(12) United States Patent
Chen et al.

(10) Patent No.: US 7,435,831 B2
(45) Date of Patent: Oct. 14, 2008

(54) BICYCLIC AND BRIDGED NITROGEN HETEROCYCLES

(75) Inventors: Wei Chen, Fremont, CA (US); Penglie Zhang, Foster City, CA (US); James B. Aggen, Burlingame, CA (US); Daniel Joseph Dairaghi, Palo Alto, CA (US); Andrew M. K. Pennell, San Francisco, CA (US); Subhabrata Sen, Bangalore Karnataka (IN); J. J. Kim Wright, Redwood City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 327 days.

(21) Appl. No.: 11/219,637

(22) Filed: Sep. 1, 2005

(65) Prior Publication Data

US 2006/0074121 A1 Apr. 6, 2006

Related U.S. Application Data

(63) Continuation-in-part of application No. 11/071,880, filed on Mar. 2, 2005.

(60) Provisional application No. 60/550,246, filed on Mar. 3, 2004.

(51) Int. Cl.
*C07D 487/04* (2006.01)
(52) U.S. Cl. .................................................. 548/453
(58) Field of Classification Search .................. 548/453
See application file for complete search history.

(56) References Cited

U.S. PATENT DOCUMENTS

| | | | |
|---|---|---|---|
| 3,362,956 A | 1/1968 | Archer | |
| 3,478,032 A | 11/1969 | Arya | |
| 3,491,098 A | 1/1970 | Archer | |
| 3,723,433 A | 3/1973 | Ueno et al. | |
| 3,950,354 A | 4/1976 | Wenzelburger et al. | |
| 3,994,890 A | 11/1976 | Fujimura et al. | |
| 4,166,452 A | 9/1979 | Generales, Jr. | |
| 4,174,393 A | 11/1979 | Van Daalen et al. | |
| 4,256,108 A | 3/1981 | Theeuwes | |
| 4,265,874 A | 5/1981 | Bonsen et al. | |
| 4,310,429 A | 1/1982 | Lai | |
| 4,442,102 A | 4/1984 | Heinemann et al. | |
| 4,547,505 A | 10/1985 | Oepen et al. | |
| 4,559,341 A | 12/1985 | Petersen et al. | |
| 4,562,189 A | 12/1985 | Tomcufcik et al. | |
| 4,672,063 A | 6/1987 | Jasserand et al. | |
| 4,772,604 A | 9/1988 | van Wijngaarden et al. | |
| 4,880,809 A | 11/1989 | Sugihara et al. | |
| 4,997,836 A | 3/1991 | Sugihara et al. | |
| 5,011,928 A | 4/1991 | Venero et al. | |
| 5,177,078 A | 1/1993 | Ward et al. | |
| 5,215,989 A | 6/1993 | Baldwin et al. | |
| 5,227,486 A | 7/1993 | Merce-Vidal et al. | |
| 5,292,739 A | 3/1994 | Merce-Vidal et al. | |
| 5,346,896 A | 9/1994 | Ward et al. | |
| 5,382,586 A | 1/1995 | Merce-Vidal et al. | |
| 5,464,788 A | 11/1995 | Bock et al. | |
| 5,580,985 A | 12/1996 | Lee et al. | |
| 5,607,936 A | 3/1997 | Chiang et al. | |
| 5,646,151 A | 7/1997 | Kruse et al. | |
| 5,681,954 A | 10/1997 | Yamamoto et al. | |
| 5,719,156 A | 2/1998 | Shue et al. | |
| 5,756,504 A | 5/1998 | Bock et al. | |
| 5,760,028 A | 6/1998 | Jadhav et al. | |
| 5,760,225 A | 6/1998 | Yuan | |
| 5,780,475 A | 7/1998 | Baker et al. | |
| 5,798,359 A | 8/1998 | Shue et al. | |
| 5,968,938 A | 10/1999 | Williams et al. | |
| 6,043,246 A | 3/2000 | Fukami et al. | |
| 6,114,334 A | 9/2000 | Kerrigan et al. | |
| 6,191,159 B1 | 2/2001 | Pinto | |
| 6,207,665 B1 | 3/2001 | Bauman et al. | |
| 6,288,083 B1 | 9/2001 | Luly et al. | |
| 6,329,385 B1 | 12/2001 | Luly et al. | |
| 6,384,035 B1 | 5/2002 | Hutchings et al. | |
| 6,451,399 B1 | 9/2002 | Boyce | |
| 6,455,544 B1 | 9/2002 | Friedhoff et al. | |

(Continued)

FOREIGN PATENT DOCUMENTS

| | | |
|---|---|---|
| EP | 0 479 546 A2 | 4/1992 |
| EP | 1 006 110 A1 | 6/2000 |
| WO | WO 97/10219 A1 | 3/1997 |
| WO | WO 97/44329 A1 | 11/1997 |
| WO | WO 98/25617 A1 | 6/1998 |
| WO | WO 98/39000 A1 | 9/1998 |
| WO | WO 98/56771 A2 | 12/1998 |
| WO | WO 99/07351 A2 | 2/1999 |
| WO | WO 99/09984 A1 | 3/1999 |
| WO | WO 99/25686 A1 | 5/1999 |

(Continued)

OTHER PUBLICATIONS

Anders, et al., "A chemokine receptor CCR-1 antagonist reduces renal fibrosis after unilateral ureter ligation." J Clin Invest. (2002) 109(2):251-9.
Badran, M. et al., "Indazole derivatives (part III): synthesis of pyrazolo-[1,2-a]indazole-1,9-dione,[1,2,4]triazino[1,2-a]indazole-1,10-dione, 3-(Indazol-1-yl)propionic acid amides and hydrazides possessing potential biological activity" *Alex. J. Pharm. Sci.* (1999) 13(2):101-106.

(Continued)

*Primary Examiner*—Laura L. Stockton
(74) *Attorney, Agent, or Firm*—Townsend and Townsend and Crew LLP

(57) ABSTRACT

Compounds are provided that act as potent modulators of one or more of the CCR1, CCR2 and CCR3 receptors. The compounds are generally fused-, spiro- or bridged-nitrogen heterocycles having an aryl and heteroaryl component and are useful in pharmaceutical compositions, methods for the treatment of CCR1-, CCR2- and/or CCR3-mediated diseases, and as controls in assays for the identification of competitive receptor antagonists for the above chemokine receptors.

14 Claims, 57 Drawing Sheets

U.S. PATENT DOCUMENTS

| | | | |
|---|---|---|---|
| 6,469,041 B2 | 10/2002 | Yuan | |
| 6,492,375 B2 | 12/2002 | Snutch | |
| 6,518,273 B1 | 2/2003 | Chapman et al. | |
| 7,157,464 B2 | 1/2007 | Pennell et al. | |
| 2002/0022624 A1 | 2/2002 | Dinnell et al. | |
| 2002/0040020 A1 | 4/2002 | Breitenbucher et al. | |
| 2002/0045613 A1 | 4/2002 | Pauls et al. | |
| 2002/0045749 A1 | 4/2002 | Li et al. | |
| 2002/0049205 A1 | 4/2002 | Li et al. | |
| 2002/0077321 A1 | 6/2002 | Khanna et al. | |
| 2002/0107255 A1 | 8/2002 | Blumberg et al. | |
| 2002/0119961 A1 | 8/2002 | Blumberg et al. | |
| 2003/0008893 A1 | 1/2003 | Colon-Cruz et al. | |
| 2003/0087917 A1 | 5/2003 | Strack et al. | |
| 2003/0139425 A1 | 7/2003 | Bauman et al. | |
| 2003/0149021 A1 | 8/2003 | Li et al. | |
| 2004/0162282 A1 | 8/2004 | Pennell et al. | |
| 2005/0234034 A1* | 10/2005 | Pennell et al. | 514/210.16 |
| 2005/0256130 A1 | 11/2005 | Pennell et al. | |
| 2006/0106218 A1 | 5/2006 | Pennell et al. | |

FOREIGN PATENT DOCUMENTS

| | | |
|---|---|---|
| WO | WO 99/32468 A1 | 7/1999 |
| WO | WO 99/37619 A1 | 7/1999 |
| WO | WO 99/37651 A1 | 7/1999 |
| WO | WO 00/31032 A1 | 6/2000 |
| WO | WO 00/46195 A1 | 8/2000 |
| WO | WO 00/46196 A1 | 8/2000 |
| WO | WO 00/46197 A1 | 8/2000 |
| WO | WO 00/46198 A1 | 8/2000 |
| WO | WO 00/46199 A1 | 8/2000 |
| WO | WO 00/47539 A1 | 8/2000 |
| WO | WO 00/53600 A1 | 9/2000 |
| WO | WO 00/69815 A1 | 11/2000 |
| WO | WO 00/69820 A1 | 11/2000 |
| WO | WO 00/69848 A1 | 11/2000 |
| WO | WO 02/08221 A3 | 1/2002 |
| WO | WO 02/14314 A2 | 2/2002 |
| WO | WO 02/070523 A1 | 9/2002 |
| WO | WO 03/008395 A1 | 1/2003 |
| WO | WO 03/024450 A1 | 3/2003 |
| WO | WO 03/051842 A2 | 6/2003 |
| WO | WO 03/105853 A1 | 12/2003 |
| WO | WO 2004/009550 A1 | 1/2004 |
| WO | WO 2005/084667 A1 | 9/2005 |

OTHER PUBLICATIONS

Bebernitz, G. et al., "The effect of 1,3-diaryl-[1H]-pyrazole-4-acetamides on glucose utilization in on/ob mice" *J. Med. Chem.* (2001) 44:2601-2611.

Bendele, et al., "Animal models of arthritis: relevance to human disease," Toxicologic Pathol. (1999) 27:134-142.

Berge, S.M., et al., "Pharmaceutical Salts," Journal of Pharmaceutical Sciences (1977) 66:1-19.

Chemcats Database, Chemical Abstracting Service, Accession No. 2003:2855298, Jan. 1, 2004 for CAS Registry No. 492422-98-7.

Chemcats Database, Chemical Abstracting Service, Accession No. 2001:2759474, Oct. 20, 2003 for CAS Registry No. 351986-92-0.

Czarnocka-Janowicz, A. et al., "Synthesis and pharmacological activity of 5-substituted-s-triazole-3-thiols" *Pharmazie* (1991) 46:109-112.

Database Crossfire Beilstein 'Online! Beilstein Institut zur Forderung der Chemischen Wissenschaften, Frankfurt am Main, DE; Database accession No. BRN 6982047 XP002254060 abstract & Varasi et al., *Farmaco Ed. Sci.* (1987) 42(6):425-436.

Database Crossfire Beilstein 'Online! Beilstein Institut zur Forderung der Chemischen Wissenschaften, Frankfurt am Main, DE; Database accession No. BRN 1159762 XP002254062 abstract & Zotta et al. *Farmacia* (1977) 25:129-134.

Database Crossfire Beilstein 'Online! Beilstein Institut zur Forderung der Chemischen Wissenschaften, Frankfurt am Main, DE; Database accession No. BRN 6000843 XP002254061 abstract & Toja et al., *Heterocycles* (1987) 26(8):2129-2138.

Database Crossfire Beilstein 'Online! Beilstein Institut zur Forderung der Chemischen Wissenschaften, Frankfurt am Main, DE; Database accession No. BRN 9229443 XP002254063 abstract & Vovk, et al., *Russ. J. Org. Chem.* (2001) 37(12).

Devries, M. et al., "On the edge: the physiological and pathophysiological role of chemokines during inflammatory and immunological responses" *Sem. Immun.* (1999) 11:95-104.

Fischer, F. et al., "Modulation of experimental autoimmune encephalomyelitis: effect of altered peptide ligand on chemokine and chemokine receptor expression" *J. Neuroimmun.* (2000) 110:195-208.

Foks, H. et al., "Synthesis of new 5-substituted 1,2,4-triazole-3-thione derivatives" *Phosphorus, Sulfur and Silicon* (2000) 164:67-81.

Gao, et al., "Targeting of the chemokine receptor CCR-1 suppresses development of acute and chronic cardiac allograft rejection," J Clin Invest. (2000) 105(1):35-44.

Hayao, S. et al., "New antihypertensive aminoalkyltetrazoles" *J. Med. Chem.* (1967) 10:400-402.

Hcaplus; Accession No. 1984:630511, Document No. 101:230511; Japanese Patent No. 59130890, issued Jul. 27, 1984; Abstract, 4 pages.

Hesselgesser, J. et al., "Identification and characterization of small molecule functional antagonists of the CCR1 chemokine receptor" *J. Biol. Chem.* (1998) 273(25):15687-15692.

International Search Report mailed on Jun. 24, 2005, for PCT Application No. PCT/US05/07166 filed on Mar. 2, 2005, three pages.

International Search Report mailed on Mar. 9, 2007, for PCT Application NO. PCT/US06/33803 filed Aug. 29, 2006, three pages.

Izikson, L. et al., "Resistance to experimental autoimmune encephalomyelitis in mice lacking the CC chemokine receptor $(CCR)^{2}$" *J. Exp. Med.* (2000) 192(7):1075-1080.

Kennedy, K. et al., "Role of chemokines in the regulation of Th1/Th2 and autoimmune encephalomyelitis" *J. Clin. Immunol.* (1999) 19(5):273-279.

Liang, M. et al., "Identification and characterization of a potent, selective, and orally active antagonist of the CC chemokine receptor" *J. Biol. Chem.* (2000) 275(25):19000-19008.

Liang, M. et al., "Species selectivity of a small molecule antagonist for the CCR1 chemokine receptor" *Eur. J. Pharmacol.* (2000) 389:41-49.

Monteclaro, et al., "The amino-terminal domain of CCR2 is both necessary and sufficient for high affinity binding of monocyte chemoattractant protein 1. Receptor activation by a pseudo-tethered ligand," J Biol Chem. (1997) 272(37):23186-90.

Ng, H. et al., "Discovery of novel non-peptide CCR1 receptor antagonists" *J. Med. Chem.* (1999) 42:4680-4694.

Nicolai, E. et al., "Synthesis and angiotensin II receptor antagonist activity of C-linkedpyrazole derivatives" *Chem. Pharm. Bull.* (1994) 42(8):1617-1630.

Patent Abstracts of Japan, vol. 007, No. 139 (C-171), Jun. 17, 1983 & JP 58 052256 A (Nippon Noyaku KK), Mar. 28, 1983 abstract.

Plater-Zyberk, C. et al., "Effect of a CC chemokine receptor antagonist on collagen induced arthritis in DBA/1 mice" *Ummun. Lett.* (1997) 57:117-120.

Podolin, et al., "A potent and selective nonpeptide antagonist of CXCR2 inhibits acute and chronic models of arthritis in the rabbit," J. Immunol. (2002) 169(11):6435-6444.

Rossi, D., et al., "The biology of chemokines and their receptors," Annu Rev Immunol. (2000) 18:217-42.

Rottman, J. et al., "Leukocyte recruitment during onset of experimental allergic encephalomyelitis is CCR1 dependent" *Eur. J. Immunol.* (2000) 30:2372-2377.

Saeki, T., et al., "CCR1 chemokine receptor antagonist," Curr Pharm Des. (2003) 9:1201-1208.

SciFinder Report; Piperazine, 1-[(2,4-dinitro-1H-Imidazol-1-yl)acetyl]-4-(4-fluorophenyl)-; Registry No. 313987-12-1; Catalogs: Exploratory Library, Interchim Intermediates, ChemDiv, Inc. Product Library, AsinEx Express Gold Collection, Pharma Library Collection; report dated Sep. 30, 2003; 7 pages.

SciFinder Report; Piperazine, 1-[(3,5-dimethyl-4-nitro-1H-pyrazol-1-yl)acetyl]-4-(4-fluorophenyl)-(9Cl); Registry No. 356039-23-1; Catalogs: STN Chemcats, Exploratory Library, ChemDiv, Inc. Product Library; report dated Sep. 30, 2003; 4 pages.

SciFinder Report; Piperazine, 1-[(4-nitro-1H-imidazol-1-yl)acetyl]-4-phenyl-(9Cl); Registry No. 312707-74-7; Catalogs: STN Chemcats, Exploratory Library, Interchem Intermediates, AsinEx Express Gold Collection, and Pharma Library Collection; report dated Sep. 30, 2003; 7 pages.

SciFinder Report; Piperazine, 1-[2-(3,5-dimethyl-4-nitro-1H-pyrazol-1-yl)-1-oxopropyl]-4-phenyl-; Registry No. 489449-56-1: Catalogs: Compounds for Screening, Interchim Intermediates; report dated Sep. 30, 2003; 3 pages.

SciFinder Report; Piperazine, 1-[2,4-dinitro-1H-imidazol-1-yl)acetyl]4-phenyl-; Registry No. 313987-13-2; Catalogs: Exploratory Library, Interchim Intermediates, Compounds for Screening, ChemDic, Inc. Product Library, AsinEx Express Gold Collection, Pharma Library Collection; report dated Sep. 30, 2003; 7 pages.

Tokuda, et al., "Pivotal role of CCR1-positive leukocytes in bleomycin-induced lung fibrosis in mice," J Immunol. (2000) 164(5):2745-51.

Trentham, et al., "Autoimmunity to type II collagen an experimental model of arthritis," J. Exp Med. (1977) 146(3):857-868.

Walsh, D. et al., "Synthesis and antiallergy activity of N-[2-(dimethylamino)ethyl]-4-aryl-1-piperazinecarboxamide derivatives" *J. Med. Chem.* (1990) 33:2028-2032.

* cited by examiner

VIy

VIz

VIaa

VIbb

VIcc

VIdd

VIee

VIff

VIgg

VIhh

VIsss

VIttt

VIuuu

VIvvv

VIwww

VIxxx

VIyyy

VIzzz

BICYCLIC AND BRIDGED NITROGEN HETEROCYCLES

CROSS-REFERENCES TO RELATED APPLICATIONS

This application is a continuation-in-part of U.S. patent application Ser. No. 11/071,880 which claims the benefit of U.S. Provisional application Ser. No. 60/550,246, filed Mar. 3, 2004, the contents of all are incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., *Semin Immunol* 11(2):95-104 (1999)). A hallmark of some demyelinating diseases such as multiple sclerosis is the chemokine-mediated monocyte/macrophage and T cell recruitment to the central nervous system (see, Kennedy, et al., *J. Clin. Immunol.* 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., *Ann. Rev. Immunol.* 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., *Current Pharmaceutical Design* 9:1201-1208 (2003)) since they have been implicated in rheumatoid arthritis, transplant rejection (see, DeVries, M. E., et al., ibid. and Gao, et al., *J. Clin. Investigation,* 105:35-44 (2000)), and multiple sclerosis (see, Fischer, et al., *J Neuroimmunol.* 110 (1-2):195-208 (2000); Izikson, et al., *J. Exp. Med.* 192(7): 1075-1080 (2000); and Rottman, et al., *Eur. J. Immunol.* 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., *Immunol Lett.* 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., *J. Biol. Chem.* 273(25):15687-15692 (1998); Ng, et al., *J. Med. Chem.* 42(22):4680-4694 (1999); Liang, et al., *J. Biol. Chem.* 275(25):19000-19008 (2000); and Liang, et al., *Eur. J. Pharmacol.* 389(1):41-49 (2000)). In view of the effectiveness demonstrated for treatment of disease in animal models (see, Liang, et al., *J. Biol. Chem.* 275(25):19000-19008 (2000)), the search has continued to identify additional compounds that can be used in the treatment of diseases mediated by CCR1 signaling.

Additionally, a chemokine receptor antagonist/modulator can have beneficial effects in the prevention of progressive fibrosis, such as renal fibrosis (see Anders, et al., *J. Clin. Investigation* 109:251-259 (2002)) and/or pulmonary fibrosis (see Tokuda, et al., *J. Immunol.* 164:2745-2751 (2000)).

A chemokine receptor antagonist/modulator can also have beneficial effects in the treatment of cancer and/or the prevention of cancer; for example. For example, this can occur by inhibiting any role of immune cells, such as macrophages, in contributing to tumor development (see Robinson, et al., *Cancer Res.* 63:8360-8365 (2003)).

The MCP-1 receptor CCR2b signals through a variety of G-proteins (see Monteclaro et al, *J. Biol. Chem.*, 37, 23186 (1997). MCP-1 interaction with the CCR2b receptor leads to various biological effects including increased histamine release, calcium influx, cAMP activation and promotion of migration of circulating monocytes into tissues.

MCP-1 has been implicated in various human diseases, including atherosclerosis, multiple sclerosis, asthma and rheumatoid arthritis (for example see Aielo et al, *Arteriosclero Throm Vasc Bio.*, 19, 1518, (1999) and Fuentes, *J. Immunology*, 155, 5769, (1995)) and various cell types including endothelial cells, smooth muscle cells, macrophages and fibroblasts produce MCP-1. Leukocyte entry into tissue involves chemotactic signaling to circulating cells, interaction with endothelial cells and transmigration through tissues. Additionally, in addition to acting as a chemoattractant, MCP-1 can further potentiate the inflammatory response by promoting integrin expression and cellular adhesion.

MCP-1 is expressed at sites of inflammation and autoimmune disease, and therefore compounds which inhibit the binding of MCP-1 to the chemokine CCR2 receptor will provide useful leads in the discovery of drugs that will inhibit the action of MCP-1 on target cells. Patent application WO 02/070523 provides a useful summary of known information in this regard. WO 02/070523 also summarises the underlying facts that homing and activation of eosinophils, basophils and memory CD4+ Th2+ lymphocytes in lung tissues are considered important to the etiology of chronic airway inflammatory diseases. Several chemokines have been shown to mediate the recruitment and activation of these cell types. Specifically, eotaxin, eotaxin 2, MCP-3, MCP-4 and Rantes are produced from human lung mast cells and other relevant cell types activate the aforementioned effector cells through binding to the CCR3 receptor. Potential therapeutic uses of CCR3 antagonists include asthma and COPD.

BRIEF SUMMARY OF THE INVENTION

The present invention provides compounds having the formula:

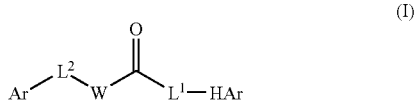

(I)

or a pharmaceutically acceptable salt or N-oxide thereof, wherein Ar, $L^1$, $L^2$, W and HAr have the meanings provided below.

In addition to the compounds provided herein, the present invention further provides pharmaceutical compositions containing one or more of these compounds, as well as methods for the use of these compounds in therapeutic methods, primarily to treat diseases associated with CCR1, CCR2 and/or CCR3 signaling activity.

DETAILED DESCRIPTION OF THE INVENTION

I. Abbreviation and Definitions

Figure 1A:
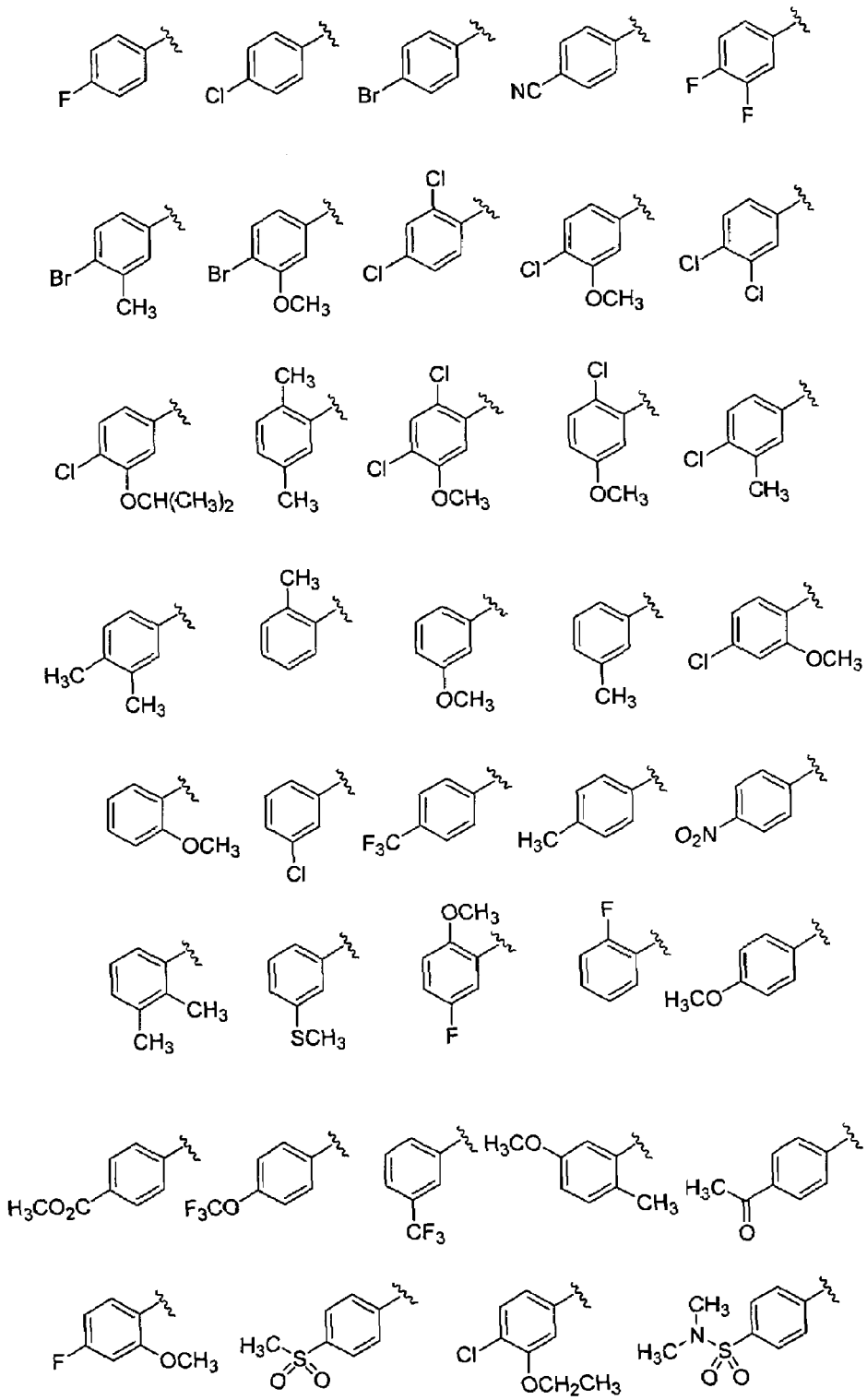
FIGS. 1A through 1G provide selected and preferred Ar groups for compounds of formula I.
Figure 1B:
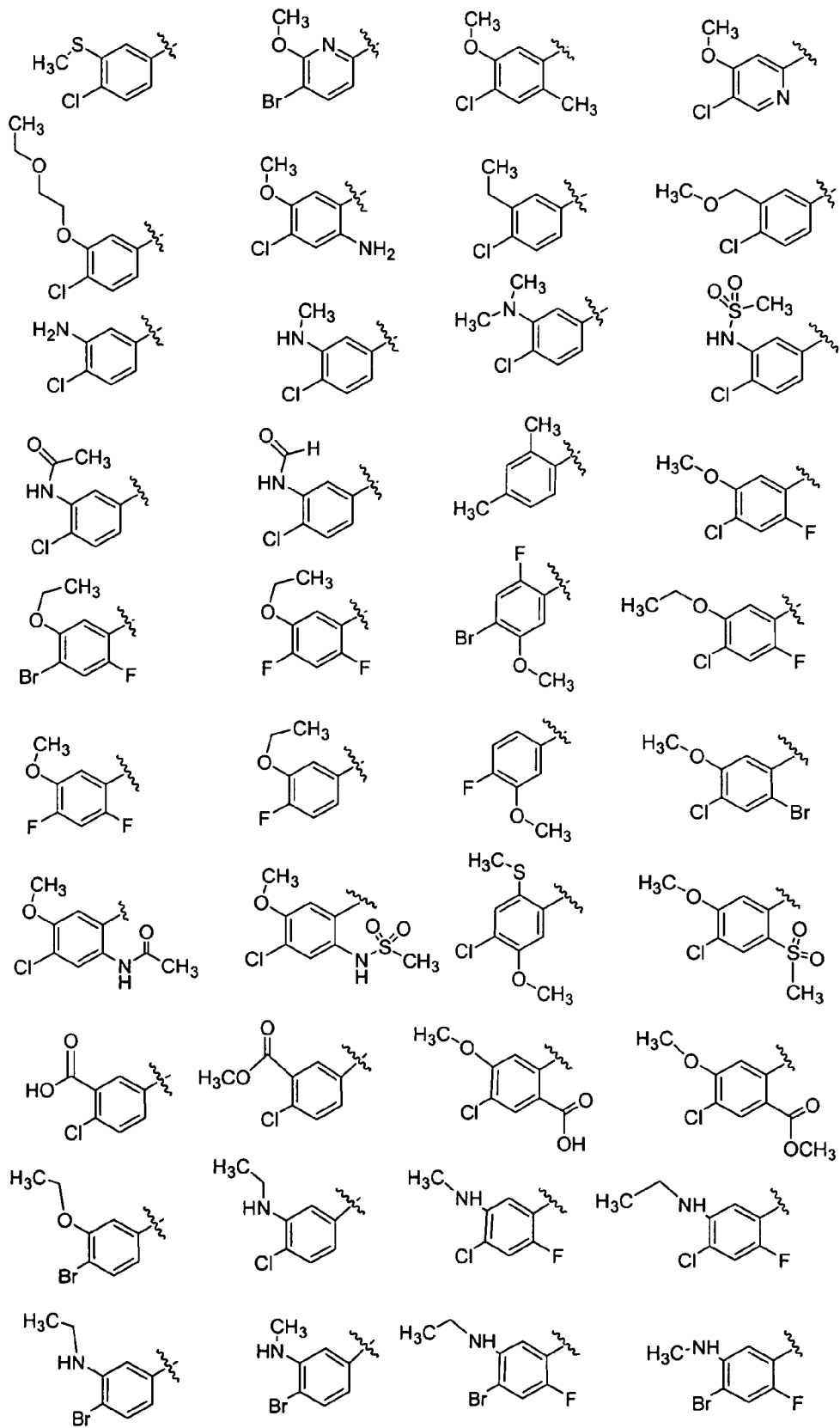
Figure 1C:
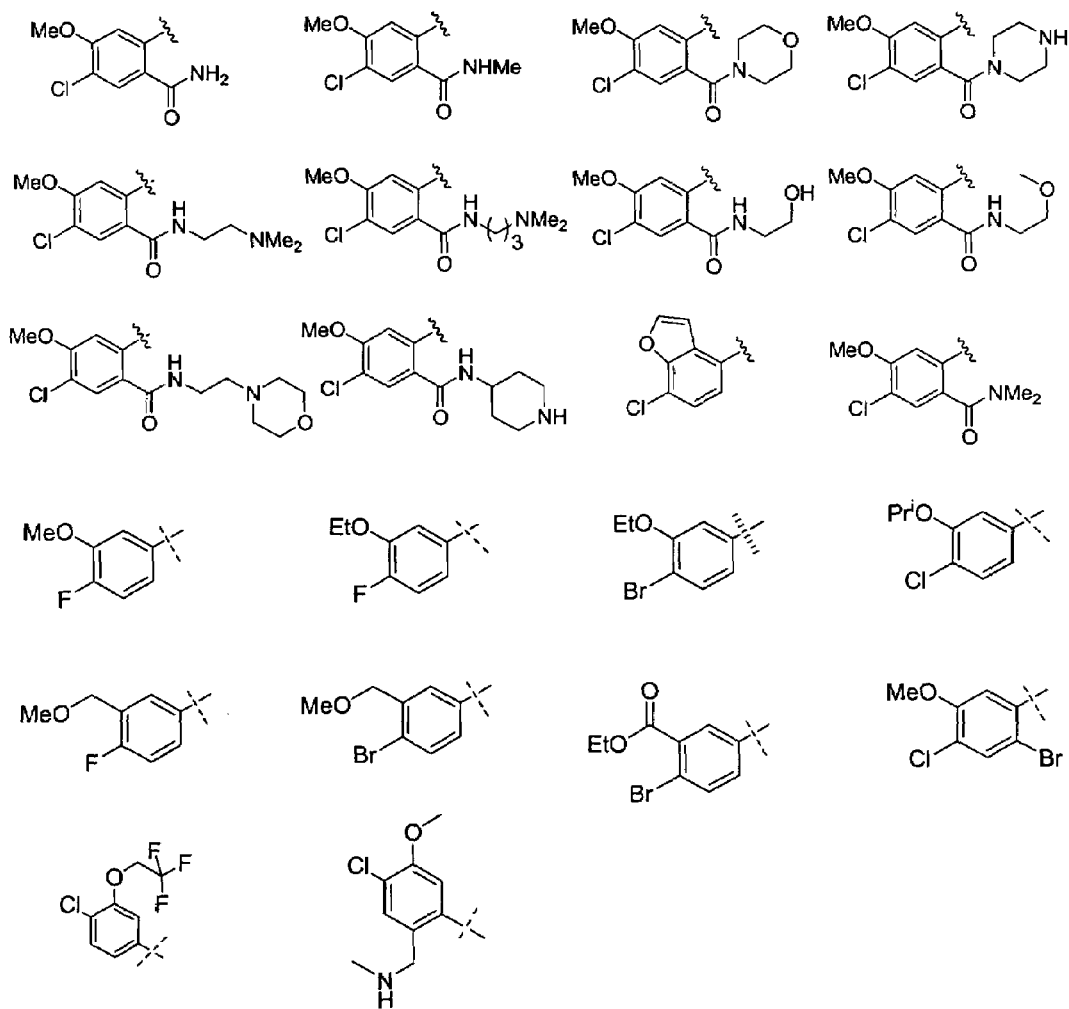
Figure 1D:
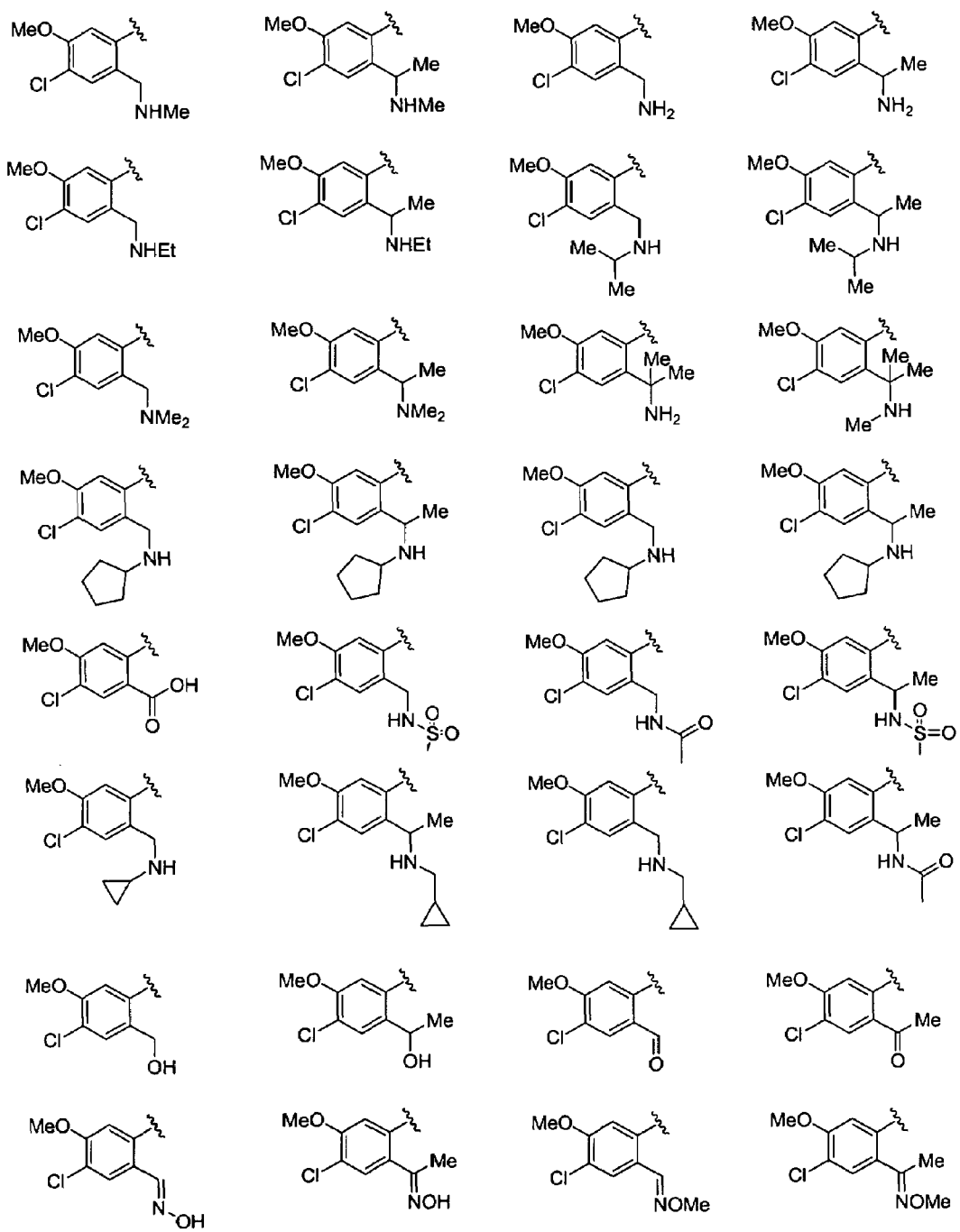
Figure 1E:
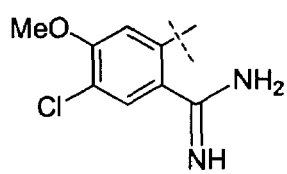
Figure 1E:
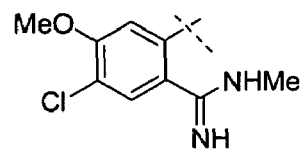
Figure 1E:
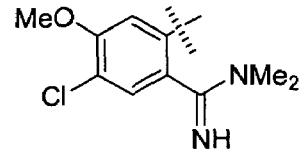
Figure 1E:
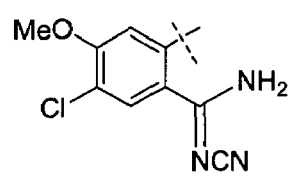
Figure 1E:
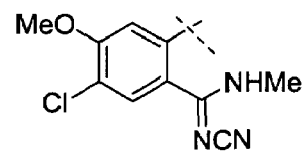
Figure 1E:
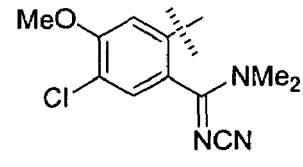
Figure 1E:
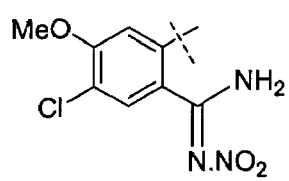
Figure 1E:
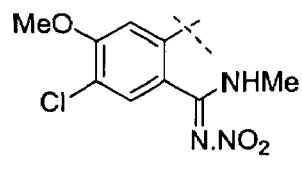
Figure 1E:
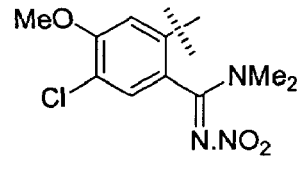
Figure 1E:
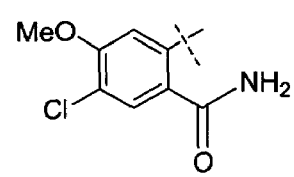
Figure 1E:
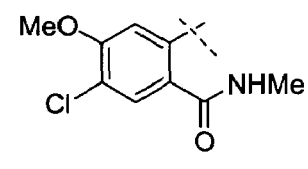
Figure 1E:
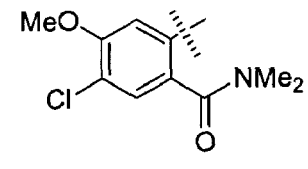
Figure 1E:
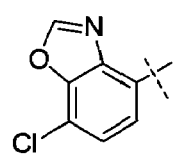
Figure 1E:
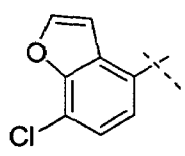
Figure 1E:
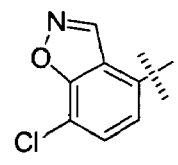
Figure 1E:
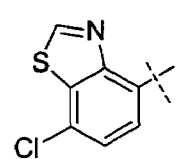
Figure 1E:
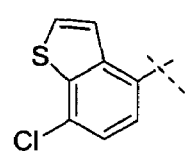
Figure 1E:
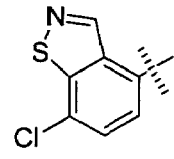
Figure 1F:
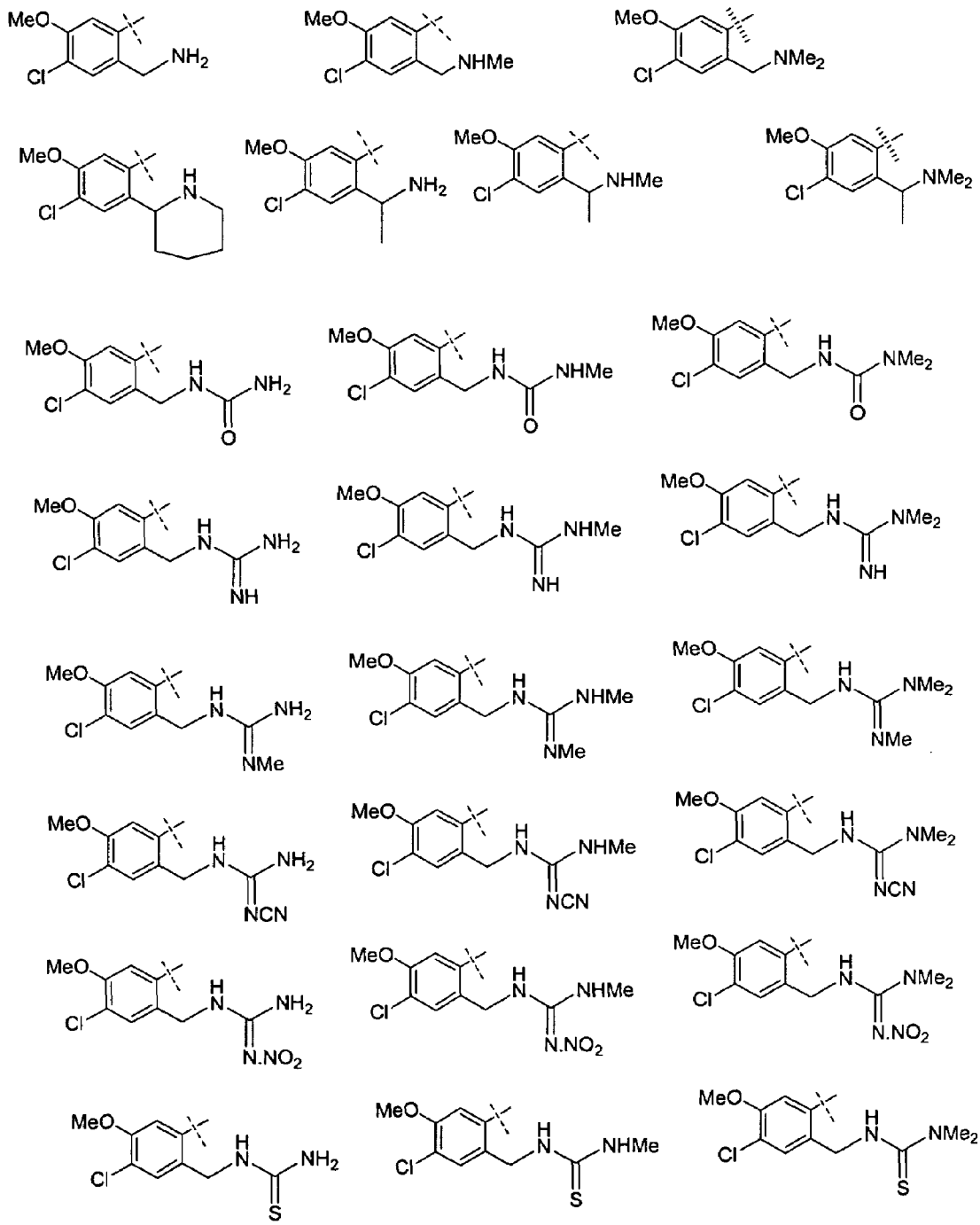
Figure 1G:
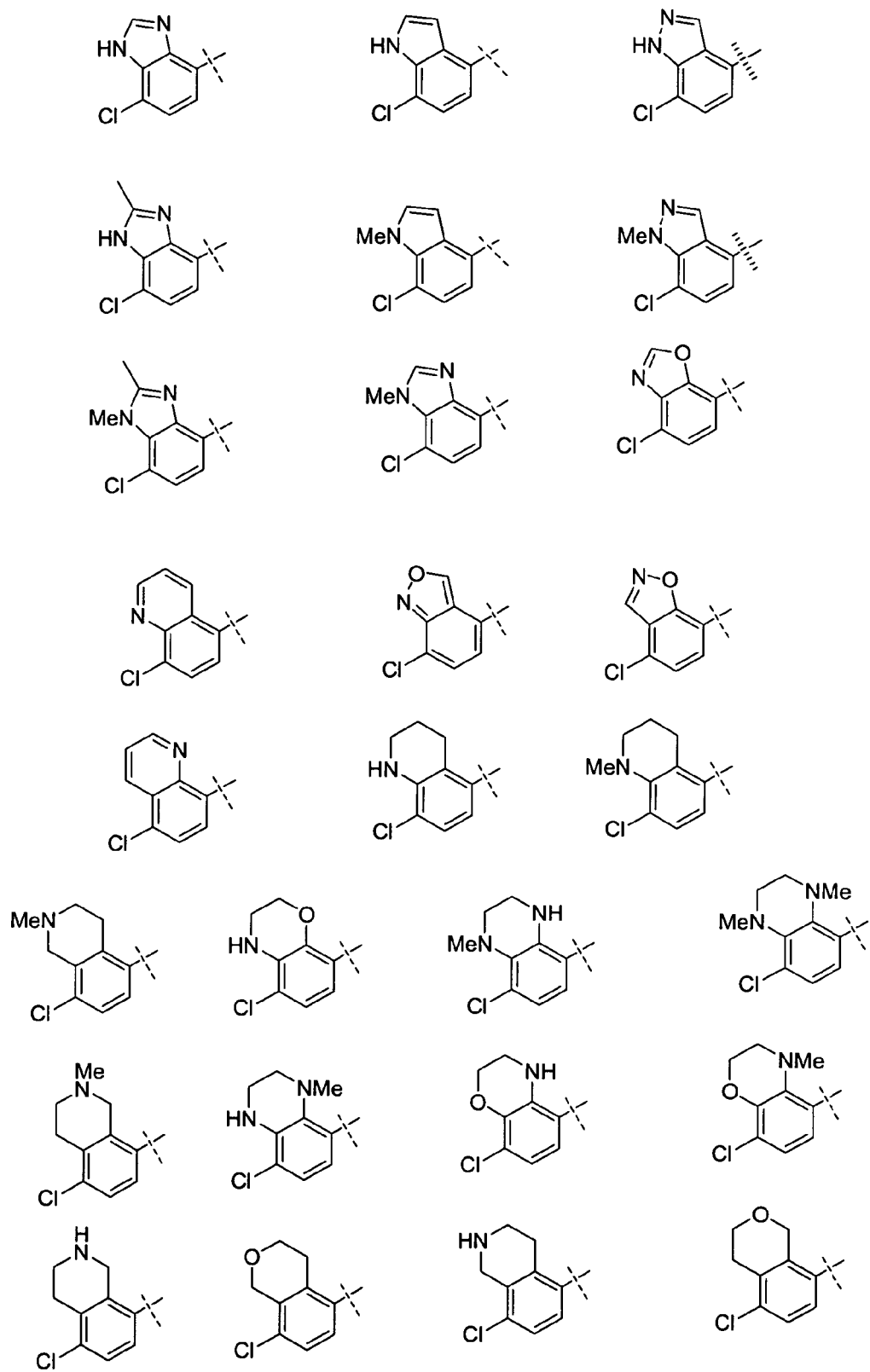

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The term "heterocycle" or "heterocyclic" refers to a saturated or unsaturated non-aromatic cyclic group containing at least one sulfur, nitrogen or oxygen heteroatom. Each heterocycle can be attached at any available ring carbon or heteroatom. Each heterocycle may have one or more rings. When multiple rings are present, they can be fused together or linked covalently. Each heterocycle must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Non-limiting examples of heterocycle groups include pyrrolidine, piperidine, imidazolidine, pyrazolidine, butyrolactam, valerolactam, imidazolidinone, hydantoin, dioxolane, phthalimide, 1,4-dioxane, morpholine, thiomorpholine, thiomorpholine-S,S-dioxide, piperazine, pyran, pyridone, 3-pyrroline, thiopyran, pyrone, tetrahydrofuran, tetrahydrothiophene and the like.

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2m'+1), where m' is the total number of carbon atoms in such radical. R', R" and R'" each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C (NH$_2$)=NR', —S(O)R', —S(O)$_2$R', —S(O)$_2$NR'R", —NR'S (O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

As used herein, a wavy line, ∿∿ that intersects a single, double or triple bond in the chemical structured depicted herein, represent the point attachment of the single, double, or triple bond to the remainder of the molecule.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. General

The present invention derives from the discovery that compounds of formula I (as well as the subgeneric formulae II, III, IV and V) act as potent antagonists of the CCR1 receptor. Another discovery underlying the present invention is that bridged and bicyclic diamine compounds provided herein as formulae A, B, C and D are useful to replace the piperazine components of compounds provided in, for example, co-pending and co-owned applications, Ser. No. 11/008,774; Ser. No. 10/979,882; Ser. No. 10/732,897; Ser. No. 10/460,752; and Ser. No. 60/453,711, the disclosures of which are incorporated herein by reference. As demonstrated herein through representative activities, the CCR1 receptors is tolerant of the changes imposed by the replacement of piperazine in the aforementioned applications with bridged, fused or spirocyclic diamines. Accordingly, the compounds provided herein are useful in pharmaceutical compositions, methods for the treatment of CCR1-mediated diseases, and as controls in assays for the identification of competitive chemokine receptor antagonists.

III. Compounds

In one aspect, the present invention provides compounds having the formula:

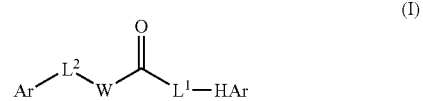

(I)

or a pharmaceutically acceptable salt or N-oxide thereof.

In the formula above, W is a bridged or fused bicyclic or spirocyclic diamine moiety selected from the group consisting of:

formula A—

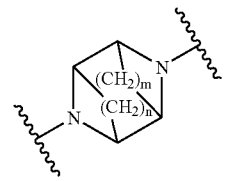

A wherein the subscripts n and m are each independently integers of from 0 to 4, and at least one of n or m is other than 0, wherein 0 indicates the absence of either a bridge or a bond;

formula B—

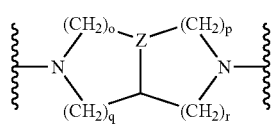

B wherein the subscripts o, p, q and r are each independently integers of from 0 to 4, and (i) when o is 0, q is other than 0; (ii) when p is 0, r is other than 0; (iii) when q is 0, r is other than 0; (iv) when p is 0, o is other than 0; (v) the sum of o, p, q and r is 3 to 10; and Z is selected from the group consisting of CH, CR$^1$ and N; and a covalent bond is indicated when any of o, p, q and r are 0;

formula C—

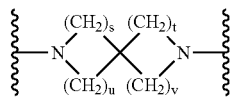

wherein the subscripts s, t, u and v are independently integers of from 0 to 4, and (i) no more than one of s, t, u and v is 0; (ii) the sum of s and u is no more than 6; and (iii) the sum of t and v is no more than 6; and a covalent bond is indicated when any of s, t, u and v are 0;

formula D—

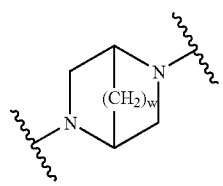

wherein the subscript w is an integer of from 1 to 3;

and wherein each of formulae A, B, C and D is optionally substituted with from 1 to 4 $R^1$ groups and optionally can further have a site of unsaturation (a double bond) between two ring vertices; and the wavy lines indicate the points of attachment to the remainder of the compound. Each $R^1$ is a substituent independently selected from $C_{1-8}$ alkyl, $C_{1-8}$ haloalkyl, $C_{3-6}$ cycloalkyl, $C_{2-8}$ alkenyl, $C_{2-8}$ alkynyl, —$COR^a$, —$CO_2R^a$, —$CONR^aR^b$, —$NR^aCOR^b$, —$SO_2R^a$, —$X^1COR^a$, —$X^1CO_2R^a$, —$X^1CONR^aR^b$, —$X^1NR^aCOR^b$, —$X^1SO_2R^a$, —$X^1SO_2NR^aR^b$, —$X^1NR^aR^b$, —$X^1OR^a$, wherein $X^1$ is selected from $C_{1-4}$ alkylene, $C_{2-4}$ alkenylene and $C_{2-4}$ alkynylene and each $R^a$ and $R^b$ is independently selected from hydrogen, $C_{1-8}$ alkyl, $C_{1-8}$ haloalkyl, $C_{3-6}$ cycloalkyl and aryl-$C_{1-4}$alkyl, or optionally $R^a$ and $R^b$ when attached to the same nitrogen atom can be combined with the nitrogen atom to form a five or six-membered ring having from 0 to 2 additional heteroatoms as ring members, and wherein the aliphatic portions of each of said $R^1$ substituents are optionally substituted with from one to three members selected from —OH, —$OR^m$, —$OC(O)NHR^m$, —$OC(O)N(R^m)_2$, —SH, —$SR^m$, —$S(O)R^m$, —$S(O)_2R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)NHR^m$, —$C(O)N(R^m)_2$, —$C(O)R^m$, —$NHC(O)R^m$, —$NR^mC(O)R^m$, —$NHC(O)NH_2$, —$NR^mC(O)NH_2$, —$NR^mC(O)NHR^m$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl. Optionally, two $R^1$ substituents on adjacent carbon atoms of formula A, B, C or D can be combined with the atoms to which each are attached to form a 5-, 6- or 7-membered carbocyclic or heterocyclic ring.

The symbol Ar represents an optionally substituted aryl or heteroaryl group. Preferred aryl groups are phenyl and naphthyl. Preferred heteroaryl groups are those having from 5 to 10 ring vertices, at least one of which is a nitrogen atom (e.g., pyridyl, pyridazinyl, pyrazinyl, pyrimidinyl, triazinyl, quinolinyl, quinoxalinyl, purinyl and the like). The Ar moiety is optionally substituted with from one to five $R^2$ substituents independently selected from the group consisting of halogen, —$OR^c$, —$OC(O)R^c$, —$NR^cR^d$, —$SR^c$, —$R^e$, —CN, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —NH—$C(NH_2)$=NH, —$NR^eC(NH_2)$=NH, —NH—$C(NH_2)$=$NR^e$, —NH—$C(NHR^e)$=NH, —$S(O)R^e$, —$S(O)_2R^e$, $NR^cS(O)_2R^e$, —$S(O)_2NR^cR^d$, —$N_3$, —$X^2OR^c$, —O—$X^2OR^c$, —$X^2OC(O)R^c$, —$X^2NR^cR^d$, —O—$X^2NR^cR^d$, —$X^2SR^c$, —$X^2CN$, —$X^2NO_2$, —$X^2CO_2R^c$, —O—$X^2CO_2R^c$, —$X^2CONR^cR^d$, —O—$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$, —$X^2N_3$, —$NR^d$—$X^2OR^c$, —$NR^d$—$X^2NR^cR^d$, —$NR^d$—$X^2CO_2R^c$, and —$NR^d$—$X^2CONR^cR^d$, wherein $X^2$ is a member selected from the group consisting of $C_{1-4}$ alkylene, $C_{2-4}$ alkenylene and $C_{2-4}$ alkynylene and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or optionally $R^c$ and $R^d$ when attached to the same nitrogen atom can be combined with the nitrogen atom to form a five or six-membered ring having from 0 to 2 additional heteroatoms as ring members; and each $R^e$ is independently selected from the group consisting of $C_{1-8}$ alkyl, $C_{18}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of $R^c$, $R^d$ and $R^e$ is optionally further substituted with from one to three members selected from the group consisting of —OH, —$OR''$, —$OC(O)NHR''$, —$OC(O)N(R'')_2$, —SH, —$SR''$, —$S(O)R''$, —$S(O)_2R''$, —$SO_2NH_2$, —$S(O)_2NHR''$, —$S(O)_2N(R'')_2$, —$NHS(O)_2R''$, —$NR''S(O)_2R''$, —$C(O)NH_2$, —$C(O)NHR''$, —$C(O)N(R'')_2$, —$C(O)R''$, —$NHC(O)R''$, —$NR''C(O)R''$, —$NHC(O)NH_2$, —$NR''C(O)NH_2$, —$NR''C(O)NHR''$, —$NHC(O)NHR''$, —$NR''C(O)N(R'')_2$, —$NHC(O)N(R'')_2$, —$CO_2H$, —$CO_2R''$, —$NHCO_2R''$, —$NR''CO_2R''$, —CN, —$NO_2$, —$NH_2$, —$NHR''$, —$N(R'')_2$, —$NR''S(O)NH_2$ and —$NR''S(O)_2NHR''$, wherein each $R''$ is independently an unsubstituted $C_{1-6}$ alkyl. Optionally, two $R^2$ substituents on adjacent carbon atoms can be combined to form a 5- or 6-membered ring having 0-3 heteroatoms as ring members.

HAr is an optionally substituted heteroaryl group or a heterocyclic group substituted with an aryl or heteroaryl group. The heteroaryl groups for HAr can be the same or different from any of the heteroaryl groups used for Ar. The HAr groups can be monocyclic, or can also be fused bicyclic systems having from 5 to 10 ring atoms, preferably wherein at least one ring atom of which is a nitrogen atom. Certain preferred heteroaryl groups are 5 or 6-membered rings having at least one nitrogen atom as a ring vertex and fused ring systems having a 5-membered ring fused to a benzene or a heteroaryl ring having up to 4 nitrogen atoms. Examples of heteroaryl groups that can be optionally substituted include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl, thienyl and the like.

In certain embodiments, HAr is a heteroaryl group selected from the group consisting of pyrazolyl, imidazolyl, triazolyl, tetrazolyl, oxazolyl, isoxazolyl, oxadiazolyl, oxathiadiazolyl, pyrrolyl, thiazolyl, isothiazolyl, benzimidazolyl, benzopyrazolyl, benzotriazolyl, benzotetrazolyl, benzooxazolyl, benzoisoxazolyl, benzooxadiazolyl, quinolinyl, isoquinolinyl, quinazolinyl, quinoxalinyl, naphthyridinyl, pyrimidinopyridinyl, pyridazinopyridinyl, pyrazinopyridinyl, pyridinopyrimidinyl, pyrimidinopyrimidinyl, pyridazinopyrimidinyl, pyrazinopyrimidinyl, pyridinopyridazinyl, pyrimidinopyridazinyl, pyridazinopyridazinyl, pyrazinopyridazinyl, pyridinopyrazinyl, pyrimidinopyrazinyl, pyridazinopyrazinyl, pyrazinopyrazinyl, pyridinoimidazolyl, purinyl, pyridazinoimidazolyl, pyrazinoimidazolyl, pyridinooxazolyl, pyrimidinooxazolyl, pyridazinooxazolyl, pyrazinooxazolyl, pyridinoisoxazolyl, pyrimidinoisoxazolyl, pyridazinoisoxazolyl, pyrazinoisoxazolyl, pyridinooxathiadiazolyl, pyrimidinooxathiadiazolyl, pyridazinooxathiadiazolyl, pyrazinooxathiadiazolyl, pyridinooxathiazolyl, pyrimidinooxathiazolyl, pyridazinooxathiazolyl, pyrazinooxathiazolyl, pyridinothiazolyl, pyrimidinothiazolyl, pyridazinothiazolyl, pyrazinothiazolyl, pyridinopyrazolyl, pyrimidinopyrazolyl, pyridazinopyrazolyl, pyrazinopyrazolyl, pyridinopyrrolyl, pyrimidinopyrrolyl, pyridazinopyrrolyl and pyrazinopyrrolyl.

In certain other embodiments, HAr is a fused bicyclic moiety, and is attached to the remainder of the molecule through the 5-member ring. Examples of such preferred HAr include benzimidazolyl, benzopyrazolyl, benzotriazolyl, pyridinopyrazolyl, indolyl, benzotetrazolyl, benzooxazolyl, benzoisoxazolyl, benzooxadiazolyl, quinolinyl, isoquinolinyl, quinazolinyl, quinoxalinyl, naphthyridinyl, pyrimidinopyridinyl, pyridazinopyridinyl, pyrazinopyridinyl, pyridinopyrimidinyl, pyrimidinopyrimidinyl, pyridazinopyrimidinyl, pyrazinopyrimidinyl, pyridinopyridazinyl, pyrimidinopyridazinyl, pyridazinopyridazinyl, pyrazinopyridazinyl, pyridinopyrazinyl, pyrimidinopyrazinyl, pyridazinopyrazinyl, pyrazinopyrazinyl, pyridinoimidazolyl, purinyl, pyridazinoimidazolyl, pyrazinoimidazolyl, pyridinooxazolyl, pyrimidinooxazolyl, pyridazinooxazolyl, pyrazinooxazolyl, pyridinoisoxazolyl, pyrimidinoisoxazolyl, pyridazinoisoxazolyl, pyrazinoisoxazolyl, pyridinooxathiadiazolyl, pyrimidinooxathiadiazolyl, pyridazinooxathiadiazolyl, pyrazinooxathiadiazolyl, pyridinooxathiazolyl, pyrimidinooxathiazolyl, pyridazinooxathiazolyl, pyrazinooxathiazolyl, pyridinothiazolyl, pyrimidinothiazolyl, pyridazinothiazolyl, pyrazinothiazolyl, pyrimidinopyrazolyl, pyridazinopyrazolyl, pyrazinopyrazolyl, pyridinopyrrolyl, pyrimidinopyrrolyl, pyridazinopyrrolyl and pyrazinopyrrolyl.

In other embodiments, HAr is a monocyclic group, preferably selected from pyrazolyl, imidazolyl, triazolyl, tetrazolyl and pyrrolyl. In certain instances, HAr is a pyrazolyl group. In some embodiments, HAr is a heteroaryl group having one or more nitrogen atoms as ring members wherein the point of attachment to the remainder of the molecule is through a nitrogen ring member. In some embodiments, HAr is a heteroaryl group having one or more nitrogen atoms as ring members wherein the point of attachment to the remainder of the molecule is through a carbon ring member.

In certain other embodiments, HAr is a heterocyclic ring substituted with an aryl or heteroaryl group. In a certain embodiment, the heterocyclic ring and the aryl or heteroaryl group are connected by a single covalent bond. In a preferred embodiment, the heterocyclic ring and the aryl or heteroaryl group are fused together.

Additionally, each of the HAr groups is substituted with from one to five $R^3$ substituents independently selected from the group consisting of halogen, —$OR^f$, —$OC(O)R^f$, —$NR^fR^g$, —$SR^f$, —$R^h$, —$CN$, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —$NH$—$C(NH_2)$=$NH$, —$NR^hC(NH_2)$=$NH$, —$NH$—$C(NH_2)$=$NR^h$, —$NH$—$C(NHR^h)$=$NH$, —$S(O)R^h$, —$S(O)_2R^h$, —$NR^fS(O)_2R^h$, —$S(O)_2NR^fR^g$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3NH$—$C(NH_2)$=$NH$, —$X^3NR^hC(NH_2)$=$NH$, —$X^3NH$—$C(NH_2)$=$NR^h$, —$X^3NH$—$C(NHR^h)$=$NH$, —$X^3S(O)R^h$, —$X^3S(O)_2R^h$, —$X^3NR^fS(O)_2R^h$, —$X^3S(O)_2NR^fR^g$, —$Y$, —$X^3Y$, —$S(O)_2Y$, —$C(O)Y$, —$X^3N_3$, —$O$—$X^3OR^f$, —$O$—$X^3NR^fR^g$, —$O$—$X^3CO_2R^f$, —$O$—$X^3CONR^fR^g$, —$NR^g$—$X^3OR^f$, —$NR^g$—$X^3NR^fR^g$, —$NR^gX^3CO_2R^f$, and —$NR^g$—$X^3CONR^fR^g$, wherein Y is a five or six-membered aryl, heteroaryl or heterocyclic ring, optionally substituted with from one to three substitutents selected from the group consisting of halogen, —$OR^f$, —$OC(O)R^f$, —$NR^fR^g$, —$R^h$, —$SR^f$, —$CN$, —$NO_2$, —$CO_2R^f$, —$CONR^fR^g$, —$C(O)R^f$, —$NR^gC(O)R^f$, —$NR^gC(O)_2R^h$, —$S(O)R^h$, —$S(O)_2R^h$, —$NR^fS(O)_2R^h$, —$S(O)_2NR^fR^g$, —$X^3OR^f$, $X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3OC(O)R^f$, —$X^3S(O)R^h$, —$X^3S(O)_2R^h$, —$X^3NR^fR^g$, —$X^3NR^fS(O)_2R^h$, —$X^3S(O)_2NR^fR^g$, —$O$—$X^3OR^f$, —$O$—$X^3NR^fR^g$, —$O$—$X^3CO_2R^f$, —$O$—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$ and wherein each $X^3$ is independently selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $X^3$, $R^f$, $R^g$ and $R^h$ are optionally further substituted with from one to three members selected from the group consisting of —$OH$, —$OR^o$, —$OC(O)NHR^o$, —$OC(O)N(R^o)_2$, —$SH$, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —$CN$, —$NO_2$, —$NH_2$, —$NHR^o$, —$N(R^o)_2$, —$NR^oS(O)NH_2$ and —$NR^oS(O)_2NHR^o$, wherein each $R^o$ is independently an unsubstituted $C_{1-6}$ alkyl. In some embodiments, two adjacent $R^3$ groups can be combined to form a 5-7 membered ring having 0-3 heteroatoms as ring members. Among the most preferred HAr groups are substituted or unsubstituted pyrazoles and substituted or unsubstituted triazoles. Preferably, substituted or unsubstituted pyrazoles are attached to the remainder of the molecule via a nitrogen atom of the pyrazole ring.

For those embodiment in which HAr is substituted with Y or a group having a Y component, preferred 6-membered heteroaryl systems are pyridyl, pyridazinyl, pyrazinyl, pyrimidinyl, triazinyl, and the like. Preferred 5-membered heteroaryl ring systems are isothiazolyl, pyrazolyl, imidazolyl, triazolyl, tetrazolyl, oxazolyl, isoxazolyl, oxadiazolyl, thiadiazolyl, pyrrolyl, thiazolyl and the like. Most preferred are those embodiments in which Y is selected from phenyl, morpholinyl, pyrazolyl, thiazolyl, isoxazolyl, oxazolyl, oxadiazolyl, piperidinyl, piperazinyl, pyrrolidinyl, pyridyl, pyrimidinyl, furyl and thienyl.

The symbol $L^1$ represents a linking group having from one to three main chain atoms selected from the group consisting of C, N, O and S and being optionally substituted with from one to three substituents selected from the group consisting of halogen, —$OR^i$, —$OC(O)R^i$, —$NR^iR^j$, —$SR^i$, —$R^k$, —CN, —$NO_2$, —$CO_2R^i$, —$CONR^iR^j$, —$C(O)R^i$, —$S(O)R^i$, —$S(O)_2R^i$, —$SO_2NH_2$, —$S(O)_2NHR^i$, —$S(O)_2NR^iR^j$, —$NHS(O)_2R^i$, —$NR^jS(O)_2R^i$, —$OC(O)NR^iR^j$, —$NR^jC(O)R^i$, —$NR^jC(O)_2R^k$, —$Y^1$, —$X^4Y^1$, —$X^4OR^i$, —$X^4OC(O)R^i$, —$X^4NR^iR^j$, —$X^4SR^i$, —$X^4S(O)_2R^i$, —$X^4S(O)_2NR^iR^j$, —$X^4CN$, —$X^4NO_2$, —$X^4CO_2R^i$, —$X^4CONR^iR^j$, —$X^4C(O)R^i$, —$X^4OC(O)NR^iR^j$, —$X^4NR^jS(O)_2R^i$, —$X^4NR^jC(O)R^i$ and —$X^4NR^jC(O)_2R^k$, wherein $Y^1$ is a five or six-membered aryl, heteroaryl or heterocyclic ring, optionally substituted with from one to three substituents independently selected from the group consisting of halogen, —$OR^i$, —$OC(O)R^i$, —$NR^iR^j$, —$SR^i$, —$R^k$, —CN, —$NO_2$, —$CO_2R^i$, —$CONR^iR^j$, —$C(O)R^i$, —$S(O)R^i$, —$S(O)_2R^i$, —$SO_2NH_2$, —$S(O)_2NHR^i$, —$S(O)_2NR^iR^j$, —$NHS(O)_2R^i$, —$NR^jS(O)_2R^i$, —$OC(O)NR^iR^j$, —$NR^jC(O)R^i$, —$NR^jC(O)_2R^i$, —$X^4OR^i$, —$X^4OC(O)R^i$, —$X^4NR^iR^j$, —$X^4SR^i$, —$X^4S(O)_2R^i$, —$X^4S(O)_2NR^iR^j$, —$X^4CN$, —$X^4NO_2$, —$X^4CO_2R^i$, —$X^4CONR^iR^j$, —$X^4C(O)R^i$, —$X^4OC(O)NR^iR^j$, —$X^4NR^jS(O)_2R^i$, —$X^4NR^jC(O)R^i$ and —$X^4NR^jC(O)_2R^i$, and wherein each $X^4$ is independently selected from the group consisting of $C_{1-4}$ alkylene, $C_{2-4}$ alkenylene and $C_{2-4}$ alkynylene and each $R^i$ and $R^j$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, or when attached to the same nitrogen atom can be combined with the nitrogen atom to form a five or six-membered ring having from 0 to 2 additional heteroatoms as ring members, and each $R^k$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, wherein the aliphatic portions of $X^4$, $R^i$, $R^j$ and $R^k$ are optionally substituted with from one to three members selected from the group consisting of —OH, —$OR^p$, —$OC(O)NHR^p$, —$OC(O)N(R^p)_2$, —SH, —$SR^p$, —$S(O)R^p$, —$S(O)_2R^p$, —$SO_2NH_2$, —$S(O)_2NHR^p$, —$S(O)_2N(R^p)_2$, —$NHS(O)_2R^p$, —$NR^pS(O)_2R^p$, —$C(O)NH_2$, —$C(O)NHR^p$, —$C(O)N(R^p)_2$, —$C(O)R^p$, —$NHC(O)R^p$, —$NR^pC(O)R^p$, —$NHC(O)NH_2$, —$NR^pC(O)NH_2$, —$NR^pC(O)NHR^p$, —$NHC(O)NHR^p$, —$NR^pC(O)N(R^p)_2$, —$NHC(O)N(R^p)_2$, —$CO_2H$, —$CO_2R^p$, —$NHCO_2R^p$, —$NR^pCO_2R^p$, —CN, —$NO_2$, —$NH_2$, —$NHR^p$, —$N(R^p)_2$, —$NR^pS(O)NH_2$ and —$NR^pS(O)_2NHR^p$, wherein each $R^p$ is independently an unsubstituted $C_{1-6}$ alkyl. In certain preferred embodiments, the linking groups are unsubstituted, while in other preferred embodiments, substituents are present that can increase partitioning into selected solvents or into selected tissues. For example, addition of a hydroxy group to a propylene linkage will generally provide compounds having more favorable solubility in water. Preferably, $L^1$ is selected from —$CH_2$—, —$CH_2CH_2$—, —$CH_2CH_2CH_2$—, —$CH_2O$—, —$CH_2NH$—, —$CH_2OCH_2$— and —$CH_2NHCH_2$—.

For those embodiments in which $Y^1$ is present, optionally substituted aryl and heteroaryl rings are preferably selected from phenyl, pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl and the like. Most preferred are those embodiments in which $Y^1$ is selected from phenyl, pyridyl, pyrimidinyl, furyl and thienyl. Optionally substituted heterocyclic groups are those selected from pyrrolidine, piperidine, imidazolidine, pyrazolidine, butyrolactam, valerolactam, imidazolidinone, hydantoin, dioxolane, 1,4-dioxane, morpholine, thiomorpholine, thiomorpholine-S,S-dioxide, piperazine, pyran, pyridine, 3-pyrroline, thiopyran, pyrone, tetrahydrofuran, tetrahydrothiophene and the like. In one embodiment, $L^1$ is —$CH_2$—, —$CH_2NH$— or —$CH_2O$— and is optionally substituted with —$R^k$, —$X^4OR^i$, —$X^4OC(O)R^i$, —$X^4NR^iR^j$, —$X^4CO_2R^i$, —$X^4CONR^iR^j$, —$X^4SR^i$, —$Y^1$, —$X^4Y^1$, —$X^4CN$ or —$X^4NO_2$. In another embodiment, $L^1$ is —$CH_2$—.

The symbol $L^2$ represents a linkage that is selected from a covalent bond, CO, $SO_2$ and $CR^qR^r$, wherein $R^q$ and $R^r$ are independently selected from the group consisting of hydrogen, halogen, $C_{1-8}$ alkyl, $C_{1-8}$ haloalkyl, $C_{3-6}$ cycloalkyl, $C_{2-8}$ alkenyl, $C_{2-8}$ alkynyl, $C_{6-10}$ aryl and $C_{5-10}$ heteroaryl wherein the aliphatic portions of $R^q$, and $R^r$ are optionally further substituted with from one to three members selected from the group consisting of —OH, —$OR^s$, —$OC(O)NHR^s$, —$OC(O)N(R^s)_2$, —SH, —$SR^s$, —$S(O)R^s$, —$S(O)_2R^s$, —$SO_2NH_2$, —$S(O)_2NHR^s$, —$S(O)_2N(R^s)_2$, —$NHS(O)_2R^s$, —$NR^sS(O)_2R^s$, —$C(O)NH_2$, —$C(O)NHR^s$, —$C(O)N(R^s)_2$, —$C(O)R^s$, —$NHC(O)R^s$, —$NR^sC(O)R^s$, —$NHC(O)NH_2$, —$NR^sC(O)NH_2$, —$NR^sC(O)NHR^s$, —$NHC(O)NHR^s$, —$NR^sC(O)N(R^s)_2$, —$NHC(O)N(R^s)_2$, —$CO_2H$, —$CO_2R^s$, —$NHCO_2R^s$, —$NR^sCO_2R^s$, —CN, —$NO_2$, —$NH_2$, —$NHR^s$, —$N(R^s)_2$, —$NR^sS(O)NH_2$ and —$NR^sS(O)_2NHR^s$, wherein each $R^s$ is independently an unsubstituted $C_{1-6}$ alkyl.

In several specific groups of embodiments defined by formulae I, II, IIa, IIb, III, IIIa, IIIb, IIIc, IIId, IIId$^1$-IIId$^4$, IV, IVa, V and Va, herein, Ar is selected from the preferred groups represented in FIGS. 1A through 1G.

Figure 2A:
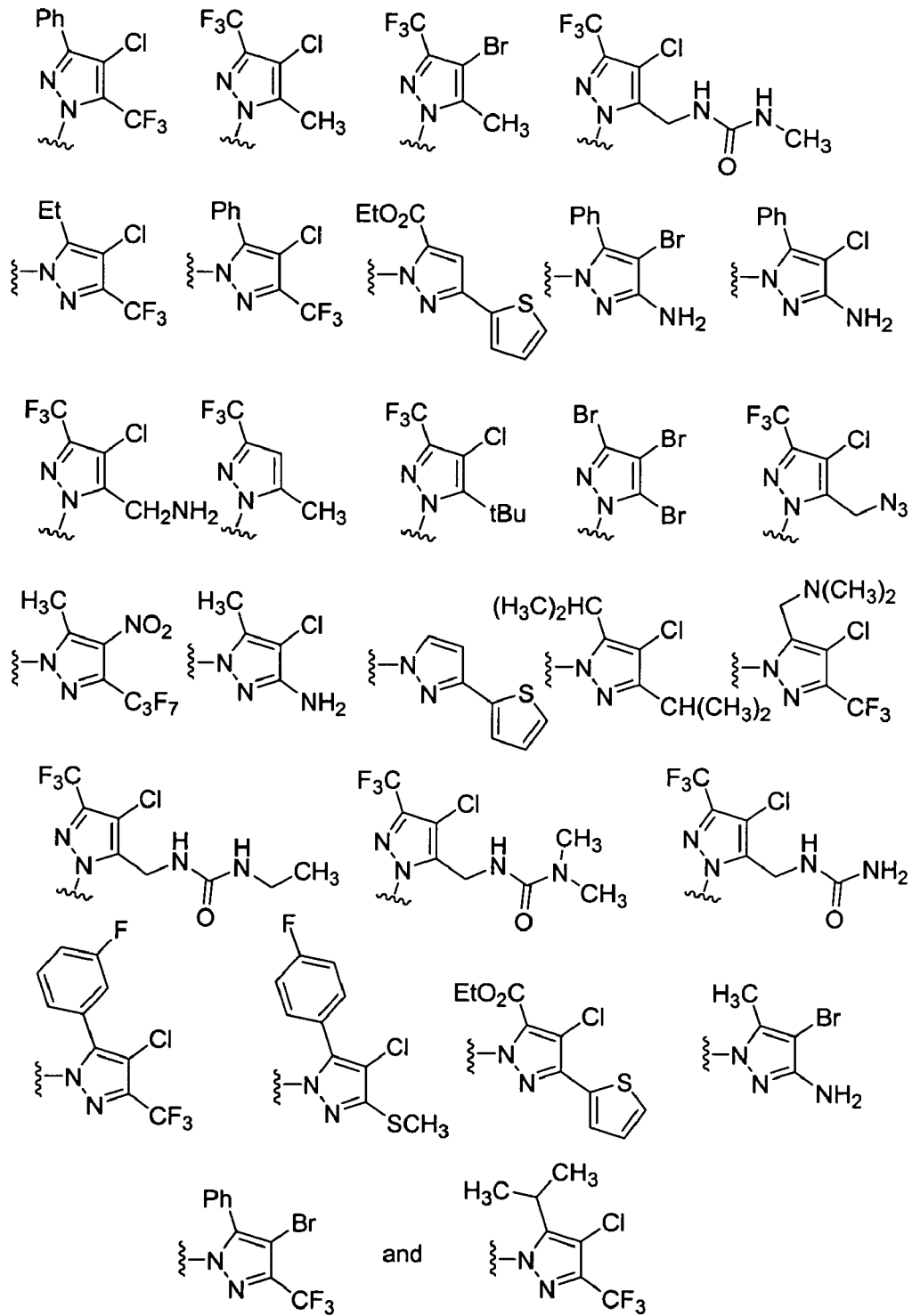
FIGS. 2A through 2Z, 2AA through 2HH and 3 provide selected and preferred HAr groups for compounds of formula I.
Figure 2B:
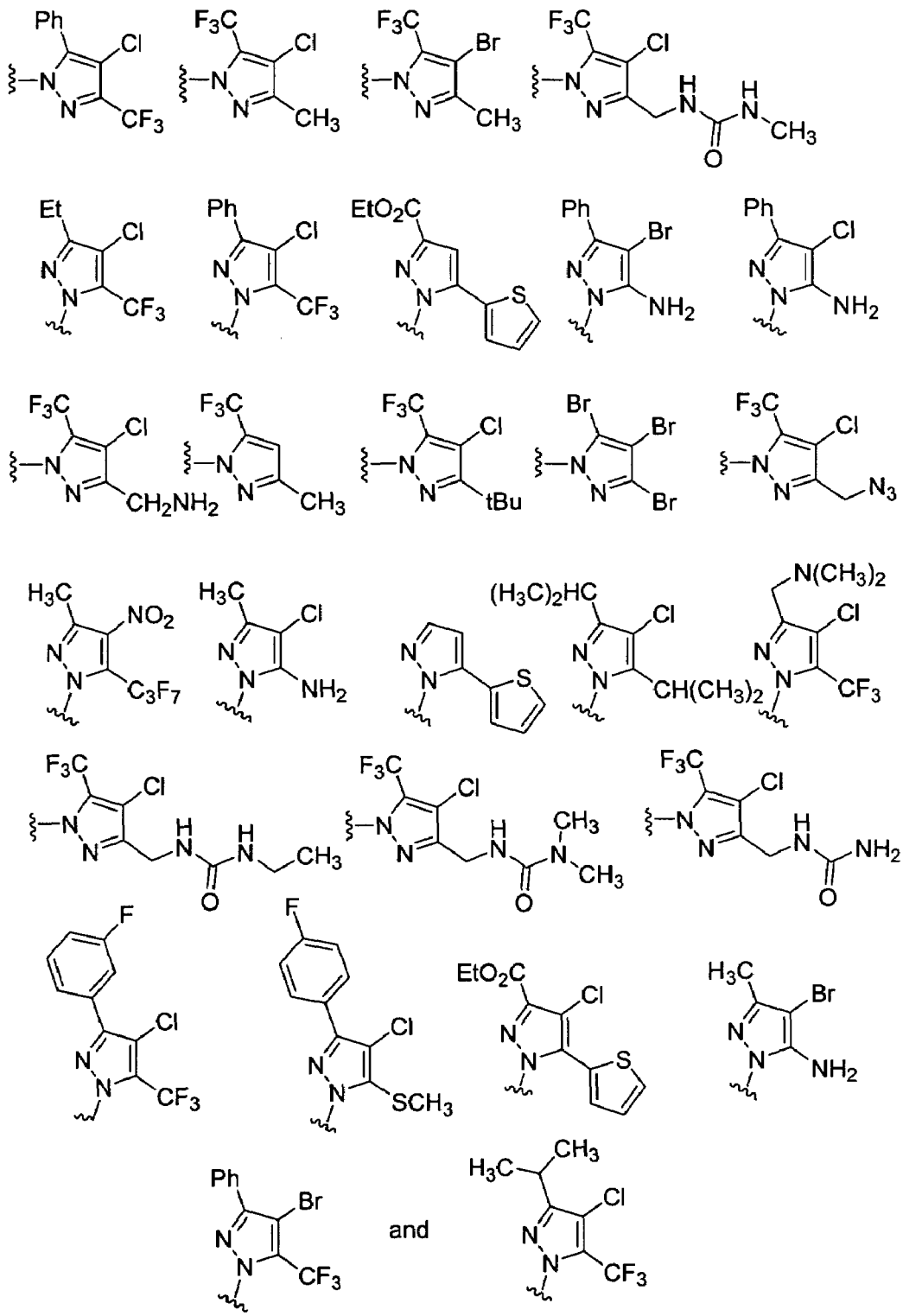
Figure 2C:
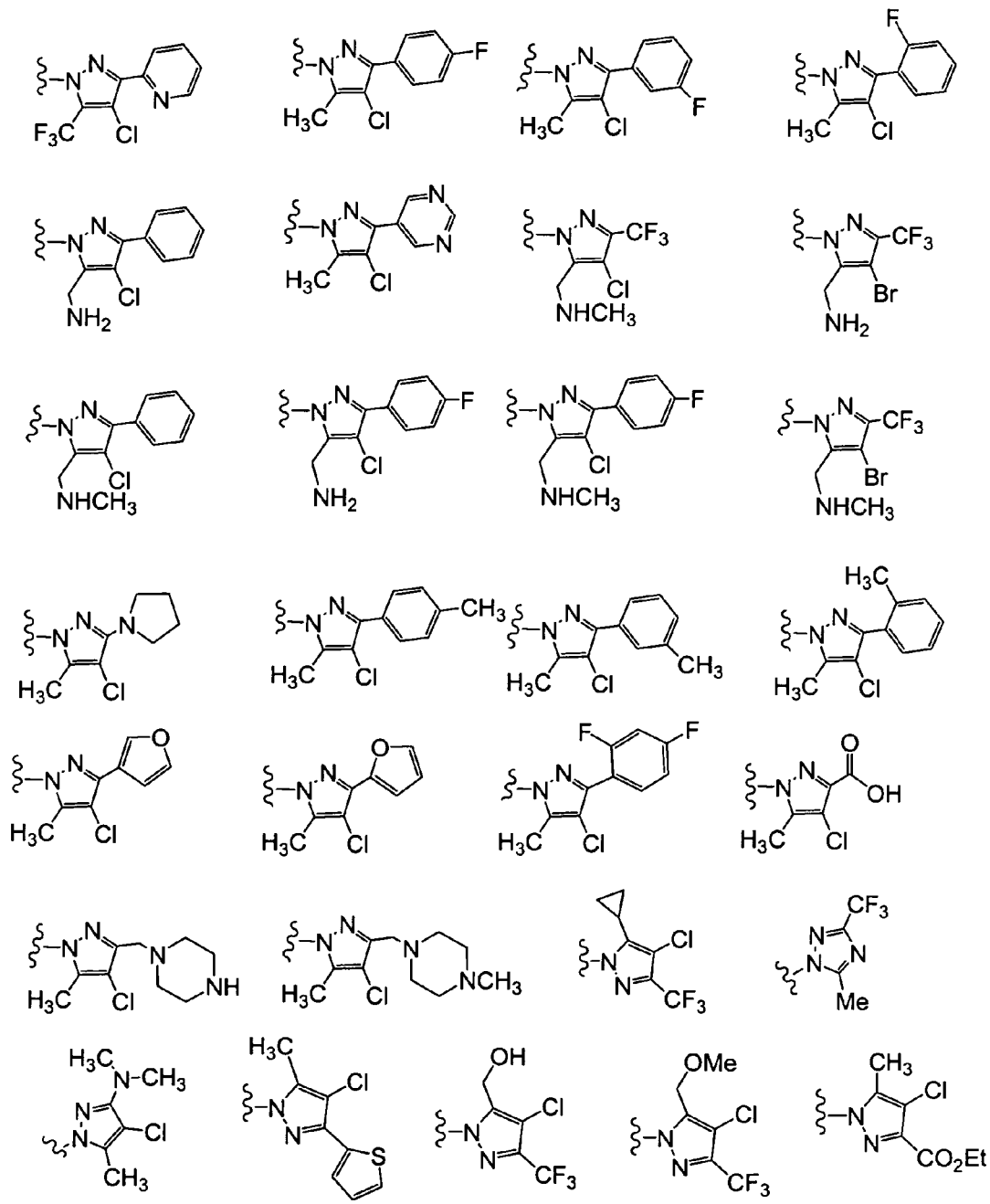
Figure 2D:
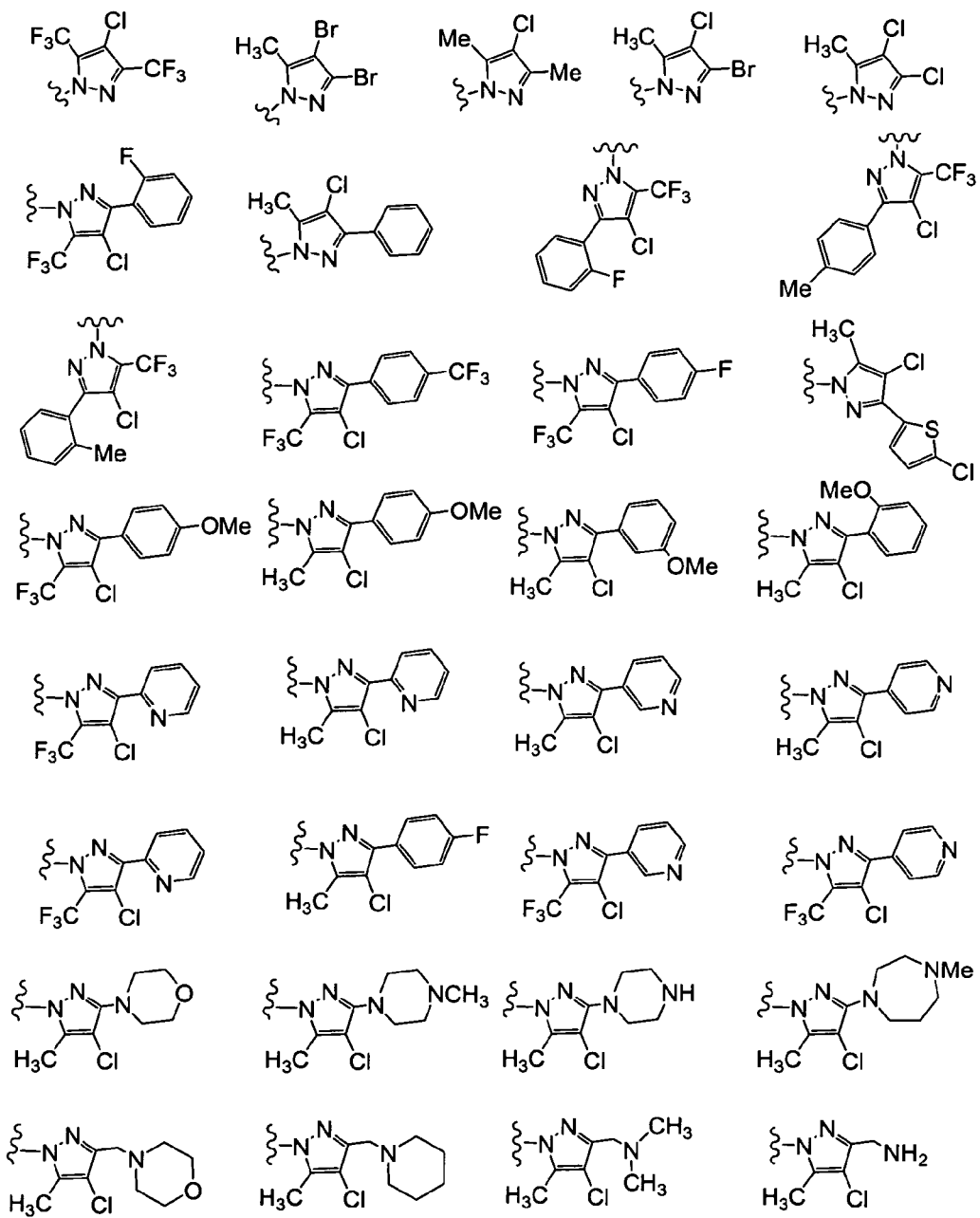
Figure 2E:
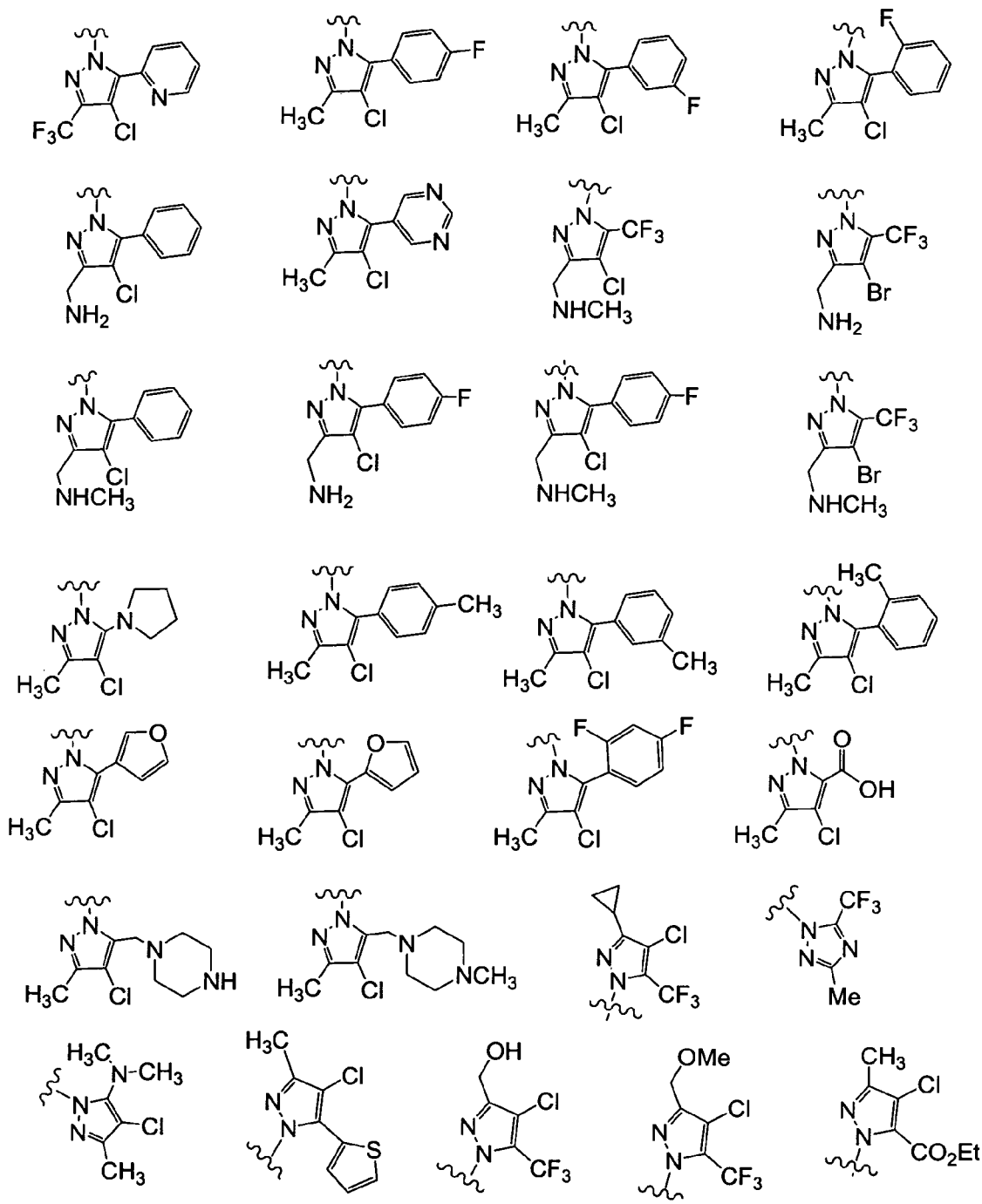
Figure 2F:
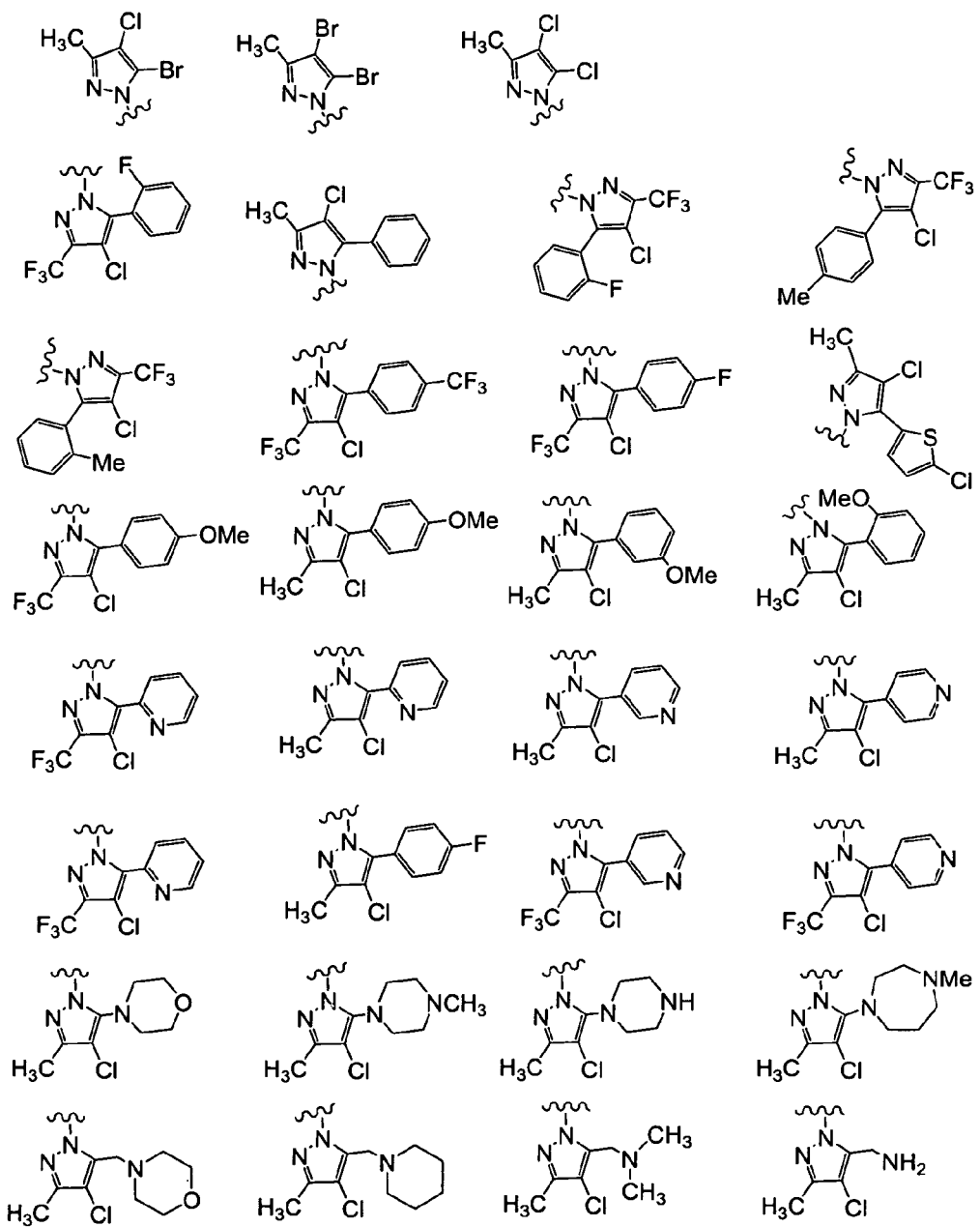
Figure 2G:
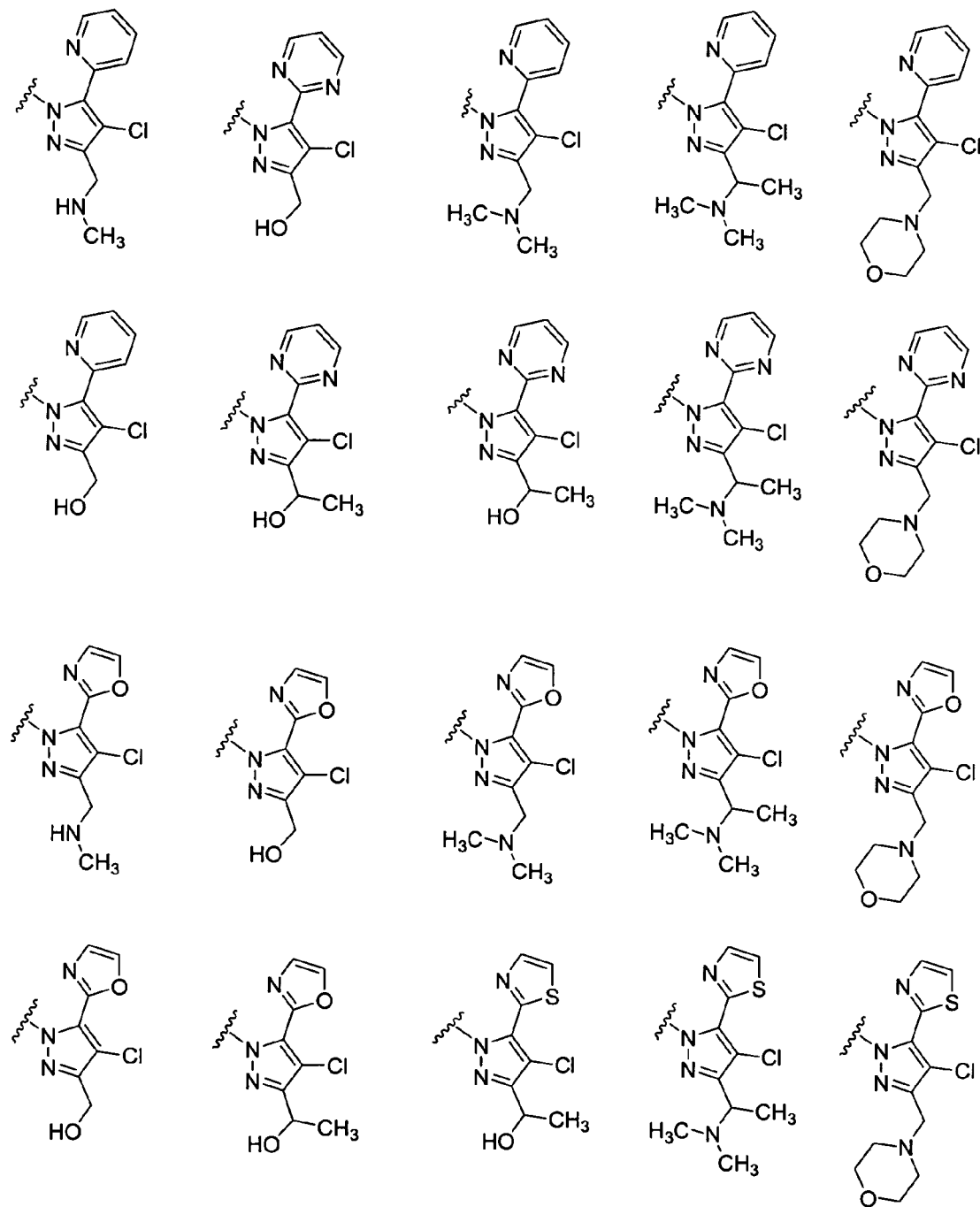
Figure 2H:
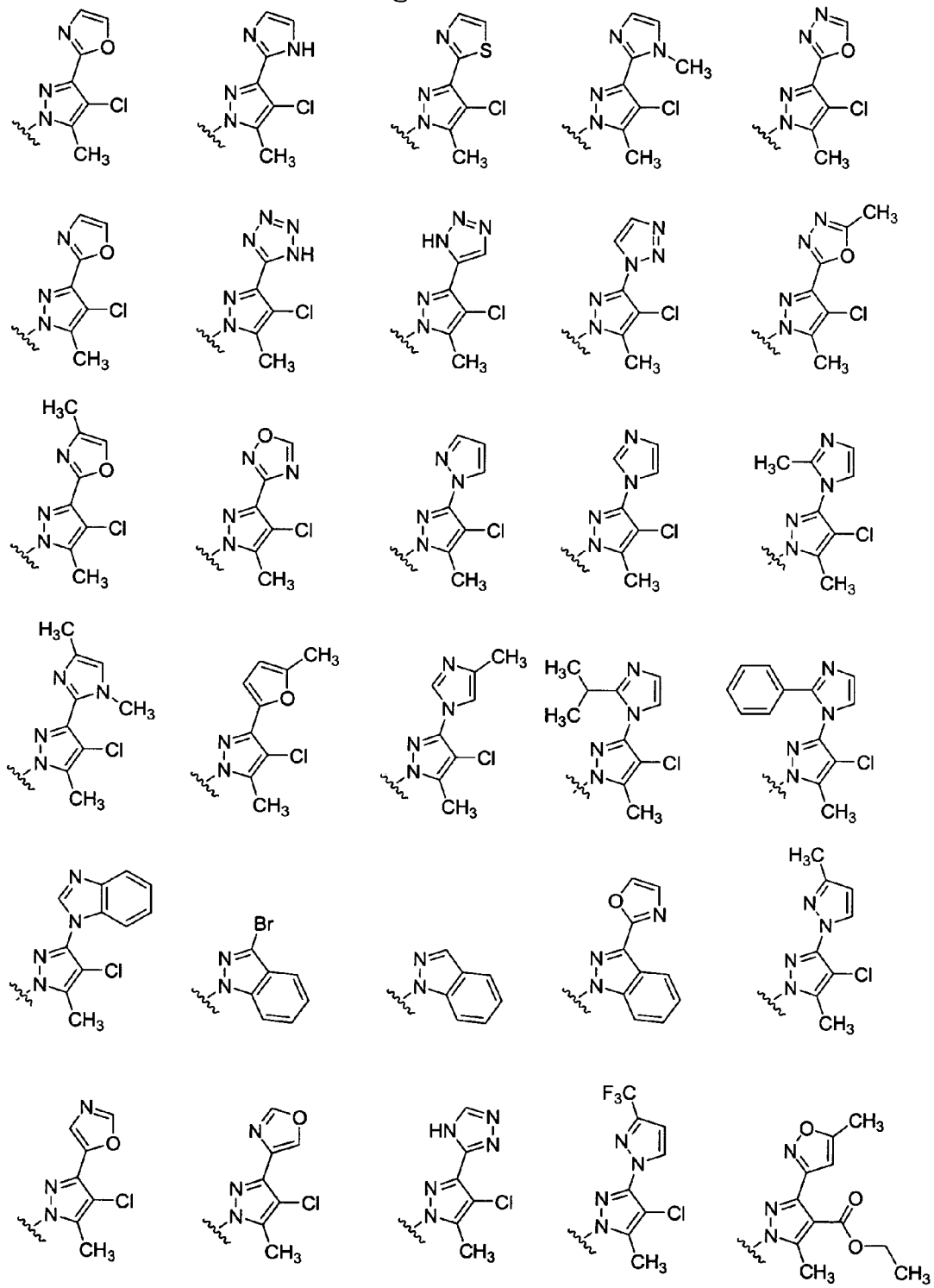
Figure 2I:
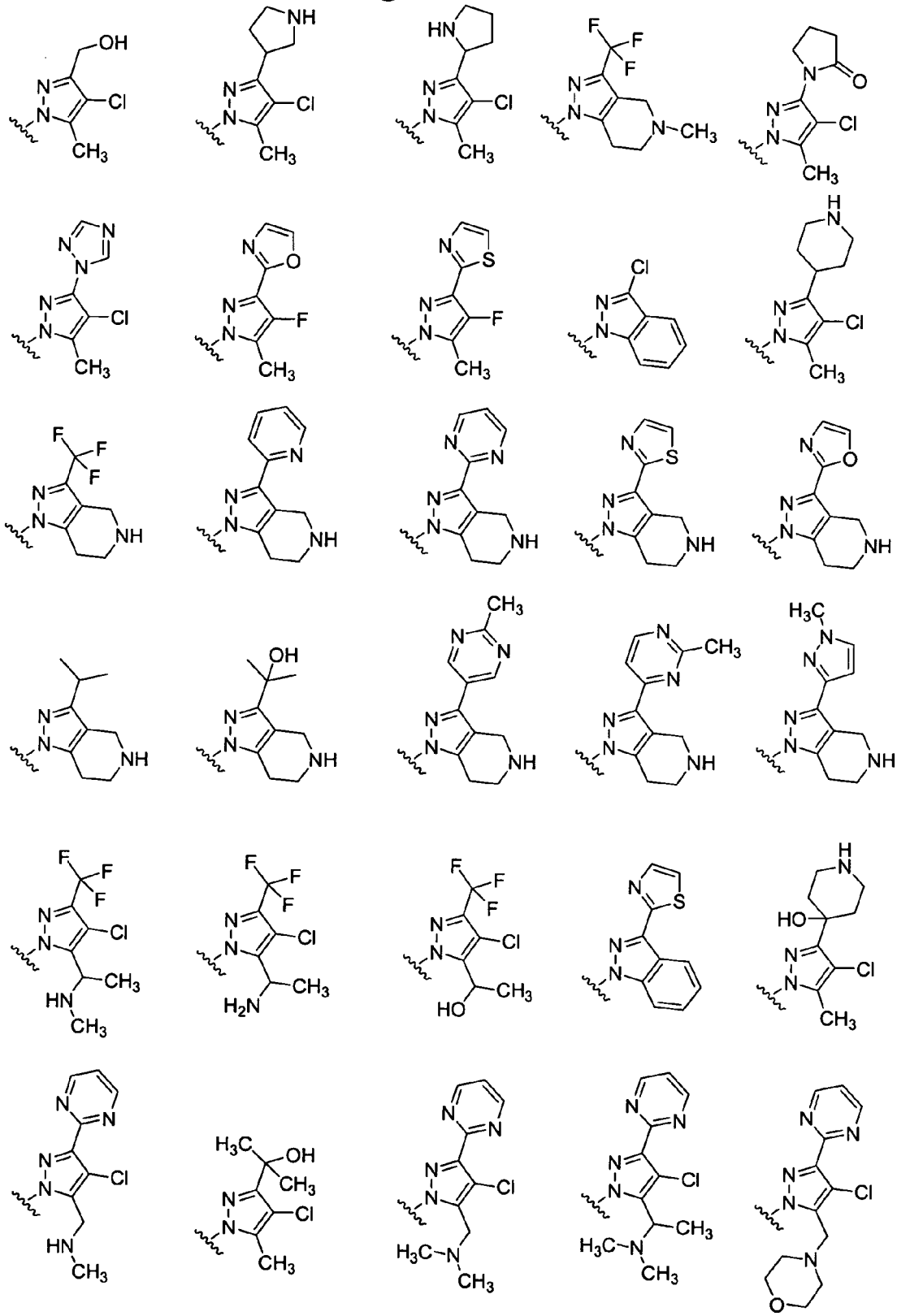
Figure 2J:
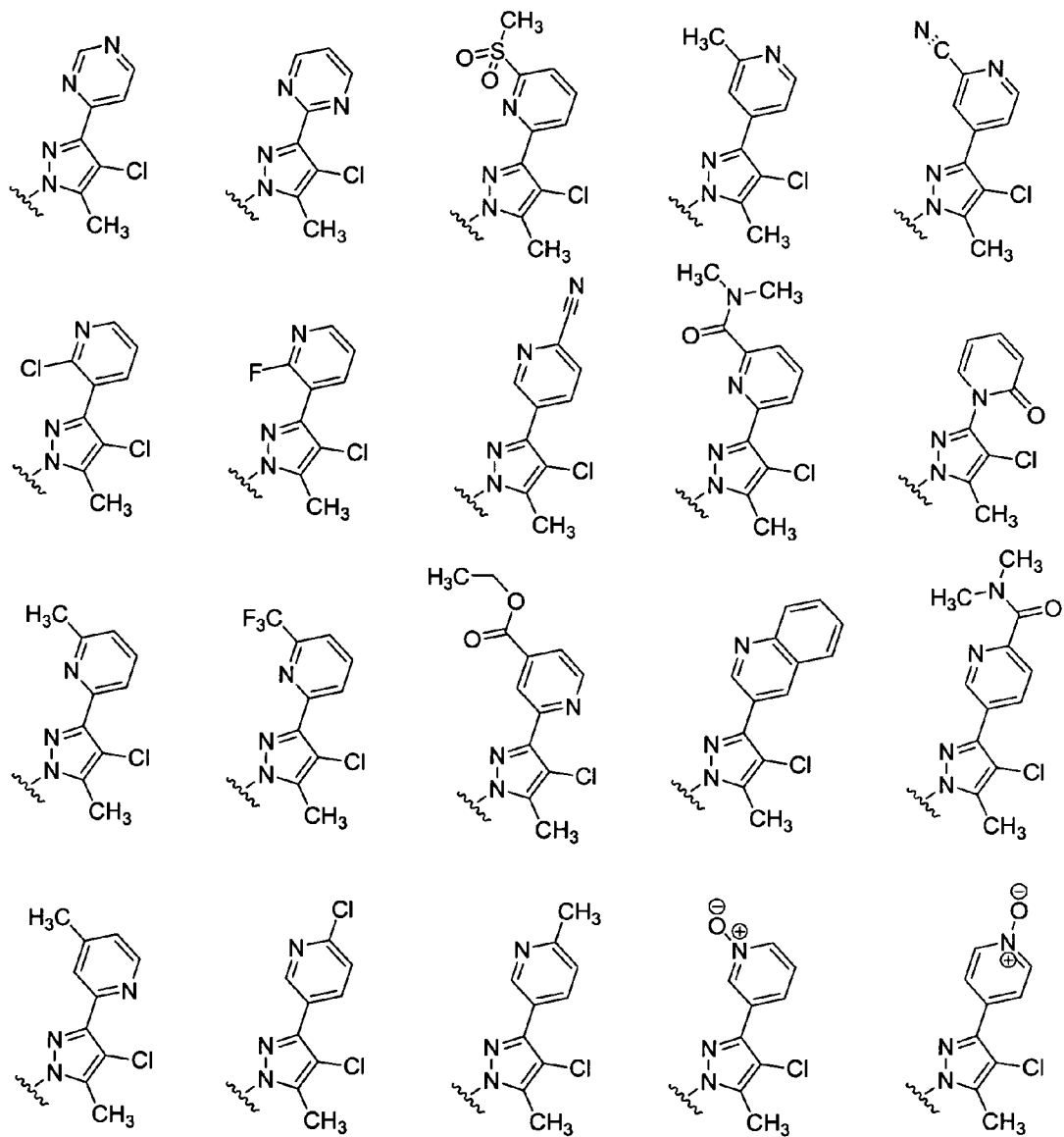
Figure 2K:
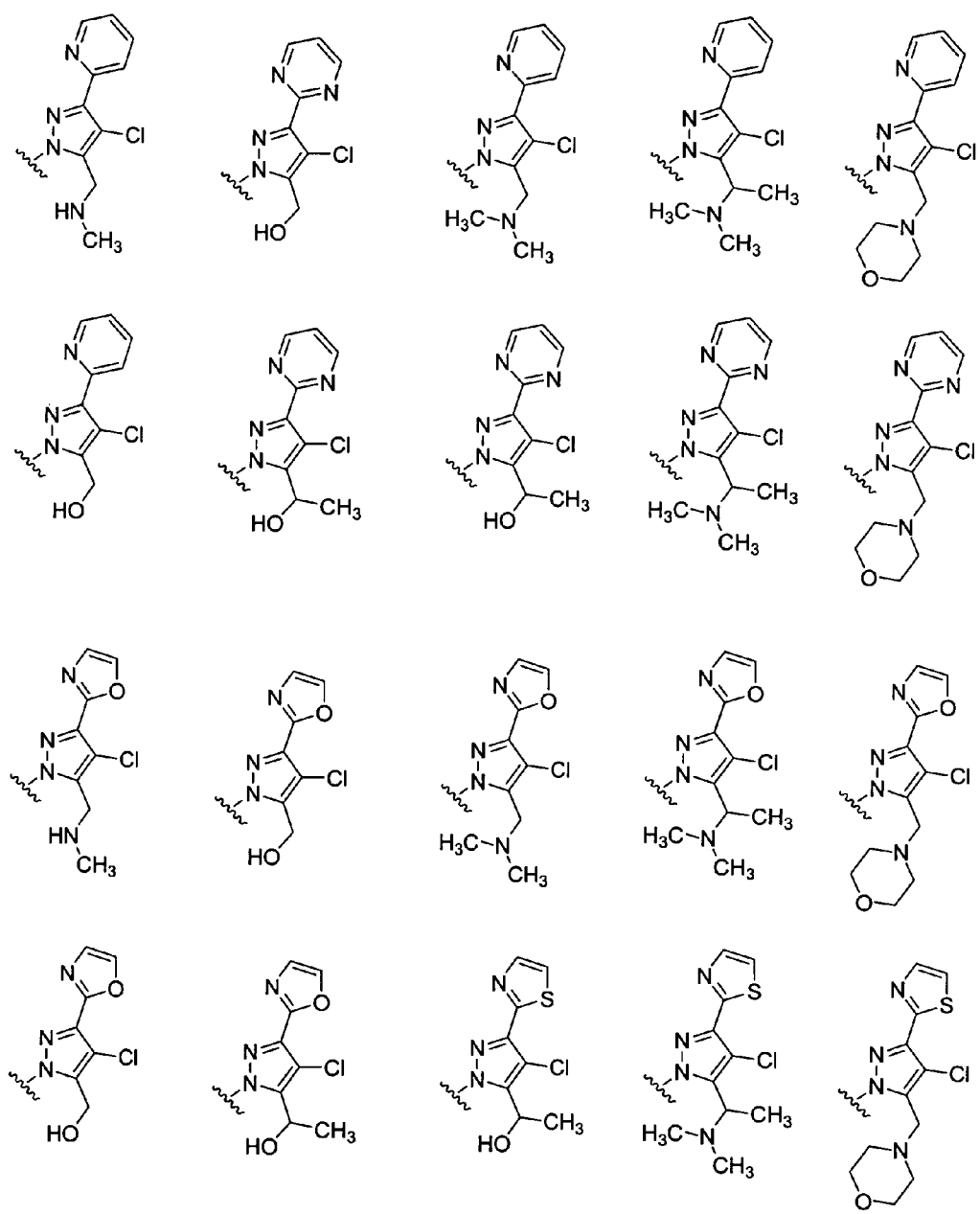
Figure 2L:
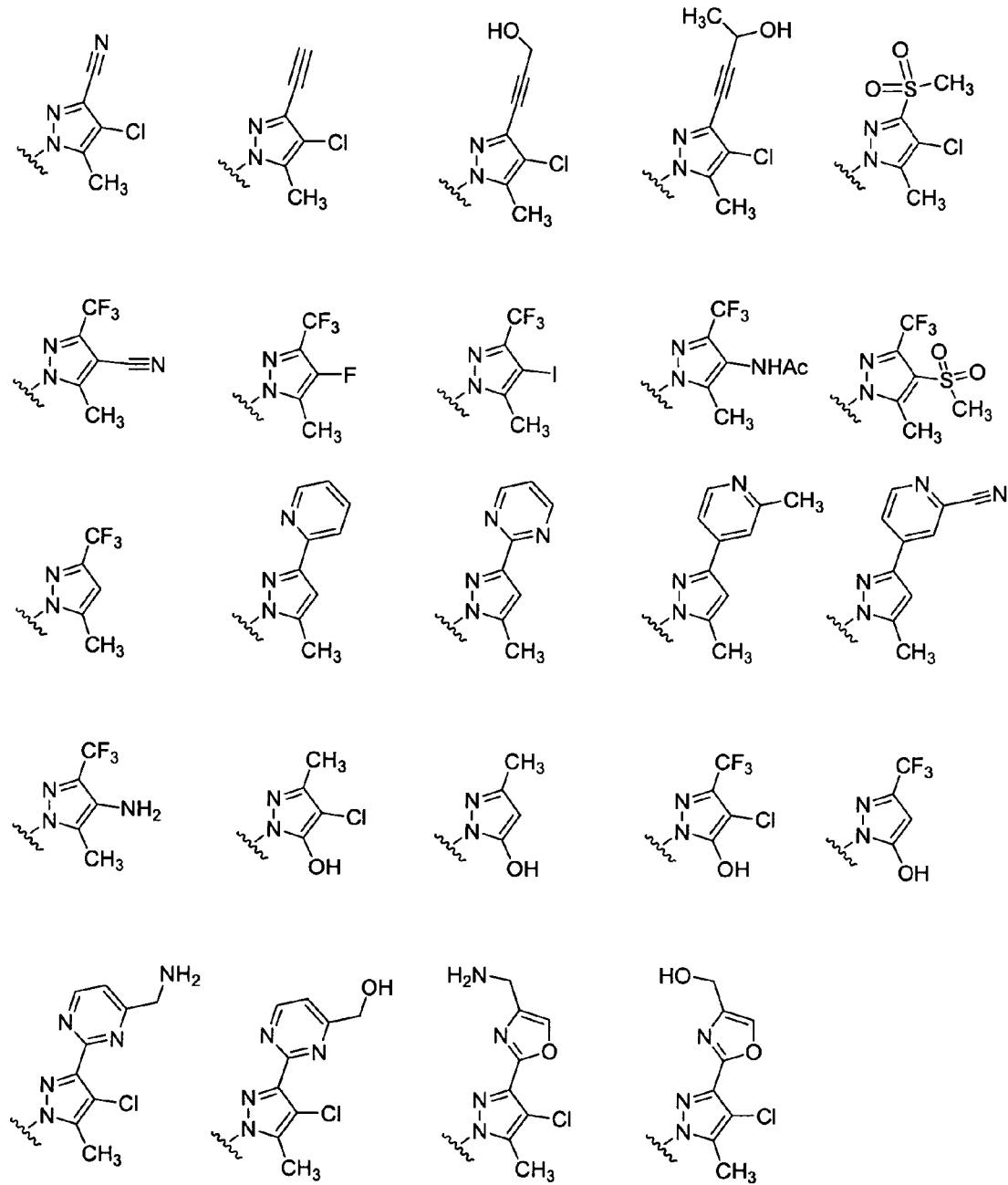
Figure 2M:
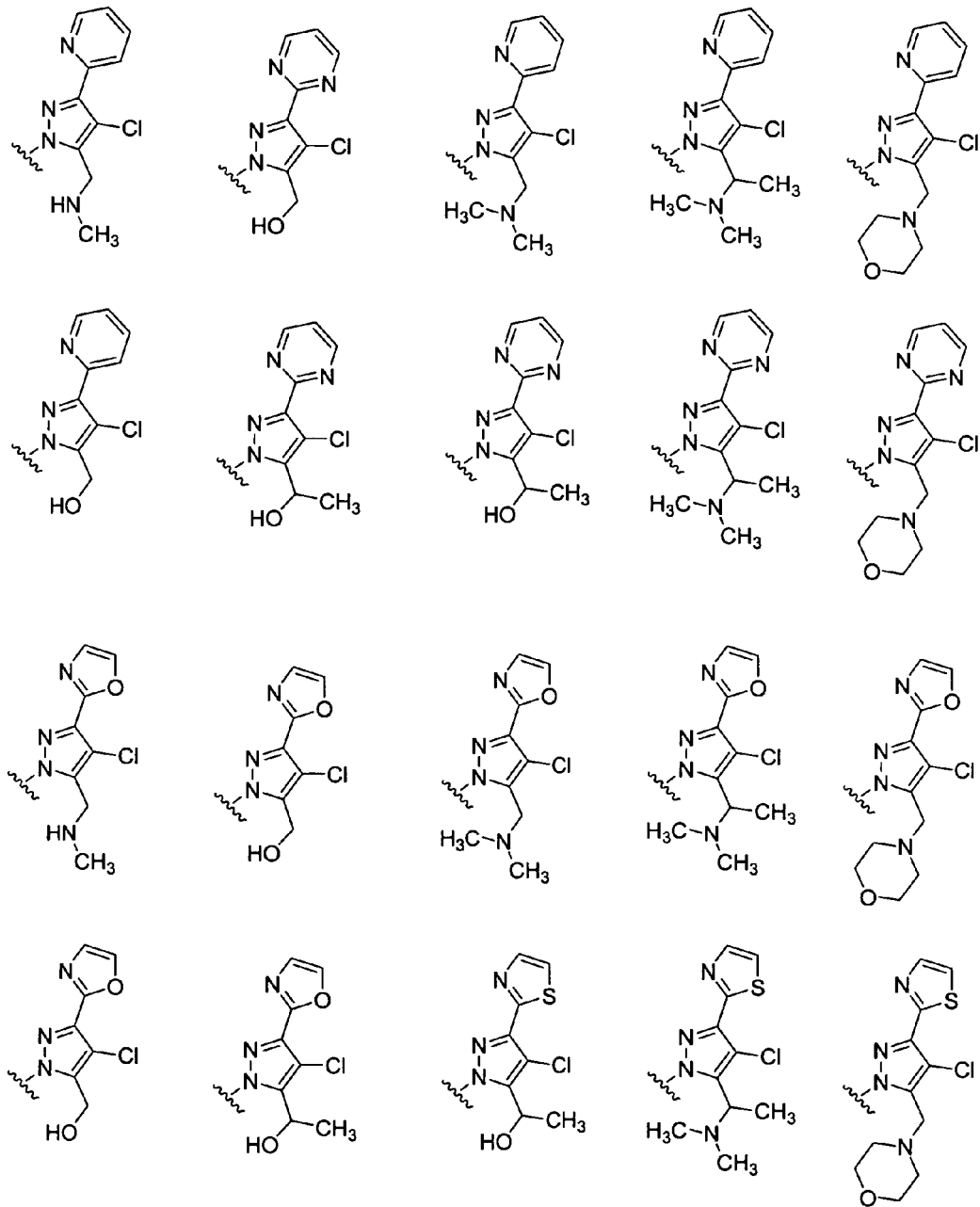
Figure 2N:
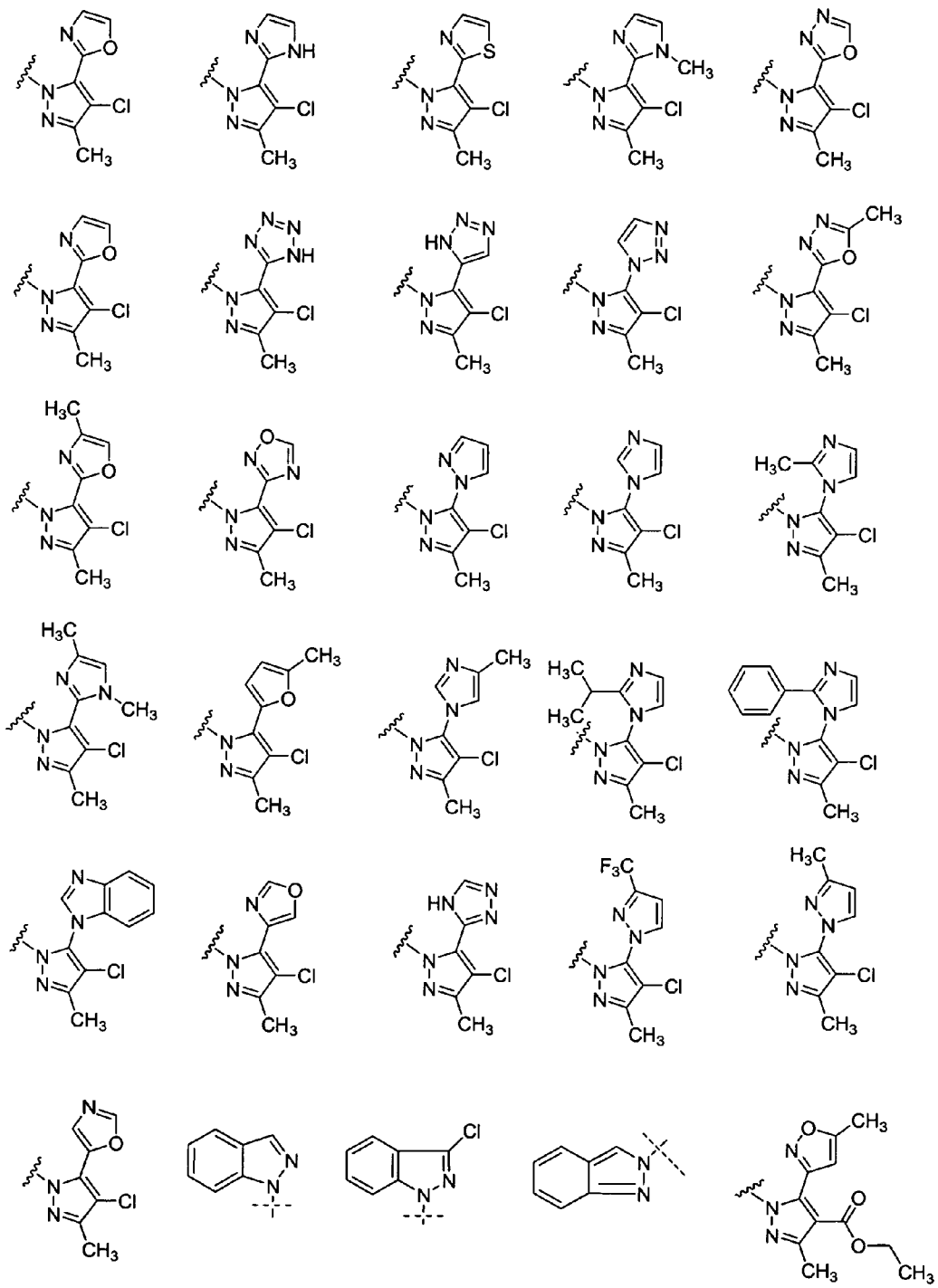
Figure 2O:
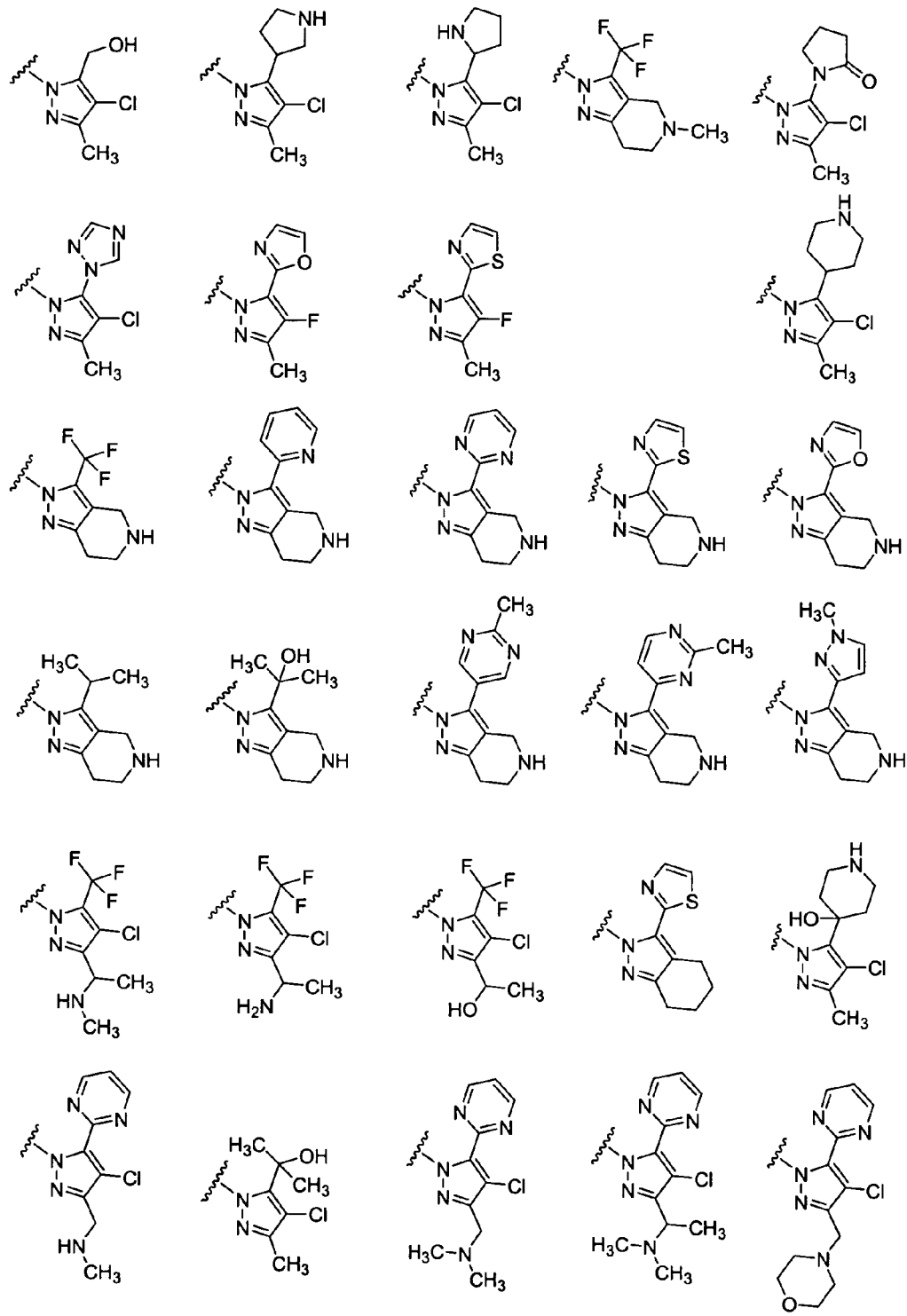
Figure 2P:
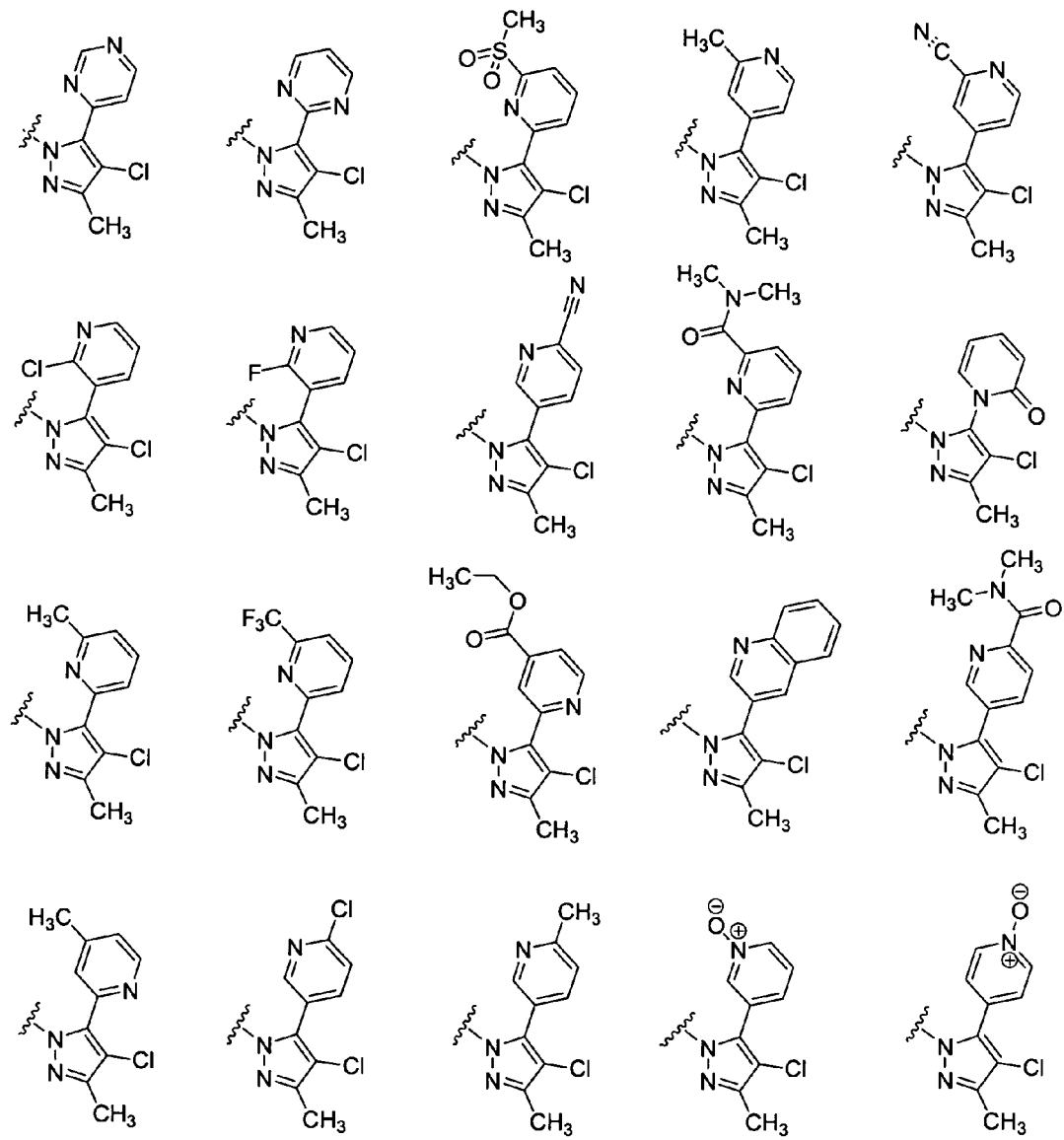
Figure 2Q:
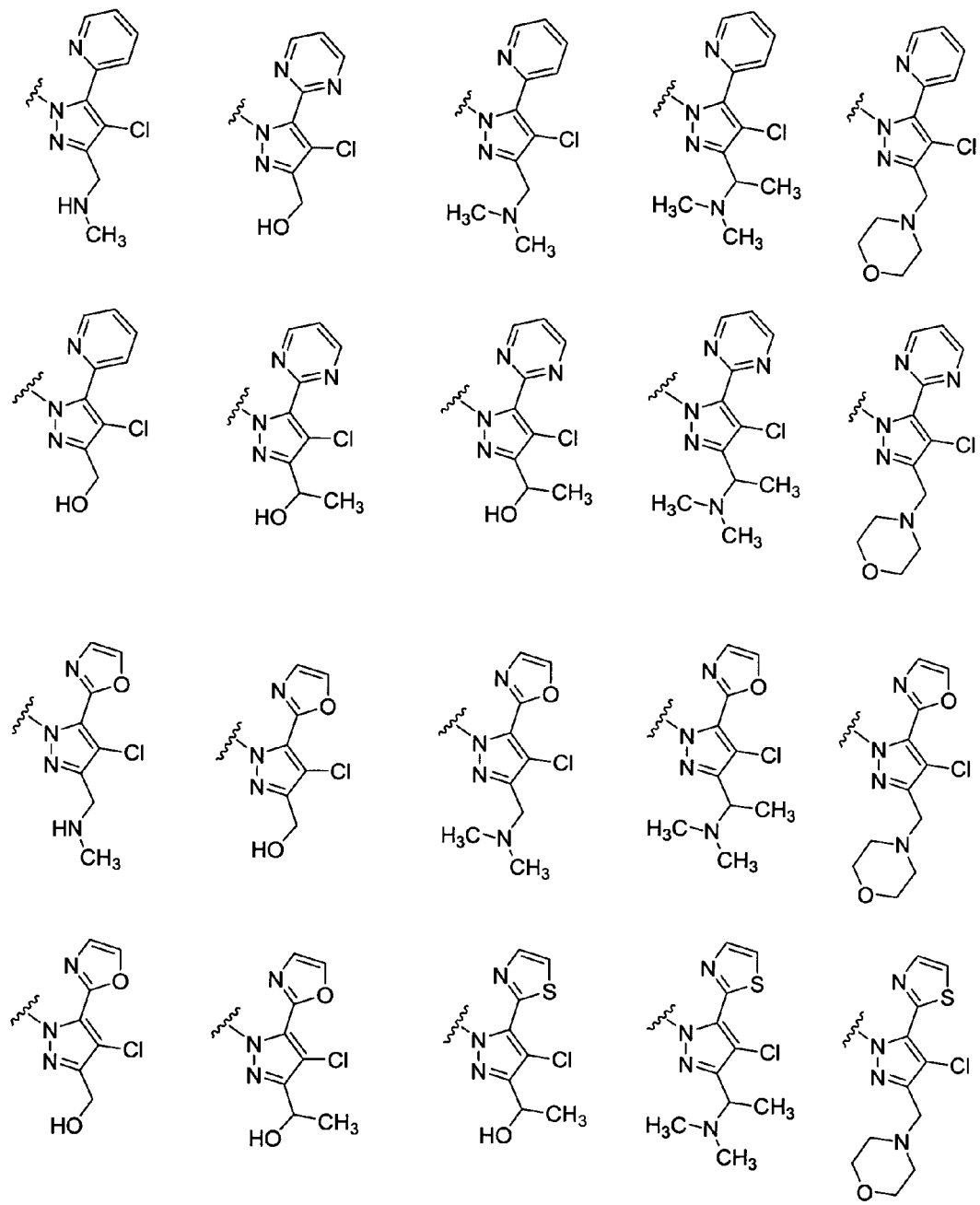
Figure 2R:
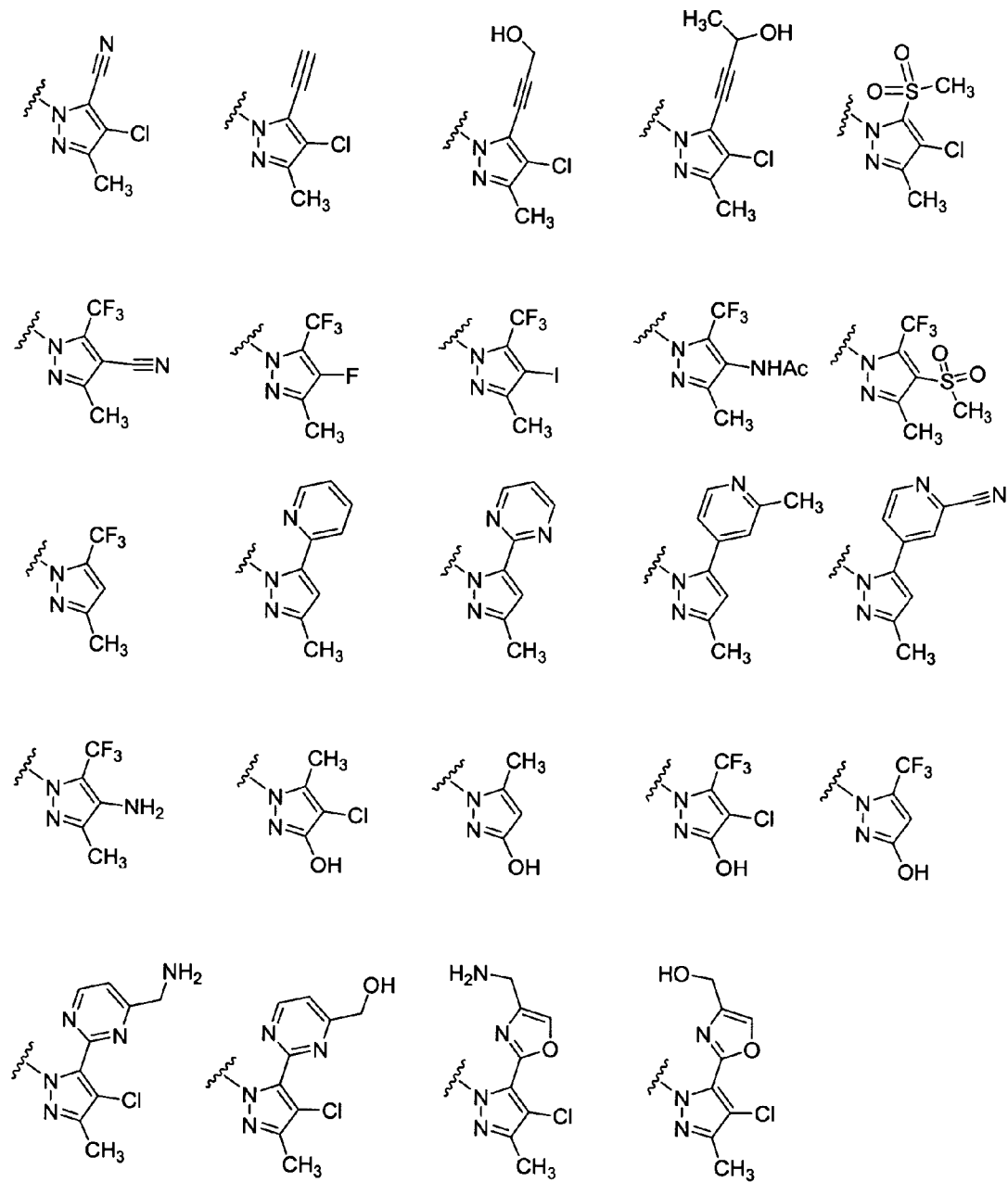
Figure 2S:
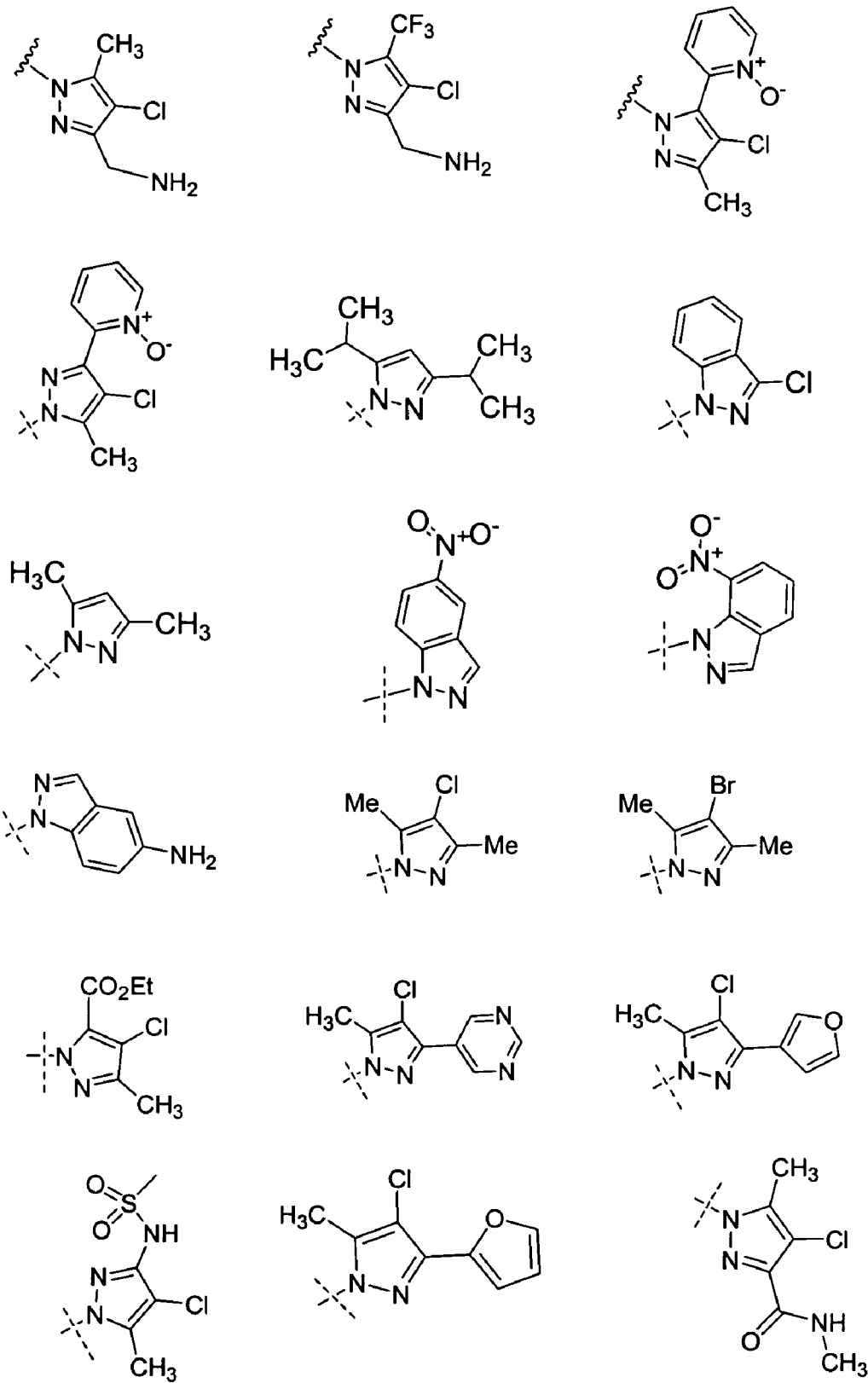
Figure 2T:
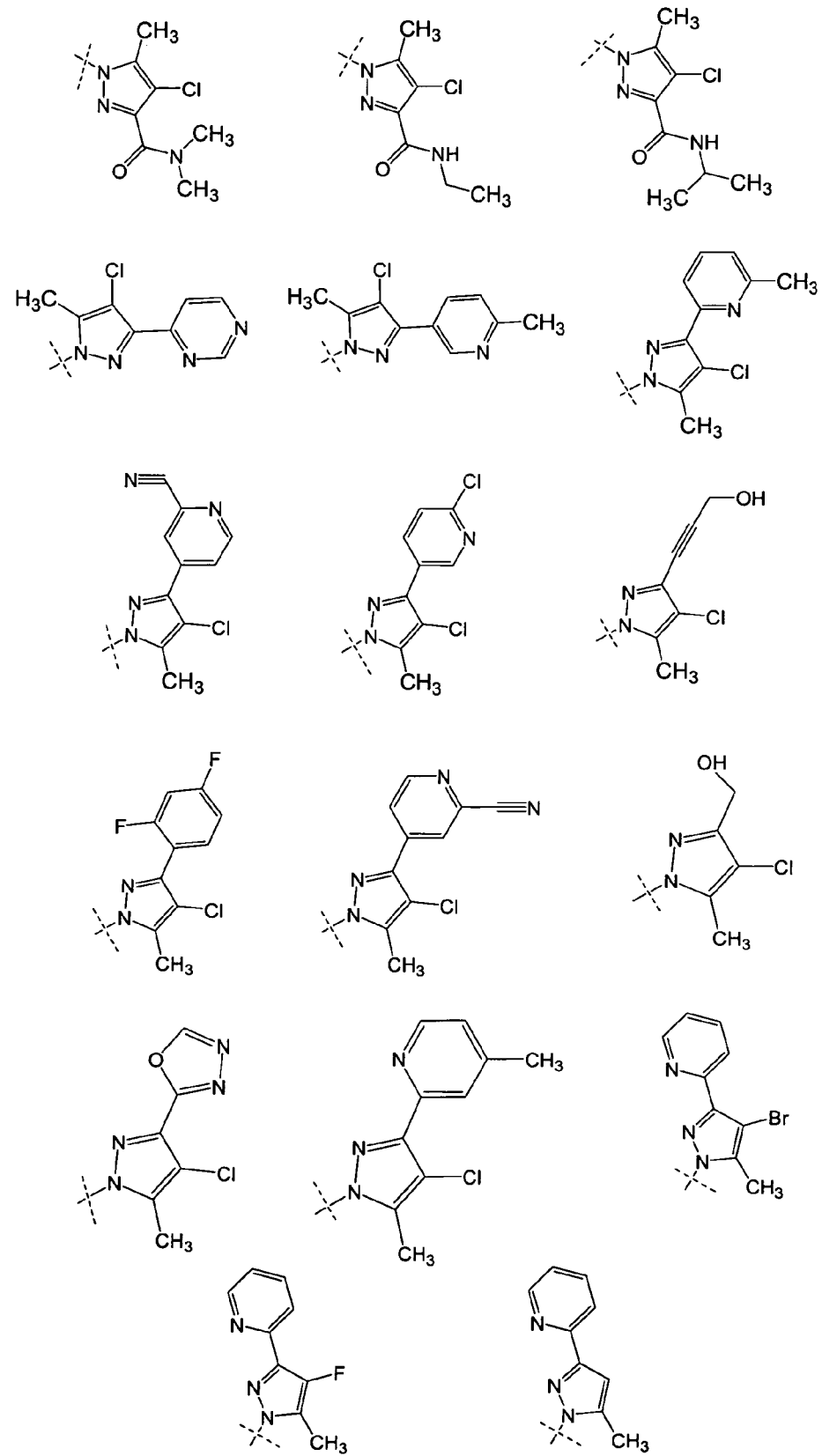
Figure 2U:
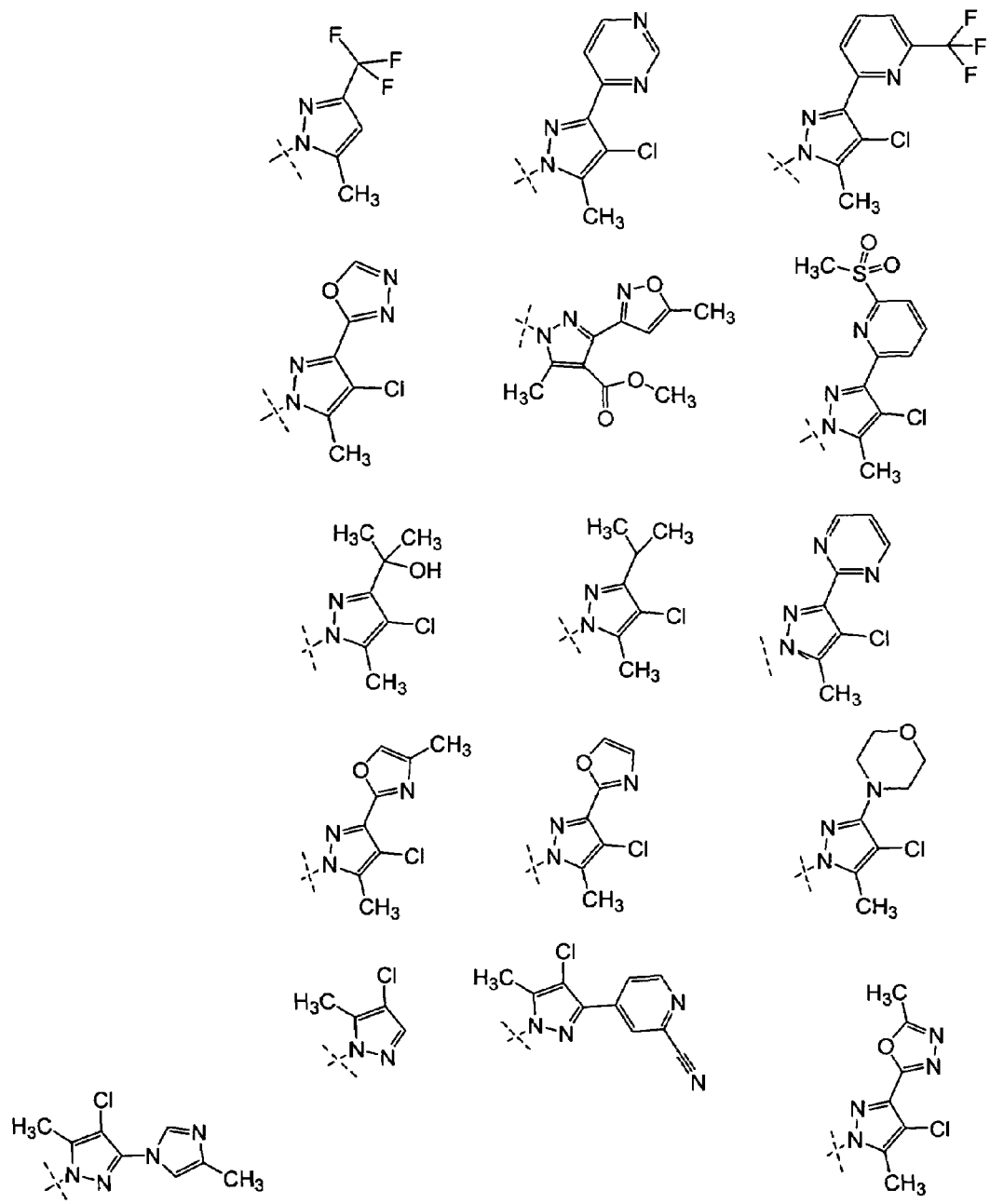
Figure 2V:
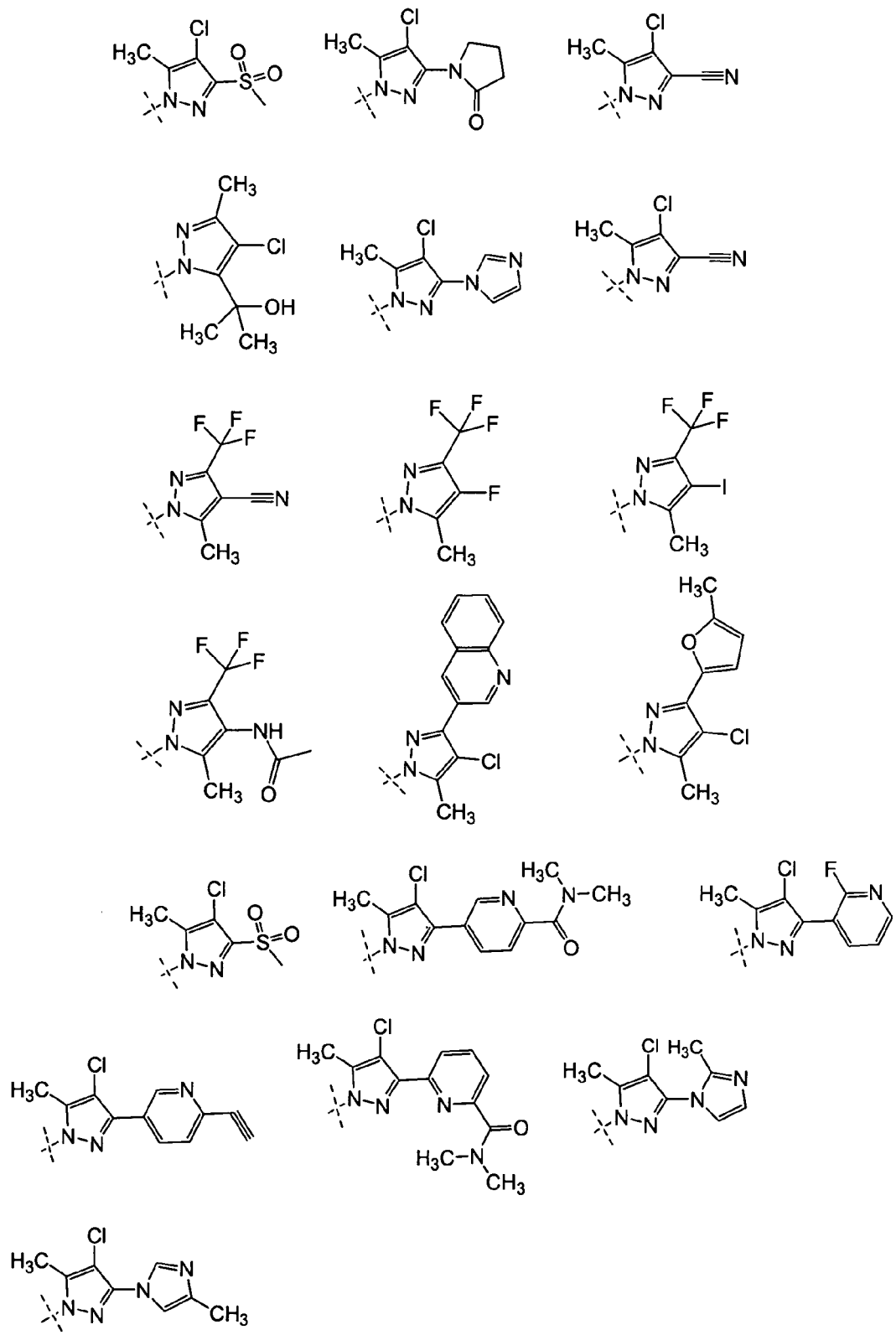
Figure 2W:
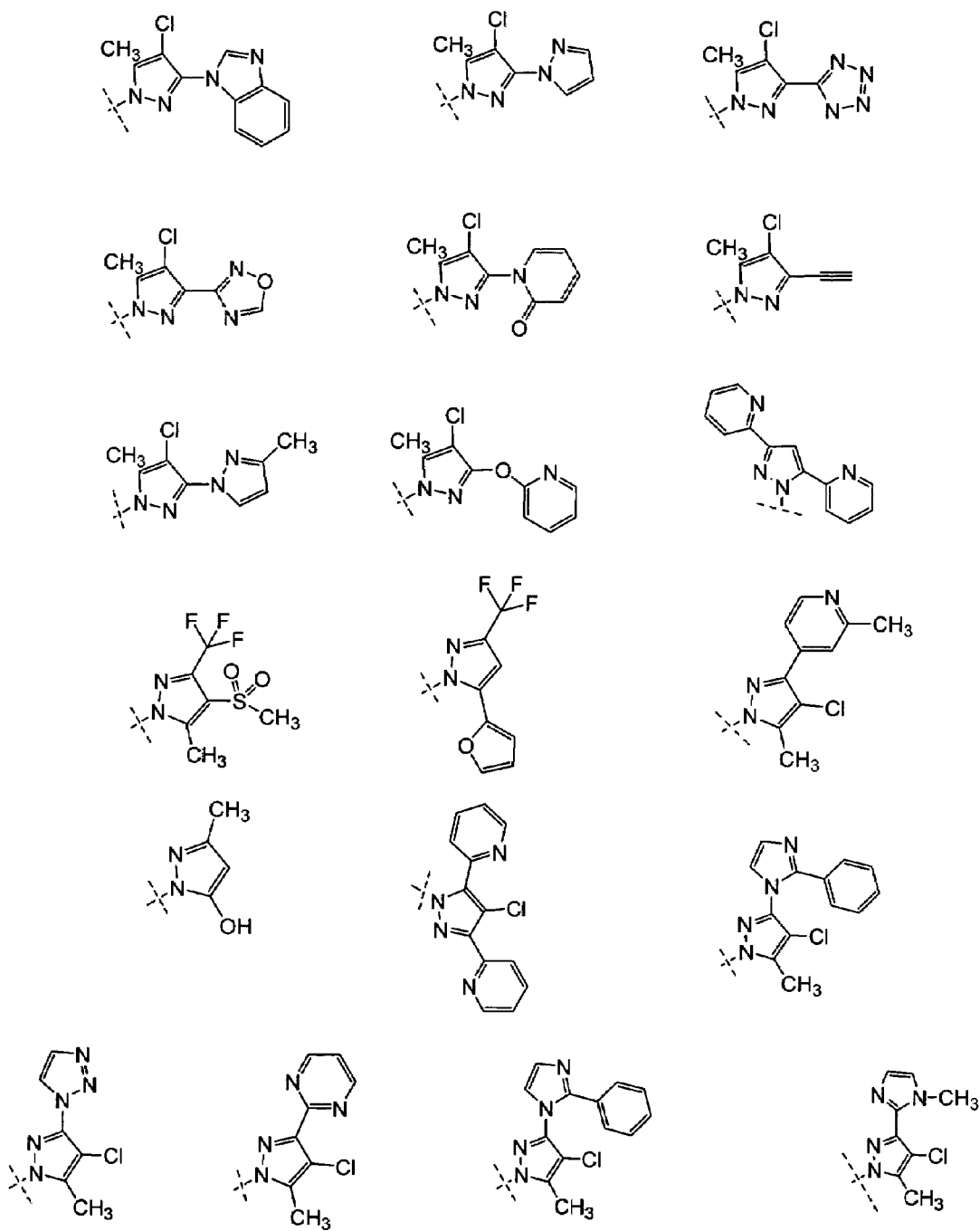
Figure 2X:
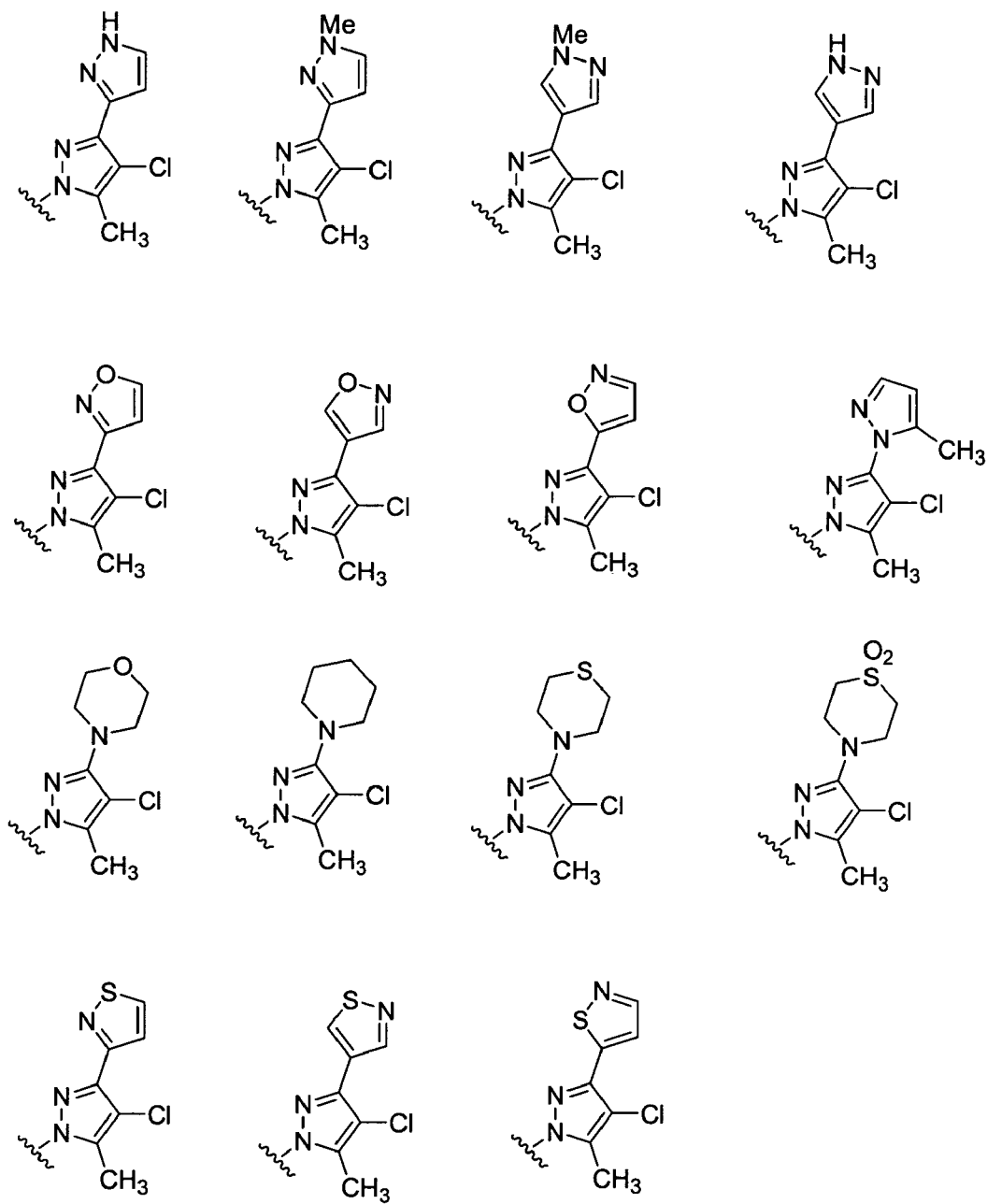
Figure 2Y:
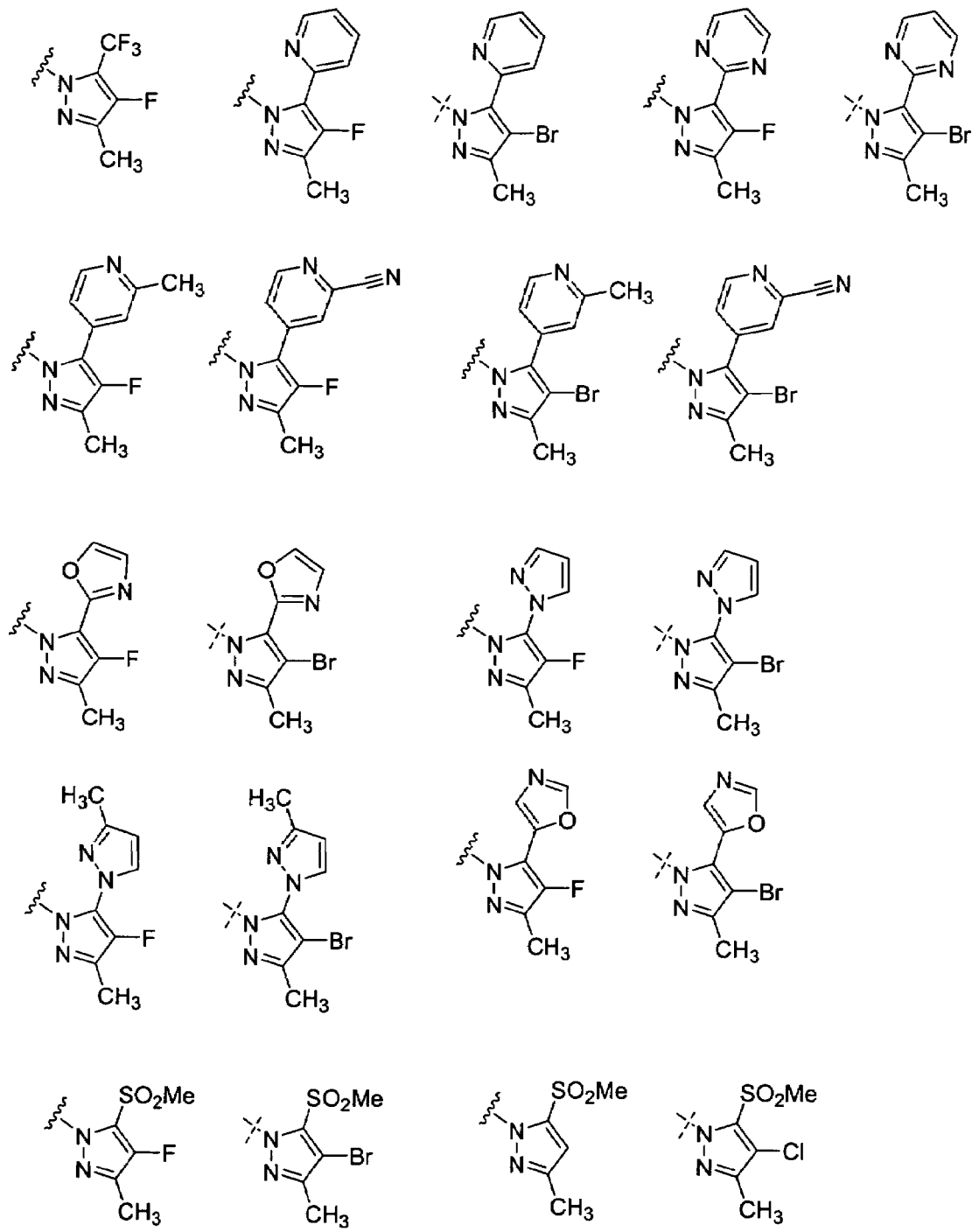
Figure 2Z:
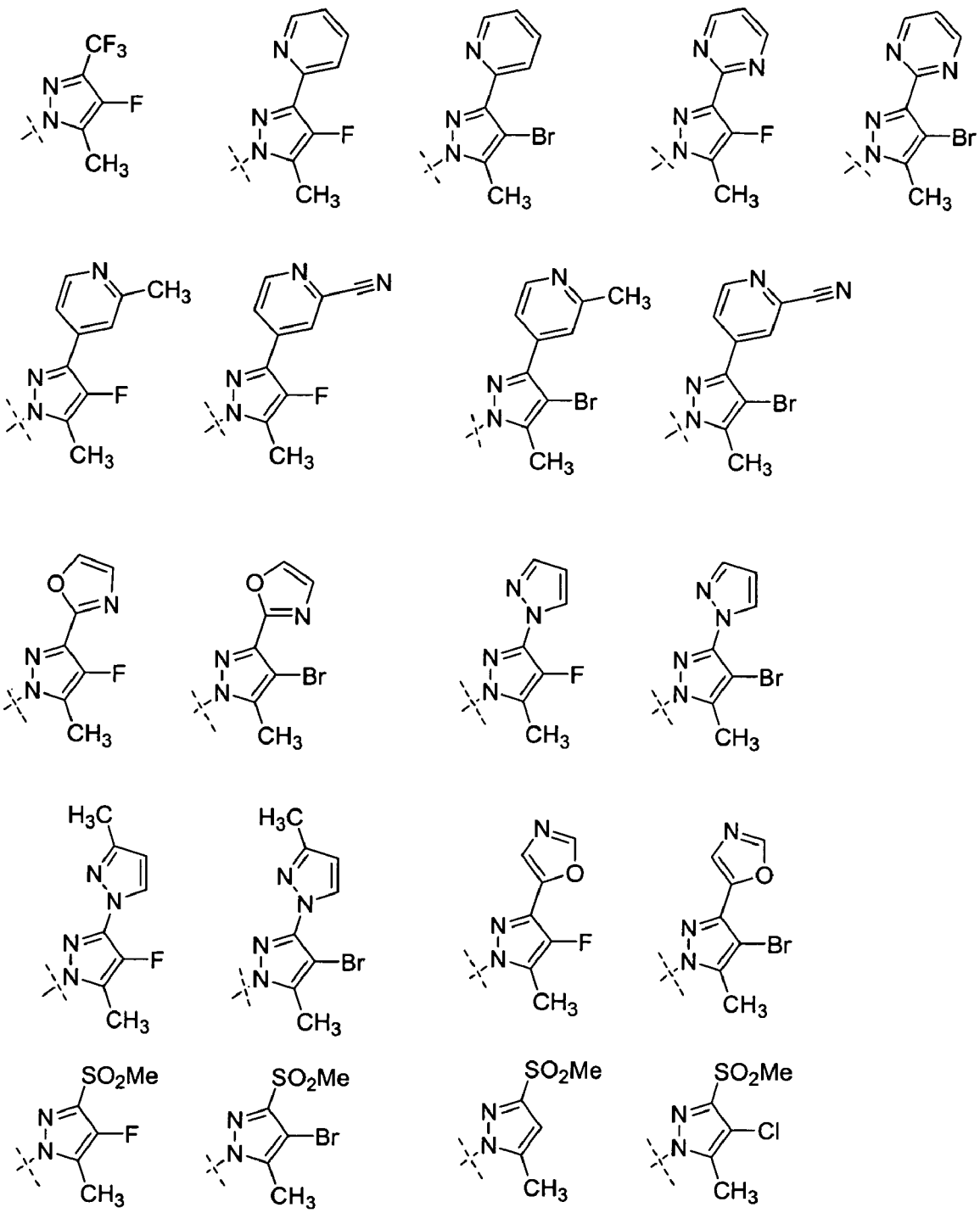
Figure 2A:
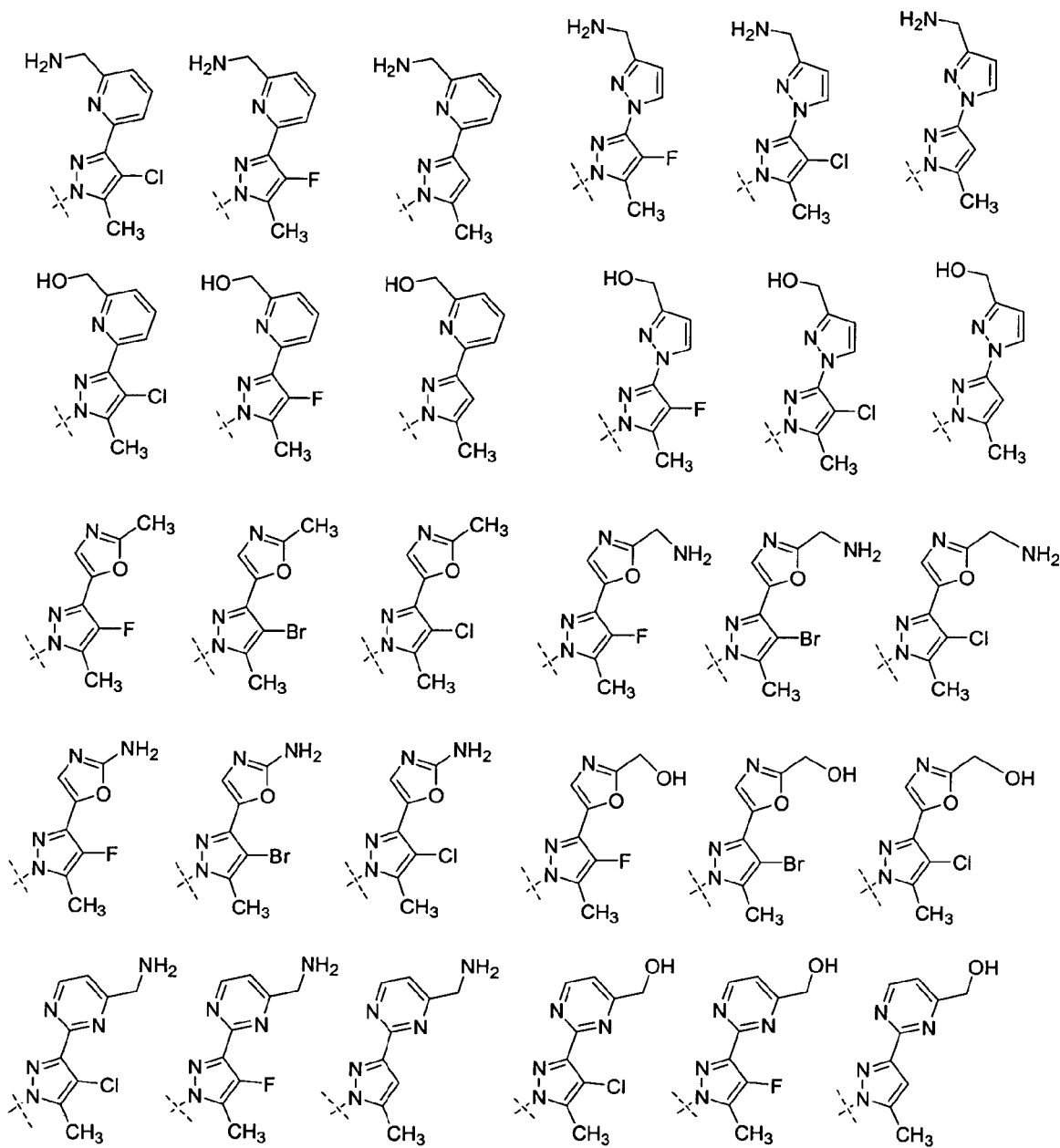
Figure 2B:
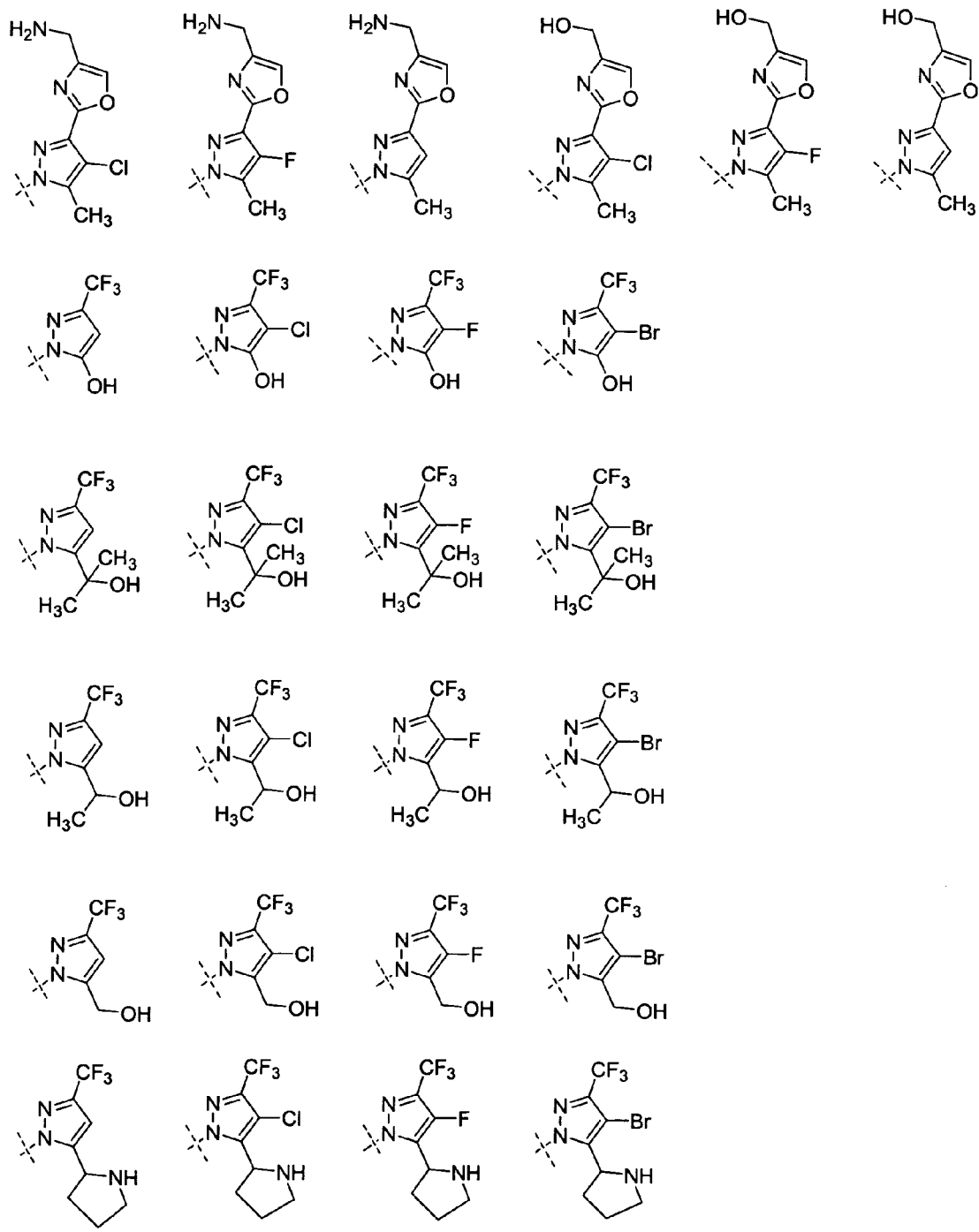
Figure 2C:
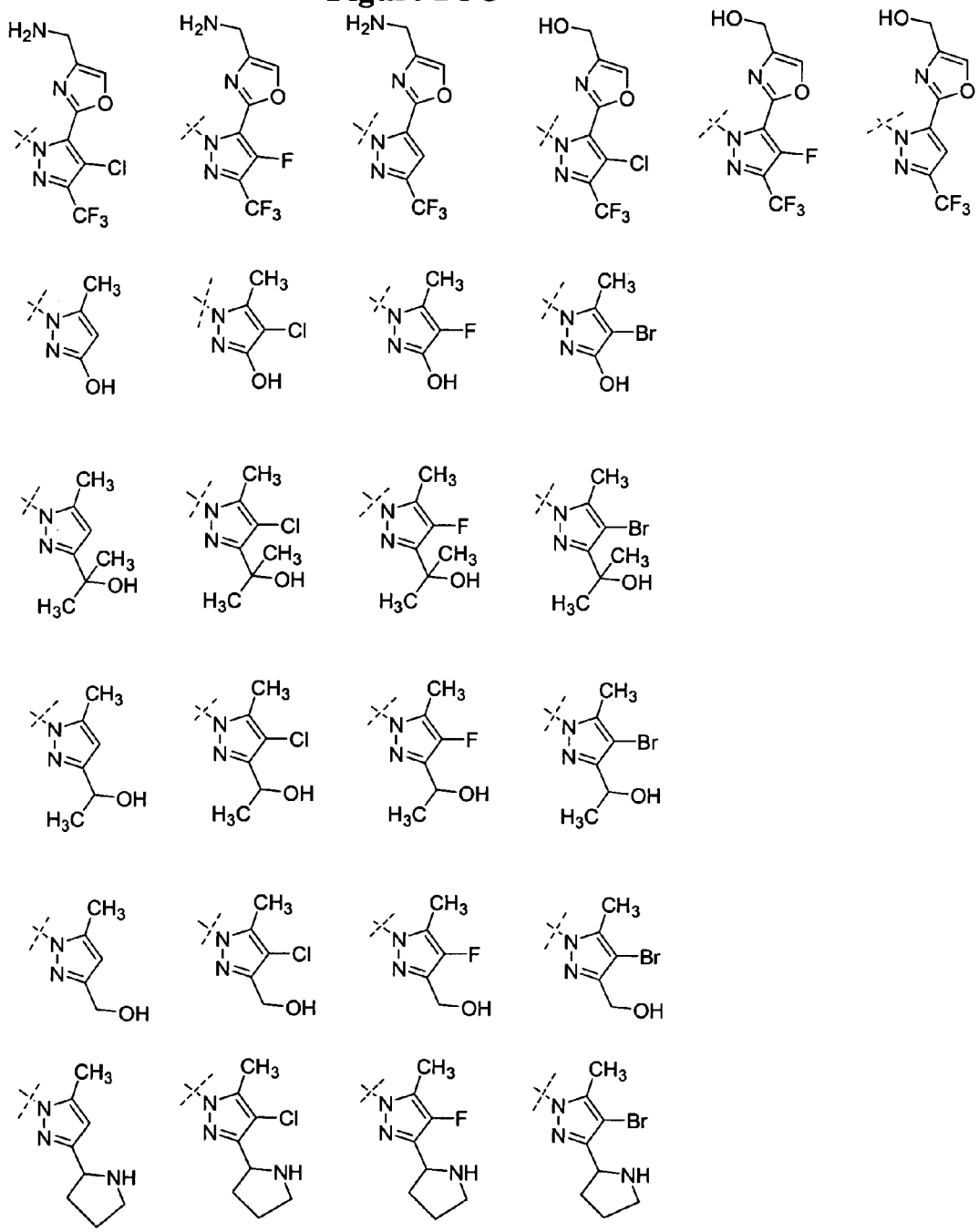
Figure 2D:
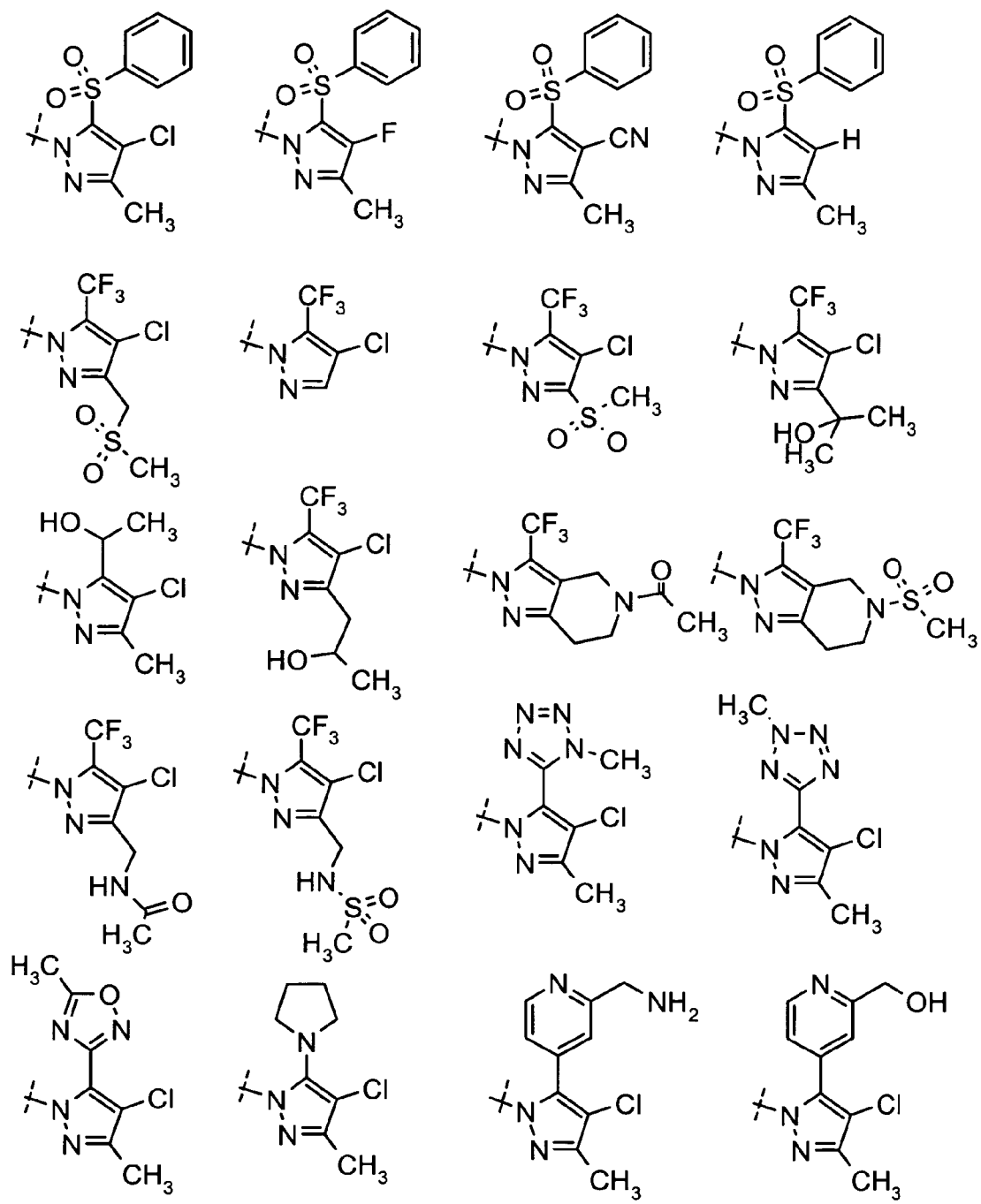
Figure 2E:
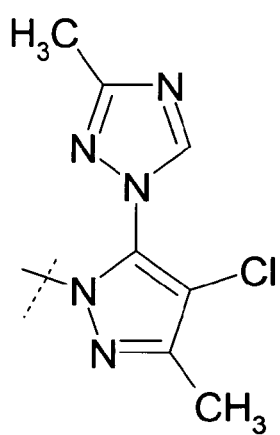
Figure 2E:
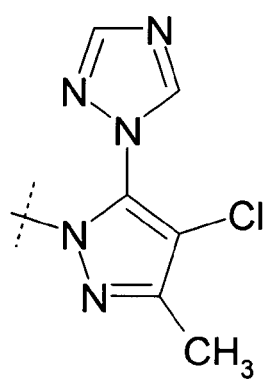
Figure 2E:
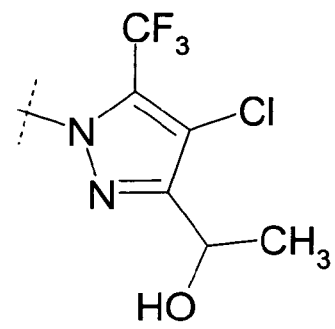
Figure 2E:
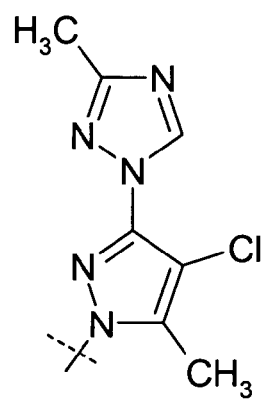
Figure 2E:
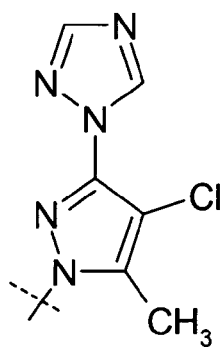
Figure 2E:
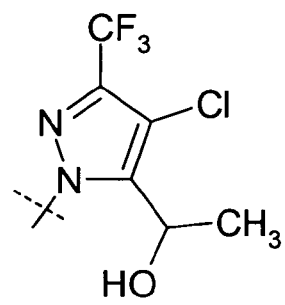
Figure 2F:
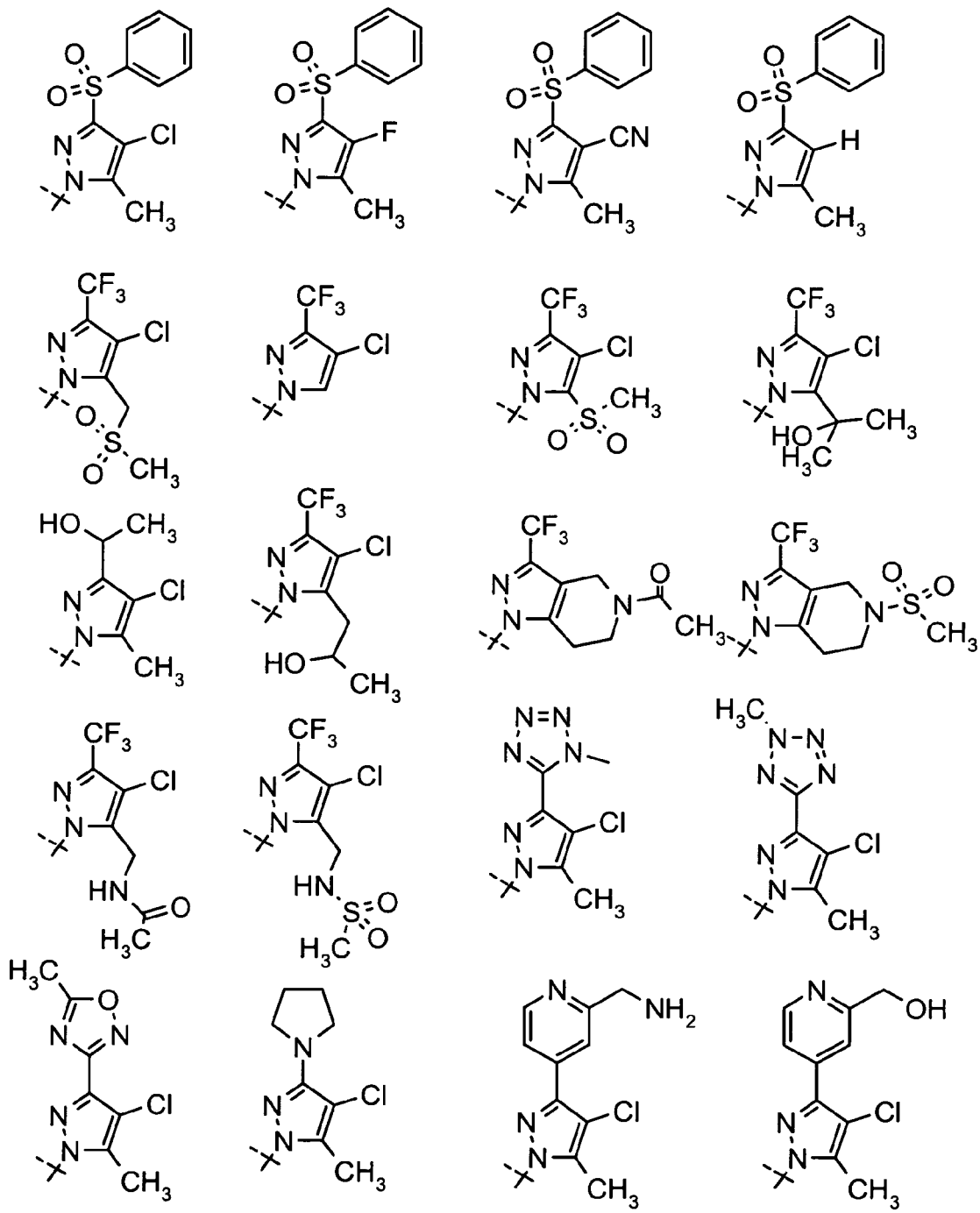
Figure 2G:
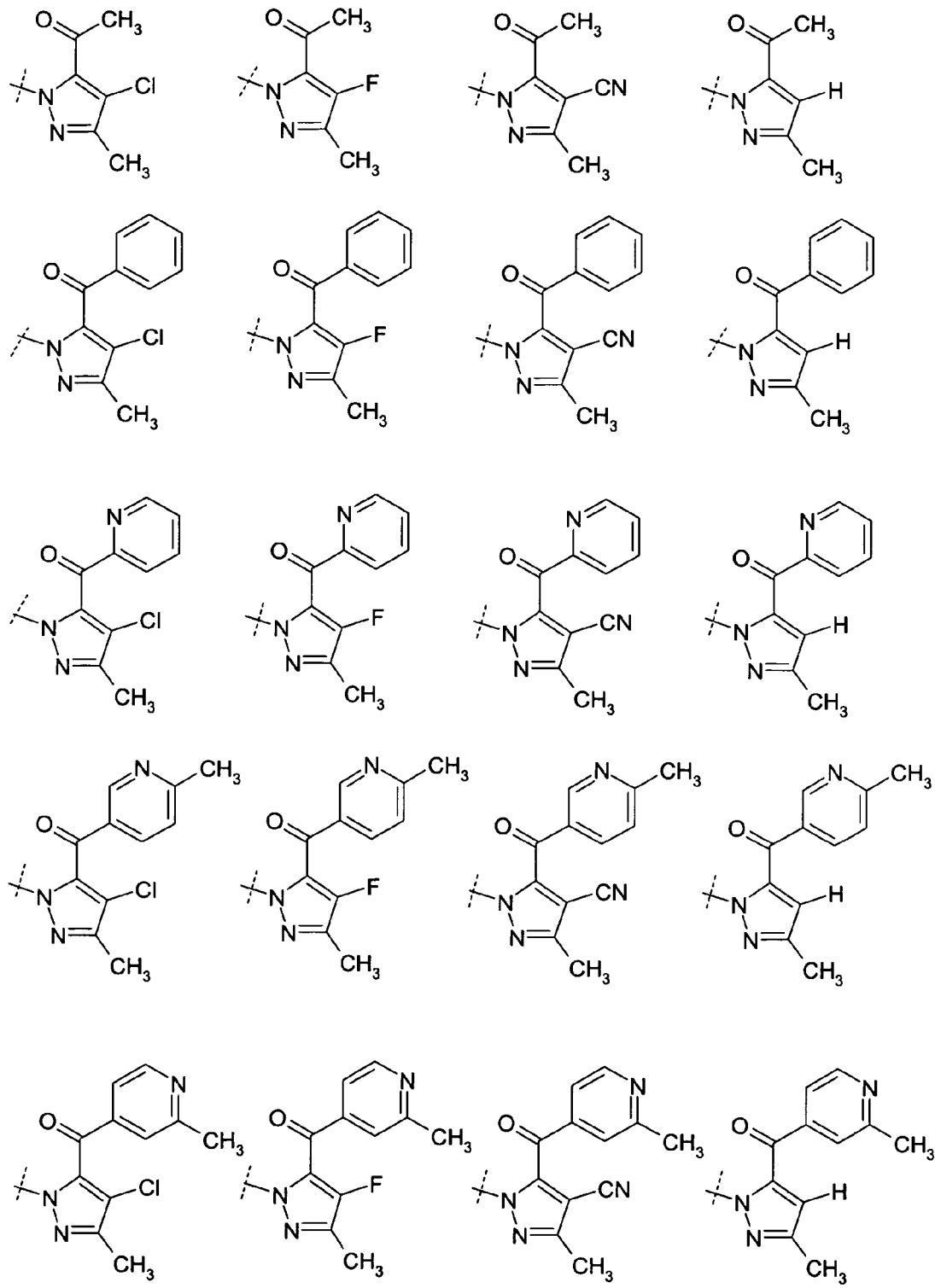
Figure 2H:
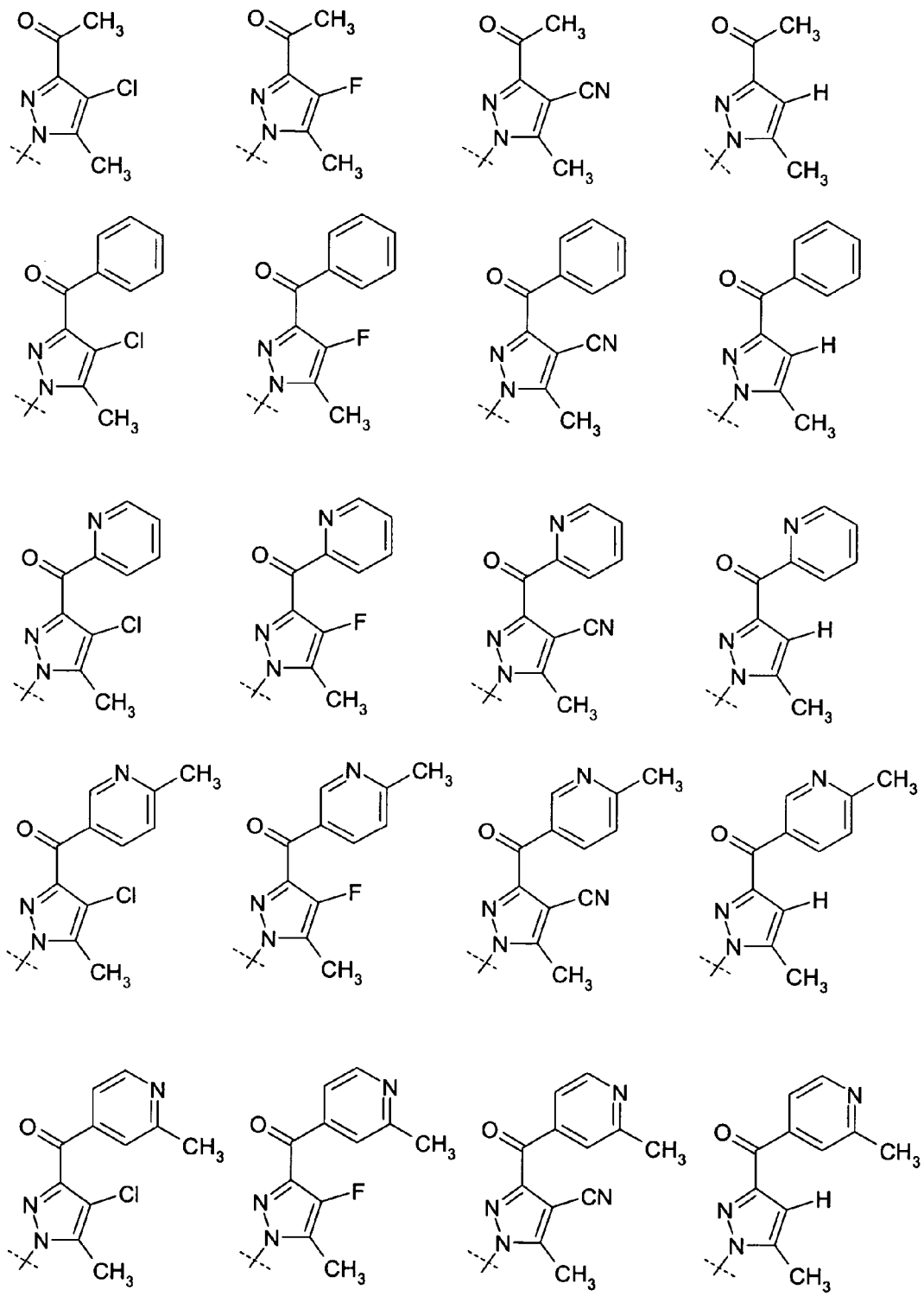

In several other specific groups of embodiments defined by formulae I, II, IIa, IIb, III, IIIa, IIIb, IIIc, IIId, IIId$^1$-IIId$^4$, IV, IVa, V and Va, herein, HAr is selected from the preferred groups represented in FIGS. 2A-2Z, 2AA-2HH, and 3

A number of groups of additional embodiments can be outlined as follows.

In a first group of embodiments, the compounds are represented by formula I in which Ar is selected from
(i) phenyl, substituted with from 1 to 5 $R^2$ groups;
(ii) pyridinyl, substituted with from 1 to 4 $R^2$ groups; and
(iii) pyrimidinyl, substituted with from 1 to 3 $R^2$ groups;
(iv) pyrazinyl, substituted with from 1 to 3 $R^2$ groups; and
(v) pyridazinyl, substituted with from 1 to 3 $R^2$ groups;

wherein each $R^2$ is a member independently selected from the group consisting of halogen, —$OR^c$, —$OC(O)R^c$, —$NR^cR^d$, —$SR^c$, —$R^e$, —CN, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —$S(O)R^e$, —$S(O)_2R^e$, —$NR^cS(O)_2R^e$, —$S(O)_2NR^cR^d$ and —$N_3$, wherein each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, wherein the aliphatic portions of $R^c$, $R^d$ and $R^e$ are optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$. More preferably, Ar is phenyl substituted with from 1 to 3 $R^2$ groups. Some preferred embodiments are those in which the Ar groups are represented by:

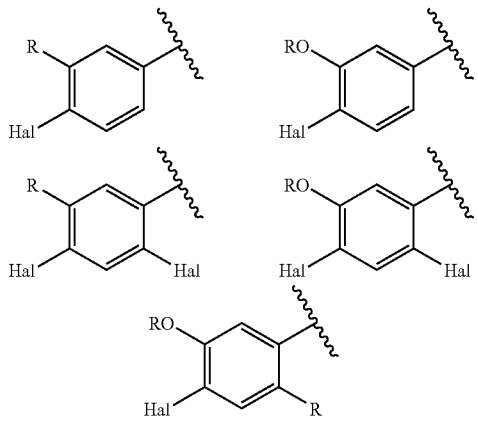

wherein Hal is F, Cl or Br and each R is independently $C_{1-6}$ alkyl or $C_{3-6}$ cycloalkyl. Still other preferred embodiments have Ar groups represented by:

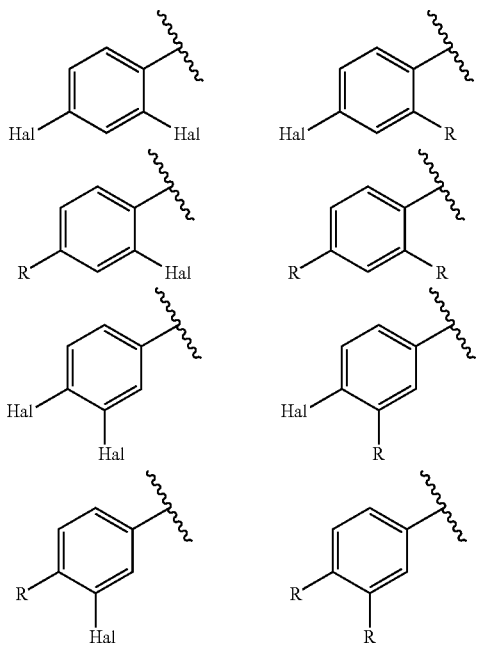

wherein Hal is F, Cl or Br and each R is independently $C_{1-6}$ alkyl or $C_{3-6}$ cycloalkyl.

In other preferred embodiments, $L^1$ is —$CH_2$— and is optionally substituted with —$R^k$, —$X^4OR^i$, —$X^4OC(O)R^i$, —$X^4NR^iR^j$, —$X^4CO_2R^i$, —$X^4CONR^iR^j$, —$X^4SR^i$, —$Y^1$, —$X^4Y^1$, —$X^4CN$ or —$X^4NO_2$. In still other preferred embodiments, HAr is selected from pyrazolyl and triazolyl, each of which is optionally substituted with from one to three $R^3$ groups independently selected from halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f(O)NR^fR^g$, —$S(O)R^h$, —$S(O)_2R^h$, —$S(O)_2NR^fR^g$, —$NR^fS(O)_2R^h$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f—C(O)NR^fR^g$, —$X^3S(O)R^h$, —$X^3S(O)_2R^h$, —$X^3NR^fS(O)_2R^h$, —$X^3S(O)_2NR^fR^g$, —Y, —$X^3Y$, —$S(O)_2Y$, —$C(O)Y$, —$O—X^3OR^f$, —$O—X^3NR^fR^g$, —$O—X^3CO_2R^f$, —$O—X^3CONR^fR^g$, —$NR^g—X^3OR^f$, —$NR^gX^3NR^fR^g$, —$NR^g—X^3CO_2R^f$, —$NR^g—X^3CONR^fR^g$, and —$X^3N_3$ wherein $R^f$ and $R^g$ are each independently selected from the group consisting of H, $C_{1-8}$ alkyl and $C_{1-8}$ haloalkyl, and each $R^h$ is independently selected from the group consisting of $C_{1-8}$ alkyl and $C_{1-8}$ haloalkyl. In still other preferred embodiments, Ar is phenyl substituted with from one to three $R^2$ groups, HAr is pyrazolyl which is substituted with three $R^3$ groups and $L^1$ is —$CH_2$—. In certain preferred embodiments in this group, Ar is selected from those substituted phenyl moieties provided in FIGS. 1A and 1B.

In a second group of embodiments, the compounds are represented by formula I in which Ar is selected from
(i) phenyl, substituted with from 1 to 5 $R^2$ groups;
(ii) pyridinyl, substituted with from 1 to 4 $R^2$ groups; and
(iii) pyrimidinyl, substituted with from 1 to 3 $R^2$ groups;
(iv) pyrazinyl, substituted with from 1 to 3 $R^2$ groups; and
(v) pyridazinyl, substituted with from 1 to 3 $R^2$ groups;

wherein each $R^2$ is a member independently selected from the group consisting of halogen, —$X^2OR^c$, —$O—X^2OR^c$, —$X^2OC(O)R^c$, —$X^2NR^cR^d$, —$O—X^2NRR^d$, —$X^2SR^c$, —$X^2CN$, —$X^2NO_2$, —$X^2CO_2R^c$, —$O—X^2CO_2R^c$, —$X^2CONR^cR^d$, —$O—X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH—C(NH_2)=NH$, —$X^2NR^eC(NH_2)=NH$, —$X^2NH—C(NH_2)=NR^e$, —$X^2NH—C(NHR^e)=NH$, —$X^2S(O)R^e$, —$X^2S(O)_2R^e$, —$X^2NR^cS(O)_2R^e$, —$X^2S(O)_2NR^cR^d$ and —$X^2N_3$.

In a third group of embodiments, the compounds are represented by formula I in which HAr is a member selected from the group consisting of pyrazolyl and benzopyrazolyl, which is optionally substituted with from one to three $R^3$ groups independently selected from the group consisting of halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f—C(O)NR^fR^g$, —$NH—C(NH_2)=NH$, —$NR^hC(NH_2)=NH$, —$NH—C(NH_2)=NR^h$, —$NH—C(NHR^h)=NH$, —$S(O)R^h$, —$S(O)_2R^h$, —$NR^fS(O)_2R^h$, —$S(O)_2NR^fR^g$, —$NR^fS(O)_2R^h$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f—C(O)NR^fR^g$, —$X^3NH—C(NH_2)=NH$, —$X^3NR^hC(NH_2)=NH$, —$X^3NH—C(NH_2)=NR^h$, —$X^3NH—C(NHR^h)=NH$, —$X^3S(O)R^h$, —$X^3S(O)_2R^h$, —$X^3NR^fS(O)_2R^h$, —$X^3S(O)_2NR^fR^g$, —Y, —$X^3Y$, —$S(O)_2Y$, —$C(O)Y$, —$O—X^3OR^f$, —$O—X^3NR^fR^g$, —$O—X^3CO_2R^f$, —$O—X^3CONR^fR^g$, —$NR^g—X^3OR^f$, —$NR^g—X^3NR^fR^g$, —$NR^g—X^3CO_2R^f$, —$NR^g—X^3CONR^fR^g$, and —$X^3N_3$ wherein Y is a five or six-membered aryl, heteroaryl or heterocyclic ring, optionally substituted with from one to three substituents selected from the group consisting of halogen, —$OR^f$, —$OC(O)R^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$NR^gC(O)_2R^h$, —$S(O)R^h$, —$S(O)_2R^h$, —$NR^fS(O)_2R^h$, —$S(O)_2NR^fR^g$, —$X^3OR^f$, $X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f—C(O)NR^fR^g$, —$X^3OC(O)NR^fR^g$, —$X^3S(O)R^h$, —$X^3S(O)_2R^h$, —$X^3NR^fR^g$, —$X^3NR^fS(O)_2R^h$, —$X^3S(O)_2NR^fR^g$, —$O$—$X^3OR^f$, —$O$—$X^3NR^fR^g$, —$O$—$X^3CO_2R^f$, —$O$—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$ and wherein each $X^3$ is independently selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $X^3$, $R^f$, $R^g$ and $R^h$ are optionally further substituted with from one to three members selected from the group consisting of —OH, —$OR^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein R$^o$ is unsubstituted $C_{1-6}$ alkyl. Within this group of embodiments, preferred compounds are those in which Ar is phenyl substituted with from one to three $R^2$ groups, HAr is pyrazolyl which is substituted with three $R^3$ groups and preferably attached to the remainder of the molecule via a ring nitrogen atom, and $L^1$ is —$CH_2$—. Other preferred embodiments are those in which Ar is selected from the substituted phenyl moieties provided in FIGS. 1A through 1G. In some preferred embodiments are those compounds in which one of the $R^3$ groups is selected from the group consisting of —Y and —$X^3$—Y. More preferably, those compounds wherein Y is selected from the group consisting of morpholinyl, pyrrolidinyl, piperidinyl, piperazinyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl and oxadiazolyl, which is optionally substituted, or phenyl which is substituted as set forth above, or more preferably, with from one to three substituents independently selected from the group consisting of halogen, —$OR^f$, —$NR^fR^g$, —$COR^f$, —$CO_2R^f$, —$CONR^fR^g$, —$NO_2$, —$R^h$, —CN, —$X^3$—$OR^f$, —$X^3$—$NR^fR^g$ and —$X^3$—$NR^fS(O)_2R^h$, wherein $R^f$ and $R^g$ are each independently selected from the group consisting of H, $C_{1-8}$ alkyl, $C_{3-6}$ cycloalkyl and $C_{1-8}$ haloalkyl, and each $R^h$ is independently selected from the group consisting of $C_{1-8}$ alkyl, $C_{3-6}$ cycloalkyl and $C_{1-8}$ haloalkyl.

In certain embodiments, the compounds are represented by formula I in which W is formula A, Ar is phenyl substituted with from one to three $R^2$ groups, HAr is pyrazolyl which is substituted with from one to three $R^3$ groups and $L^1$ is —$CH_2$—. Within this group of embodiments are further subgroups of embodiments, for example, those in which $L^2$ is a covalent bond, those in which $L^2$ is CO (a carbonyl moiety), those in which $L^2$ is SO$_2$ (a sulfonyl moiety) and those in which $L^2$ is CR$^q$R$^r$.

In other embodiments, the compounds are represented by formula I in which W is formula B, Ar is phenyl substituted with from one to three $R^2$ groups, HAr is pyrazolyl which is substituted with from one to three $R^3$ groups and $L^1$ is —$CH_2$—. Within this group of embodiments are further subgroups of embodiments, for example, those in which $L^2$ is a covalent bond, those in which $L^2$ is CO, those in which $L^2$ is SO$_2$, and those in which $L^2$ is CR$^q$R$^r$.

In still other embodiments, the compounds are represented by formula I in which W is formula C, Ar is phenyl substituted with from one to three $R^2$ groups, HAr is pyrazolyl which is substituted with from one to three $R^3$ groups and $L^1$ is —$CH_2$—. Within this group of embodiments are further subgroups of embodiments, for example, those in which $L^2$ is a covalent bond, those in which $L^2$ is CO, those in which $L^2$ is SO$_2$, and those in which $L^2$ is CR$^q$R$^r$.

In yet other embodiments, the compounds are represented by formula I in which W is formula D, Ar is phenyl substituted with from one to three $R^2$ groups, HAr is pyrazolyl which is substituted with from one to three $R^3$ groups and $L^1$ is —$CH_2$—. Within this group of embodiments are further subgroups of embodiments, for example, those in which $L^2$ is a covalent bond, those in which $L^2$ is CO, those in which $L^2$ is SO$_2$, and those in which $L^2$ is CR$^q$R$^r$.

In another group of embodiments, the compounds are represented by formula II:

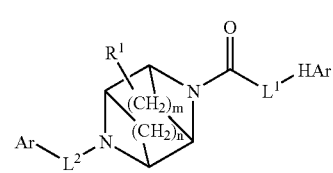

II or a pharmaceutically acceptable salt or N-oxide thereof, wherein one of the subscripts m and n is zero such that a bridge or bond is absent, and the other is 1, 2 or 3; Ar is phenyl substituted with from 1 to 5 $R^2$ groups; $L^1$ is —$CH_2$— and is optionally substituted with —$R^k$, —$X^4OR^i$, —$X^4OC(O)R^i$, —$X^4NR^iR^j$, —$X^4CO_2R^i$, —$X^4CONR^iR^j$, —$X^4SR^i$, —$Y^1$, —$X^4Y^1$, —$X^4CN$ or —$X^4NO_2$; $L^2$ is as defined above; HAr is pyrazole substituted with from 1 to 3 $R^3$ groups and is linked to $L^1$ via a nitrogen atom of the pyrazole ring; and $R^1$ represents 0, 1, 2 or 3 substituents selected from those described above with reference to formula I. Preferably, $R^1$ represents 0, 1 or 2 substituents selected from those described above. More preferably, $R^1$ is H or $C_{1-8}$ alkyl.

In a related group of embodiments, compounds have a formula selected from

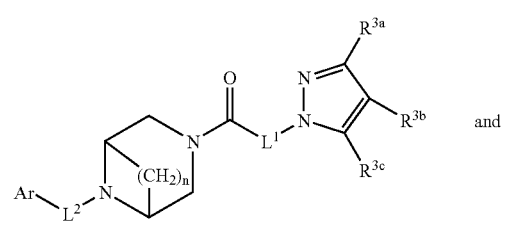

IIa and

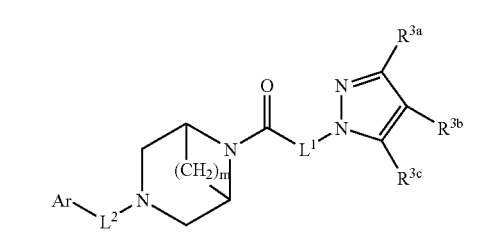

IIb and their pharmaceutically acceptable salts and N-oxides thereof, wherein the subscripts n and m are each 1, 2 or 3 and wherein $R^{3a}$, $R^{3b}$ and $R^{3c}$ are each members independently selected from the group consisting of hydrogen, halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —NH—$C(NH_2)$=NH, —$NR^hC(NH_2)$=NH, —NH—$C(NH_2)$=$NR^h$, —NH—$C(NHR^h)$=NH, —$S(O)R^h$, —$S(O)_2R^h$, —$NR^fS(O)_2R^h$, —$S(O)_2NR^fR^g$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^fC(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2NR^fR^g$, —Y, —$X^3Y$, —$S(O)_2Y$, —C(O)Y, —$X^3N_3$, —O—$X^3OR^f$, —O—$X^3NR^fR^g$, —O—$X^3CO_2R^f$, —O—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$, wherein Y is a five or six-membered aryl, heteroaryl or heterocyclic ring, optionally substituted with from one to three substituents selected from the group consisting of halogen, —$OR^f$, —$OC(O)R^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$NR^gC(O)_2R^h$, —$S(O)R^h$, —$S(O)_2R^h$, —$NR^fS(O)_2R^h$, —$S(O)_2NR^fR^g$, —$X^3OR^f$, $X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3OC(O)R^f$, —$X^3S(O)R^h$, —$X^3S(O)_2R^h$, —$X^3NR^fR^g$, —$X^3NR^fS(O)_2R^h$, —$X^3S(O)_2NR^fR^g$, —O—$X^3OR^f$, —O—$X^3NR^fR^g$, —O—$X^3CO_2R^f$, —O—$X^3CONR^fR^g$, —$NR^g$—$X^3OR^f$, —NR—$X^3NR^fR^g$, —$NR^g$—$X^3CO_2R^f$, and —$NR^g$—$X^3CONR^fR^g$, and wherein each $X^3$ is independently selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $R^f$, $R^g$ and $R^h$ is optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein each $R^o$ is independently an unsubstituted $C_{1-6}$ alkyl. Preferably, at least one of $R^{3a}$, $R^{3b}$ and $R^{3c}$ is other than H. The remaining groups have the meanings provided above with reference to formula I in their most complete interpretation. Preferably, Ar is phenyl, optionally substituted with from one to five $R^2$ substituents. Still more preferably, $L^1$ is —$CH_2$—. Further preferred are those compounds in which Ar is phenyl substituted with from one to three independently selected $R^2$ substituents. In still further preferred embodiments, Ar is a substituted phenyl selected from those provided in FIGS. 1A through 1G. Even further preferred are those compounds in which the substituted pyrazole moiety is selected from the appropriately oriented substituted pyrazoles provided in FIGS. 2A-2Z, 2AA-2HH and 3. In related subgroups of embodiments, the subscripts n and m are 2; $L^1$ is —$CH_2$—; and $L^2$ is a covalent bond. In another related subgroup of embodiments, $L^2$ is CO, $SO_2$ or $CR^qR^r$ and $L^1$ is —$CH_2$— and is optionally substituted with —$R^k$, —$X^4OR^i$, —$X^4OC(O)R^i$, —$X^4NR^iR^j$, —$X^4CO_2R^i$, —$X^4CONR^iR^j$, —$X^4SR^i$, —$Y^1$, —$X^4Y^1$, —$X^4CN$ or —$X^4NO_2$.

In other embodiments of formula Ia and IIb, Ar is phenyl, substituted with $R^{2a}$, $R^{2b}$, $R^{2c}$, $R^{2d}$ and $R^{2e}$, wherein selected embodiments are those embodiments provided below with reference to each of formula IIIa and IIIb.

In yet another group of embodiments, compounds are provided having formula III:

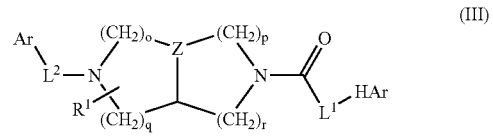

or a pharmaceutically acceptable salt or N-oxide thereof, wherein the subscripts o, p, q and r are 0 to 3; Ar is phenyl substituted with from 1 to 5 $R^2$ groups; $L^1$ is —$CH_2$— and is optionally substituted with —$R^k$, —$X^4OR^i$, —$X^4OC(O)R^i$, —$X^4NR^iR^j$, —$X^4CO_2R^i$, —$X^4CONR^iR^j$, —$X^4SR^i$, —$Y^1$, —$X^4Y^1$, —$X^4CN$ or —$X^4NO_2$; HAr is pyrazole substituted with from 1 to 3 $R^3$ groups and is linked to $L^1$ via a nitrogen atom of the pyrazole ring; and $R^1$ represents 0, 1, 2 or 3 substituents selected from those described above with reference to formula I. Preferably, $R^1$ represents 0, 1 or 2 substituents selected from those described above, and optionally two $R^1$ groups on adjacent carbon atoms can be combined with the atoms to which each are attached to form a 5-, 6- or 7-membered carbocyclic or heterocyclic ring. More preferably, $R^1$ is H or $C_{1-8}$ alkyl. The remaining groups have the meanings provided above with reference to formula I.

In a related group of embodiments, the compounds of formula III have the subformula:

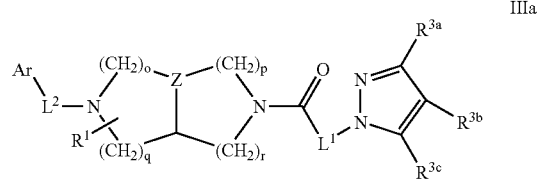

wherein $R^{3a}$, $R^{3b}$ and $R^{3c}$ are each members independently selected from the group consisting of hydrogen, halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —NH—$C(NH_2)$=NH, —$NR^hC(NH_2)$=NH, —NH—$C(NH_2)$=$NR^h$, —NH—$C(NHR^h)$=NH, —$S(O)R^h$, —$S(O)_2R^h$, —$NR^fS(O)_2R^h$, —$S(O)_2NR^fR^g$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3NH$—$C(NH_2)$=NH, —X₃NRʰC(NH₂)=NH,    —X³NH—C(NH₂)=NRʰ, —X³NH—C(NHRʰ)=NH, —X³S(O)Rʰ, —X³S(O)₂Rʰ, —X³NRᶠS(O)₂Rʰ, —X³S(O)₂NRᶠRᵍ, —Y, —X³Y, —S(O)₂Y, —C(O)Y, —X³N₃, —O—X³ORᶠ, —O—X³NRᶠRᵍ, —O—X³CO₂Rᶠ, —O—X³CONRᶠRᵍ, —NRᵍ—X³ORᶠ, —NRᵍ—X³NRᶠRᵍ, —NRᵍ—X³CO₂Rᶠ, and —NRᵍX³CONRᶠRᵍ, wherein Y is a five or six-membered aryl, heteroaryl or heterocyclic ring, optionally substituted with from one to three substitutents selected from the group consisting of halogen, —ORᶠ, —OC(O)Rᶠ, —NRᶠRᵍ, —Rʰ, —SRᶠ, —CN, —NO₂, —CO₂Rᶠ, —CONRᶠRᵍ, —C(O)Rᶠ, —NRᵍC(O)Rᶠ, —NRᵍC(O)₂Rʰ, —S(O)Rʰ, —S(O)₂Rʰ, —NRᶠS(O)₂Rʰ, —S(O)₂NRᶠRᵍ, —X³ORᶠ, X³SRᶠ, —X³CN, —X³NO₂, —X³CO₂Rᶠ, —X³CONRᶠRᵍ, —X³C(O)Rᶠ, —X³OC(O)NRᶠRᵍ, —X³NRᵍC(O)Rᶠ, —X³NRᵍC(O)₂Rʰ, —X³NRᶠ—C(O)NRᶠRᵍ, —X³OC(O)Rᶠ, —X³S(O)Rʰ, —X³S(O)₂Rʰ, —X³NRᶠRᵍ, —X³NRᶠS(O)₂Rʰ, —X³S(O)₂NRᶠRᵍ, —O—X³ORᶠ, —O—X³NRᶠRᵍ, —O—X³CO₂Rᶠ, —O—X³CONRᶠRᵍ, —NRᵍ—X³ORᶠ, —NRᵍ—X³NRᶠRᵍ, —NRᵍ—X³CO₂Rᶠ, and —NRᵍ—X³CONRᶠRᵍ, and wherein each X³ is independently selected from the group consisting of C₁₋₄ alkylene, C₂₋₄ alkenylene and C₂₋₄ alkynylene and each Rᶠ and Rᵍ is independently selected from hydrogen, C₁₋₈ alkyl, C₁₋₈ haloalkyl, C₃₋₆ cycloalkyl, C₂₋₈ alkenyl, C₂₋₈ alkynyl, aryl, heteroaryl, aryl-C₁₋₄ alkyl, and aryloxy-C₁₋₄ alkyl, or when attached to the same nitrogen atom can be combined with the nitrogen atom to form a five or six-membered ring having from 0 to 2 additional heteroatoms as ring members, and each Rʰ is independently selected from the group consisting of C₁₋₈ alkyl, C₁₋₈ haloalkyl, C₃₋₆ cycloalkyl, C₂₋₈ alkenyl, C₂₋₈ alkynyl, aryl, heteroaryl, aryl-C₁₋₄ alkyl, and aryloxy-C₁₋₄ alkyl, wherein the aliphatic portions of Rᶠ, Rᵍ and Rʰ is optionally further substituted with from one to three members selected from the group consisting of —OH, —ORᵒ, —OC(O)NHRᵒ, —OC(O)N(Rᵒ)₂, —SH, —SRᵒ, —S(O)Rᵒ, —S(O)₂Rᵒ, —SO₂NH₂, —S(O)₂NHRᵒ, —S(O)₂N(Rᵒ)₂, —NHS(O)₂Rᵒ, —NRᵒS(O)₂Rᵒ, —C(O)NH₂, —C(O)NHRᵒ, —C(O)N(Rᵒ)₂, —C(O)Rᵒ, —NHC(O)Rᵒ, —NRᵒC(O)Rᵒ, —NHC(O)NH₂, —NRᵒC(O)NH₂, —NRᵒC(O)NHRᵒ, —NHC(O)NHRᵒ, —NRᵒC(O)N(Rᵒ)₂, —NHC(O)N(Rᵒ)₂, —CO₂H, —CO₂Rᵒ, —NHCO₂Rᵒ, —NRᵒCO₂Rᵒ, —CN, —NO₂, —NH₂, —NHRᵒ, —N(Rᵒ)₂, —NRᵒS(O)NH₂ and —NRᵒS(O)₂NHRᵒ, wherein each Rᵒ is independently an unsubstituted C₁₋₆ alkyl. Preferably, at least one of R³ᵃ, R³ᵇ and R³ᶜ is other than H. R¹ represents 0, 1, 2 or 3 substituents selected from those described above with reference to formula I. Preferably, R¹ represents 0, 1 or 2 substituents selected from those described above, and optionally two R¹ groups on adjacent carbon atoms can be combined with the atoms to which each are attached to form a 5-, 6- or 7-membered carbocyclic or heterocyclic ring. The remaining groups have the meanings provided above with reference to formula I. In some embodiments, Ar is phenyl, optionally substituted with from one to five R² substitutents. Still more preferably, L¹ is —CH₂—. Further preferred are those compounds in which Ar is phenyl substituted with from one to three independently selected R² substituents. In still further preferred embodiments, Ar is a substituted phenyl selected from those provided in FIGS. 1A through 1G. Even further preferred are those compounds in which the substituted pyrazole moiety is selected from the appropriately oriented substituted pyrazoles provided in FIGS. 2A-2Z, 2AA-2HH and 3.

Within the group of formula IIIa above, certain groups of embodiments are particularly preferred. In one group of particularly preferred embodiments, the subscripts o, p, q and r are each 1; and L² is a covalent bond. In another related subgroup of embodiments, L² is CO, SO₂ or CRᵠRʳ. In each of these groups, L¹ is —CH₂— and is optionally substituted with —Rᵏ, —X⁴ORⁱ, —X⁴OC(O)Rⁱ, —X⁴NRⁱRʲ, —X⁴CO₂Rⁱ, —X⁴CONRⁱRʲ, —X⁴SRⁱ, —Y¹, —X⁴Y¹, —X⁴CN or —X⁴NO₂; and Z is preferably CH.

In a related group of embodiments, the compounds have the formula:

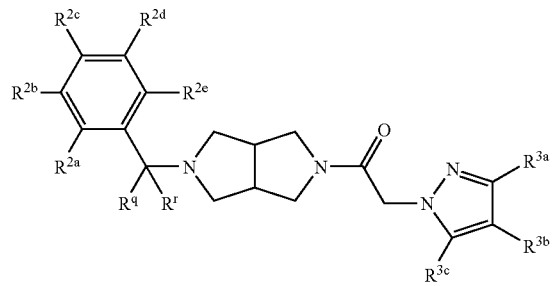

IIIb and the pharmaceutically acceptable salts and N-oxides thereof, wherein R²ᵃ, R²ᵇ, R²ᶜ, R²ᵈ and R²ᵉ are each members independently selected from the group consisting of hydrogen, halogen, —ORᶜ, —OC(O)Rᶜ, —NRᶜRᵈ, —SRᶜ, —Rᵉ, —CN, —NO₂, —CO₂Rᶜ, —CONRᶜRᵈ, —C(O)Rᶜ, —OC(O)NRᶜRᵈ, —NRᵈC(O)Rᶜ, —NRᵈC(O)₂Rᵉ, —NRᶜ—C(O)NRᶜRᵈ, —NH—C(NH₂)=NH, —NRᵉC(NH₂)=NH, —NH—C(NH₂)=NRᵉ, —NH—C(NHRᵉ)=NH, —S(O)Rᵉ, —S(O)₂Rᵉ, —NRᶜS(O)₂Rᵉ, —S(O)₂NRᶜRᵈ, —N₃, —X²ORᶜ, —O—X²ORᶜ, —X²OC(O)Rᶜ, —X²NRᶜRᵈ, —O—X²NRᶜRᵈ, —X²SRᶜ, —X²CN, —X²NO₂, —X²CO₂Rᶜ, —O—X²CO₂Rᶜ, —X²CONRᶜRᵈ, —O—X²CONRᶜRᵈ, —X²C(O)Rᶜ, —X²OC(O)NRᶜRᵈ, —X²NRᵈC(O)Rᶜ, —X²NRᵈC(O)₂Rᵉ, —X²NRᶜC(O)NRᶜRᵈ, —X²NH—C(NH₂)=NH, —X²NRᵉC(NH₂)=NH, —X²NH—C(NH₂)=NRᵉ, —X²NH—C(NHRᵉ)=NH, —X²S(O)Rᵉ, —X²S(O)₂Rᵉ, —X²NRᶜS(O)₂Rᵉ, —X²S(O)₂NRᶜRᵈ, —X²N₃, —NRᵈ—X²ORᶜ, —NRᵈ—X²NRᶜRᵈ, —NRᵈ—X²CO₂Rᶜ, and —NRᵈ—X²CONRᶜRᵈ, wherein X² is a member selected from the group consisting of C₁₋₄ alkylene, C₂₋₄ alkenylene and C₂₋₄ alkynylene and each Rᶜ and Rᵈ is independently selected from hydrogen, C₁₋₈ alkyl, C₁₋₈ haloalkyl, C₃₋₆ cycloalkyl, C₂₋₈ alkenyl, C₂₋₈ alkynyl, aryl, heteroaryl, aryl-C₁₋₄ alkyl, and aryloxy-C₁₋₄ alkyl, or optionally Rᶜ and Rᵈ when attached to the same nitrogen atom can be combined with the nitrogen atom to form a five or six-membered ring having from 0 to 2 additional heteroatoms as ring members; and each Rᵉ is independently selected from the group consisting of C₁₋₈ alkyl, C₁₋₈ haloalkyl, C₃₋₆ cycloalkyl, C₂₋₈ alkenyl, C₂₋₈ alkynyl, aryl, heteroaryl, aryl-C₁₋₄ alkyl, and aryloxy-C₁₋₄ alkyl, and each of Rᶜ, Rᵈ and Rᵉ is optionally further substituted with from one to three members selected from the group consisting of —OH, —ORⁿ, —OC(O)NHRⁿ, —OC(O)N(Rⁿ)₂, —SH, —SRⁿ, —S(O)Rⁿ, —S(O)₂Rⁿ, —SO₂NH₂, —S(O)₂NHRⁿ, —S(O)₂N(Rⁿ)₂, —NHS(O)₂Rⁿ, —NRⁿS(O)₂Rⁿ, —C(O)NH₂, —C(O)NHRⁿ, —C(O)N(Rⁿ)₂, —C(O)Rⁿ, —NHC(O)Rⁿ, —NRⁿC(O)Rⁿ, —NHC(O)NH₂, —NRⁿC(O)NH₂, —NRⁿC(O)NHRⁿ, —NHC(O)NHRⁿ, —NRⁿC(O)N(Rⁿ)₂, —NHC(O)N(Rⁿ)₂, —CO₂H, —CO₂Rⁿ, —NHCO₂Rⁿ, —NRⁿCO₂Rⁿ, —CN, —NO₂, —NH₂, —NHRⁿ, —N(Rⁿ)₂, —NRⁿS(O)NH₂ and —NRⁿS(O)₂NHRⁿ, wherein each Rⁿ is independently an unsubstituted C₁₋₆ alkyl, such that at least one of R²ᵃ, R²ᵇ, R²ᶜ, R²ᵈ and R²ᵉ is other than H; R³ᵃ, R³ᵇ and R³ᶜ are each members independently selected from the group consisting of hydrogen, halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —NH—C(NH$_2$)=NH, —NR$^h$C(NH$_2$)=NH, —NH—C(NH$_2$)=NR$^h$, —NH—C(NHR$^h$)=NH, —S(O)R$^h$, —S(O)$_2$R$^h$, —NR$^f$S(O)$_2$R$^h$, —S(O)$_2$NR$^f$R$^g$, —NR$^f$S(O)$_2$NR$^f$R$^g$, —N$_3$, —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —Y, —X$^3$Y, —S(O)$_2$Y, —C(O)Y, —X$^3$N$_3$, —O—X$^3$OR$^f$, —O—X$^3$NR$^f$R$^g$, —O—X$^3$CO$_2$R$^f$, —O—X$^3$CONR$^f$R$^g$, —NR$^g$—X$^3$OR$^f$, —NR$^g$—X$^3$NR$^f$R$^g$, —NR$^g$—X$^3$CO$_2$R$^f$, and —NR$^g$—X$^3$CONR$^f$R$^g$, wherein Y is a five or six-membered aryl, heteroaryl or heterocyclic ring, optionally substituted with from one to three substituents selected from the group consisting of halogen, —OR$^f$, —OC(O)R$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —NR$^g$C(O)$_2$R$^h$, —S(O)R$^h$, —S(O)$_2$R$^h$, —NR$^f$S(O)$_2$R$^h$, —S(O)$_2$NR$^f$R$^g$, —X$^3$OR$^f$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$OC(O)R$^f$, —X$^3$S(O)R$^h$, —X$^3$S(O)$_2$R$^h$, —X$^3$NR$^f$R$^g$, —X$^3$NR$^f$S(O)$_2$R$^h$, —X$^3$S(O)$_2$NR$^f$R$^g$, —O—X$^3$OR$^f$, —O—X$^3$NR$^f$R$^g$, —O—X$^3$CO$_2$R$^f$, —O—X$^3$CONR$^f$R$^g$, —NR$^g$—X$^3$OR$^f$, —NR$^g$—X$^3$NR$^f$R$^g$, —NR$^g$—X$^3$CO$_2$R$^f$, and —NR$^g$—X$^3$CONR$^f$R$^g$ and wherein each X$^3$ is independently selected from the group consisting of C$_{1-4}$ alkylene, C$_{2-4}$ alkenylene and C$_{2-4}$ alkynylene and each R$^f$ and R$^g$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, or when attached to the same nitrogen atom can be combined with the nitrogen atom to form a five or six-membered ring having from 0 to 2 additional heteroatoms as ring members, and each R$^h$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, wherein the aliphatic portions of R$^f$, R$^g$ and R$^h$ are optionally further substituted with from one to three members selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein each R$^o$ is independently an unsubstituted C$_{1-6}$ alkyl, such that at least one of R$^{3a}$, R$^{3b}$ and R$^{3c}$ is other than H. Additionally, the groups R$^q$ and R$^r$ are independently selected from hydrogen, C$_{1-6}$ alkyl and C$_{1-6}$ haloalkyl wherein the aliphatic portions of R$^q$ and R$^r$ are optionally further substituted with from one to three members selected from the group consisting of —OH, —OR$^s$, —OC(O)NHR$^s$, —OC(O)N(R$^s$)$_2$, —SH, —SR$^s$, —S(O)R$^s$, —S(O)$_2$R$^s$, —SO$_2$NH$_2$, —S(O)$_2$NHR$^s$, —S(O)$_2$N(R$^s$)$_2$, —NHS(O)$_2$R$^s$, —NR$^s$S(O)$_2$R$^s$, —C(O)NH$_2$, —C(O)NHR$^s$, —C(O)N(R$^s$)$_2$, —C(O)R$^s$, —NHC(O)R$^s$, —NR$^s$C(O)R$^s$, —NHC(O)NH$_2$, —NR$^s$C(O)NH$_2$, —NR$^s$C(O)NHR$^s$, —NHC(O)NHR$^s$, —NR$^s$C(O)N(R$^s$)$_2$, —NHC(O)N(R$^s$)$_2$, —CO$_2$H, —CO$_2$R$^s$, —NHCO$_2$R$^s$, —NR$^s$CO$_2$R$^s$, —CN, —NO$_2$, —NH$_2$, —NHR$^s$, —N(R$^s$)$_2$, —NR$^s$S(O)NH$_2$ and —NR$^s$S(O)$_2$NHR$^s$, wherein each R$^s$ is independently an unsubstituted C$_{1-6}$ alkyl. In some embodiments, R$^q$ and R$^r$ are independently selected from hydrogen, trifluoromethyl, methyl and ethyl. In other embodiments, R$^q$ and R$^r$ are both hydrogen.

Certain subgroups are provided as additional embodiments of the invention. In one embodiment, compounds are represented by formula IIIb, above in which one of the R$^3$ groups (e.g., R$^{3a}$, R$^{3b}$ and R$^{3c}$) is selected from —Y and —X$^3$—Y. In other embodiments, at least one of R$^{2a}$ and R$^{2e}$ is hydrogen. In still other embodiments, R$^{2b}$ is halogen. In other embodiments, at least one of R$^{3a}$, R$^{3b}$ and R$^{3c}$ is selected from halogen and C$_{1-4}$ haloalkyl. In other embodiments, R$^{2d}$ is hydrogen and at least two of R$^{3a}$, R$^{3b}$ and R$^{3c}$ are selected from halogen, C$_{1-4}$ haloalkyl and C$_{1-4}$ alkyl. In still other embodiments, the substituted phenyl moiety is selected from those provided in FIGS. 1A through 1G. Even further preferred are those compounds in which the substituted pyrazole moiety is selected from the appropriately oriented substituted pyrazoles provided in FIGS. 2A-2Z, 2AA-2HH and 3.

In still other embodiments, the compound is represented by formula IIIb wherein R$^{2c}$ is halogen or —R$^e$; R$^{2b}$ and R$^{2e}$ are each hydrogen; R$^{2a}$ is hydrogen, halogen, —CN, —C(O)R$^c$, —X$^2$NR$^c$R$^d$, or —R$^e$; R$^{2d}$ is selected from hydrogen, —SR$^c$, —O—X$^2$—OR$^c$, —X$^2$—OR$^c$, —R$^e$, —OR$^c$, —NR$^c$R$^d$, —NR$^c$S(O)$_2$R$^e$ and —NR$^d$C(O)R$^c$; R$^{3b}$ is halogen; and R$^{3a}$ and R$^{3c}$ are each independently selected from halogen, cyano, —NO$_2$, —CO$_2$R$^f$, —CONR$^f$R$^g$, —C(O)R$^f$, —NR$^f$R$^g$, —SR$^f$, —S(O)R$^h$, —S(O)$_2$R$^h$, —C(O)Y, —SO$_2$Y, —X$^3$Y, Y, C$_{1-6}$ alkyl, C$_{1-6}$ haloalkyl or C$_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$. In some embodiments, one of R$^{3a}$ or R$^{3c}$ is Y.

In still other embodiments, compounds are represented by formula IIIb, above in which R$^{2c}$ is selected from F, Cl, Br, CN, NO$_2$, CO$_2$CH$_3$, C(O)CH$_3$ and S(O)$_2$CH$_3$, and —R$^e$ and one, two or all three of R$^{3a}$, R$^{3b}$ and R$^{3c}$ is other than hydrogen.

In still other embodiments, compounds are represented by formula IIIb, above wherein at least one of R$^{2a}$ and R$^{2e}$ is hydrogen and R$^{2c}$ is halogen. Within this group of embodiments, a subgroup are those in which R$^{3a}$ and R$^{3c}$ are each independently selected from C$_{1-6}$ alkyl, C$_{1-6}$ haloalkyl, C$_{3-6}$ cycloalkyl and —Y; and R$^{3b}$ is halogen. Still further embodiments are those in which one of R$^{3a}$ and R$^{3c}$ is selected from C$_{1-6}$ alkyl, optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein each R$^o$ is independently an unsubstituted C$_{1-6}$ alkyl. Additional embodiments are those in which $R^{2d}$ is hydrogen and at least two of $R^{3a}$, $R^{3b}$ and $R^{3c}$ are selected from the group consisting of halogen, $C_{1-4}$ alkyl and $C_{1-4}$ haloalkyl, wherein the aliphatic portions are optionally substituted with from one to three members selected from the group consisting of —OH, —OR°, —OC(O)NHR°, —OC(O)N(R°)$_2$, —SH, —SR°, —S(O)R°, —S(O)$_2$R°, —SO$_2$NH$_2$, —S(O)$_2$NHR°, —S(O)$_2$N(R°)$_2$, —NHS(O)$_2$R°, —NR°S(O)$_2$R°, —C(O)NH$_2$, —C(O)NHR°, —C(O)N(R°)$_2$, —C(O)R°, —NHC(O)R°, —NR°C(O)R°, —NHC(O)NH$_2$, —NR°C(O)NH$_2$, —NR°C(O)NHR°, —NHC(O)NHR°, —NR°C(O)N(R°)$_2$, —NHC(O)N(R°)$_2$, —CO$_2$H, —CO$_2$R°, —NHCO$_2$R°, —NR°CO$_2$R°, —CN, —NO$_2$, —NH$_2$, —NHR°, —N(R°)$_2$, —NR°S(O)NH$_2$ and —NR°S(O)$_2$NHR°, wherein each R° is independently an unsubstituted $C_{1-6}$ alkyl.

In still other embodiments, compounds are represented by formula IIIb, above wherein $R^{2c}$ is selected from the group consisting of F, Cl, Br, CN, NO$_2$, CO$_2$CH$_3$, C(O)CH$_3$ and S(O)$_2$CH$_3$, and one, two or all three of $R^{3a}$, $R^{3b}$ and $R^{3c}$ is other than hydrogen.

In some embodiments related to formula IIIb, compounds are provided having the formula:

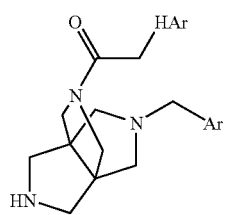

IIIc wherein Ar and HAr have the meanings provided with reference to formula I above, and are preferably selected from the preferred groups provided with reference to formula IIIb, above.

In another group of embodiments, the compounds of the invention have formula IIId

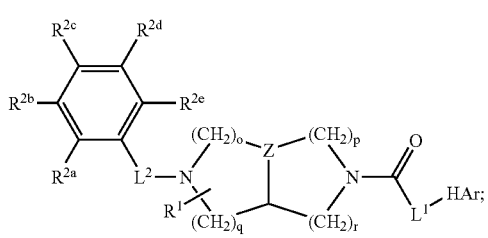

IIId in which the subscripts o, p, q and r are 0 to 3. In certain preferred embodiments, the subscripts o, p, q and r are each 1. Z is CH, CR$^1$ or N. The substituents $R^{2a}$, $R^{2b}$, $R^{2c}$, $R^{2d}$ and $R^{2e}$ are each members independently selected from the group consisting of hydrogen, halogen, —OR$^c$, —OC(O)R$^c$, —NR$^c$R$^d$, —SR$^c$, —R$^c$, —CN, —NO$_2$, —CO$_2$R$^c$, —CONR$^c$R$^d$, —C(O)R$^c$, —OC(O)NR$^c$R$^d$, —NR$^d$C(O)R$^c$, —NR$^d$C(O)$_2$R$^e$, —NR$^c$—C(O)NR$^c$R$^d$, —NH—C(NH$_2$)=NH, —NR$^e$C(NH$_2$)=NH, —NH—C(NH$_2$)=NR$^e$, —NH—C(NHR$^e$)=NH, —S(O)R$^e$, —S(O)$_2$R$^e$, —NR$^c$S(O)$_2$R$^e$, —S(O)$_2$NR$^c$R$^d$, —N$_3$, —X$^2$OR$^c$, —O—X$^2$OR$^c$, —X$^2$OC(O)R$^c$, —X$^2$NR$^c$R$^d$, —O—X$^2$NR$^c$R$^d$, —X$^2$SR$^c$, —X$^2$CN, —X$^2$NO$_2$, —X$^2$CO$_2$R$^c$, —O—X$^2$CO$_2$R$^c$, —X$^2$CONR$^c$R$^d$, —O—X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, —X$^2$N$_3$, —NR$^d$—X$^2$OR$^c$, —NR$^d$—X$^2$NR$^c$R$^d$, —NR$^d$—X$^2$CO$_2$R$^c$, and —NR$^d$—X$^2$CONR$^c$R$^d$, wherein X$^2$ is a member selected from the group consisting of $C_{1-4}$ alkylene, $C_{2-4}$ alkenylene and $C_{2-4}$ alkynylene and each R$^c$ and R$^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or optionally R$^c$ and R$^d$ when attached to the same nitrogen atom can be combined with the nitrogen atom to form a five or six-membered ring having from 0 to 2 additional heteroatoms as ring members; and each R$^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of R$^c$, R$^d$ and R$^e$ is optionally further substituted with from one to three members selected from the group consisting of —OH, —OR″, —OC(O)NHR″, —OC(O)N(R″)$_2$, —SH, —SR″, —S(O)R″, —S(O)$_2$R″, —SO$_2$NH$_2$, —S(O)$_2$NHR″, —S(O)$_2$N(R″)$_2$, —NHS(O)$_2$R″, —NR″S(O)$_2$R″, —C(O)NH$_2$, —C(O)NHR″, —C(O)N(R″)$_2$, —C(O)R″, —NHC(O)R″, —NR″C(O)R″, —NHC(O)NH$_2$, —NR″C(O)NH$_2$, —NR″C(O)NHR″, —NHC(O)NHR″, —NR″C(O)N(R″)$_2$, —NHC(O)N(R″)$_2$, —CO$_2$H, —CO$_2$R″, —NHCO$_2$R″, —NR″CO$_2$R″, —CN, —NO$_2$, —NH$_2$, —NHR″, —N(R″)$_2$, —NR″S(O)NH$_2$ and —NR″S(O)$_2$NHR″, wherein each R″ is independently an unsubstituted $C_{1-6}$ alkyl, such that at least one of $R^{2a}$, $R^{2b}$, $R^{2c}$, $R^{2d}$ and $R^{2e}$ is other than H. L$^1$ is —CH$_2$—, —CH$_2$NH— or —CH$_2$O— and is optionally substituted with —R$^k$, —X$^4$OR$^i$, —X$^4$OC(O)R$^i$, —X$^4$NR$^i$R$^j$, —X$^4$CO$_2$R$^i$, —X$^4$CONR$^i$R$^j$, —X$^4$SR$^i$, —Y$^1$, —X$^4$Y$^1$, —X$^4$CN or —X$^4$NO$_2$. In one preferred embodiment, L$^1$ is —CH$^2$—. L$^2$ is, in certain embodiments, a covalent bond or —C(R$^p$)(R$^r$)—, preferably —CH$_2$—.

In formula IIId, HAr is benzimidazolyl, benzopyrazolyl, benzotriazolyl, benzotetrazolyl, benzooxazolyl, benzoisoxazolyl, benzooxadiazolyl, quinolinyl, isoquinolinyl, quinazolinyl, quinoxalinyl, naphthyridinyl, pyrimidinopyridinyl, pyridazinopyridinyl, pyrazinopyridinyl, pyridinopyrimidinyl, pyrimidinopyrimidinyl, pyridazinopyrimidinyl, pyrazinopyrimidinyl, pyridinopyridazinyl, pyrimidinopyridazinyl, pyridazinopyridazinyl, pyrazinopyridazinyl, pyridinopyrazinyl, pyrimidinopyrazinyl, pyridazinopyrazinyl, pyrazinopyrazinyl, pyridinoimidazolyl, purinyl, pyridazinoimidazolyl, pyrazinoimidazolyl, pyridinooxazolyl, pyrimidinooxazolyl, pyridazinooxazolyl, pyrazinooxazolyl, pyridinoisoxazolyl, pyrimidinoisoxazolyl, pyridazinoisoxazolyl, pyrazinoisoxazolyl, pyridinooxathiadiazolyl, pyrimidinooxathiadiazolyl, pyridazinooxathiadiazolyl, pyrazinooxathiadiazolyl, pyridinooxathiazolyl, pyrimidinooxathiazolyl, pyridazinooxathiazolyl, pyrazinooxathiazolyl, pyridinothiazolyl, pyrimidinothiazolyl, pyridazinothiazolyl, pyrazinothiazolyl, pyridinopyrazolyl, pyrimidinopyrazolyl, pyridazinopyrazolyl, pyrazinopyrazolyl, pyridinopyrrolyl, pyrimidinopyrrolyl, pyridazinopyrrolyl, pyrazinopyrrolyl; or alternatively is a heterocyclic ring substituted with an aryl or heteroaryl group; and wherein the HAr group is substituted with from 0 to 5 R$^3$ groups.

In one embodiment, HAr is selected from the group consisting of pyridinoimidazolyl, purinyl, pyridazinoimidazolyl, pyrazinoimidazolyl, pyridinooxazolyl, pyrimidinooxazolyl, pyridazinooxazolyl, pyrazinooxazolyl, pyridinoisoxazolyl, pyrimidinoisoxazolyl, pyridazinoisoxazolyl, pyrazinoisoxazolyl, pyridinooxathiadiazolyl, pyrimidinooxathiadiazolyl, pyridazinooxathiadiazolyl, pyrazinooxathiadiazolyl, pyridinooxathiazolyl, pyrimidinooxathiazolyl, pyrazinooxathiazolyl, pyrimidinothiazolyl, pyridinothiazolyl, pyrimidinothiazolyl, pyridazinothiazolyl, pyrazinothiazolyl, pyridinopyrazolyl, pyrimidinopyrazolyl, pyridazinopyrazolyl, pyrazinopyrazolyl, pyridinopyrrolyl, pyrimidinopyrrolyl, pyridazinopyrrolyl and pyrazinopyrrolyl, wherein the HAr group is substituted with from 0 to 5 $R^3$ groups.

In certain embodiments of formula IIId, the HAr group has formula

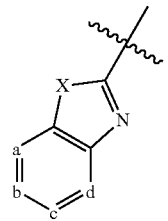

wherein X is N(H), N($R^{3a}$), C($R^{3a}$)$_2$, O or S; and each of ring vertices a, b, c and d is each independently selected from N, $N^+$—$O^-$, C(H) and C($R^{3a}$), and from 0 to 2 of said ring vertices is N.

In another embodiment of formula IIId, HAr is selected from the group consisting of

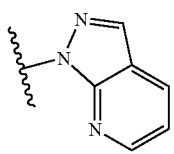 and 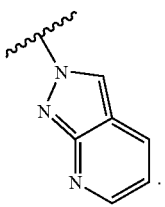

In certain embodiments of the invention, compounds of formula IIId have the subformulae selected from the group consisting of:

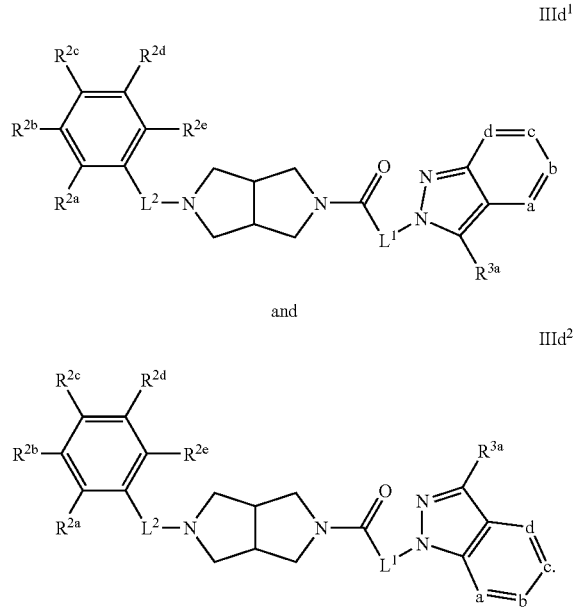

Each of ring vertices a, b, c and d in formulae IIId$^1$ and IIId$^2$ is each independently selected from N, N—O and C($R^{3a}$), and from one to two of said ring vertices is N or N—O. The substituent $R^{2a}$ is selected from the group consisting of hydrogen, halogen, cyano, heteroaryl, —NO$_2$, —CO$_2R^c$, —CONR$^c$R$^d$, —C(O)R$^c$, —S(O)R$^e$, —S(O)$_2$R$^e$, —R$^e$, —C(NOR$^c$)R$^d$, —C(NR$^c$V)=NV, —N(V)C(R$^c$)=NV, —X$^2$C(NOR$^c$)R$^d$, —X$^2$C(NR$^c$V)=NV, —X$^2$N(V)C(R$^c$) =NV, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O) NR$^c$R$^d$, —X$^2$NR$^d$C(O)R$^c$, —X$^2$NR$^d$C(O)$_2$R$^e$, —X$^2$NR$^c$C (O)NR$^c$R$^d$, —X$^2$NH—C(NH$_2$)=NH, —X$^2$NR$^e$C(NH$_2$) =NH, —X$^2$NH—C(NH$_2$)=NR$^e$, —X$^2$NH—C(NHR$^e$) =NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$ and —X$^2$N$_3$; $R^{2b}$ and $R^{2e}$ are each hydrogen; and $R^{2c}$ and $R^{2d}$ are each independently selected from the group consisting of hydrogen halogen, —OR$^c$, —SR$^c$, —R$^e$, —CN, —NO$_2$, —CO$_2$R$^c$, —C(O)R$^c$, —NR$^d$C(O)R$^c$, —NR$^d$C(O)$_2$R$^e$, —S(O)$_2$R$^e$, —S(O)$_2$NR$^c$R$^d$, —X$^2$OR$^c$, —O—X$^2$OR$^c$, —X$^2$NR$^c$R$^d$, —O—X$^2$NR$^c$R$^d$ and —NR$^d$—X$^2$CO$_2$R$^c$.

In formula IIId$^1$ and IIId$^2$, L$^1$ is —CH$_2$—, —CH$_2$NH— or —CH$_2$O— and is optionally substituted with —R$^k$, —X$^4$OR$^i$, —X$^4$OC(O)R$^i$, —X$^4$NR$^i$R$^j$, —X$^4$CO$_2$R$^i$, —X$^4$CONR$^i$R$^j$, —X$^4$SR$^i$, —Y$^1$, —X$^1$Y$^1$, —X$^4$CN or —X$^4$NO$_2$; L$^2$ is, a covalent bond or —C(R$^p$)(R$^r$)—.

The $R^{3a}$ substituent in formulae IIId$^1$ and IIId$^2$, at each occurrence, is independently selected from the group consisting of hydrogen, halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O) R$^f$, —OC(O)NR$^f$R$^g$, —NR$^g$C(O)R$^f$, —NR$^g$C(O)$_2$R$^h$, —NR$^f$—C(O)NR$^f$R$^g$, —S(O)R$^h$, —S(O)$_2$R$^h$, —NR$^f$S (O)$_2$R$^h$, —S(O)$_2$NR$^f$R$^g$, —NR$^f$S(O)$_2$NR$^f$R$^g$, —X$^3$OR$^f$, —X$^3$NR$^f$R$^g$, —X$^3$SR$^f$, —X$^3$CN, —X$^3$CO$_2$R$^f$, —X$^3$CONR$^f$R$^g$, —X$^3$C(O)R$^f$, —X$^3$NR$^g$C(O)R$^f$, —X$^3$NR$^g$C (O)$_2$R$^h$, —Y and —X$^3$Y, wherein Y is selected from the group consisting of a five or six-membered aryl ring, a five or six-membered heteroaryl ring and three to eight membered heterocycloalkyl ring, wherein said Y group is optionally substituted with from one to three substitutents selected from the group consisting of halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$ and —S(O)$_2$NR$^f$R$^g$, and wherein each X$^3$ is independently C$_{1-4}$ alkylene, and each R$^f$ and R$^g$ is independently selected from hydrogen, C$_{1-8}$ alkyl, C$_{1-8}$ haloalkyl and C$_{3-6}$ cycloalkyl, and each R$^h$ is independently selected from the group consisting of C$_{1-8}$ alkyl, C$_{1-8}$ haloalkyl and C$_{3-6}$ cycloalkyl, wherein the aliphatic portions of X$^3$, R$^f$, R$^g$ and R$^h$ is optionally further substituted with from one to three members selected from the group consisting of —OH, —OR$^o$, —OC(O)NHR$^o$, —OC (O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S (O)$_2$NHR$^o$, wherein each R$^o$ is independently an unsubstituted C$_{1-6}$ alkyl.

Certain preferred embodiments of compounds having subformulae IIId$^1$ and IIId$^2$ are set forth below. In one embodiment, L$^1$ is —CH$_2$— and L$^2$ is a covalent bond. In another embodiment, the fused six membered ring having vertices a, b, c and d is a fused pyridine or an N-oxide thereof. Alternatively, in another embodiment, the fused six membered ring having vertices a, b, c and d is a fused pyrazine ring, or an N-oxide thereof. In yet another embodiment, the fused six membered ring having vertices a, b, c and d is a fused pyrimidine ring, or an N-oxide thereof. In yet another embodiment, the fused six membered ring having vertices a, b, c and d is a fused pyridazine ring, or an N-oxide thereof. In a certain other embodiment, in formula IIId¹ and IIId², the $R^{3a}$ moiety on the pyrazole ring is a member independently selected from the group consisting of hydrogen, halogen, —OR$^f$, —NR$^f$R$^g$, —C(O)R$^f$, —C(O)OR$^f$, —S(O)R$^f$, —S(O)$_2$R$^f$, —S(O)$_2$NR$^f$R$^g$, —R$^h$, —CN, and —Y. In another embodiment of formulae IIId¹ and IIId², the $R^{3a}$ moiety on the pyrazole ring is hydrogen, fluoro, chloro, bromo, iodo, oxazolyl, pyridyl, thiazolyl, —R$^h$ or cyano. In yet another embodiment, $R^{2c}$ is selected from the group consisting of F, Cl, Br, I, CN, NO$_2$, —CO$_2$CH$_3$, —C(O)CH$_3$ and —S(O)$_2$CH$_3$. In another embodiment, $R^{2d}$ is selected from the group consisting of —SR$^c$, —O—X²—OR$^c$, —X²—OR$^c$, —R$^e$ and —OR$^c$. In yet another embodiment, in formula IIId¹ and IIId², the $R^{2a}$ moiety, is selected from the group consisting of F, Cl, Br, I, —CO$_2$Me, —CONH$_2$, CN, oxazolyl, —CH$_2$NH$_2$, —CH$_2$NHMe, —CH$_2$NMe$_2$ and —CH=N—OH; $R^{2b}$ and $R^{2e}$ are each hydrogen; $R^{2c}$ is halogen, cyano or nitro; $R^{2d}$ is selected from —SR$^c$, —O—X²—OR$^c$, —X²—OR$^c$, —R$^e$, —OR$^c$, —NR$^c$R$^d$, —NR$^c$S(O)$_2$R$^e$ and —NR$^d$C(O)R$^c$; and $R^{3a}$ is independently selected from the group consisting of hydrogen, halogen, C$_{1-6}$ alkyl, C$_{1-6}$ haloalkyl, C$_{3-6}$ cycloalkyl, amino, phenyl, pyridyl, isoxazolyl and thiazolyl. In yet another embodiment $R^{2a}$, $R^{2b}$ and $R^{2e}$ in formula IIId¹ and IIId² are hydrogen; $R^{2c}$ is halogen, cyano or nitro; $R^{2d}$ is selected from —SR$^c$, —O—X²—OR$^c$, —X²—OR$^c$, —R$^e$, —OR$^c$ and —NR$^d$C(O)R$^c$; and $R^{3a}$ is independently selected from the group consisting of hydrogen, halogen, C$_{1-6}$ alkyl, C$_{1-6}$ haloalkyl, C$_{3-6}$ cycloalkyl, amino, phenyl, pyridyl, isoxazolyl and thiazolyl.

In another embodiment of compound having formula IIId, HAr is a heterocyclic ring substituted with an aryl or heteroaryl group. In a certain embodiment the heterocyclic ring and the aryl or heteroaryl group are connected by a single covalent bond. In a preferred embodiment, the heterocyclic ring and the aryl or heteroaryl group are fused together.

In certain embodiment of compounds having formula IIId, HAr is a heterocyclic ring substituted with an aryl or heteroaryl group selected from the group consisting of

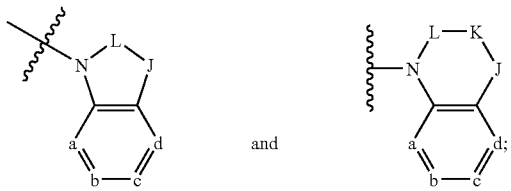

wherein J, K and L are each independently selected from the group consisting of —CH$_2$—, —CHR$^{3a}$—, —C(R)$^{3a}$)$_2$—, —NR$^{3a}$—, —NH—, —S—, —O—, —C(O)—, —S(O)— and —S(O)$_2$—; or optionally any two substituents on the adjacent atoms of K and L, or J and K may be absent and replaced with a bond to form a double bond between K and L, or J and K; and each of ring vertices a, b, c and d is independently selected from the group consisting of N, N$^+$—O$^-$, C(H) and C(R$^{3a}$), and from 0-2 ring vertices is N or N$^+$—O$^-$.

In another embodiment of the invention, compounds having formula IIId, are those having subformulae selected from the group consisting of

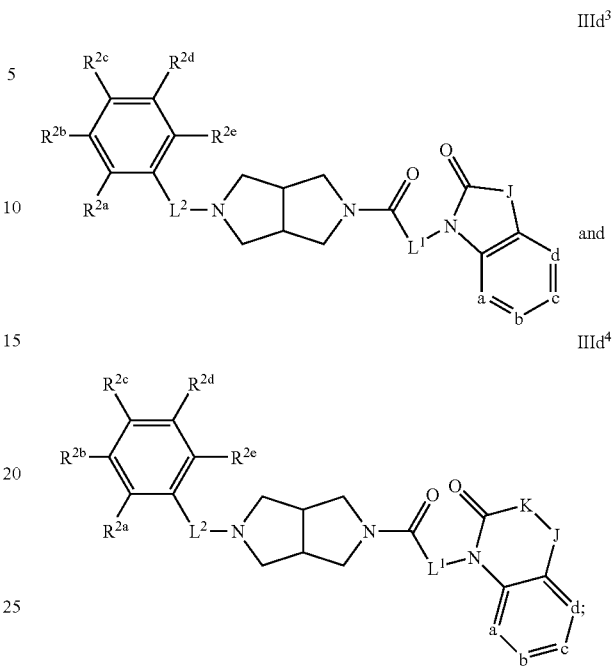

in which each of ring vertices a, b, c and d in formulae IIId³ and IIId⁴ is each independently selected from N, N—O, C(H) and C(R$^{3a}$), and from one to two of said ring vertices is N or N—O; J and K are each independently —CH$_2$—, —CHR$^{3a}$—, —C(R$^{3a}$)$_2$—, —NR$^{3a}$—, —NH—, —S—, or —O—; each R$^{3a}$ substituent is preferably independently selected from the group consisting of halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$C(O)NR$^f$R$^g$, —S(O)R$^h$, —S(O)$_2$R$^h$, —NR$^f$S(O)$_2$R$^h$, —S(O)$_2$NR$^f$R$^g$, —NR$^f$S(O)$_2$NR$^f$R$^g$, —X³OR$^f$, —X³NR$^f$R$^g$, —X³SR$^f$, —X³CN, —X³CO$_2$R$^f$, —X³CONR$^f$R$^g$, —X³C(O)R$^f$, —X³NR$^g$C(O)R$^f$, —X³NR$^g$C(O)$_2$R$^h$, —Y and —X³Y, wherein Y is selected from the group consisting of a five or six-membered aryl ring, a five or six-membered heteroaryl ring and three to eight membered heterocycloalkyl ring, wherein said Y group is optionally substituted with from one to three substituents selected from the group consisting of halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$ and —S(O)$_2$NR$^f$R$^g$, and wherein each X³ is independently C$_{1-4}$ alkylene, and each R$^f$ and R$^g$ is independently selected from hydrogen, C$_{1-8}$ alkyl, C$_{1-8}$ haloalkyl and C$_{3-6}$ cycloalkyl, and each R$^h$ is independently selected from the group consisting of C$_{1-8}$ alkyl, C$_{1-8}$ haloalkyl and C$_{3-6}$ cycloalkyl, wherein the aliphatic portions of X³, R$^f$, R$^g$ and R$^h$ is optionally further substituted with from one to three members selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein each R$^o$ is independently an unsubstituted C$_{1-6}$ alkyl;

In formula IIId³ and IIId⁴, $R^{2a}$ is preferably a substituent selected from the group consisting of hydrogen, halogen, cyano, heteroaryl, —NO₂, —CO₂R^c, —CONR^cR^d, C(O)R^c, —S(O)R^e, —S(O)₂R^e, —R^e, —C(NOR^c)R^d, —C(NR^cV)=NV, —N(V)C(R^c)=NV, —X²C(NOR^c)R^d, —X²C(NR^cV)=NV, —X²N(V)C(R^c)=NV, —X²NR^cR^d, —X²SR^c, —X²CN, —X²NO₂, —X²CO₂R^c, —X²CONR^cR^d, —X²C(O)R^c, —X²OC(O)NR^cR^d, —X²NR^dC(O)R^c, —X²NR^dC(O)₂R^e, —X²NR^cC(O)NR^cR^d, —X²NH—C(NH₂)=NH, —X²NR^eC(NH₂)=NH, —X²NH—C(NH₂)=NR^e, —X²NH—C(NHR^e)=NH, —X²S(O)R^e, —X²S(O)₂R^c, —X³NR^cS(O)₂R^e, —X²S(O)₂NR^cR^d and —X²N₃; and $R^{2b}$ and $R^{2e}$ are each hydrogen; and $R^{2c}$ and $R^{2d}$ are each independently selected from the group consisting of hydrogen halogen, —OR^c, —SR^c, —R^e, —CN, —NO₂, —CO₂R^c, —C(O)R^c, —NR^dC(O)R^c, —NR^dC(O)₂R^e, —S(O)₂R^e, —S(O)₂NR^cR^d, —X²OR^c, —O—X²OR^e, —X²NR^cR^d, —O—X²NR^cR^d and —NR^d—X²CO₂R^c.

In formula IIId³ and IIId⁴, $L^1$ is —CH₂—, —CH₂NH— or —CH₂O— and is optionally substituted with —R^k, —X⁴OR^i, —X⁴OC(O)R^i, —X⁴NR^iR^j, —X⁴CO₂R^i, —X⁴CONR^iR^j, —X⁴SR^i, —Y¹, —X⁴Y¹, —X⁴CN or —X⁴NO₂; $L^2$ is, a covalent bond or —C(R^p)(R^r)—.

Certain embodiments of compounds having formulae IIId³ or IIId⁴ are set forth below. In a certain embodiment, the $R^{3a}$ of the heterocyclic ring of HAr is selected from the group consisting of halogen, —R^h, —OR^f, —OC(O)R^f, —NR^fR^g, —SR^f, CO₂R^f and —CONR^fR^g, —X₃OR^f, —X₃NR^fR^g, —X₃CO₂R^f and —X₃CONR^fR^g. In a second embodiment, $L^1$ is —CH₂—, and $L^2$ is a bond or —CH₂—. In another embodiment J is —O—, —CR^{3a}R^{3a}, —CH₂—, NR^{3a}. Preferably J is —O—. In another embodiment, K is —C(R^{3a})₂—, preferably —CH₂—. In another embodiment, 1 or 2 of said ring vertices a, b, c and d of formulae IIId³ or IIId⁴ are N or N⁺—O⁻. More particularly, in one embodiment, the ring vertices a, b, c, d form a fused pyridine ring or an N-oxide thereof. In a second another embodiment, the ring vertices a, b, c, d form a fused pyrimidine ring or an N-oxide thereof. In a third embodiment of the invention, the ring vertices a, b, c, d form a fused pyridazine ring or an N-oxide thereof. In a fourth embodiment of the invention, the ring vertices a, b, c, d form a fused pyrazine ring or an N-oxide thereof. In yet another embodiment, in formula IIId³ and IIId⁴, the vertices a, b, c and d are C(H) or C(R^{3a}), wherein $R^3$ is halogen. More particularly, in one embodiment of the invention, the ring vertices a, b, d are each C(H) and c is C(R^{3a}), wherein $R^3$ is fluoro, chloro, bromo or iodo. In a second embodiment of the invention, the ring vertices a, c, d are each C(H) and b is C(R^{3a}), wherein $R^3$ is fluoro, chloro, bromo or iodo.

In a certain embodiment of the invention, the compounds having formula IIId³ have HAr group selected from the group consisting of

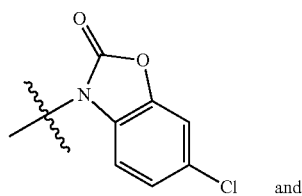

and

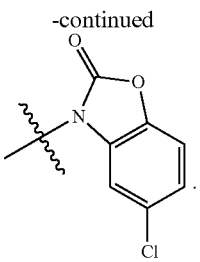

.

In another embodiment of the invention, the compounds having formula IIId⁴ have HAr group selected from the group consisting of

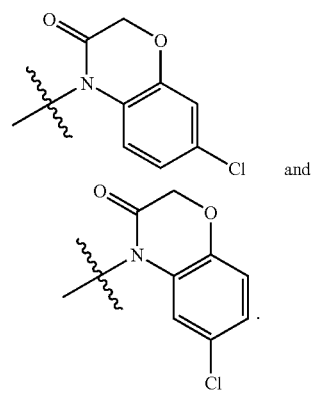

In another group of embodiments, compounds are provided having the formula

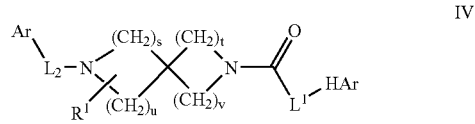

IV or a pharmaceutically acceptable salt or N-oxide thereof, wherein the subscripts s, t, u and v are 0 to 4 (within the meanings provided for formula I, above); $L^1$ is —CH₂— and is optionally substituted with —R^k, —X⁴OR^i, —X⁴OC(O)R^i, —X⁴NR^iR^j, —X⁴CO₂R^i, —X⁴CONR^iR^j, —X⁴SR^i, —Y¹, —X⁴Y¹, —X⁴CN or —X⁴NO₂; HAr is pyrazole linked via a ring nitrogen atom to $L^1$ and is substituted with from 1 to 3 $R^3$ groups; and $R^1$ represents 0, 1, 2 or 3 substituents selected from those described above with reference to formula I. Preferably, $R^1$ represents 0, 1 or 2 substituents selected from those described above. More preferably, $R^1$ is H or $C_{1-8}$ alkyl. The remaining groups have the meanings provided above with reference to formula I.

In certain embodiments within formula IV, compounds are provided having the formula

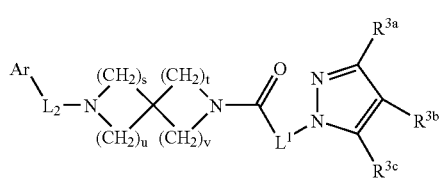

IVa wherein $R^{3a}$, $R^{3b}$ and $R^{3c}$ are each members independently selected from the group consisting of hydrogen, halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f(O)NR^fR^g$, —NH—C(NH$_2$)=NH, —$NR^hC(NH_2)$=NH, —NH—C(NH$_2$)=$NR^h$, —NH—C(NHR$^h$)=NH, —$S(O)R^h$, —$S(O)_2R^h$, —$NR^fS(O)_2R^h$, —$S(O)^2NR^fR^g$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3$NH—C(NH$_2$)=NH, —$X^3NR^hC(NH_2)$=NH, —$X^3$NH—C(NH$_2$)=$NR^h$, —$X^3$NH—C(NHR$^h$)=NH, —$X^3S(O)R^h$, —$X^3S(O)_2R^h$, —$X^3NR^fS(O)_2R^h$, —$X^3S(O)NR^fR^g$, —Y, —$X^3Y$, —$S(O)_2Y$, —C(O)Y, —$X^3N_3$, —O—$X^3OR^f$, —O—$X^3NR^fR^g$, —O—$X^3CO_2R^f$, —O—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$, wherein Y is a five or six-membered aryl, heteroaryl or heterocyclic ring, optionally substituted with from one to three substituents selected from the group consisting of halogen, —$OR^f$, —$OC(O)R^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$NR^gC(O)_2R^h$, —$S(O)R^h$, —$S(O)_2R^h$, —$NR^fS(O)_2R^h$, —$S(O)_2NR^fR^g$, —$X^3OR^f$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3OC(O)R^f$, —$X^3S(O)R^h$, —$X^3S(O)_2R^h$, —$X^3NR^fR^g$, —$X^3NR^fS(O)_2R^h$, —$X^3S(O)_2NR^fR^g$, —O—$X^3OR^f$, —O—$X^3NR^fR^g$, —O—$X^3CO_2R^f$, —O—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$, and wherein each $X^3$ is independently selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $R^f$, $R^g$ and $R^h$ is optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein each $R^o$ is independently an unsubstituted $C_{1-6}$ alkyl. Preferably, at least one of $R^{3a}$, $R^{3b}$ and $R^{3c}$ is other than H. In one selected group of embodiments, $L^1$ is —$CH_2$—; and $L^2$ is a covalent bond. In another selected group of embodiments, $L^2$ is CO, SO$_2$ or $CR^qR^r$ and $L^1$ is —$CH_2$— and is optionally substituted with —$R^k$, —$X^4OR^i$, —$X^4OC(O)R^i$, —$X^4NR^iR^j$, —$X^4CO_2R^i$, —$X^4CONR^iR^j$, —$X^4SR^i$, —$Y^1$, —$X^4Y^1$, —$X^4CN$ or —$X^4NO_2$. In still further preferred embodiments, Ar is selected from the components provided in FIGS. 1A through 1G. Even more preferred are those embodiments in which the pyrazolyl moiety (with $R^{3a}$, $R^{3b}$ and $R^{3c}$ substituents) is selected from the pyrazolyl moieties provided in FIGS. 2A-2Z, 2AA-2HH and 3.

In other embodiments of formula IVa, Ar is phenyl, substituted with $R^{2a}$, $R^{2b}$, $R^{2c}$, $R^{2d}$ and $R^{2e}$, wherein selected embodiments are those embodiments provided above with reference to each of formula IIIa and IIIb.

In another group of embodiments, compounds are provided having the formula

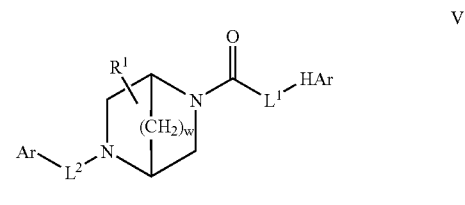

V or a pharmaceutically acceptable salt or N-oxide thereof, wherein the subscript w is an integer of from 1 to 2; $L^1$ is —$CH_2$— and is optionally substituted with —$R^k$, —$X^4OR^i$, —$X^4OC(O)R^i$, —$X^4NR^iR^j$, —$X^4CO_2R^i$, —$X^4CONR^iR^j$, —$X^4SR^i$, —$Y^1$, —$X^4Y^1$, —$X^4CN$ or —$X^4NO_2$; HAr is pyrazole linked via a ring nitrogen atom to $L^1$ and is substituted with from 1 to 3 $R^3$ groups; and $R^1$ represents 0, 1, 2 or 3 substituents selected from those described above with reference to formula I. Preferably, $R^1$ represents 0, 1 or 2 substituents selected from those described above. More preferably, $R^1$ is selected from H and $C_{1-8}$ alkyl. The remaining groups have the meanings provided above with reference to formula I.

In certain embodiments within formula V, compounds are provided having the formula

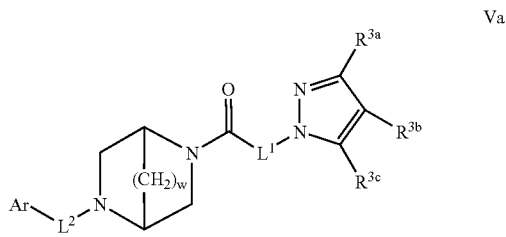

Va wherein $R^{3a}$, $R^{3b}$ and $R^{3c}$ are each members independently selected from the group consisting of hydrogen, halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —NH—C(NH$_2$)=NH, —$NR^hC(NH_2)$=NH, —NH—C(NH$_2$)=$NR^h$, —NH—C(NHR$^h$)=NH, —$S(O)R^h$, —$S(O)_2R^h$, —$NR^fS(O)_2R^h$, —$S(O)_2NR^fR^g$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3$NH—C(NH$_2$)=NH, $X^3NR^hC(NH_2)$=NH, —$X^3$NH—C(NH$_2$)=$NR^h$, —$X^3$NH—C(NHR$^h$)=NH, —$X^3S(O)R^h$, —$X^3S(O)_2R^h$, —$X^3NR^fS(O)_2R^h$, —$X^3S(O)_2NR^fR^g$, —Y, —$X^3Y$, —$S(O)_2Y$, —C(O)Y, —$X^3N_3$, —O—$X^3OR^f$, —O—$X^3NR^fR^g$, —O—$X^3CO_2R^f$, —O—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$, wherein Y is a five or six-membered aryl, heteroaryl or heterocyclic ring, optionally substituted with from one to three substitutents selected from the group consisting of halogen, —OR$^f$, —OC(O)R$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —NR$^g$C(O)$_2$R$^h$, —S(O)R$^h$, —S(O)$_2$R$^h$, NR$^f$S(O)$_2$R$^h$, —S(O)$_2$NR$^f$R$^g$, —X$^3$OR$^f$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$OC(O)R$^f$, —X$^3$S(O)R$^h$, —X$^3$S(O)$_2$R$^h$, —X$^3$NR$^f$R$^g$, —X$^3$NR$^f$S(O)$_2$R$^h$, —X$^3$S(O)$_2$NR$^f$R$^g$, —O—X$^3$OR$^f$, —O—X$^3$NR$^f$R$^g$, —O—X$^3$CO$_2$R$^f$, —O—X$^3$CONR$^f$R$^g$, —NR$^g$—X$^3$OR$^f$, —NR$^g$—X$^3$NR$^f$R$^g$, —NR$^g$—X$^3$CO$_2$R$^f$, and —NR$^g$—X$^3$CONR$^f$R$^g$, and wherein each X$^3$ is independently selected from the group consisting of C$_{1-4}$ alkylene, C$_{2-4}$ alkenylene and C$_{2-4}$ alkynylene and each R$^f$ and R$^g$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl aryloxy-C$_{1-4}$ alkyl, or when attached to the same nitrogen atom can be combined with the nitrogen atom to form a five or six-membered ring having from 0 to 2 additional heteroatoms as ring members, and each R$^h$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, wherein the aliphatic portions of R$^f$, R$^g$ and R$^h$ is optionally further substituted with from one to three members selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein each R$^o$ is independently an unsubstituted C$_{1-6}$ alkyl. Preferably, at least one of R$^{3a}$, R$^{3b}$ and R$^{3c}$ is other than H. In one selected group of embodiments, L$^2$ is a covalent bond. In another selected group of embodiments, L$^2$ is CO, SO$_2$ or CR$^q$R$^r$. In these embodiments, L$^1$ is —CH$_2$— and is optionally substituted with —R$^k$, —X$^4$OR$^i$, —X$^4$OC(O)R$^i$, —X$^4$NR$^i$R$^j$, —X$^4$CO$_2$R$^i$, —X$^4$CONR$^i$R$^j$, —X$^4$SR$^i$, —Y$^1$, —X$^4$Y$^1$, —X$^4$CN or —X$^4$NO$_2$.

In other embodiments of formula Va, Ar is phenyl, substituted with R$^{2a}$, R$^{2b}$, R$^{2c}$, R$^{2d}$ and R$^{2e}$, wherein selected embodiments are those embodiments provided above with reference to each of formula IIIa and IIIb.

Returning to formula I, other specific embodiments are provided in FIGS. 5A through 5L (as formulae VIa through VIdddd). In each of these embodiments, W is selected from formula A, B, C and D; and L$^2$ is selected from a bond, CO, SO$_2$ and CR$^q$R$^r$. With reference to the embodiments shown in those Figures, Ar is a substituted phenyl; L$^1$ is CH$_2$; and HAr is a nitrogen-linked pyrazolyl group bearing at least one heteroaryl or heterocyclic substituent. Further preferred are those embodiments in which W is selected from the bridged and bicyclic diamines provided in Schemes 1A through 1I and in Examples 1-16. Still further preferred are those embodiments in which W is selected from

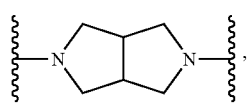

-continued

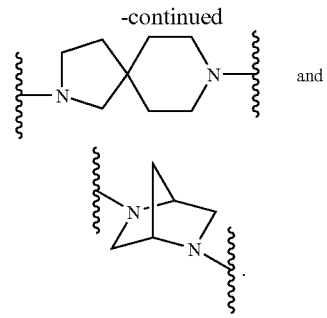

and

More particularly, for the compounds of formula VIa, VIc, VIe, VIg, VIi, VIk, VIm, VIo, VIq, VIs, VIu, VIw, VIy, VIaa, VIcc, VIee, VIgg, VIii, VIkk, VImm, VIoo, VIqq, VIss, VIuu, VIww, VIyy, VIaaa, VIccc, VIeee, VIggg, VIiii, VIkkk, VImmm, VIooo and VIqqq, R$^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^e$, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)═NH, —X$^2$NR$^e$C(NH$_2$)═NH, —X$^2$NH—C(NH$_2$)═NR$^e$, —X$^2$NH—C(NHR$^e$)═NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; R$^{2c}$ is halogen, cyano or nitro; R$^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; R$^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)═NH, —X$^3$NR$^h$C(NH$_2$)═NH, —X$^3$NH—C(NH$_2$)═NR$^h$, —X$^3$NH—C(NHR$^h$)═NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; R$^{3c}$ is preferably halogen, cyano, —NO$_2$, —CO$_2$R$^f$, —CONR$^f$R$^g$, —C(O)R$^f$, NR$^f$R$^g$, SR$^f$, —S(O)R$^h$, —S(O)$_2$R$^h$, —C(O)Y, —SO$_2$Y, —X$^3$Y, Y, C$_{1-6}$ alkyl, C$_{1-6}$ haloalkyl or C$_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; R$^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$NR$^f$R$^g$; R$^5$ is attached to a ring nitrogen and is preferably hydrogen, —R$^h$, —S(O)$_2$R$^h$, —X$^3$OR$^f$, —X$^3$NR$^f$R$^g$, —X$^3$NR$^f$S(O)$_2$R$^h$ and —X$^3$S(O)$_2$NR$^f$R$^g$; n (as a subscript for R$^4$) is preferably 0-3. Further preferred are those compounds in which each R$^1$, when present in each of formulae A, B, C and D, is selected from the group consisting of C$_{1-4}$ alkyl, optionally substituted with a member selected from the group consisting of —OH, —OR$^m$, —S(O)$_2$R$^m$, —CO$_2$H and —CO$_2$R$^m$; when n is 1 or more, at least one R$^4$ substituent is attached to a ring carbon atom adjacent to a ring heteroatom. Even more preferably, $R^{2a}$ is hydrogen, halogen, —CN, —C(O)$R^c$, —$X^2$NR$^c$R$^d$, or —$R^e$; $R^{2c}$ is halogen or cyano; $R^5$ is hydrogen, $C_{1-4}$ alkyl, or $C_{3-6}$ cycloalkyl. Still more preferably, n is 0 or 1, and $R^1$ when present is —CH$_3$. In the most preferred embodiments, $R^{2d}$ is —SR$^c$, —R$^e$, or —OR$^c$; $R^{3b}$ is hydrogen, halogen, cyano, or —NO$_2$; $R^{3c}$ is $C_{1-6}$ alkyl, $C_{1-6}$ haloalkyl or $C_{3-6}$ cycloalkyl which are optionally substituted as set forth above; and $R^4$ when present is —CH$_3$, —CF$_3$ or —CN.

For compounds of formula VIb, VId, VIf, VIh, VIj, VIl, VIn, VIp, VIr, VIt, VIv, VIx, VIz, VIbb, VIdd, VIff, VIhh, VIjj, VIll, VInn, VIpp, VIrr, VItt, VIvv, VIxx, VIzz, VIbbb, VIddd, VIfff, VIhhh, VIjjj, VIlll, VInnn, VIppp and VIrrr, $R^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^e$, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; $R^{2c}$ is halogen, cyano or nitro; $R^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; $R^{3a}$ is preferably halogen, cyano, —NO$_2$, —CO$_2$R$^f$, —CONR$^f$R$^g$, —C(O)R$^f$, NR$^f$R$^g$, SR$^f$, —S(O)R$^h$, —S(O)$_2$R$^h$, —C(O)Y, —SO$_2$Y, —X$^3$Y, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; $R^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$^2$NR$^f$R$^g$, —X$^3$N$_3$, Y, or —X$^3$Y; $R^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$NR$^f$R$^g$; $R^5$ is attached to a ring nitrogen and is preferably hydrogen, —R$^h$, —S(O)$_2$R$^h$, —X$^3$OR$^f$, —X$^3$NR$^f$R$^g$, —X$^3$NR$^f$S(O)$_2$R$^h$ and —X$^3$S(O)$_2$NR$^f$R$^g$; n (as a subscript for $R^4$) is preferably 0-3. Further preferred are those compounds in which each $R^1$, when present in each of formulae A, B, C and D, is selected from the group consisting of $C_{1-4}$ alkyl, optionally substituted with a member selected from the group consisting of —OH, —OR$^m$, —S(O)R$^m$, —CO$_2$H and —CO$_2$R$^m$; when n is 1 or more, at least one $R^4$ substituent is attached to a ring carbon atom adjacent to a ring heteroatom. Even more preferably, $R^{2a}$ is hydrogen, halogen, —CN, —C(O)R$^c$, —X$^2$NR$^c$R$^d$, or —R$^e$; $R^{2c}$ is halogen or cyano; $R^5$ is hydrogen, $C_{1-4}$ alkyl, or $C_{3-6}$ cycloalkyl. Still more preferably, n is 0 or 1, and $R^1$ when present is —CH$_3$. In the most preferred embodiments, $R^{2d}$ is —SR$^c$, —R$^e$, or —OR$^c$; $R^{3a}$ is halogen, cyano, $C_{1-6}$ alkyl, $C_{1-6}$ haloalkyl, $C_{3-6}$ cycloalkyl, —C(O)R$^f$ or —SO$_2$R$^h$ wherein the aliphatic portions are optionally substituted as set forth above; $R^{3b}$ is hydrogen, halogen, cyano, or —NO$_2$; $R^4$when present is —CH$_3$, —CF$_3$, —CN, —C(O)R$^f$ or —SO$_2$R$^h$.

N-linked heteroaryls

Figure 5A:
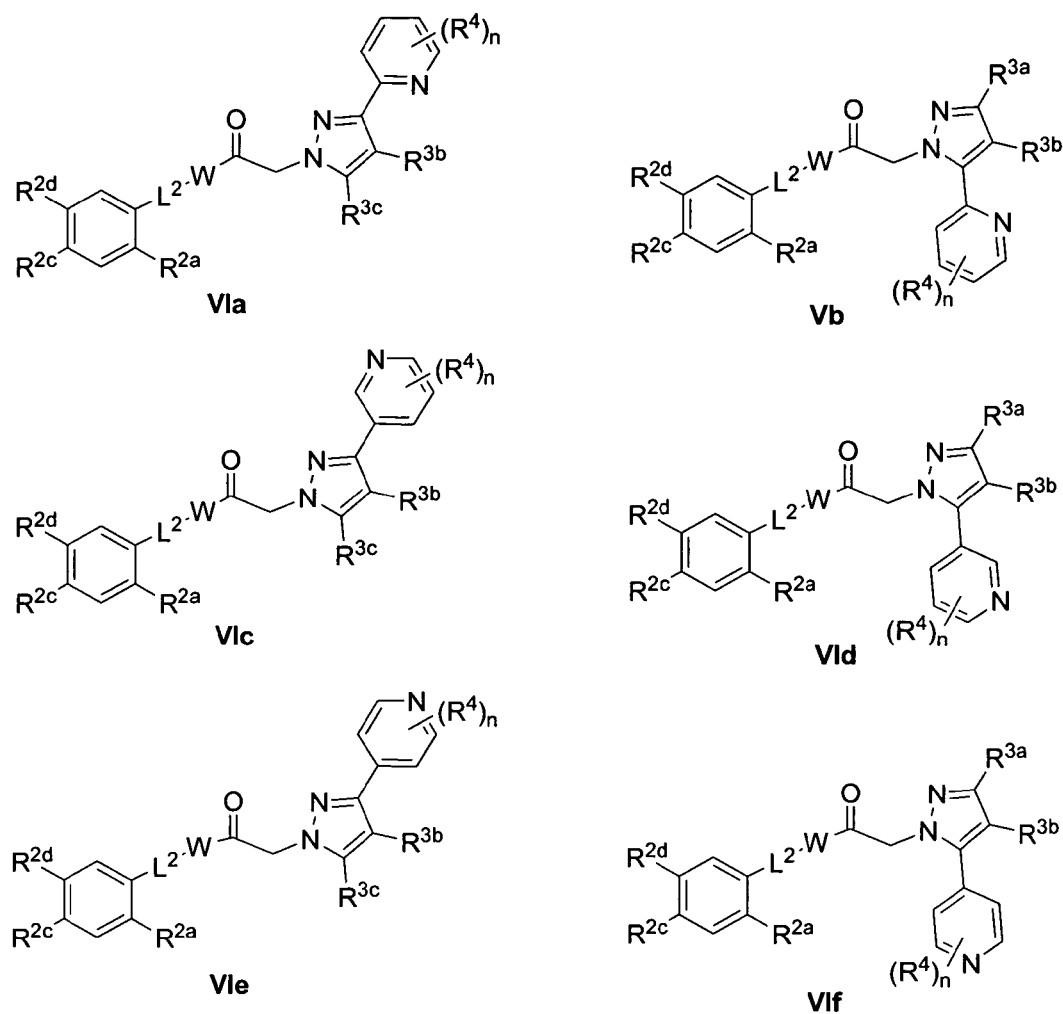
FIGS. 5A through 5L provide generic formulae for some preferred embodiments of the invention.
Figure 5B:
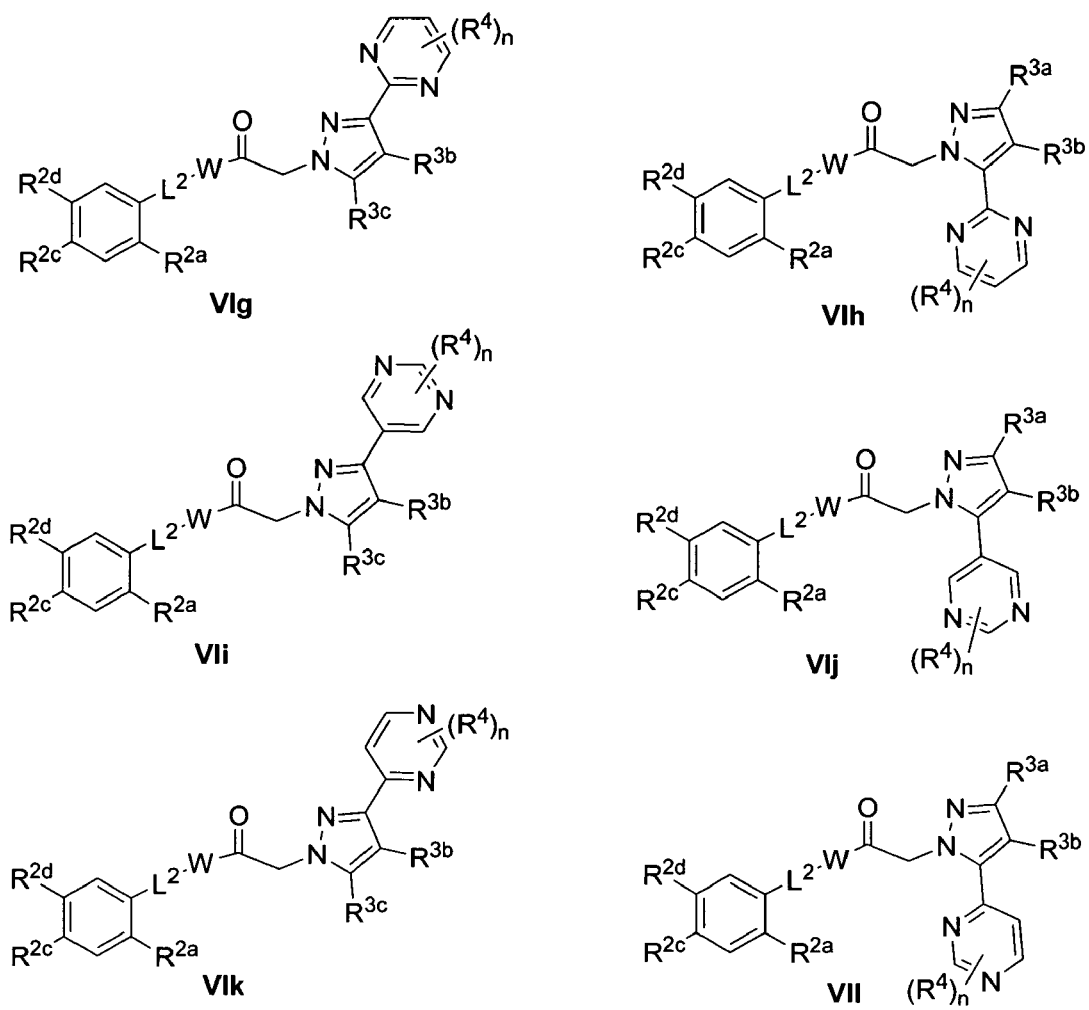
Figure 5C:
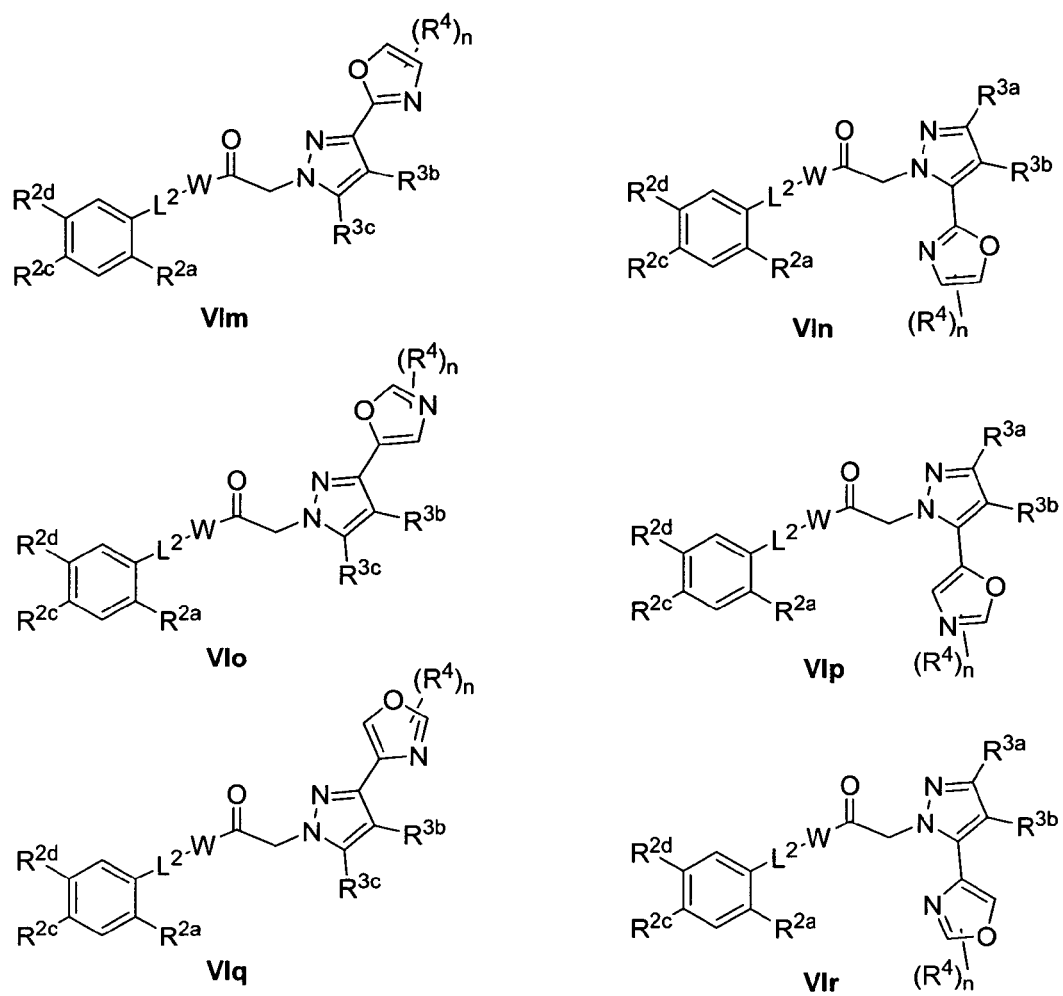
Figure 5D:
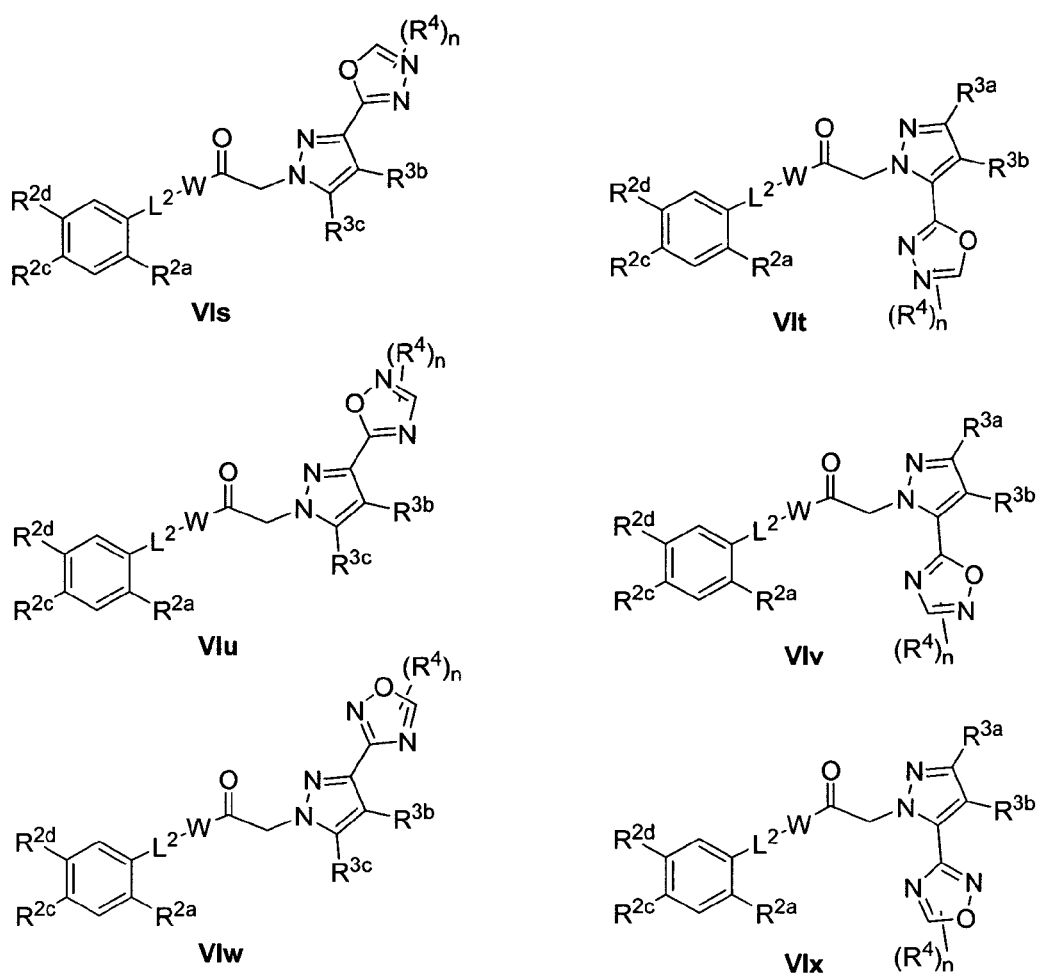
Figure 5E:
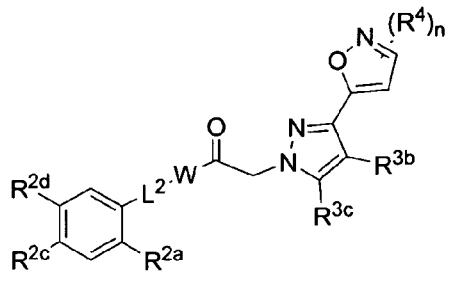
Figure 5E:
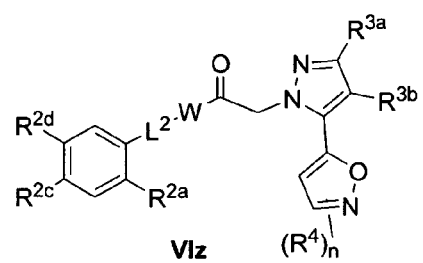
Figure 5E:
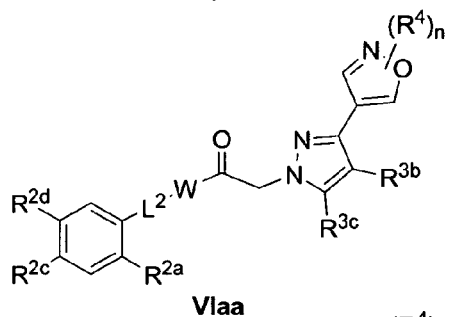
Figure 5E:
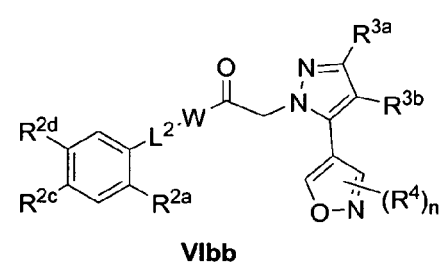
Figure 5E:
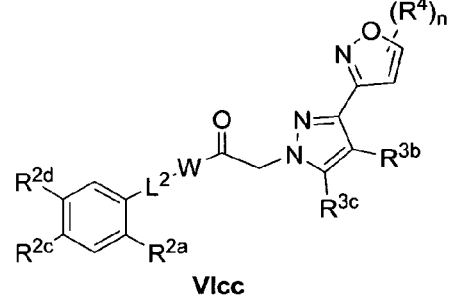
Figure 5E:
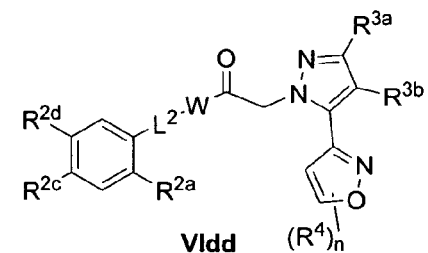
Figure 5E:
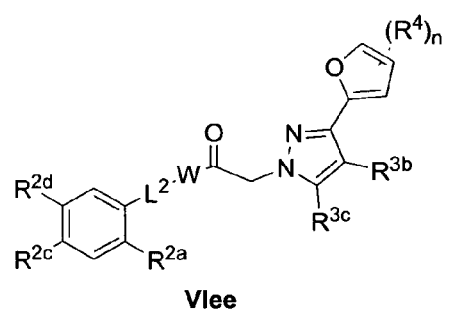
Figure 5E:
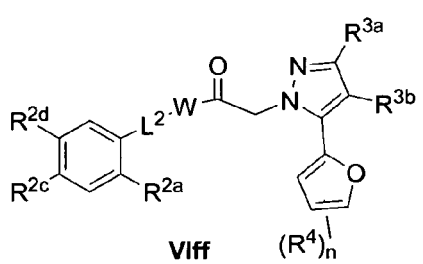
Figure 5E:
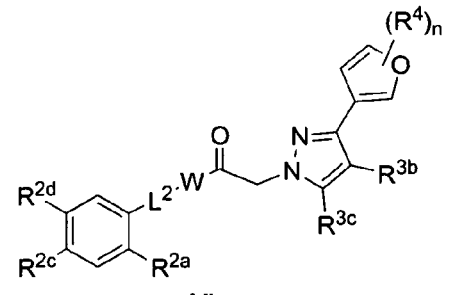
Figure 5E:
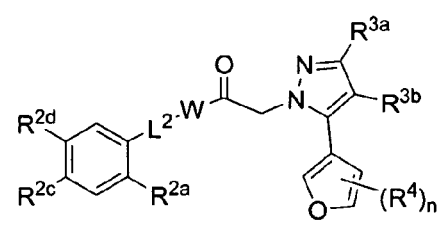
Figure 5F:
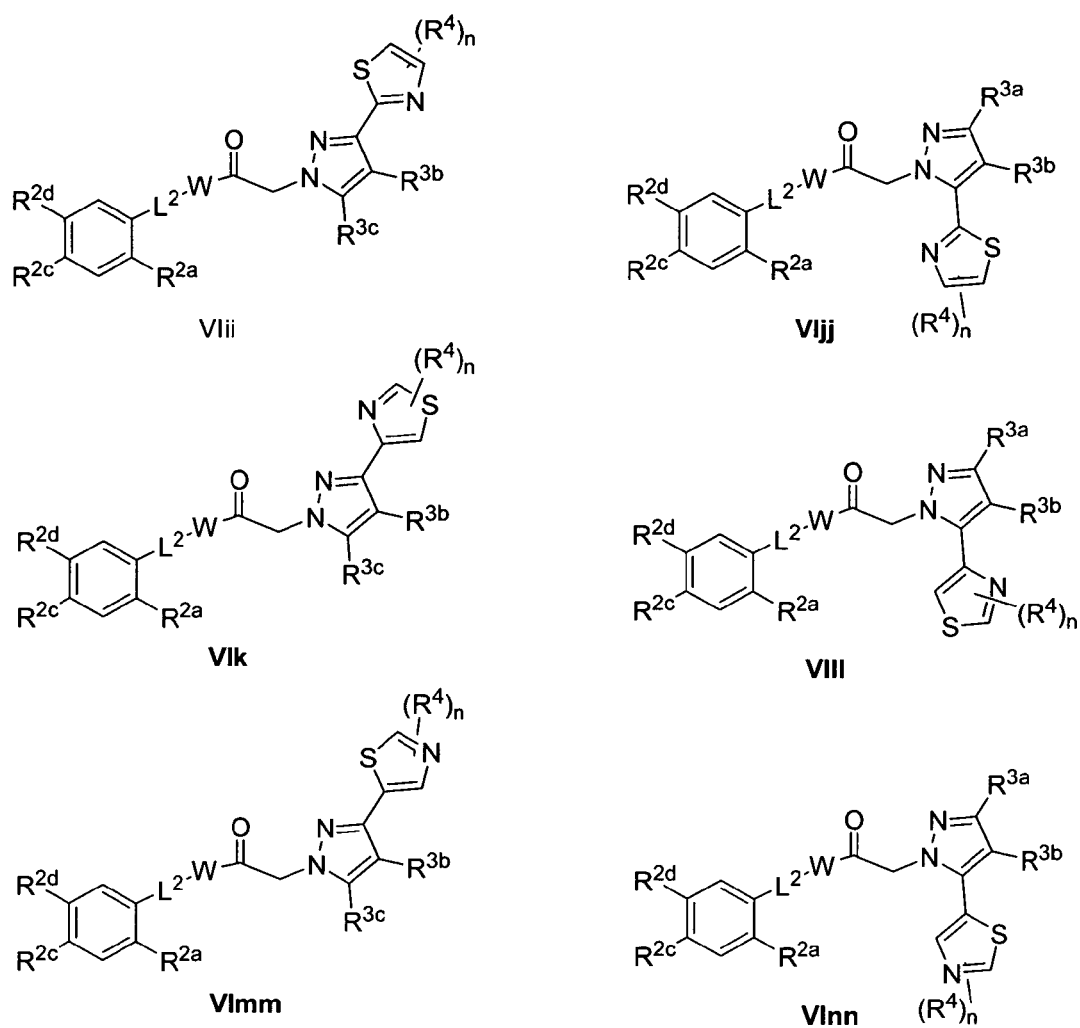
Figure 5G:
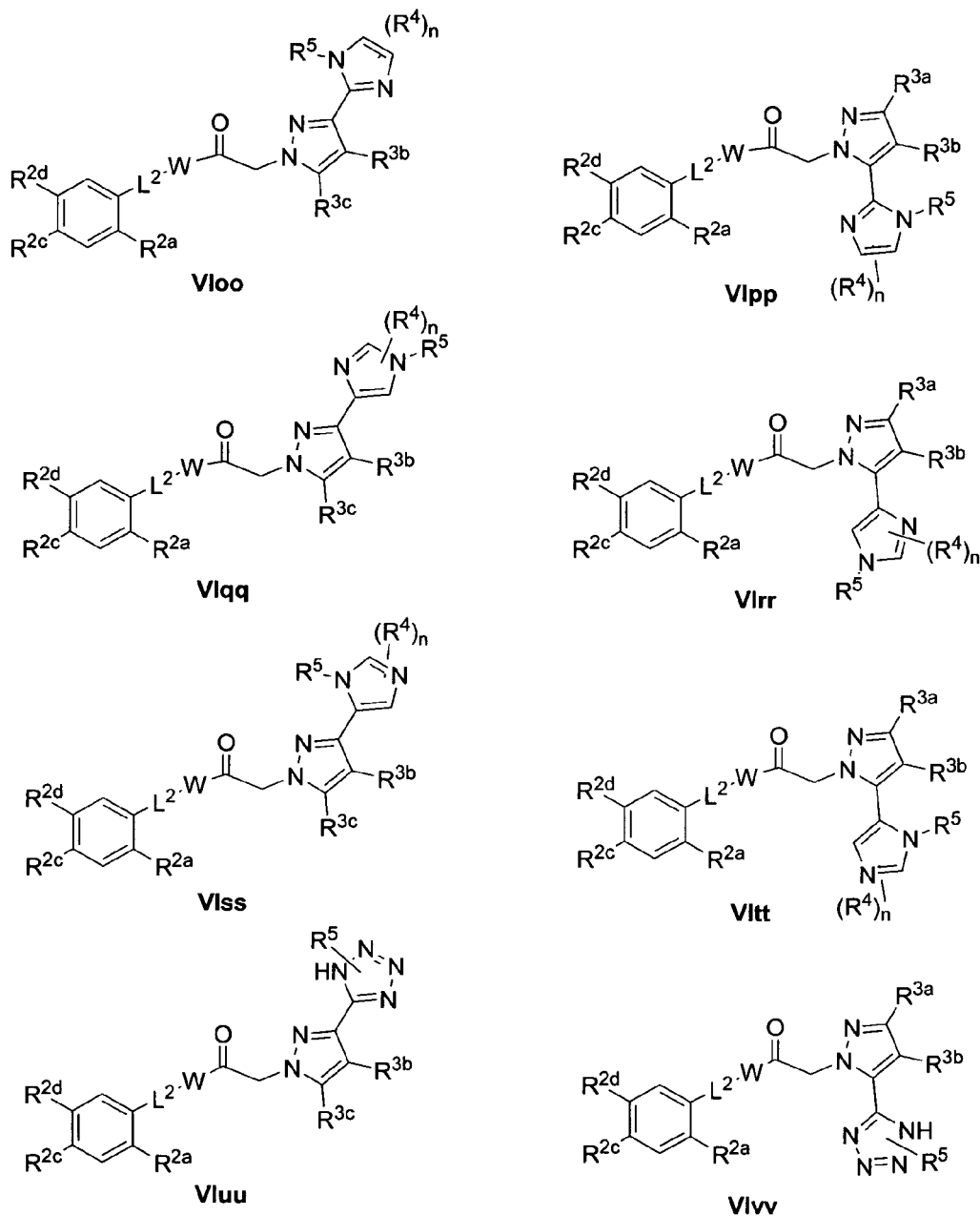
Figure 5H:
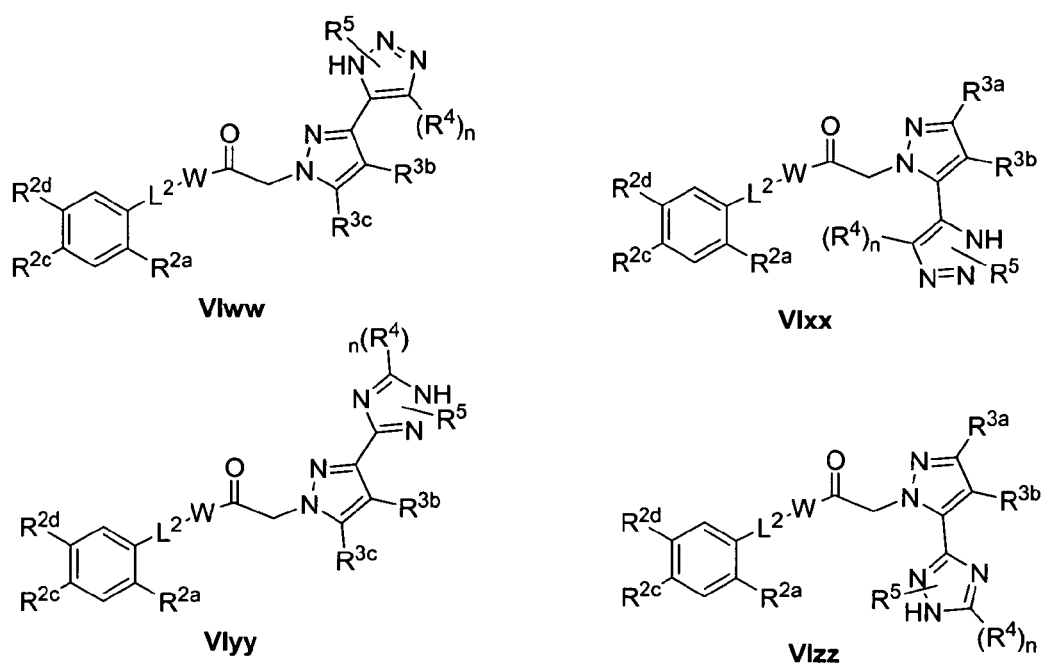
Figure 5I:
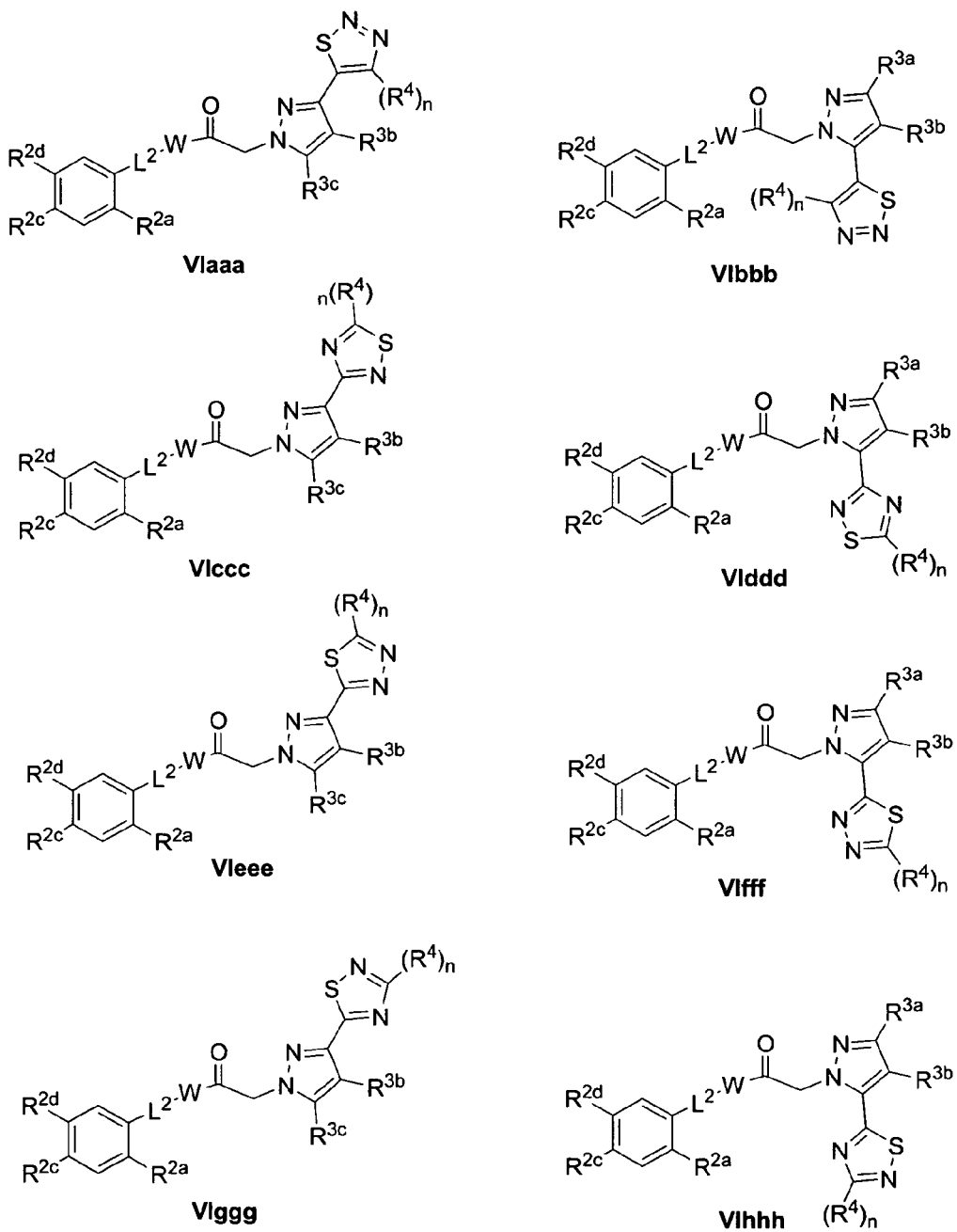
Figure 5J:
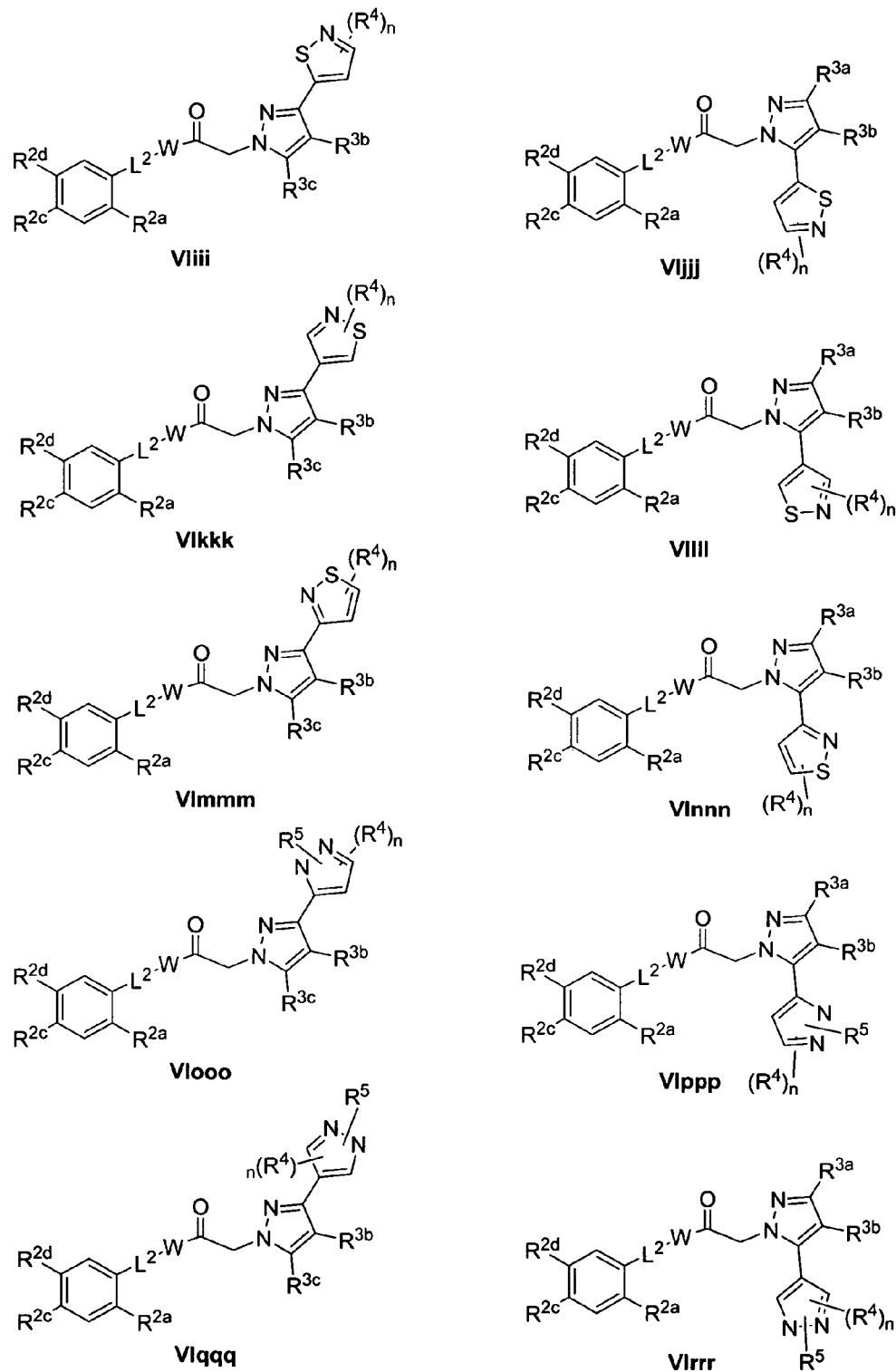
Figure 5K:
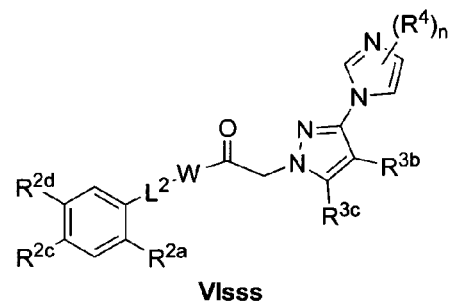
Figure 5K:
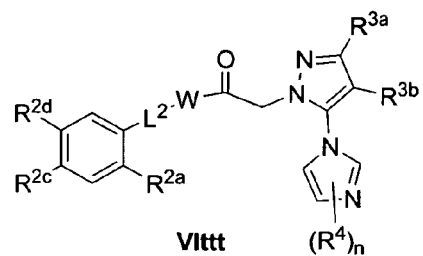
Figure 5K:
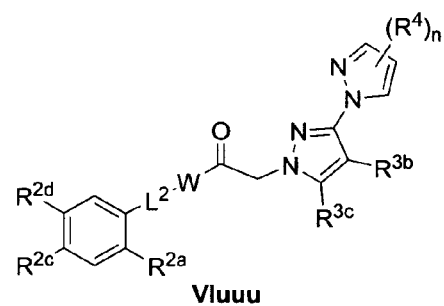
Figure 5K:
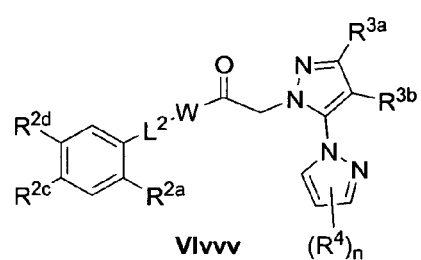
Figure 5K:
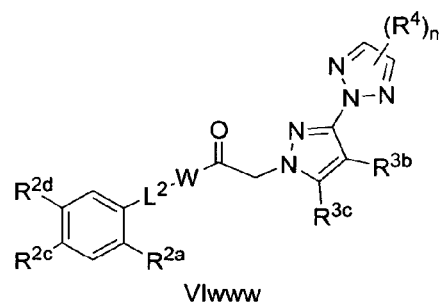
Figure 5K:
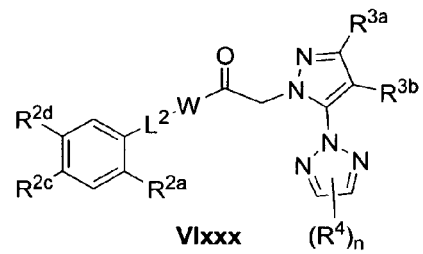
Figure 5K:
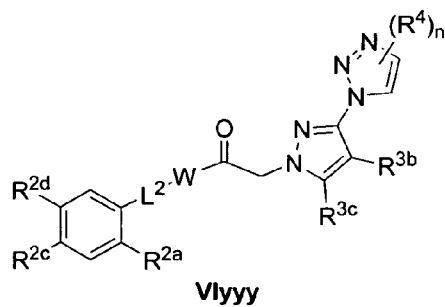
Figure 5K:
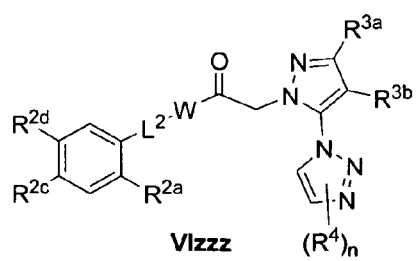

In other preferred groups of formula I, the compounds have a formula selected from formulae VIsss through VIzzz, FIG. 5K, wherein the substituents have the meanings provided with respect to formula I and III above. Turning first to the compounds of formula VIsss, VIuuu, VIwww and VIyyy, $R^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^e$, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$, $R^{2c}$ is halogen, cyano or nitro; $R^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; $R^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; $R^{3c}$ is preferably halogen, cyano, —NO$_2$, —CO$_2$R$^f$, —CONR$^f$R$^g$, —C(O)R$^f$, —NR$^f$R$^g$, —SR$^f$, —S(O)R$^h$, —S(O)$_2$R$^h$, —C(O)Y, —SO$_2$Y, —X$^3$Y, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; $R^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$NR$^f$R$^g$, and two adjacent $R^4$ groups can form a five or six-membered saturated or unsaturated ring having from 0 to 2 additional heteroatoms as ring members; n (as a subscript for $R^4$) is preferably 0-3. Further preferred are those compounds in which each $R^1$, when present in each of formulae A, B, C and D, is selected from the group consisting of $C_{1-4}$ alkyl, optionally substituted with a member selected from the group consisting of —OH, —OR$^m$, —S(O)$_2$R$^m$, —CO$_2$H and —CO$_2$R$^m$; when n is 1 or more, at least one $R^4$ substituent is attached to a ring carbon atom adjacent to a ring heteroatom. Even more preferably, $R^{2a}$ is hydrogen, halogen, —CN, —C(O)R$^c$, —X$^2$NR$^c$R$^d$, or —R$^e$; $R^{2c}$ is halogen or cyano. Still more preferably, n is 0 or 1, and $R^1$ when present is —CH$_3$. In the most preferred embodiments, $R^{2d}$ is —SR$^c$, —R$^e$, or —OR$^c$; $R^{3b}$ is hydrogen, halogen, cyano, or —NO$_2$; $R^{3c}$ is halogen, cyano, —C(O)R$^f$, —SO$_2$R$^h$, $C_{1-6}$ alkyl, $C_{1-6}$ haloalkyl or $C_{3-6}$ cycloalkyl wherein the aliphatic portions are substituted as set forth above; and $R^4$ when present is —CH$_3$, —CF$_3$ or —CN.

For compounds of formula VIttt, VIvvv, VIxxx and VIzzz, $R^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —$R^e$, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$, or —$X^2N_3$; $R^{2c}$ is halogen, cyano or nitro; $R^{2d}$ is —$SR^c$, —O—$X^2$—$OR^c$, —$X^2$—$OR^c$, —$R^e$, —$OR^c$, —$NR^cR^d$, or —$NR^cSO_2R^d$; $R^{3a}$ is preferably halogen, cyano, —$NO_2$, —$CO_2R^f$, —$CONR^fR^g$, —$C(O)R^f$, —$NR^fR^g$, —$SR^f$, —$S(O)R^h$, —$S(O)_2R^h$, —$C(O)Y$, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$; $R^{3b}$ is preferably hydrogen, halogen, cyano, —$NO_2$, —$CO_2R^f$, —$CONR^fR^g$, —$C(O)R^f$, —$S(O)R^h$, —$S(O)_2R^h$, —$R^h$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^fC(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2NR^fR^g$, —$X^3N_3$, Y, or —$X^3Y$; $R^4$ is preferably halogen, —$OR^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$, —$S(O)_2NR^fR^g$, —$X^3OR^f$, —$X^3NR^fR^g$, —$X^3NR^fS(O)_2R^h$ and —$X^3S(O)_2NR^fR^g$, and two adjacent $R^4$ groups can form a five or six-membered saturated or unsaturated ring having from 0 to 2 additional heteroatoms as ring members; n (as a subscript for $R^4$) is preferably 0-3. Further preferred are those compounds in which each $R^1$, when present on each of formulae A, B, C and D, is selected from the group consisting of $C_{1-4}$ alkyl, optionally substituted with a member selected from the group consisting of —OH, —$OR^m$, —$S(O)_2R^m$, —$CO_2H$ and —$CO_2R^m$; when n is 1 or more, at least one $R^4$ substituent is attached to a ring carbon atom adjacent to a ring heteroatom. Even more preferably, $R^{2a}$ is hydrogen, halogen, —CN, —$C(O)R^c$, —$X^2NR^cR^d$, or —$R^e$; $R^{2c}$ is halogen or cyano. Still more preferably, n is 0 or 1, and $R^1$ when present is —$CH_3$. In the most preferred embodiments, $R^{2d}$ is —$SR^c$, —$R^e$, or —$OR^c$; $R^{3a}$ is halogen, cyano, —$C(O)R^f$, —$S(O)_2R^h$, $C_{1-6}$ alkyl, $C_{1-6}$ haloalkyl or $C_{3-6}$ cycloalkyl, where the alkyl and cycloalkyl substituents can be optionally substituted as noted above; $R^{3b}$ is hydrogen, halogen, cyano or —$NO_2$; $R^4$ when present is —$CH_3$, —$CF_3$ or —CN.

Figure 5L:
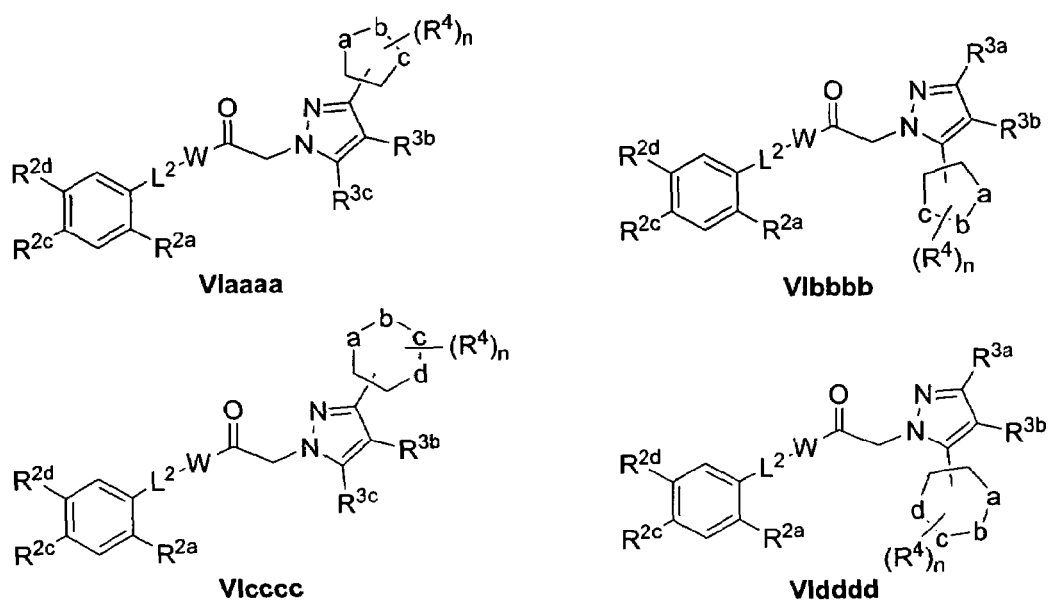

5-membered C- and N-linked Heterocycles:

In other preferred groups of formula I, the compounds have a formula selected from formulae VIaaaa and VIbbbb, FIG. 5L, wherein $R^{2a}$, $R^{2c}$, $R^{2d}$, $R^{3a}$, $R^{3b}$, $R^{3c}$, $R^4$, W and $L^2$ have the meanings provided above for other compounds of formula VI. Turning first to the compounds of formula VIaaaa, $R^{2a}$ is preferably hydrogen, halogen, cyano, —$NO_2$, —$CO_2R^c$, —$CONR^cR^d$, —$C(O)R^c$, —$S(O)R^e$, —$S(O)_2R^e$, —$R^e$, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$, or —$X^2N_3$, $R^{2c}$ is halogen, cyano or nitro; $R^{2d}$ is —$SR^c$, —O—$X^2$—$OR^c$, —$X^2$—$OR^c$, —$R^e$, —$OR^c$, —$NR^cR^d$, or —$NR^cSO_2R^d$; $R^{3b}$ is preferably hydrogen, halogen, cyano, —$NO_2$, —$CO_2R^f$, —$CONR^fR^g$, —$C(O)R^f$, —$S(O)R^h$, —$S(O)_2R^h$, —$R^h$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^fC(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2NR^fR^g$, —$X^3N_3$, Y, or —$X^3Y$; $R^{3c}$ is preferably halogen, cyano, —$NO_2$, —$CO_2R^f$, —$CONR^fR^g$, —$C(O)R^f$, —$NR^fR^g$, —$SR^f$, —$S(O)R^h$, —$S(O)_2R^h$, —$C(O)Y$, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$; $R^4$ is preferably halogen, —$OR^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$, —$S(O)_2NR^fR^g$, —$X^3OR^f$, —$X^3NR^fR^g$, —$X^3NR^fS(O)_2R^h$, —$X^3S(O)_2NR^fR^g$, and two adjacent $R^4$ groups can form a five or six-membered saturated or unsaturated ring having from 0 to 2 additional heteroatoms as ring members; n (as a subscript for $R^4$) is preferably 0-3; a, b, and c can be N, $NR^5$, S, SO, $SO_2$, O, or $C(R^4)_o$, where o (as a subscript for $R^4$) can be 0-2; $R^5$ is preferably hydrogen, —$R^h$, —$S(O)_2R^h$, —$X^3OR^f$, —$X^3NR^fR^g$, —$X^3NR^fS(O)_2R^h$ and —$X^3S(O)_2NR^fR^g$, —$CO_2R^f$, —$CONR^fR^g$, or —$C(O)R^f$. Further preferred are those compounds in which each $R^1$, when present in each of formulae A, B, C and D, is selected from the group consisting of $C_{1-4}$ alkyl, optionally substituted with a member selected from the group consisting of —OH, —$OR^m$, —$S(O)_2R^m$, —$CO_2H$ and —$CO_2R^m$; when a and c are other than $C(R^4)_o$, b must be $C(R^4)_o$ or $SO_2$; when a and b are other than $C(R^4)_o$, then c must be $C(R^4)_o$ or $SO_2$. Even more preferably, $R^{2a}$ is hydrogen, halogen, —CN, —$C(O)R^c$, —$X^2NR^cR^d$, or —$R^e$; $R^{2c}$ is halogen or cyano. Still more preferably, n is 0 or 1, and $R^1$ when present is —$CH_3$. In the most preferred embodiments, $R^{2d}$ is —$SR^c$, —$R^e$, or —$OR^c$; $R^{3b}$ is hydrogen, halogen, cyano or —$NO_2$; $R^{3c}$ is halogen, cyano, —$C(O)R^f$, —$SO_2R^h$, $C_{1-6}$ alkyl, $C_{1-6}$ haloalkyl or $C_{3-6}$ cycloalkyl wherein the aliphatic portions are substituted as set forth above.

For compounds of Formula VIbbbb, $R^{2a}$ is preferably hydrogen, halogen, cyano, —$NO_2$, —$CO_2R^c$, —$CONR^cR^d$, —$C(O)R^c$, —$S(O)R^e$, —$S(O)_2R^e$, —$R^e$, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, $X^2NR^cS(O)_2R^e$, —$X^2S(O)_2NR^cR^d$, or —$X^2N_3$; $R^{2c}$ is halogen, cyano or nitro; $R^{2d}$ is —$SR^c$, —O—$X^2$—$OR^c$, —$X^2$—$OR^c$, —$R^e$, —$OR^c$, —$NR^cR^d$, or —$NR^cSO_2R^d$; $R^{3a}$ is preferably halogen, cyano, —$NO_2$, —$CO_2R^f$, —$CONR^fR^g$, —$C(O)R^f$, —$NR^fR^g$, —$SR^f$, —$S(O)R^h$, —$S(O)_2R^h$, —$C(O)Y$, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; R$^{3b}$ is preferably hydrogen, halogen, cyano, —NO$_2$, —CO$_2$R$^f$, —CONR$^f$R$^g$, —S(O)R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$C(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; R$^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$NR$^f$R$^g$, and two adjacent R$^4$ groups can form a five or six-membered saturated or unsaturated ring having from 0 to 2 additional heteroatoms as ring members; n (as a subscript for R$^4$) is preferably 0-3; a, b, and c can be N, NR$^5$, S, SO, SO$_2$, O, or C(R$^4$)$_o$, where o (as a subscript for R$^4$) can be 0-2; R$^5$ is preferably hydrogen, —R$^h$, —S(O)$_2$R$^h$, —X$^3$OR$^f$, —X$^3$NR$^f$R$^g$, —X$^3$NR$^f$S(O)$_2$R$^h$, —X$^3$S(O)$_2$NR$^f$R$^g$, —CO$_2$R$^f$, —CONR$^f$R$^g$, or —C(O)R$^f$. Further preferred are those compounds in which each R$^1$, when present, is selected from the group consisting of $C_{1-4}$ alkyl, optionally substituted with a member selected from the group consisting of —OH, —OR$^m$, —S(O)$_2$R$^m$, —CO$_2$H and —CO$_2$R$^m$; when a and c are other than C(R$^4$)$_o$, b must be C(R$^4$)$_o$ or SO$_2$; when a and b are other than C(R$^4$)$_o$, then c must be C(R$^4$)$_o$ or SO$_2$. Even more preferably, R$^{2a}$ is hydrogen, halogen, —CN, —C(O)R$^c$, —X$^2$NR$^c$R$^d$, or —R$^e$; R$^{2c}$ is halogen or cyano. Still more preferably, n is 0 or 1, and R$^1$ when present is —CH$_3$. In the most preferred embodiments, R$^{2d}$ is —SR$^c$, —R$^e$, or —OR$^c$; R$^{3a}$ is halogen, cyano, —C(O)R$^f$, —S(O)$_2$R$^h$, $C_{1-6}$ alkyl, $C_{1-6}$ haloalkyl or $C_{3-6}$ cycloalkyl, where the alkyl and cycloalkyl substituents can be optionally substituted as noted above; and R$^{3b}$ is hydrogen, halogen, cyano or —NO$_2$.

6-membered C— and N-linked Heterocycles:

In other preferred groups of formula I, the compounds have a formula selected from formulae VIcccc and VIdddd, FIG. 5L, wherein R$^{2a}$, R$^{2c}$, R$^{2d}$, R$^{3a}$, R$^{3b}$, R$^{3c}$, R$^4$, W and L$^2$ have the meanings provided above for other compounds of formula VI. Turning first to the compounds of formula VIcccc, R$^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^e$, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^c$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; R$^{2c}$ is halogen, cyano or nitro; R$^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; R$^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; R$^{3c}$ is preferably halogen, cyano, —NO$_2$, —CO$_2$R$^f$, —CONR$^f$R$^g$, —C(O)R$^f$, NR$^f$R$^g$, SR$^f$, —S(O)R$^h$, —S(O)$_2$R$^h$, —C(O)Y, —SO$_2$Y, —X$^3$Y, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; R$^4$ is preferably halogen, O, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$, —X$^3$S(O)$_2$NR$^f$R$^g$, and two adjacent R$^4$ groups can form a five or six-membered saturated or unsaturated ring having from 0 to 2 additional heteroatoms as ring members; n (as a subscript for R$^4$) is preferably 0-3; a, b, c, and d can be N, NR$^5$, S, SO, SO$_2$, O, or C(R$^4$)$_o$, where o (as a subscript for R$^4$) can be 0-2; R$^5$ is preferably hydrogen, —R$^h$, —S(O)$_2$R$^h$, —X$^3$OR$^f$, —X$^3$NR$^f$R$^g$, —X$^3$NR$^f$S(O)$_2$R$^h$ and —X$^3$S(O)$_2$NR$^f$R$^g$, —CO$_2$R$^f$, —CONR$^f$R$^g$, or —C(O)R$^f$. Further preferred are those compounds in which each R$^1$, when present, is selected from the group consisting of $C_{1-4}$ alkyl, optionally substituted with a member selected from the group consisting of —OH, —OR$^m$, —S(O)$_2$R$^m$, —CO$_2$H and —CO$_2$R$^m$; when b and d are other than C(R$^4$)$_o$, c must be C(R$^4$)$_o$ or SO$_2$; when b and c are other than C(R$^4$)$_o$, then d must be C(R$^4$)$_o$ or SO$_2$; when a and d are other than C(R$^4$)$_o$, then at least one of a and b must be C(R$^4$)$_o$ or SO$_2$. Even more preferably, R$^{2a}$ is hydrogen, halogen, —CN, —C(O)R$^c$, —X$^2$NR$^c$R$^d$, or —R$^e$; R$^{2c}$ is halogen or cyano. Still more preferably, n is 0 or 1, and R$^1$ when present is —CH$_3$. In the most preferred embodiments, R$^{2d}$ is —SR$^c$, —R$^e$, or —OR$^c$; R$^{3b}$ is hydrogen, halogen, cyano, or —NO$_2$; R$^{3c}$ is halogen, cyano, —C(O)R$^f$, —SO$_2$R$^h$, $C_{1-6}$ alkyl, $C_{1-6}$ haloalkyl or $C_{3-6}$ cycloalkyl wherein the aliphatic portions are substituted as set forth above.

For compounds of Formula VIdddd, R$^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^c$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; R$^{2c}$ is halogen, cyano or nitro; R$^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; R$^{3a}$ is preferably halogen, cyano, —NO$_2$, —CO$_2$R$^f$, —CONR$^f$R$^g$, —C(O)R$^f$, NR$^f$R$^g$, SR$^f$, —S(O)R$^h$, —S(O)$_2$R$^h$, —C(O)Y, —SO$_2$Y, —X$^3$Y, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; R$^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, —R$^h$, —X$^3$NR$^f$R$^g$, —X$^3$SR$^f$, —X$^3$CN, —$X^3NO_2$, —$X^3CO_2R^f$, —$X^3CONR^fR^g$, —$X^3C(O)R^f$, —$X^3C(O)NR^fR^g$, —$X^3NR^gC(O)R^f$, —$X^3NR^gC(O)_2R^h$, —$X^3NR^fC(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2NR^fR^g$, —$X^3N_3$, Y, or —$X^3Y$; $R^4$ is preferably halogen, —$OR^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$, —$S(O)_2NR^fR^g$, —$X^3OR^f$, —$X^3NR^fR^g$, —$X^3NR^fS(O)_2R^h$ and —$X^3S(O)_2NR^fR^g$, and two adjacent $R^4$ groups can form a five or six-membered saturated or unsaturated ring having from 0 to 2 additional heteroatoms as ring members; n (as a subscript for $R^4$) is preferably 0-3; a, b, c, and d can be N, $NR^5$, S, SO, $SO_2$, O, or $C(R^4)_o$, where o (as a subscript for $R^4$) can be 0-2; $R^5$ is preferably hydrogen, —$R^h$, —$S(O)_2R^h$, —$X^3OR^f$, —$X^3NR^fR^g$, —$X^3NR^fS(O)_2R^h$, —$X^3S(O)_2NR^fR^g$, —$CO_2R^f$, —$CONR^fR^g$, or —$C(O)R^f$. Further preferred are those compounds in which each $R^1$, when present on each of formulae A, B, C and D, is selected from the group consisting of $C_{1-4}$ alkyl, optionally substituted with a member selected from the group consisting of —OH, —$OR^m$, —$S(O)_2R^m$, —$CO_2H$ and —$CO_2R^m$; when b and d are other than$C(R^4)_o$, c must be $C(R^4)_o$ or $SO_2$; when b and c are other than $C(R^4)_o$, then d must be $C(R^4)_o$ or $SO_2$; when a and d are other than $C(R^4)_o$, then at least one of b and c must be $C(R^4)_o$ or $SO_2$. Even more preferably, $R^{2a}$ is hydrogen, halogen, —CN, —$C(O)R^c$, —$X^2NR^cR^d$, or —$R^e$; $R^{2c}$ is halogen or cyano. Still more preferably, n is 0 or 1, and $R^1$ when present is —$CH_3$. In the most preferred embodiments, $R^{2d}$ is —$SR^c$, —$R^e$, or —$OR^c$; $R^{3a}$ is halogen, cyano, $C_{1-6}$ alkyl, $C_{1-6}$ haloalkyl, $C_{3-6}$ cycloalkyl, —$C(O)R^f$ or —$SO_2R^h$ wherein the aliphatic portions are optionally substituted as set forth above; $R^{3b}$ is hydrogen, halogen, cyano, or —$NO_2$.

For each of the groups of embodiments of formula VI (e.g., VIa through VIdddd) additional preferred embodiments of the invention are those in which two adjacent $R^{3a}$, $R^{3b}$ or $R^{3c}$ substituents are combined to form a fused five or six-membered ring, having from 0-3 additional heteroatoms as ring members. Further preferred are those embodiments in which the ring is a fused six-membered ring, preferably a fused benzene, pyridine or piperidine ring.

Any substituents not particularly set forth above for the various embodiments of formula VI (e.g., VIa through VIdddd) are meant to have their most complete meaning with reference to formula I, II, III, IV or V. Additionally, all compounds are meant to include their pharmaceutically acceptable salts, as well as any N-oxides thereof. Still further, the preferred compounds of the present invention are those having a molecular weight (exclusive of any salt) of less than 800, more preferably less than 700 and still more preferably less than 600. Additionally, the preferred compounds exhibit an $IC_{50}$ in the CCR1 assay described below of less than 100 micromolar, more preferably less than 10 micromolar and still more preferably less than 1 micromolar.

Preparation of Compounds

As provided in the examples below, the compounds of the present invention can be prepared by one of skill in the art in a component assembly manner, generally following synthesis strategies outlined in, for example, co-pending U.S. applications Ser. Nos. 10/460,752 and 10/732,897, as well as PCT/US03/18660. In these applications, compounds are prepared using an orthogonally protected bicyclic or spirocyclic diamine component. The term "orthogonally protected" refers to a component having two independently removable protecting groups (see, for example, compound 4, below). A first protecting group can be removed and the liberated amine reacted with a first reactant (or $L^1$-HAr component), followed by removal of the second protecting group and reaction with a second reactant (or $L^2$-Ar component). The order of component assembly can be reversed.

Bicyclic Diamine Syntheses

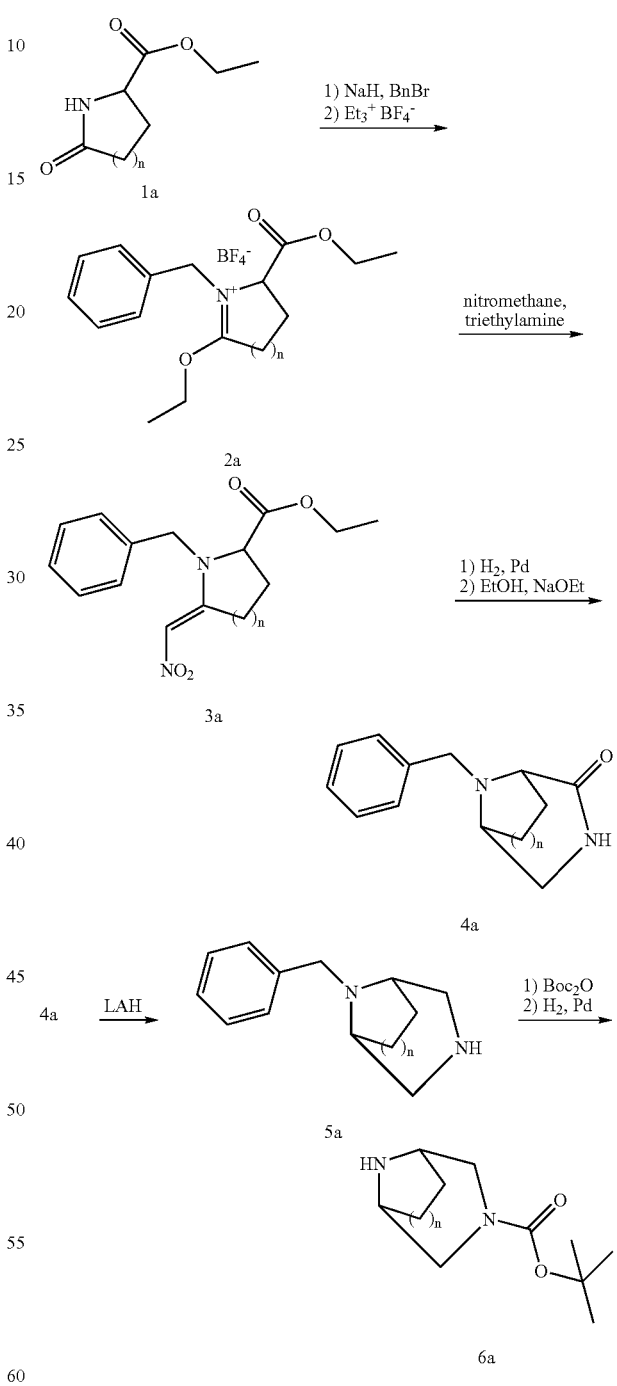

One common synthetic sequence for preparing differentially protected diamine intermediates of formula A is shown in Scheme 1A. Starting from the esters 1a, readily prepared from commercially available materials (*Chem. Pharm. Bull.*, 32, 1984, p 1303; *Synth. Commun.* 19, 1989, p 3485), the amide is first N-alkylated with benzylbromide or benzylchloride, and the product is then O-alkylated using an oxophillic electrophile, such as triethyloxonium tetrafluoroborate, to give the salts 2a. The salts 2a are then reacted with nitromethane, in the presence of triethylamine, to give the condensation products 3a. These products are then first reacted with hydrogen, using a catalyst such as palladium, and the corresponding reduction products are cyclized by heating in an alcohol, in the presence of a basic catalyst to give the bicyclic products 4a. The bicyclic products 4a are then reduced with a reductant, such as lithium aluminum hydride, to give the mono-protected diamines 5a. The diamines 5a are converted to the differentially protected diamines 6a by first reacting them with di-tert-butyldicarbonate, followed by removal of the N-benzyl group with hydrogen in the presence of a catalyst, such as palladium hydroxide.

Scheme 1B:
Formula A, Protocol B.

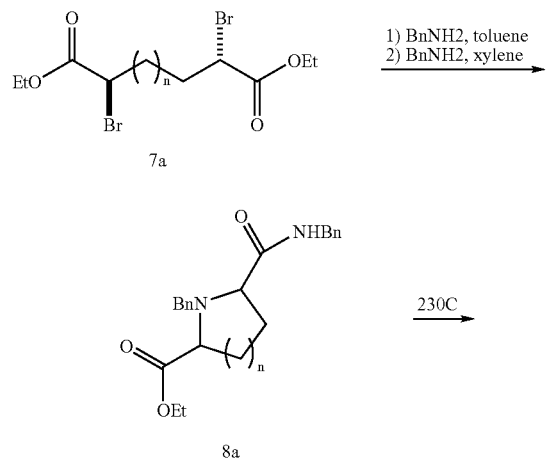

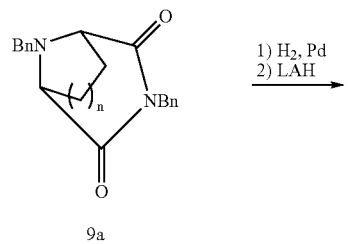

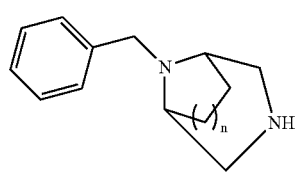

An alternate approach to differentially protected diamine intermediates of the type 10a and 9a is shown in Scheme 1B. The dibromodiesters 7a, readily prepared from the corresponding di-acids using standard methods well know to those in the art, are reacted first with benzylamine by heating in toluene. These products are then reacted with benzylamine by heating in xylene to product the cyclic monoamides 8a (*Tetrahedron. Lett.* 43, 2002, p 899). The monocyclic amides 8a are then heated at 230° C. to form the bicyclic imides 9a.

These products are selectively de-benzylated at the imide nitrogen, using hydrogen and palladium, followed by reduction by lithium aluminum hydride to give the diamines 10a.

Scheme 1C:
Formula D, Protocol C.

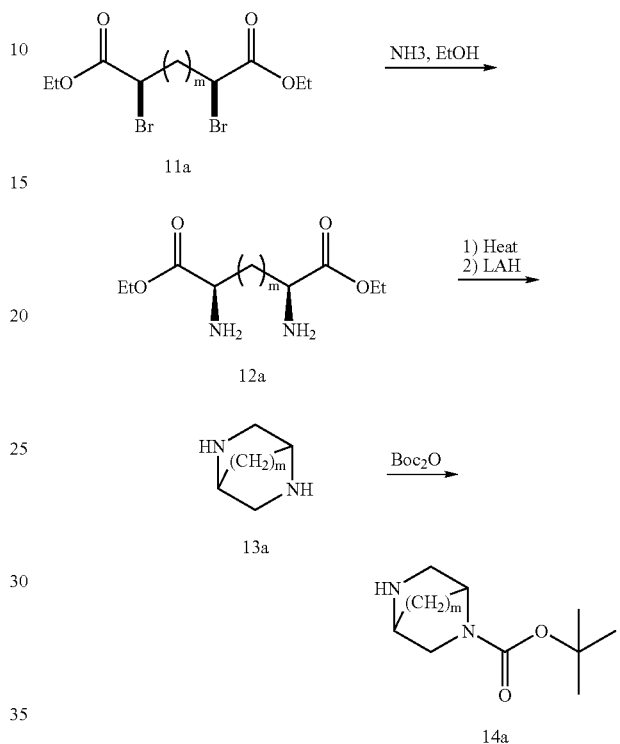

To prepare alternatively bridged diamines, one applicable route is shown in Scheme 1C. The dibromodiesters 11a, readily prepared from the corresponding di-acids using standard methods well know to those in the art, are reacted first with ammonia in ethanol, to give the diamines 12a. The diamines are then heated in an alcohol, such as ethanol, in the presence of a base, such as sodium ethoxide, to form the bicyclic piperazine-diones. These products are reduced, using a reducing agent such as lithium aluminum hydride, to give the bicyclic diamines 13a. The diamines are reacted with di-tert-butyl dicarbonate to prepare the mono-protected diamines 14a.

Scheme 1D:
Formula D, protocol D.

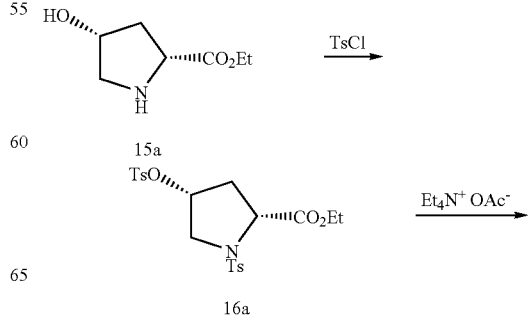

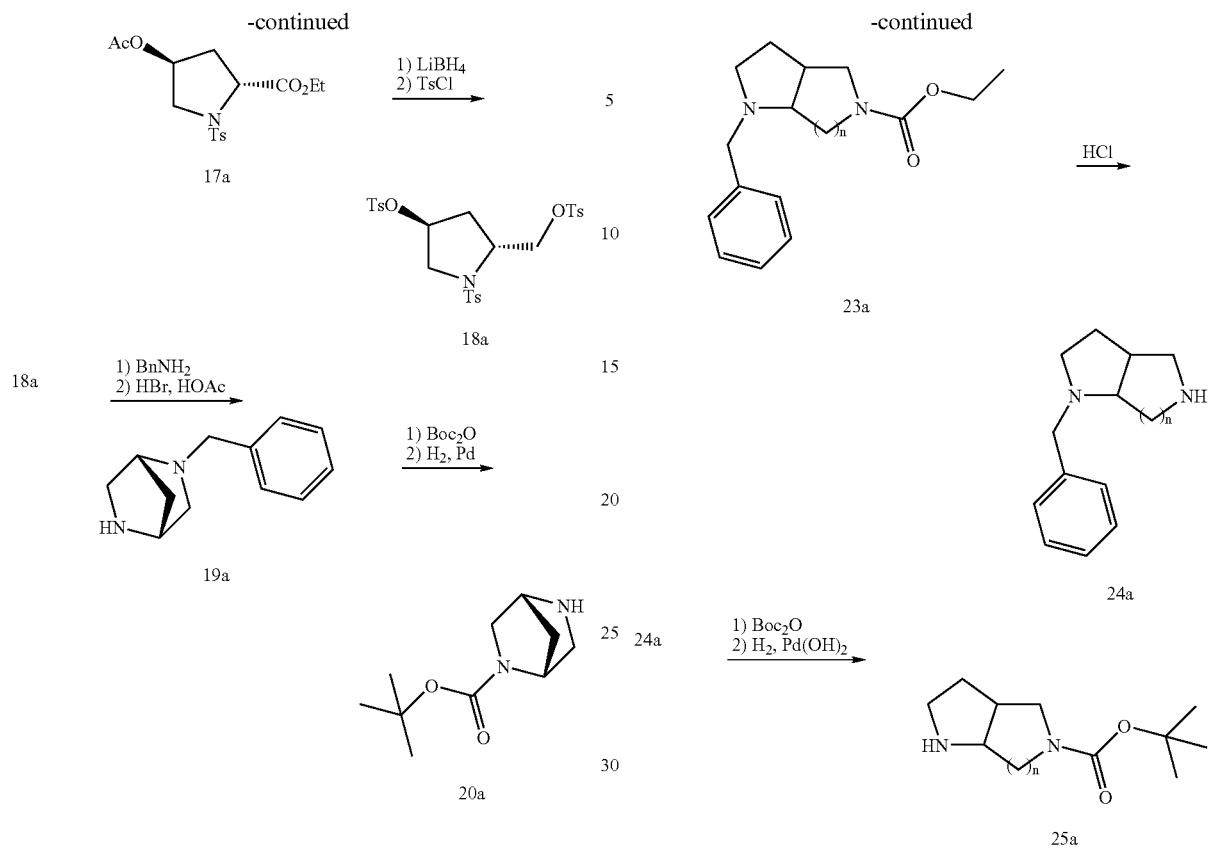

An alternative route to preparing the mono-protected bridged piperazine derivatives 19a and 20a is shown in Scheme 1D. The ethyl ester of cis-4-hydroxy-L-proline is reacted with p-toluenesulfonyl chloride to give 16a (*J. Med. Chem.* 33, 1990, p 1344). This product is reacted with tetraethylammonium acetate to give 17a, which is then reduced to the bis-alcohol, using lithium borohydride, followed by reaction with p-toluenesulfonylchloride to form 18a. Reaction with benzylamine, followed by N-tosyl removal with HBr in acetic acid, gives the mono-benzyl protected diamine 19a. This product can be differentially protected by first reacting with di-tert-butyldicarbonate, followed by treatment with hydrogen in the presence of palladium hydroxide, to give 20a.

In addition to the methods in the experimental section detailing the preparation of certain diamines of formula B, other methods allow preparation of diamines of this class wherein the subscripts o, p, q, or r equal 0. The first of these methods, protocol E, is shown in Scheme 1E (*Bioorg. Med. Chem. Lett.* 9, 1999, p 2491). The aminoacetals 21a are first reacted with ethylchloroformate, followed by alkylation with allylbromide, and finally treated with formic acid to give the aldehydes 22a. Heating of these aldehydes in toluene, in the presence of N-benzylglycine, gives the bicyclic compounds 23a. The ethoxycarbonyl group is hydrolyzed using hydrochloric acid, to give the mono-benzyl protected diamine 24a. This product can be differentially protected by first treating with di-tert-butyldicarbonate, followed by N-debenzylation using hydrogen and a palladium catalyst, to give 25a.

Scheme 1E:
Formula B, protocol E.

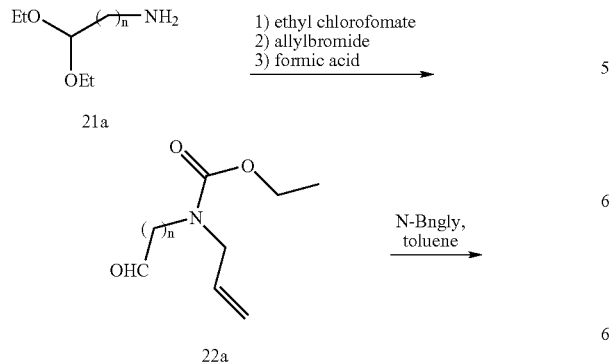

Scheme 1F:
Formula B, protocol F.

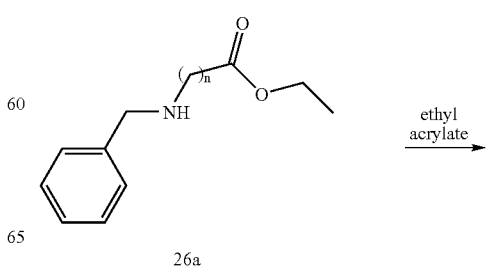

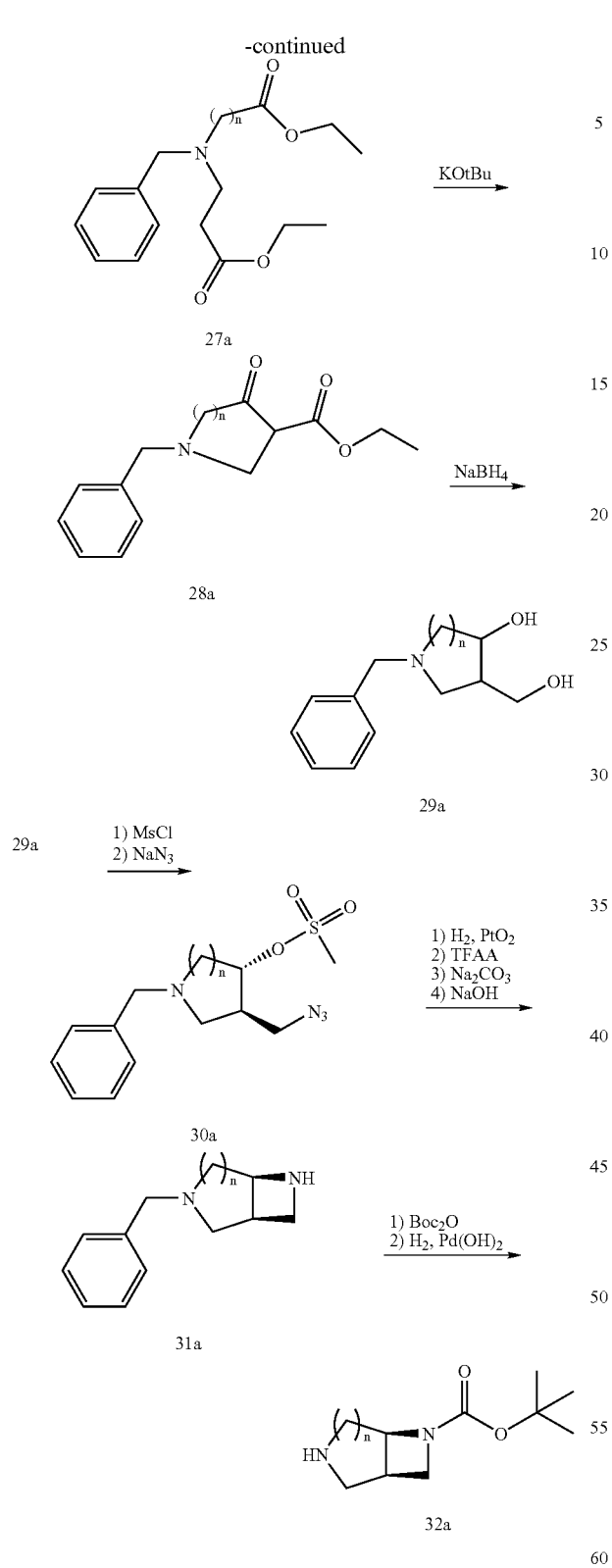

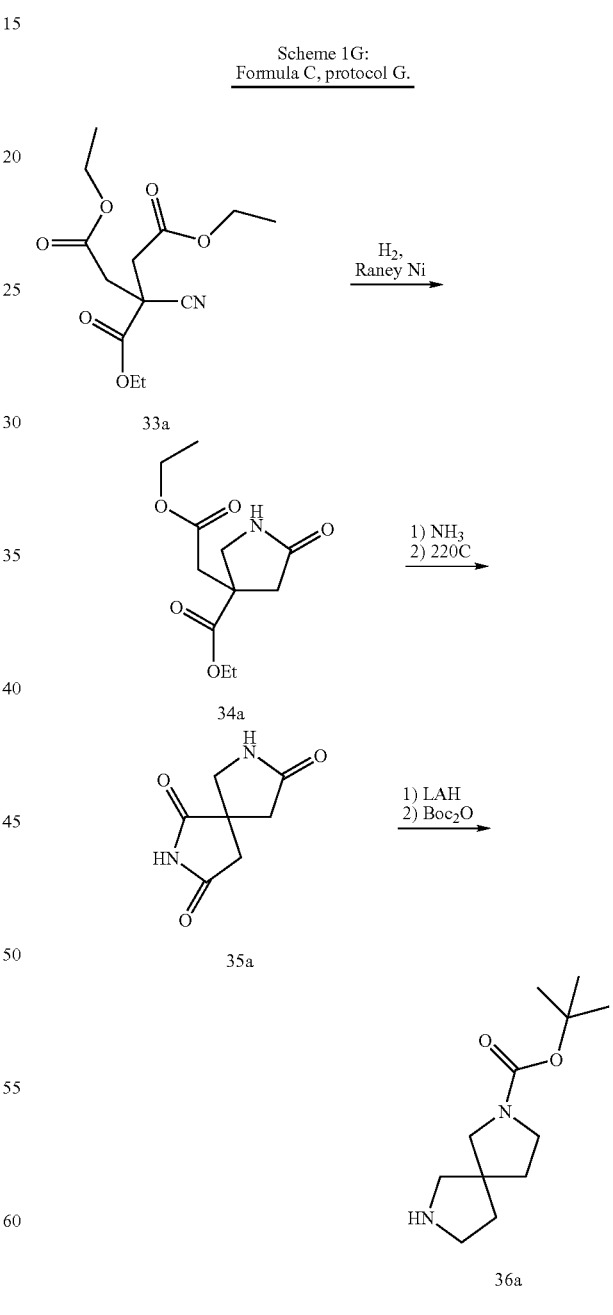

borohydride, for example, to give the aminodiols 29a. Treatment of these with methanesulfonyl chloride, followed by sodium azide, gives the compounds 30a. The azide groups are reduced, using conditions such as hydrogen with platinum oxide as catalyst, and the resulting primary amines are treated with trifluoroacetic anhydride. These materials are further heated under mild basic conditions, using non-protic solvents, to form bicyclic intermediates. Final treatment with sodium hydroxide, and an alcoholic solvent, gives the monobenzyl protected diamines 31a. These products can be differentially protected by first treating with di-tert-butyldicarbonate, followed by N-debenzylation using hydrogen and a palladium catalyst, to give the compounds 32a.

Scheme 1G:
Formula C, protocol G.

The second additional method for preparing diamines of formula B is shown in Scheme 1F (*Tetrahedron Lett.* 32, 1991, p 1565). The readily prepared aminoesters 26a, this can be treated with ethyl acrylate to form tertiary amines 27a. Treatment with potassium tert-butoxide forms cyclic compounds 28a. These compounds are reduced with sodium One method for preparing certain diamines of formula C is shown in Scheme 1G. The readily prepared triester 33a (*J. Org. Chem.* 46, 1981, p 2757) is converted to the pyrrolidinone 34a by reduction with hydrogen catalyzed by Raney nickel. 34a is treated with ammonia in an alcoholic solvent, and the product is concentrated and heated to produce the spirocyclic trione 35a. This product is reduced to the diamine, using lithium aluminum hydride, followed by treatment with di-tert-butyl dicarbonate, to give the mono-protected diamine 36a.

A method for preparing additional compounds containing the diamine of formula C is shown in Scheme 1H. Boc-piperidinone is homologated via a Wittig reaction, followed by treatment with nitromethane under basic conditions to give 38a (*J. Med. Chem.* 38, 1995, p 3772). Reduction with hydrogen, catalyzed by Raney nickel, results in formation of the spirocyclic system. Treatment of this with sodium hydride and benzyl bromide gives 39a. Removal of the Boc group using trifluoroacetic acid, followed by reduction with borane-dimethylsulfide, gives the mono-benzyl protected diamine 40a. This product can be differentially protected by treatment with di-tert-butyldicarbonate, followed by hydrogenolysis of the benzyl group using hydrogen and palladium hydroxide, to give 41a.

Scheme 1H:
Formula C, protocol H.

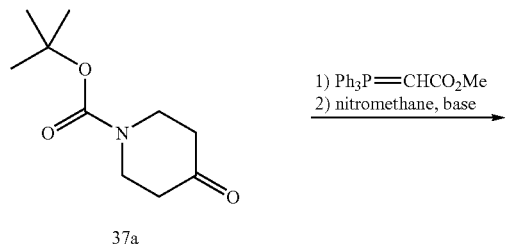

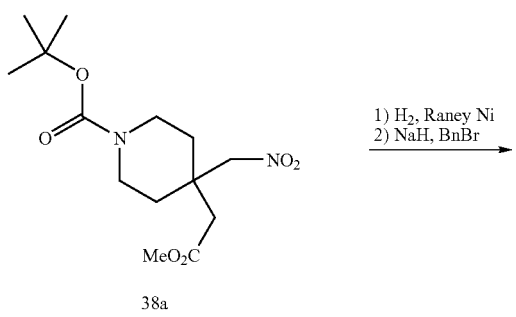

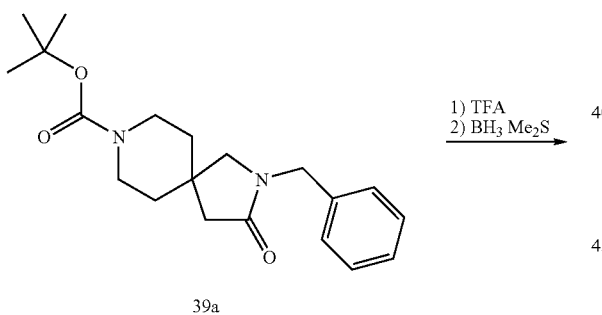

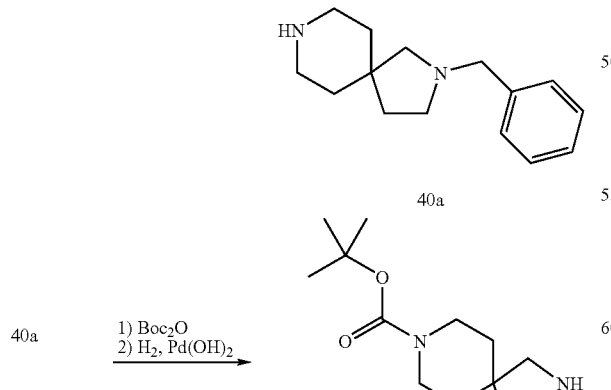

Scheme 1I:
Formula C, protocol I.

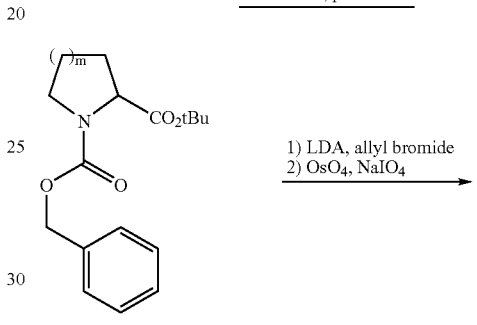

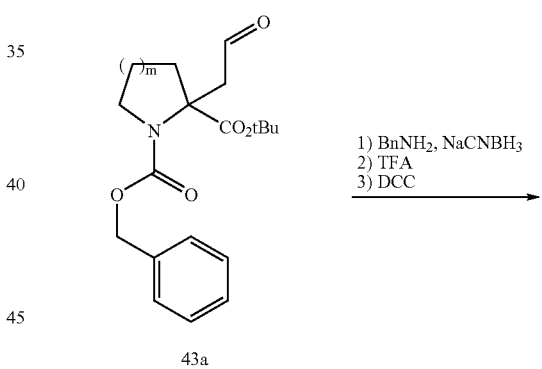

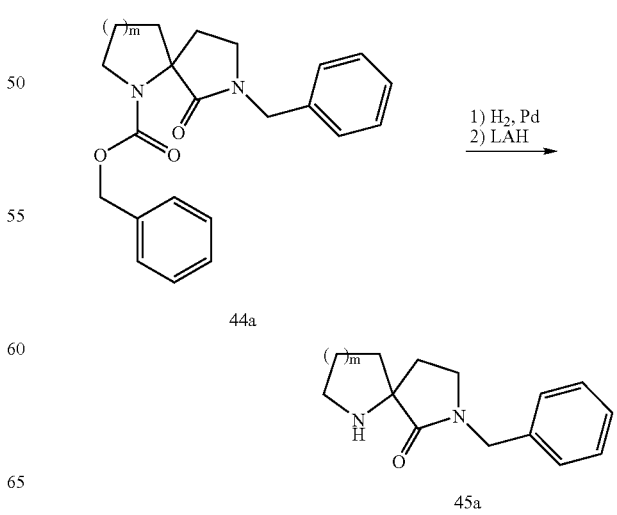

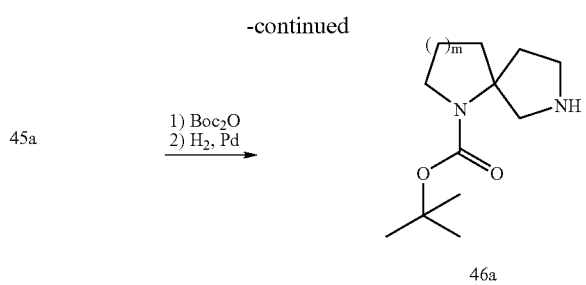

One method that is useful for preparing compounds of formula C, wherein one of the subscripts s, t, u, or v is 0, is shown in Scheme 1I. Treatment of the readily prepared derivatives 42a with lithium diisopropylamide and allyl bromide, followed by oxidative cleavage of the allyl moiety with osmium tetroxide and sodium periodate, gives aldehydes 43a (*J. Org. Chem.* 58, 1993, p 860). Reductive alkylation with benzylamine, ester hydrolysis with trifluoroacetic acid, and cyclization promoted by dicylohexylcarbodiimide, gives the spirocyclic compounds 44a. Selective Cbz removal with hydrogen and palladium, followed by reduction with a reducing agent, such as lithium aluminum hydride, gives the monobenzyl protected diamines 45a. These products can be differentially protected by treatment with di-tert-butyldicarbonate, followed by hydrogenolysis of the benzyl group using hydrogen and palladium hydroxide, to give the amines 46a.

Scheme 1J:
Protocol for Formula C wherein two $R^1$ groups form an additional ring.

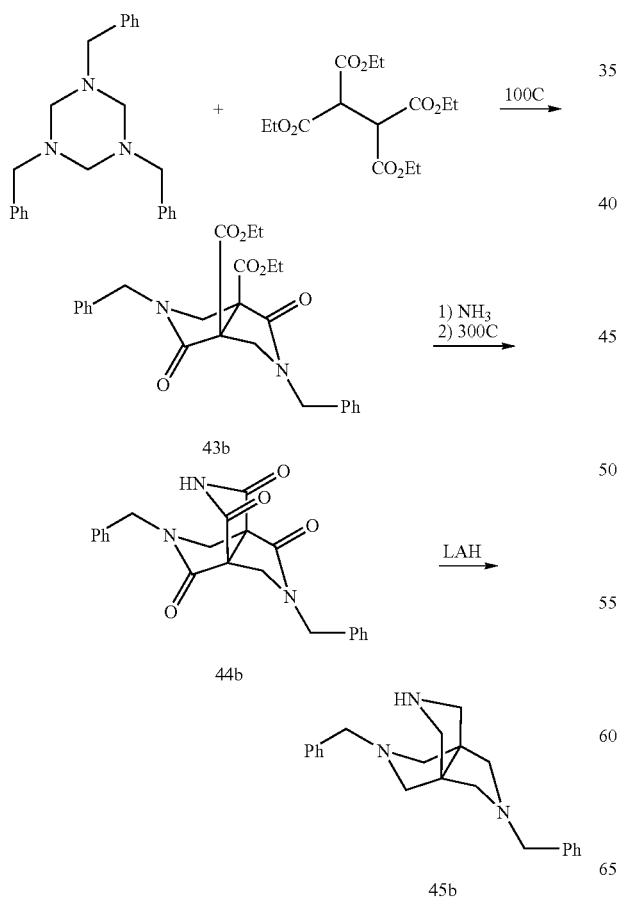

Of particular interest are a class of diamine moieties W with two $R^1$ groups joined in a cyclic alkyl or heteroalkyl ring. One example of methods used to prepare such functionalized bicyclic diamines is shown in Scheme 1J above (P. Knowles, et.al, *J. Chem. Soc. Perkin Trans.* 1, 1983, 1475). 1,3,5-tribenzylhexahydrotriazine is heated with tetraethyl ethane-1,1,2,2-tetracarboxylate at 100° C. to give the diamide 43b. This product is first treated with ammonia at 100° C. to form the tetraamide, followed by heating at 300° C. to eliminate ammonia and form the imide 44b. Reduction of 44b with lithium aluminum hydride gives the bis-benzyl protected triamine 45b.

Scheme 1K:
Protocol for Unsaturated Diamines of Formula B.

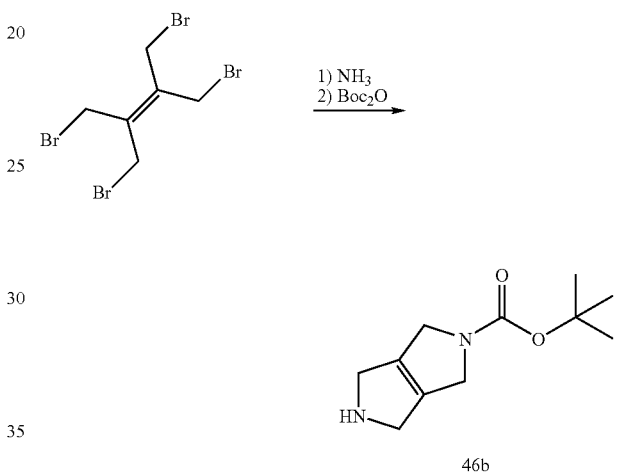

An additional class of diamines of interest are unsaturated variants of formula B. One example of methods used to prepare these diamines is shown in Scheme 1K (P. W. le Quesne, et. al., *J. Org. Chem.,* 1975, V40, 142). Treatment of tetrakis (bromomethyl)ethylene with ammonia in an alcohol solvent with heating results in formation of 3,7-diazabicyclo[3.3.0] oct-1(5)-ene. Mono-boc protection, using 1 equivalent of di-tert-butyldicarbonate, gives 46b. Compound 46b can be incorporated into Formula I using the standard chemistries outlined.

Many other methods are well known in the art for preparing compounds of formulae A, B, C and D. The methods shown should be considered as examples only, and not comprehensive as to the breadth of related structures that can be accessed via reliable means. In addition, where asymmetry is present in the compounds claimed in the present invention, one of skill in the art will appreciate that they can be readily resolved, using methods common to those practiced in the art, into their single and separate enantiomers or diastereomers, and that these single and separate isomers are also within the scope of the present invention. Additionally, those skilled in the art will recognize that methods are known for the chiral synthesis of certain materials that are useful as starting materials. Such approaches include the use of the chiral pool, the use of chiral auxiliaries, chiral synthesis using chiral catalysts and reagents and chiral resolutions. All the standard methodologies for chiral synthesis are envisaged as part of this application.

Pyrazole Synthesis

A number of compounds are prepared beginning with preparation of a suitably substituted pyrazoles (or other HAr component). Schemes 2A-2K illustrate a variety of methods for the preparation of substituted pyrazoles (see also co-pending U.S. applications Ser. Nos. 10/460,752 and 10/732,897, as well as PCT/US03/18660). In each of these schemes, non-interfering substituents are provided as —R, —$R^w$, —$R^x$, —$R^y$ and $R^z$.

Scheme 2A
Arylpyrazoles via Suzuki Coupling:

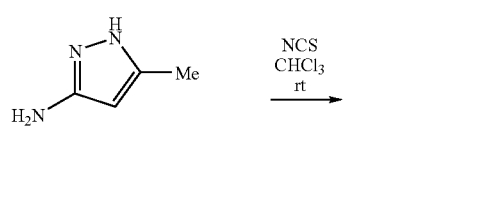

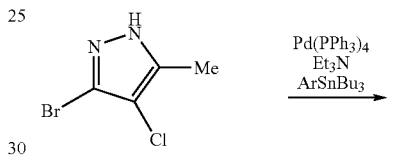

R = H, o-OMe, p-OMe, m-OMe, o-Cl, p-Cl, m-Cl
o-Me, m-Me, p-Me

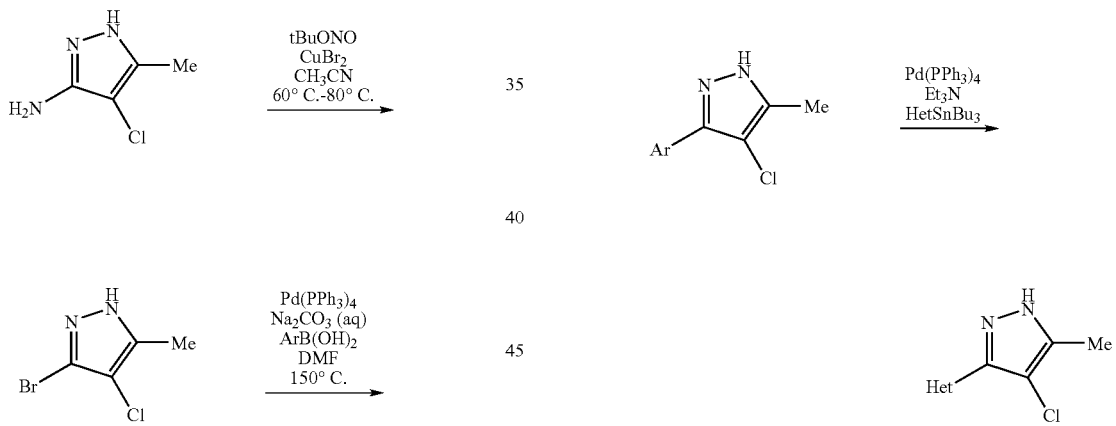

Scheme 2B
Arylpyrazoles via Stille Coupling:

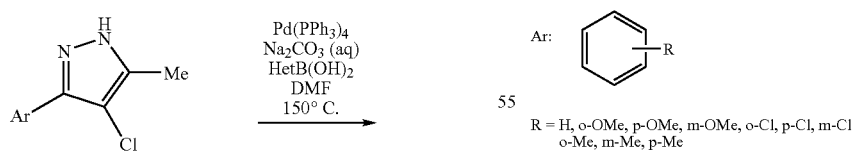

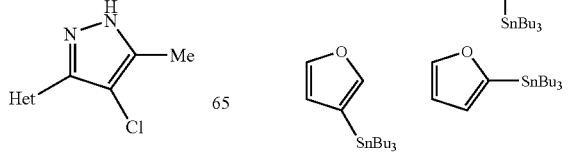

R = H, o-OMe, p-OMe, m-OMe, o-Cl, p-Cl, m-Cl
o-Me, m-Me, p-Me

Scheme 2C
Arylpyrazoles via Negishi Cross-Coupling reactions:
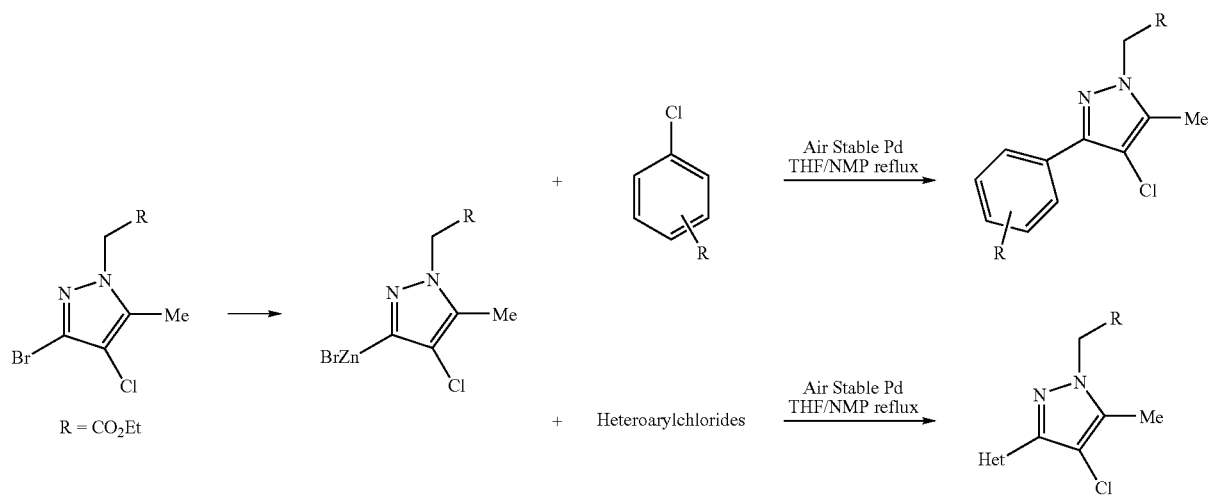
Scheme 2D
Arylpyrazoles via Kumada-Tamao-Corriu Cross-Coupling reactions:
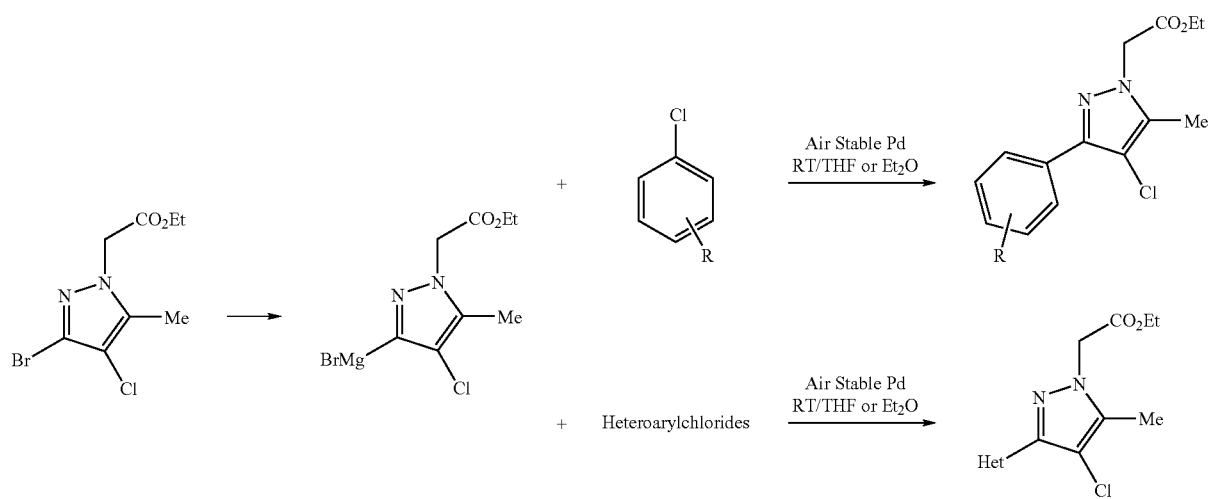

Scheme 2E

Substituted pyrazoles via Buchwald Chemistry:

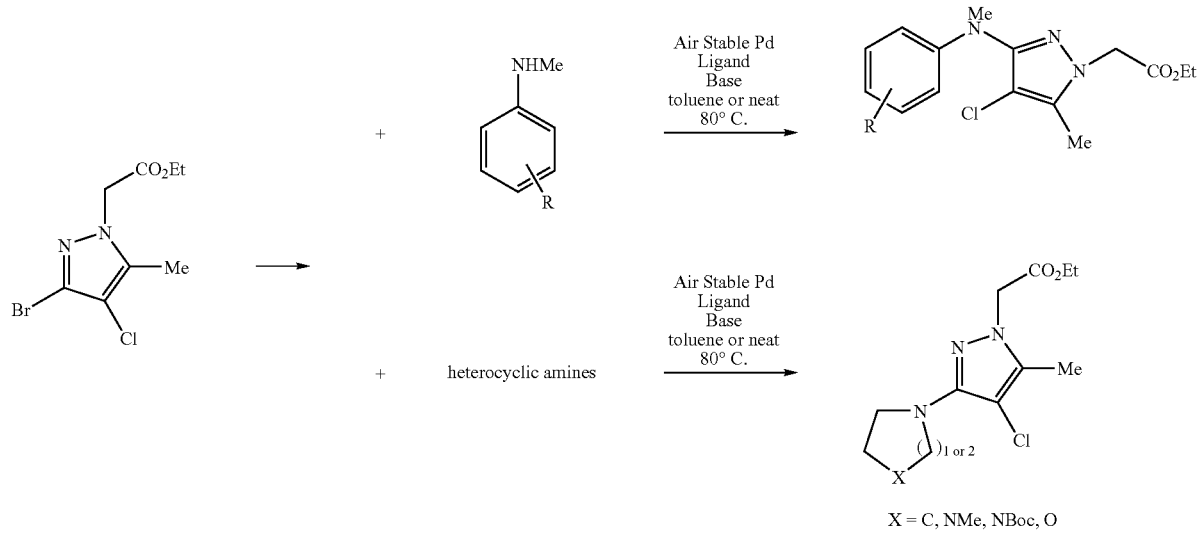

Scheme 2F

Arylpyrazoles by condensation of 1,3-diketones with hydrazines:

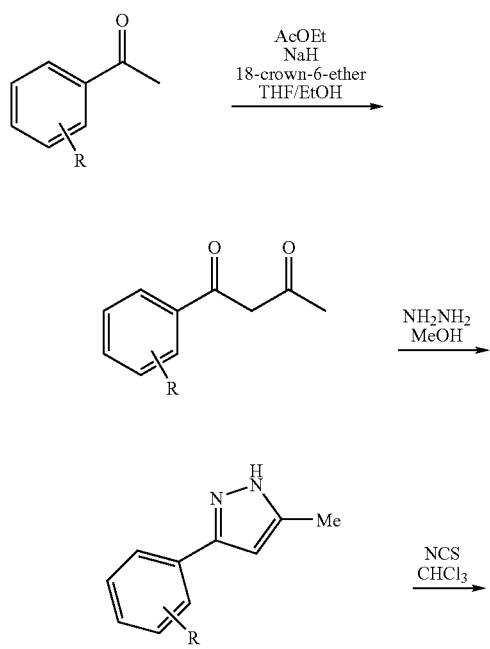

Scheme 2G

Heteroarylpyrazoles by condensation of 1,3-diketones with hydrazines:

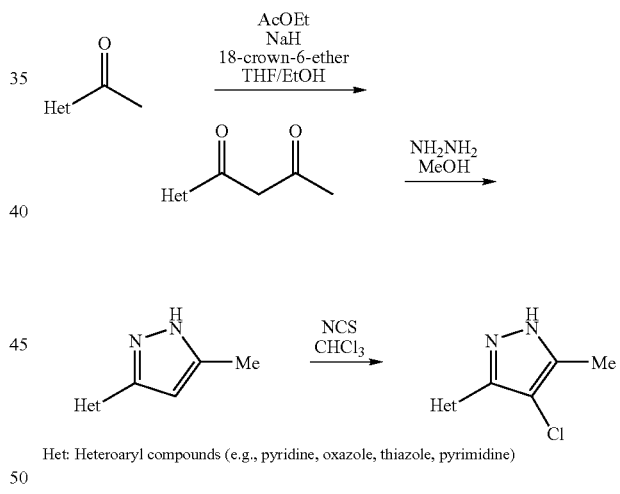

Het: Heteroaryl compounds (e.g., pyridine, oxazole, thiazole, pyrimidine)

Scheme 2H

Substituted pyrazoles via Sonogashira Coupling followed by Diels-Alder reaction on the exocyclic triple bond:

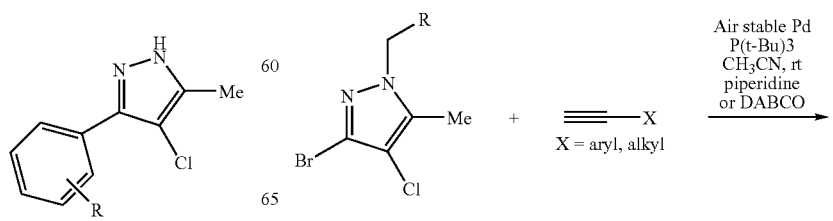

-continued
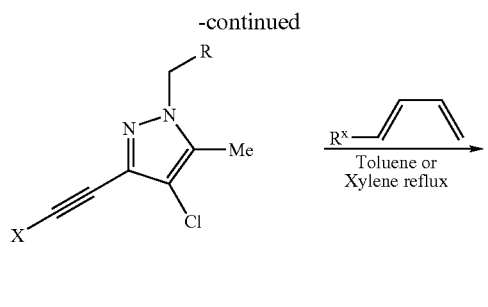
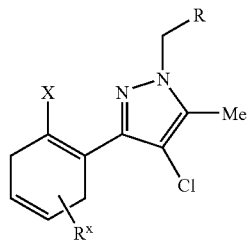
Scheme 2I
Substituted pyrazoles via Heck coupling followed by Diels-Alder reaction on the exocyclic double bond:
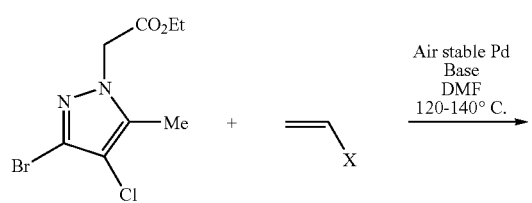
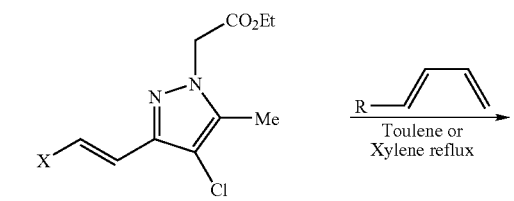
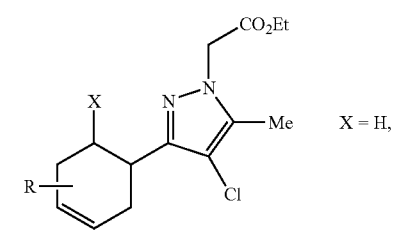
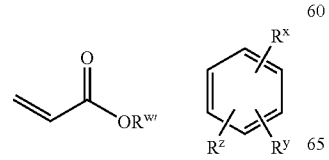
Scheme 2J
Substituted arylpyrazoles via Ullmann coupling:
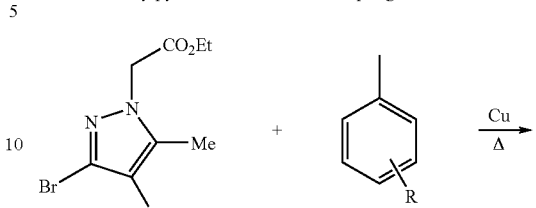
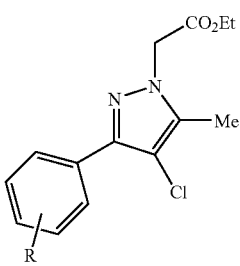
Scheme 2K
Substituted aminopyrazoles via curtius rearrangement and reductive amination:
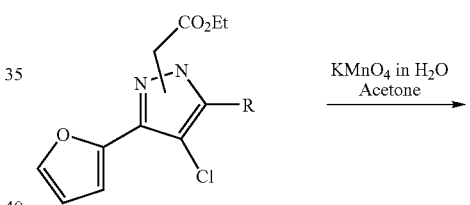
R = Me, CF$_3$
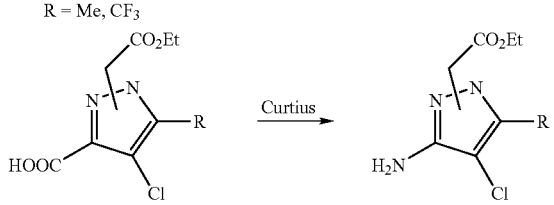
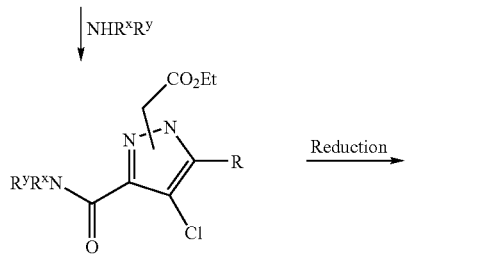
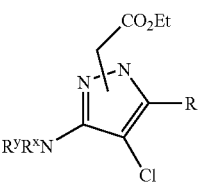

Assembly of Final Compounds of Formula I

Many routes are evident to those skilled in the art for assembly of the various fragments in formula I to synthesize the chemical entities claimed, and related examples are described in co-pending U.S. applications Ser. Nos. 10/460,752 and 10/732,897, as well as PCT/US03/18660. Additionally, a variety of appropriate synthetic approaches to final molecules of formulae A, B, C and D are indicated in the literature. WO 02/070523 provides a useful recent summary of a variety of previously known synthetic approaches and reactions.

Several variations proceed from a mono-N-benzyl protected diamine moiety 5a, according to Scheme 3A.

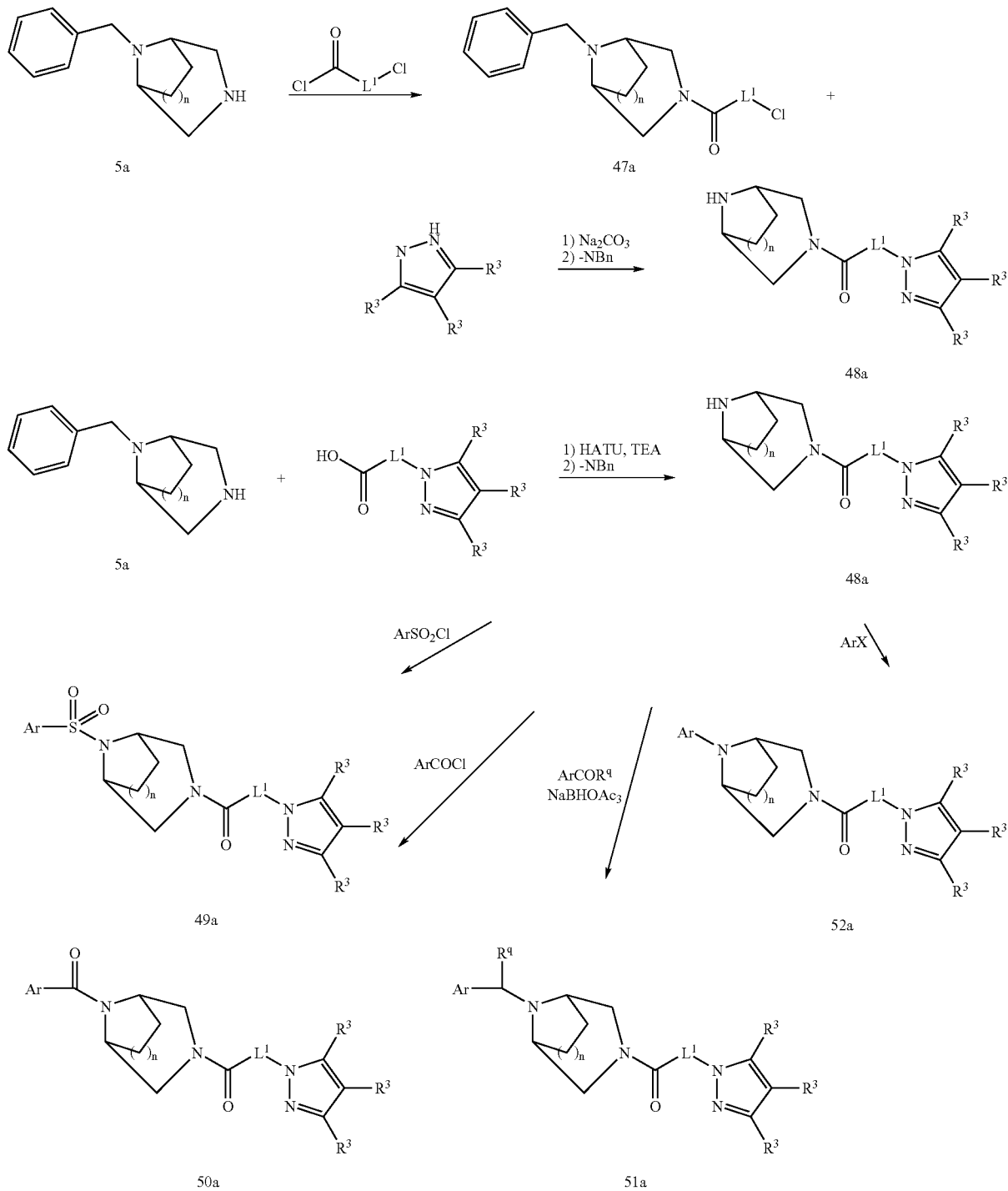

Acylation of the secondary nitrogen in intermediates such as 47a can proceed prior to the pyrazole attachment, or after (shown above), followed by N-benzyl cleavage, to give the compounds 48a. These intermediates can be coupled to Ar-L² fragments via reaction with sulfonylchlorides, acylchlorides, reductive alkylation with aldehydes or ketones, and coupled directly to Ar moieties using the various well known various methods catalyzed by palladium.

Where the diamine moiety is of formula B and is mono-protected with a tert-butoxycarbonyl (Boc) group, the assembly sequences can be similar to those shown above in Scheme 3A, leading to the complimentary set of compounds. This is of particular interest when there is no plane of symmetry perpendicular to the plane connecting the two secondary nitrogen atoms in 5a, or when 5a is a single enantiomer or diastereomer.

Alternatively, the order of assembly can vary; examples are shown in Scheme 3B below.

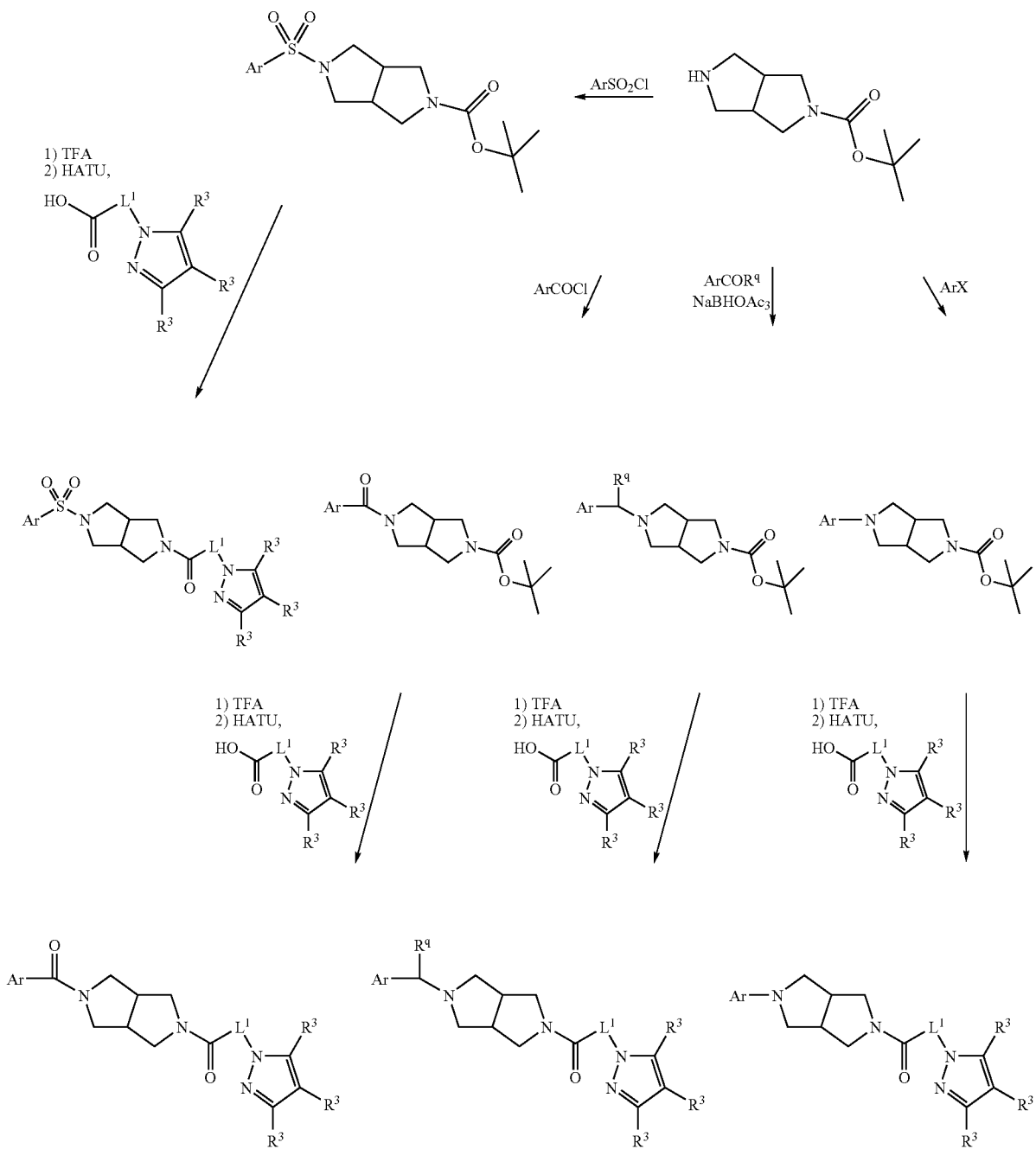

The compound 45b from Scheme 1J can be incorporated into compounds of Formula I using a variety of standard reactions, some of which are shown in Scheme 3C.
Scheme 3C
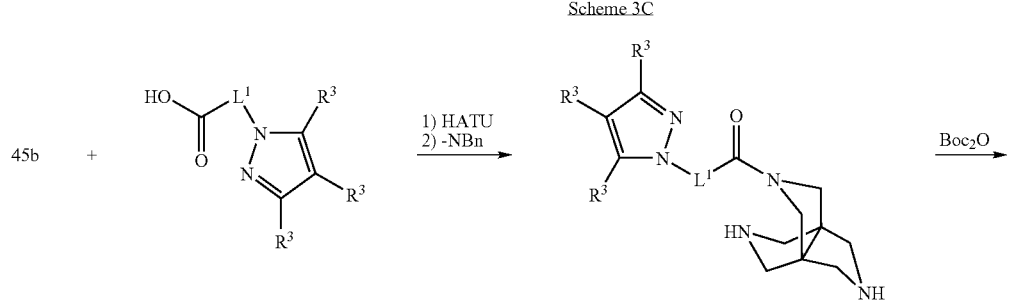
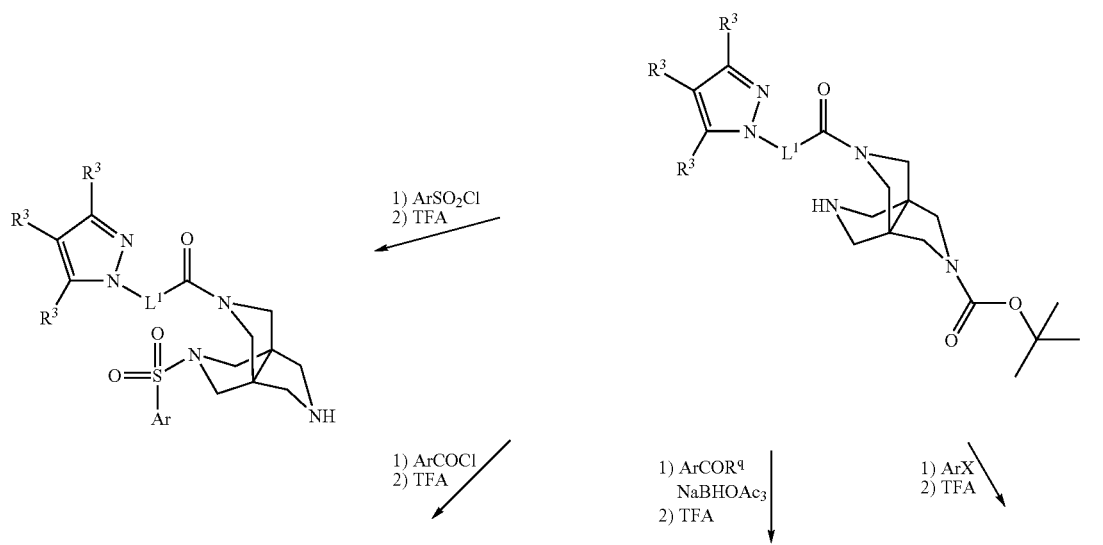
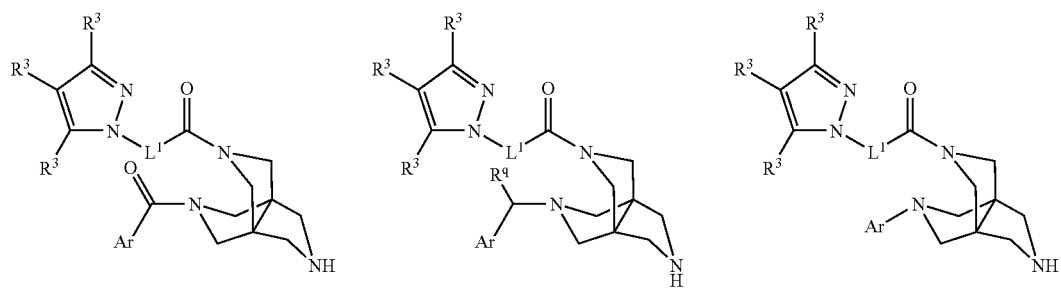

Similarly, compound 46b from Scheme 1K can be incorporated into compounds of Formula I using a variety of standard reactions, some of which are shown in Scheme 3D.

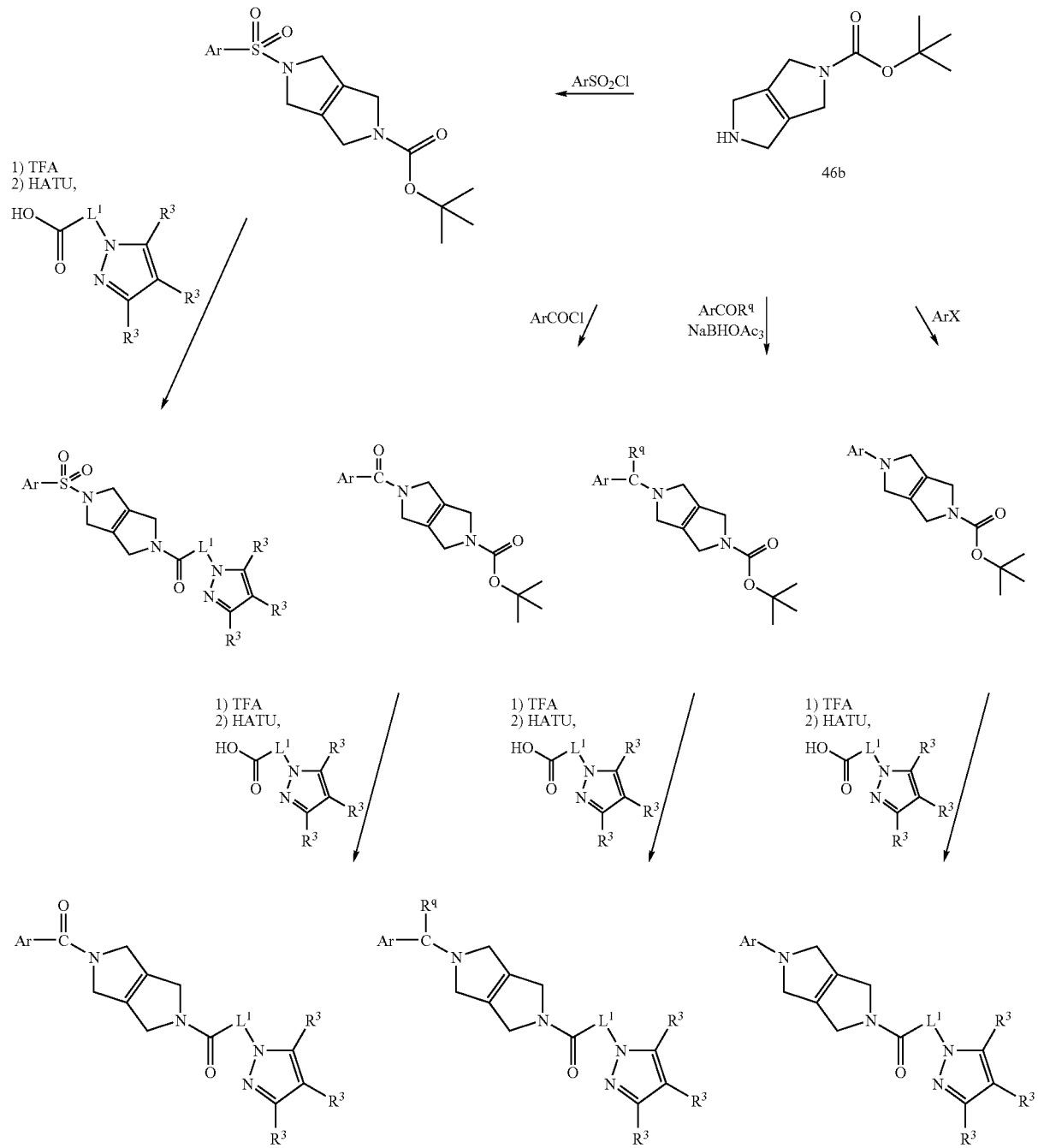

The compound S can be incorporated into compounds of Formula I using a variety of standard reactions, some of which are shown in Scheme 3D.

These chemistries outlined above, along with various applicable methodology in the literature, enable the synthesis of molecules of the invention of formula C and D as well as A and B depicted above.

IV. Pharmaceutical Compositions

In addition to the compounds provided above, compositions for modulating CCR1, CCR2 and CCR3 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. Nos. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. patent application Ser. No. 08/746,404, filed Nov. 8, 1996 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly (ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefm copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. patent application 20040243225A1, the entire disclosure of which is incorporated in its entirety.

Moreover, as described for example in U.S. Pat. No. 6,770,729, which is incorporated herein in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

V. Methods of Treating Diseases Modulated by CCR1, CCR2 and/or CCR3

In yet another aspect, the present invention provides methods of treating CCR1-, CCR2- and/or CCR3-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1, CCR2 or CCR3 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as asthma, allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, Takuyasu arthritis, rheumatoid arthritis, psoriatic arthritis, osteoarthritis, polyarticular arthritis, multiple sclerosis, systemic lupus erythematosus, type I diabetes, type II diabetes, type I diabetes (recent onset), optic neuritis, glomerulonephritis, and the like, (10) graft rejection including allograft rejection and acute and chronic graft-vs-host disease, (11) fibrosis (e.g. pulmonary fibrosis (i.e. idiopathic pulmonary fibrosis, interstitial pulmonary fibrosis), fibrosis associated with end-stage renal disease, fibrosis caused by radiation, tubulointerstitial fibrosis, subepithelieal fibrosis, scleroderma (progressive systemic sclerosis), hepatic fibrosis (including that caused by alcoholic or viral hepatitis), primary and secondary cirrhosis), (12) acute and chronic lung inflammation (chronic obstructive pulmonary disease, chronic bronchitis, adult respiratory distress syndrome, respiratory distress syndrome of infancy, immune complex alveolitis) and (13) other diseases in which undesired inflammatory responses or immune disorders are to be inhibited, such as cardiovascular disease including atherosclerosis, vascular inflammation resulting from tissue transplant or during restenosis (including, but not limited to restenosis following angioplasty and/or stent insertion), other acute and chronic inflammatory conditions such as myositis, neurodegenerative diseases (e.g., Alzheimer's disease), encephalitis, meningitis, hepatitis, nephritis, sepsis, sarcoidosis, allergic conjunctivitis, otitis, sinusitis, synovial inflammation caused by arthroscopy, hyperuremia, trauma, ischaemia reperfusion injury, nasal polyosis, preeclampsia, oral lichen planus, Guillina-Barre syndrome, granulomatous diseases, conditions associated with leptin production, Behcet's syndrome and gout and in wound healing applications (14) immune mediated food allergies such as Celiac disease.

In another group of embodiments, diseases or conditions can be treated with modulators of CCR1 function. Examples of diseases to be treated with modulators of CCR1 function include cancers (both primary and metastatic), cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Pharmaceutical compositions of this invention can also inhibit the production of metalloproteinases and cytokines at inflammatory sites, either directly or indirectly (as a consequence of decreasing cell infiltration) thus providing benefit for diseases or conditions linked to these cytokines.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefore, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, aldlofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α(Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

EXAMPLES

The following examples are offered to illustrate, but not to limit the claimed invention.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

Figure 3:
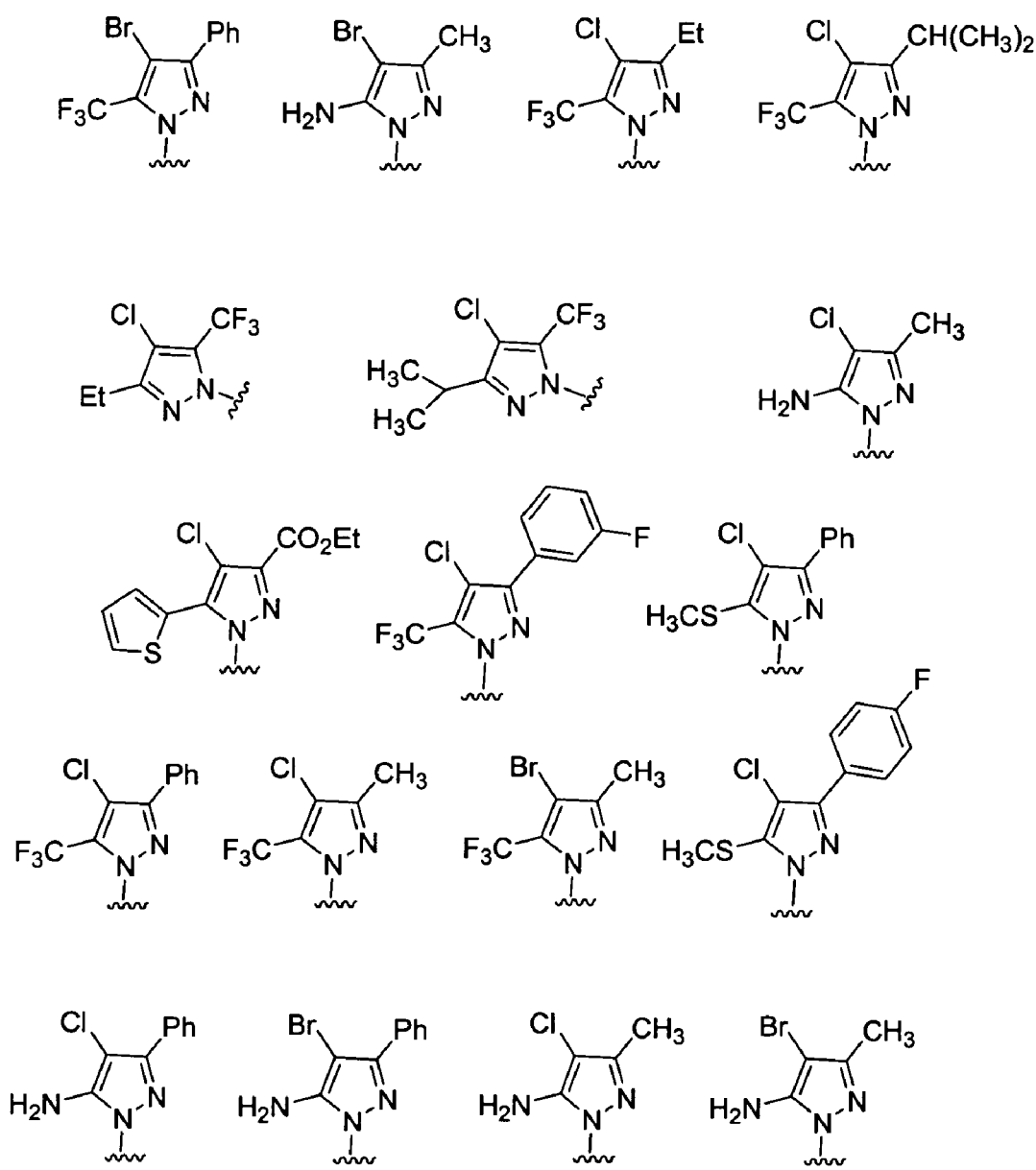
Figure 4A:
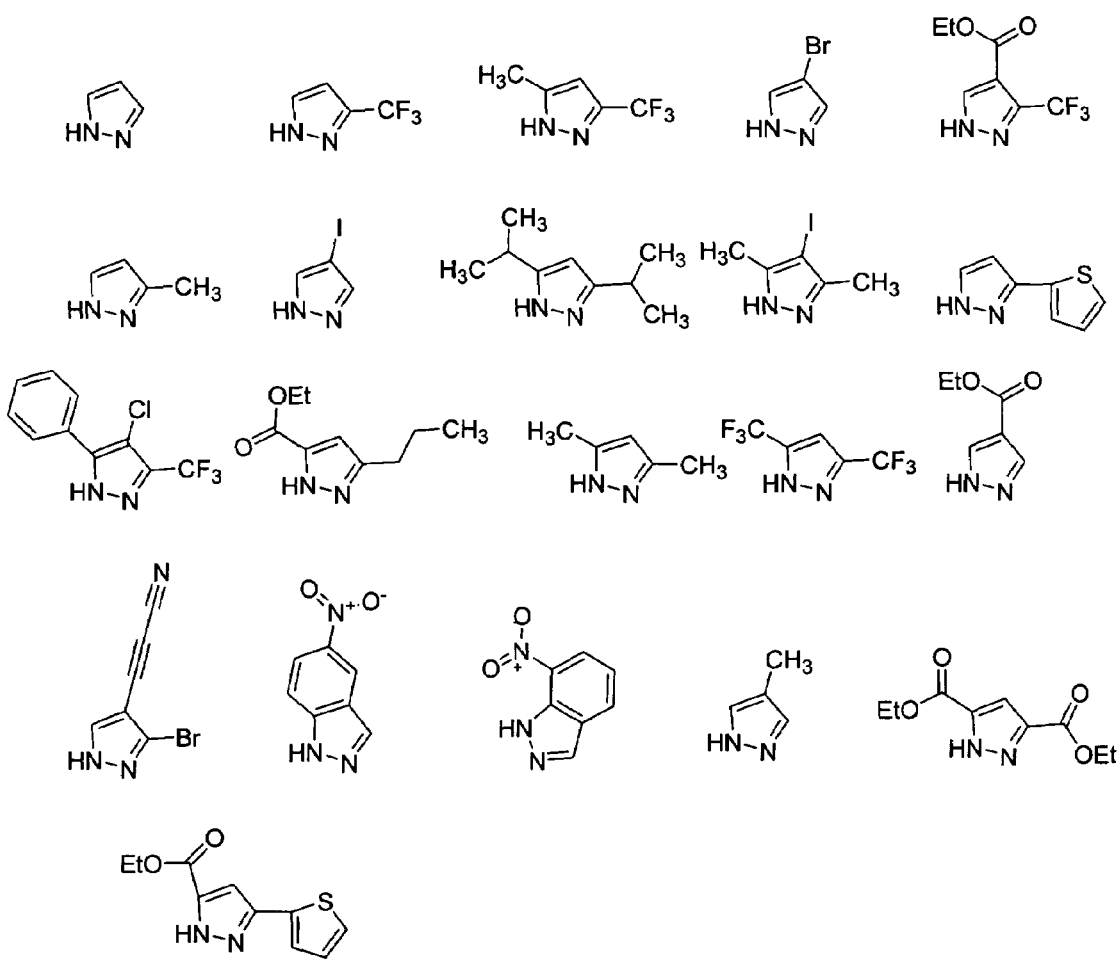
FIGS. 4A-4C provide structures of some commercially-available HAr groups, useful in preparing compounds of the present invention.
Figure 4B:
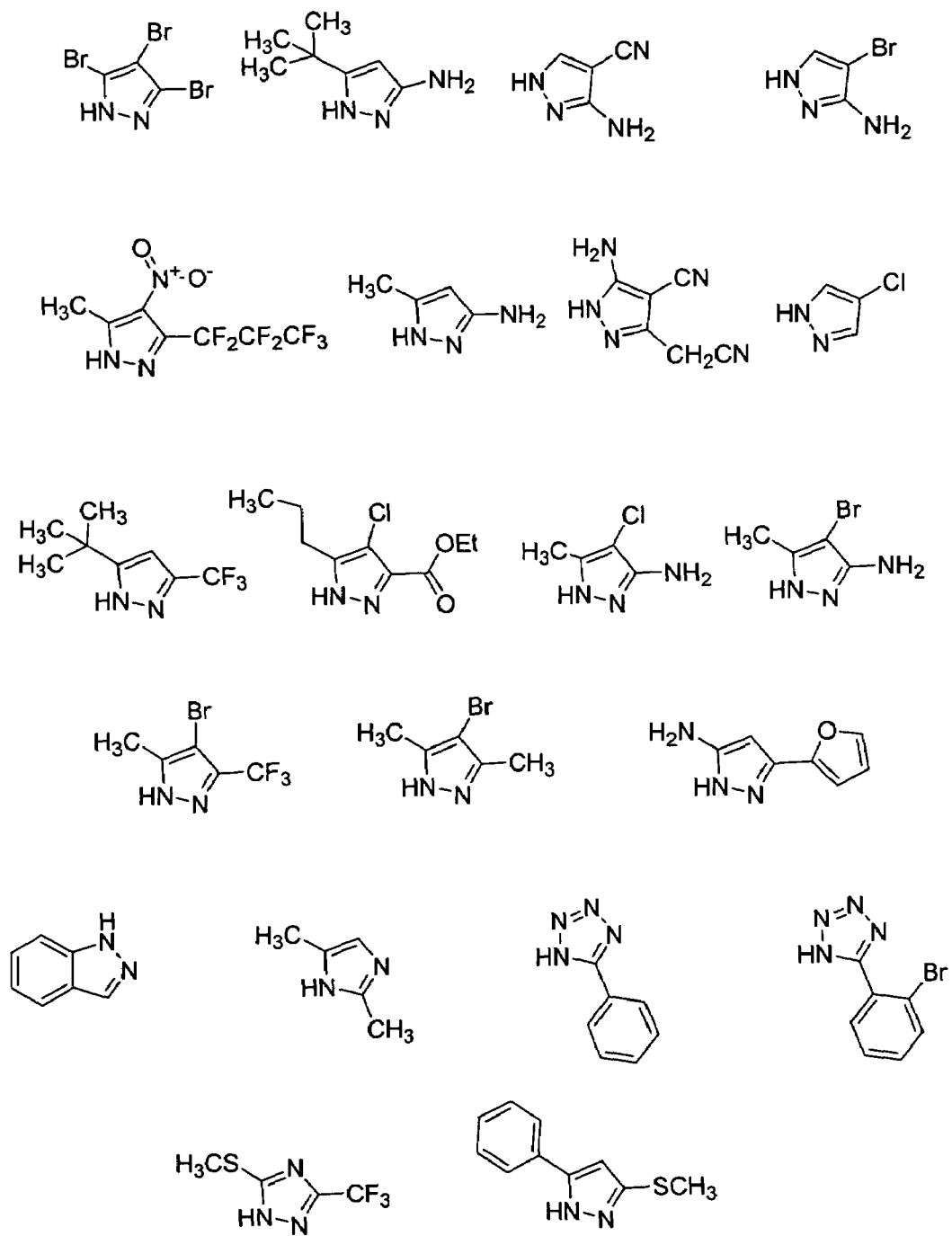
Figure 4C:
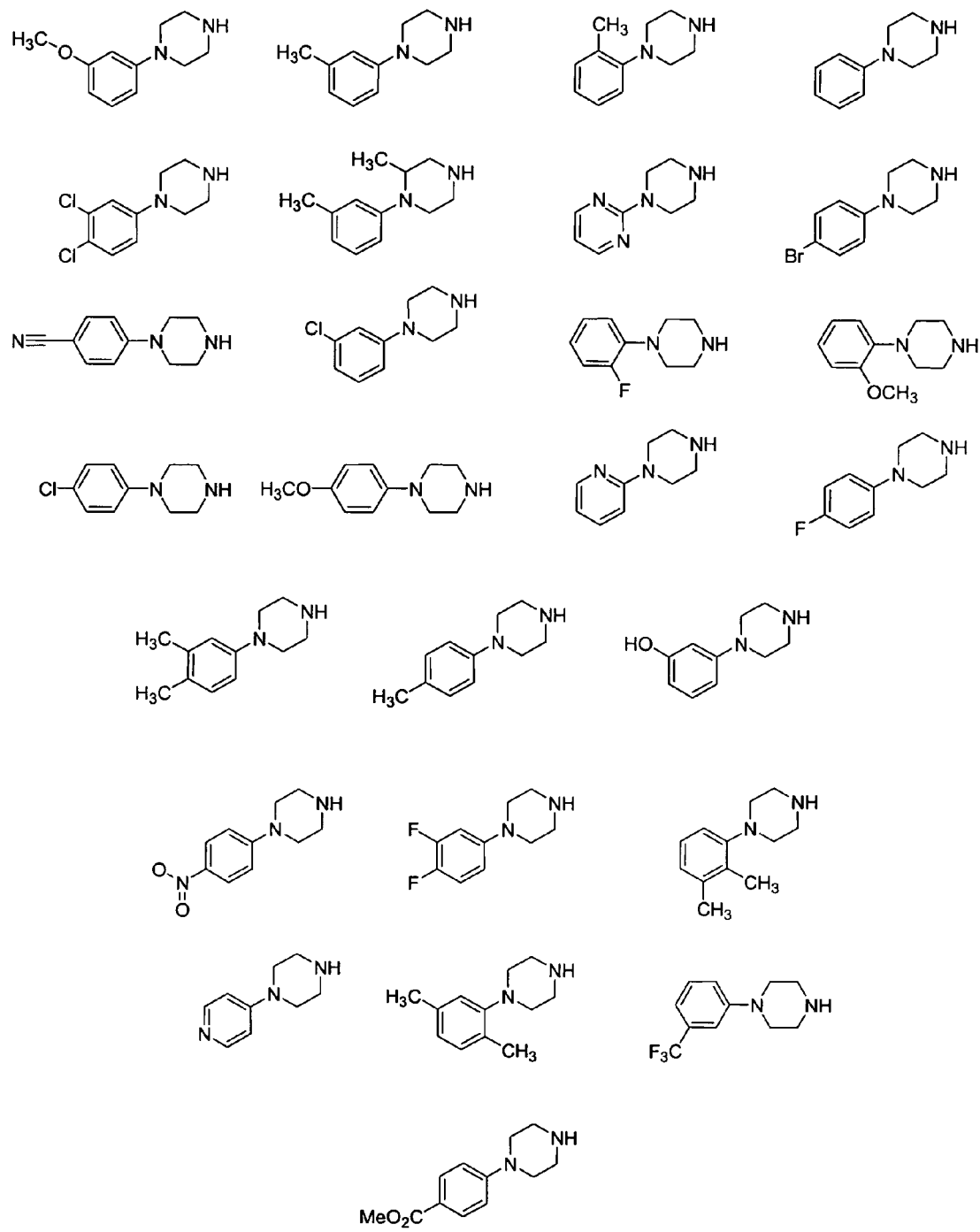

Compounds within the scope of this invention can be synthesized as described below, using a variety of reactions known to the skilled artisan. Certain pyrazole precursors can be obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals. Some examples of these commercially available compounds are shown in the FIGS. 3A-3B.

One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

Regioisomerism is a common property in organic chemistry, and is especially common with regards to certain structural types provided herein. Those skilled in the art will recognize, with respect to the compounds described herein, that the coupling reactions with the heteroaromatic ring systems can lead to either one of or a mixture of detectable regioisomers.

The detailed description of the experimental procedures used to synthesize key compounds in this text lead to molecules that are described by the physical data identifying them as well as by the structural depictions associated with them.

Two regioisomers can sometimes exist for certain compounds of the invention. For example, compounds such as those of formula III can be prepared wherein a pyrazole moiety is linked to the remainder of the molecule via either of the nitrogen atoms in the pyrazole ring. In these cases, both regioisomeric types have demonstrated biological properties and are meant to be within the scope of all the appended claims, whether explicitly drawn or not.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

This example illustrates the preparation of 1-[5-(4-Chloro-3-methoxy-benzyl)hexahydropyrrolo[3,4-c]pyrrol-2-yl]-2-

(4-chloro-5-methyl-3-trifluoromethylpyrazol-1-yl)ethanone, as an example of the compounds of formula IB.

1) Preparation of 2,5-Dibenzyltetrahydropyrrolo[3,4-c]pyrrole-1,3-dione (1)

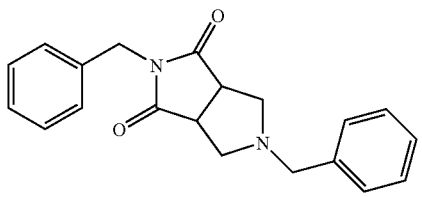

1

A mixture of paraformaldehyde (3.37 g), N-benzylmaleimide (2.80 g) and N-benzylglycine hydrochloride (3.02 g) in toluene (100 mL) was heated to reflux with azeotropic removal of water for 16 hours. The mixture was cooled to room temperature, filtered and concentrated in vacuo. The residue was purified by flash chromatography (20% EtOAc/hexane) to afford the title compound 1 as a low melting white solid (3.60 g, 75%). LCMS: $R_f$: 2.616 min, M+H$^+$: 321.

2) Preparation of 2-Benzyltetrahydropyrrolo[3,4-c]pyrrole-1,3-dione (2)

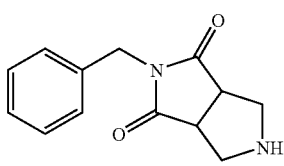

2

1-Chloroethylchloroformate (3.24 mL) was added dropwise to a solution of compound 1 (5.22 g) in dichloromethane (75 mL) at 0° C. The solution was then heated to reflux for 3 hours, cooled to room temperature and concentrated in vacuo. The residue was then dissolved in methanol (75 mL) and heated to reflux for another 3 hours. The mixture was cooled to 0° C. and ether (200 mL) was added. Filtration afforded the title compound 2 as a white solid (3.38 g, 90%). LCMS: $R_f$: 0.380 min, M+H$^+$: 231.

3) Preparation of 2-Benzyloctahydropyrrolo[3,4-c]pyrrole (3)

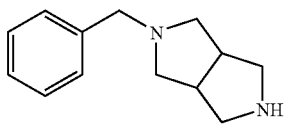

3

A solution of lithium aluminum hydride (15.0 mL, 1.0 M solution in ether) was added dropwise to a solution of compound 2 (1.15 g) in THF (50 mL) and dichloromethane (40 mL) at 0° C. The reaction mixture was stirred an additional 1.5 hour at 0° C. and water (0.5 mL) was added followed by the addition of aqueous NaOH solution (0.5 mL, 20%) and then water (1.5 mL). The resulting solids was filtered off and the filtrate was concentrated in vacuo. The residue was purified by flash chromatography to provide the title compound 3 as a pale yellow oil (0.93 g, 92%). LCMS: $R_f$: 0.368 min, M+H$^+$: 203.

4) Preparation of 5-Benzylhexahydropyrrolo[3,4-c]pyrrole-2-carboxylic acid tert-butyl ester (4)

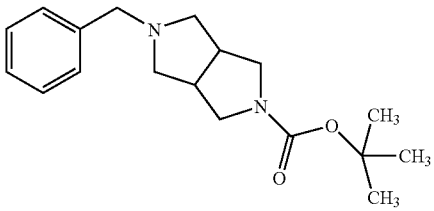

4

Boc-anhydride (0.28 mL) was added in one portion to a solution of compound 3 in dichloromethane (4 mL) at room temperature. The mixture was stirred overnight at room temperature and concentrated in vacuo. The residue was purified by preparative HPLC to provide title compound 4 as a pale yellow oil (130 mg, 43%). LCMS: $R_f$: 0.613 min, M+H$^+$: 303.

5) Preparation of Hexahydropyrrolo[3,4-c]pyrrole-2-carboxylic acid tert-butyl ester (5)

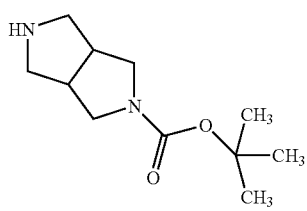

5

A mixture of compound 4 (130 mg), Pd/C (100 mg, 10%) and ammonium formate (160 mg) in ethanol (10 mL) was heated to reflux for 2 hours and then allowed to cool to room temperature. The solid was filtered off and the filtrate was concentrated in vacuo. The residue was purified by preparative HPLC to provide title compound 5 as a pale yellow oil (76 mg, 84%). LCMS: $R_f$: 0.371 min, M+H$^+$: 213.

6) Preparation of 5-[2-(4-Chloro-5-methyl-3-trifluoromethylpyrazol-1-yl)acetyl]-hexahydropyrrolo[3,4-c]-pyrrole-2-carboxylic acid tert-butyl ester (6)

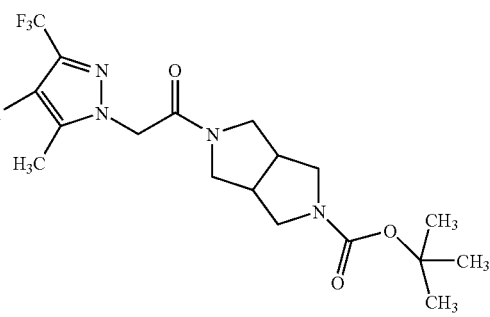

6

A solution of(4-Chloro-5-methyl-3-trifluoromethylpyrazol-1-yl)acetic acid (97 mg), triethylamine (0.2 mL) and compound 5 (76 mg) in DMF (2 mL) was stirred at 0° C. and 1-propanephosphonic acid cyclic anhydride (0.55 mL, 50% in EtOAc) was added dropwise. The reaction mixture was stirred another 30 min at 0° C. and directly purified by preparative HPLC to provide the title compound 6 as a pale yellow oil (146 mg, 93%). LCMS: $R_f$: 4.495 min, M+H$^+$: 459.

7) 2-(4-Chloro-5-methyl-3-trifluoromethylpyrazol-1-yl)-1-(hexahydropyrrolo[3,4 c]-pyrrol-2-yl)ethanone (7)

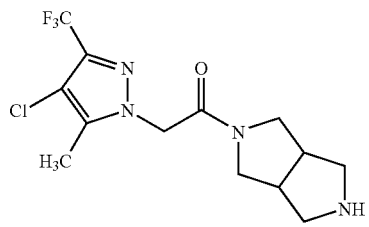

A mixture of compound 6 (146 mg) and trifluoroacetic acid (2 mL) was stirred at room temperature for 30 min and concentrated in vacuo to provide the title compound 7 as a pale yellow oil (111 mg, 99%). LCMS: R$_f$: 0.612 min, M+H$^+$: 303.

8) 1-[5-(4-Chloro-3-methoxy-benzyl)hexahydropyrrolo[3,4-c]pyrrol-2-yl]-2-(4-chloro-5-methyl-3-trifluoromethylpyrazol-1-yl)ethanone (8)

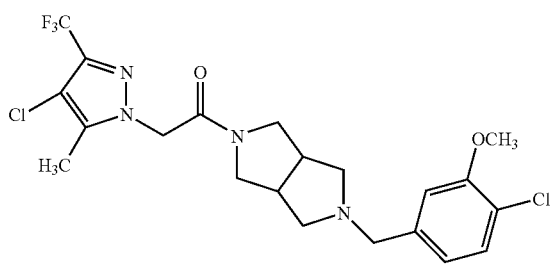

A solution of 4-chloro-3-methoxybenzaldehyde (34 mg) and compound 7 (35 mg) in THF (1 mL) was stirred at room temperature for 1 hour and then sodium triacetoxyborohydride (85 mg) was added in one portion. The mixture was stirred at room temperature for another hour and EtOAc (1 mL) was added followed by the addition of saturated aqueous ammonium chloride (1 mL). The aqueous phase was extracted by EtOAc (3×1 mL) and the combined organic extractants was dried, filtered and concentrated in vacuo. The residue was purified by preparative HPLC to afford the title compound 8 as a white solid (36 mg, 95%). LCMS: R$_f$: 3.460 min, M+H$^+$: 491.

Example 2

This example illustrates the preparation of 2-(4-Chloro-5-methyl-3-trifluoromethyl-pyrazol-1-yl)-1-[5-(2,4-dichloro-benzyl)-hexahydropyrrolo[3,4-c]pyrrol-2-yl]ethanone, as another example of the compounds of formula IB.

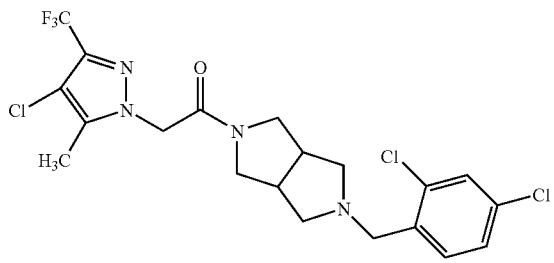

2-(4-Chloro-5-methyl-3-trifluoromethyl-pyrazol-1-yl)-1-[5-(2,4-dichloro-benzyl)-hexahydropyrrolo[3,4-c]pyrrol-2-yl]ethanone (9)

A solution of 2,4-dichlorobenzaldehyde (18 mg) and compound 7 (17 mg) in THF (1 mL) was stirred at room temperature for 1 hour and then sodium triacetoxyborohydride (42 mg) was added in one portion. The mixture was stirred at room temperature for another hour and EtOAc (1 mL) was added followed by the addition of saturated aqueous ammonium chloride (1 mL). The aqueous phase was extracted by EtOAc (3×1 mL) and the combined organic extractants was dried, filtered and concentrated in vacuo. The residue was purified by preparative HPLC to afford the title compound 9 as a white solid (15 mg, 80%). LCMS: R$_f$: 3.605 min, M+H$^+$: 495.

Example 3

This example illustrates the preparation of 2-(4-Chloro-5-methyl-3-trifluoromethylpyrazol-1-yl)-1-[5-(2,4-dimethyl-benzyl)-hexahydropyrrolo[3,4-c]pyrrol-2-yl]ethanone, as another example of the compounds of formula IB.

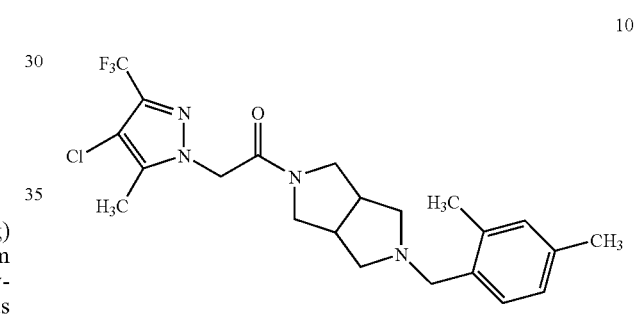

2-(4-Chloro-5-methyl-3-trifluoromethylpyrazol-1-yl)-1-[5-(2,4-dimethylbenzyl)-hexahydropyrrolo[3,4-c]pyrrol-2-yl]ethanone (10)

A solution of 2,4-dimethylbenzaldehyde (14 μL) and compound 7 (17 mg) in THF (1 mL) was stirred at room temperature for 1 hour and then sodium triacetoxyborohydride (42 mg) was added in one portion. The mixture was stirred at room temperature for another hour and EtOAc (1 mL) was added followed by the addition of saturated aqueous ammonium chloride (1 mL). The aqueous phase was extracted by EtOAc (3×1 mL) and the combined organic extracts were dried, filtered and concentrated in vacuo. The residue was purified by preparative HPLC to afford the title compound 9 as a white solid (16 mg, 86%). LCMS: R$_f$: 3.552 min, M+H$^+$: 455.

Example 4

This example illustrates the synthesis of 1-{5-[1-(4-Chloro-3-methoxyphenyl)ethyl]hexahydro-pyrrolo[3,4-c]pyrrol-2-yl}-2-(4-chloro-5-methyl-3-trifluoromethylpyrazol-1-yl)ethanone.

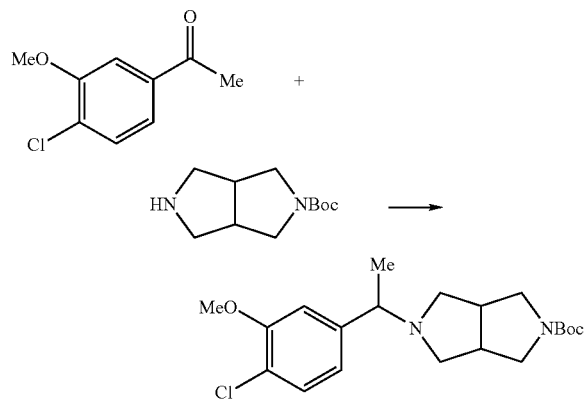

A solution of 4-chloro-3-methoxybenzoketone (220 mg), hexahydropyrrolo[3,4-c]pyrrole-2-carboxylic acid tert-butyl ester (212 mg) in THF (5 mL) was stirred at room temperature for 1 h followed by the addition of NaBH(OAc)$_3$ (818 mg). The reaction was stirred another 2 h and aqueous NaHCO$_3$ solution (5 mL) was added followed by the addition of EtOAc(5 mL). The organic layer was separated and the aqueous phase was extracted with EtOAc (3×5 mL). The combined organic layer was dried (Na$_2$SO$_4$), filtered and evaporated in vacuo. The crude material was carried on without further purification.

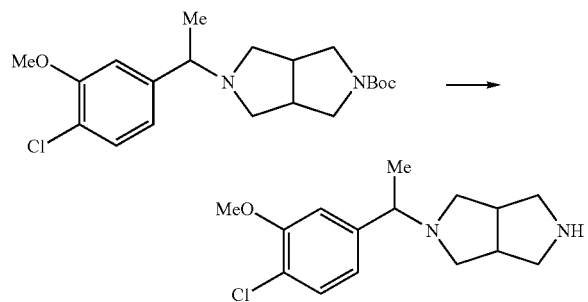

To a solution of crude material from the above reaction in CH$_2$Cl$_2$ (10 mL) was slowly added trifluoacetic acid (5 mL). The mixture was stirred at room temperature for 30 minutes and evaporated in vacuo. The resulting crude was dissolved in methanol (0.2 mL) and a solution of hexanes and ether (1:1, 5 mL) was slowly added. The resulting precipitate was filtered and dried to give the title compound as a TFA salt.

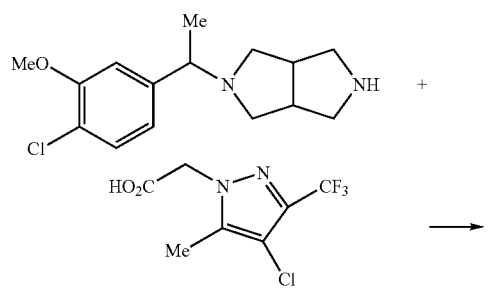

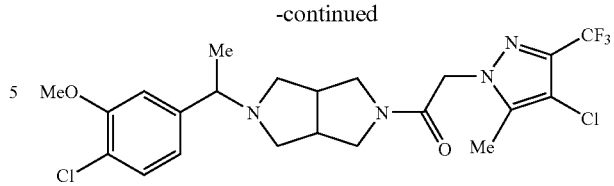

A solution of the above TFA salt (116 mg), (4-Chloro-5-methyl-3-trifluoromethyl-pyrazol-1-yl)acetic acid (48.2 mg), triethylamine (0.12 mL) in acetonitrile (1 mL) was stirring at room temperature and a solution of T3P (50% in EtOAc, 0.30 mL) was slowly added. The reaction mixture was then heated up to 60° C. for 1 h and cooled to room temperature and purified on preparative HPLC to afford the title compound. LCMS (ES) M+H 505.4. Retention time: 4.25 minutes (Agilent Zorbax SB-C18, 2.1×50 mm, 5μ, 35° C.) using a 4.5 minutes gradient of 20% to 95% B with a 1.1 minutes wash at 95% B (A=0.1% formic acid/5% acetonitrile/94.9% water, B=0.1% formic acid/99.9% acetonitrile).

Example 5

This example illustrates the synthesis of 1-[5-(4-Chloro-3-methoxyphenyl)hexahydropyrrolo[3,4-c]pyrrol-2-yl]-2-(4-chloro-5-methyl-3-trifluoromethylpyrazol-1-yl)ethanone.

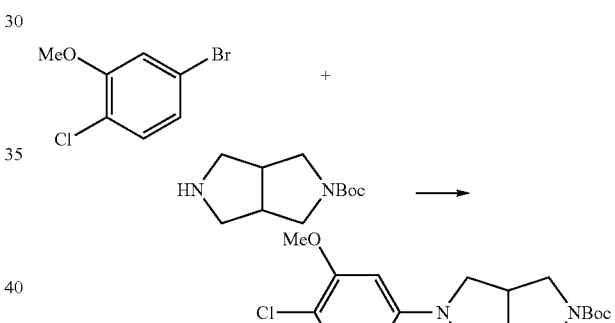

A solution of 4-bromo-2-chloroanisole (240 mg), hexahydropyrrolo[3,4-c]pyrrole-2-carboxylic acid tert-butyl ester (212 mg), sodium tert-butoxide (135 mg), BINAP (2 mg), Pd$_2$(dba)$_3$ (2 mg) in toluene (5 mL) was heated to 90° C. for 12 h, cooled to room temperature and evaporated in vacuo. The crude was dissolved in EtOAc (10 mL) and washed by aqueous HCl solution (1M, 1 mL), saturated aqueous NaCl solution (1 mL) and saturated aqueous NaHCO$_3$ solution (1 mL). The organic phase was dried (Na$_2$SO$_4$), filtered and evaporated in vacuo. The crude was used as it was.

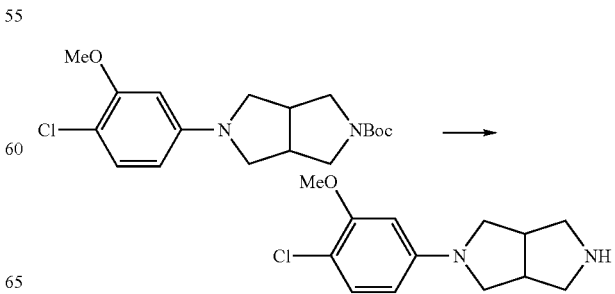

A solution of crude of the above reaction in CH₂Cl₂ (10 mL) was slowly added trifluoacetic acid (5 mL). The mixture was stirred at room temperature for 30 minutes and evaporated in vacuo. The crude was dissolved in methanol (0.2 mL) and a solution of hexanes and ether (1:1, 5 mL) was slowly added. The resulting precipitate was filtered and dried to give the title compound as a TFA salt.

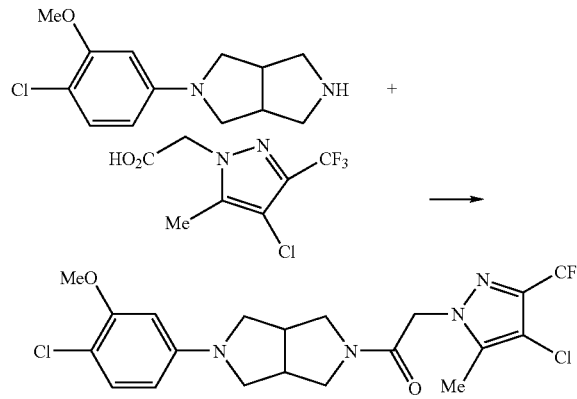

A solution of the above TFA salt (106 mg), (4-Chloro-5-methyl-3-trifluoromethyl-pyrazol-1-yl)acetic acid (48 mg), triethylamine (0.12 mL) in acetonitrile (1 mL) was stirring at room temperature and a solution of T3P (50% in EtOAc, 0.30 mL) was slowly added. The reaction mixture was then heated up to 60° C. for 1 h and cooled to room temperature and purified on preparative HPLC to afford the title compound. LCMS (ES) M+H 477.7. Retention time: 4.89 minutes (Agilent Zorbax SB-C18, 2.1×50 mm, 5μ, 35° C.) using a 4.5 minutes gradient of 20% to 95% B with a 1.1 minutes wash at 95% B (A=0.1% formic acid/5% acetonitrile/94.9% water, B=0.1% formic acid/99.9% acetonitrile).

Example 6

This example illustrates the synthesis of 2-(4-Chloro-3-methoxy-phenyl)-8-[2-(4-chloro-5-methyl-3-trifluoromethyl-pyrazol-1-yl)-acetyl]-2,8-diaza-spiro[4.5]decan-1-one.

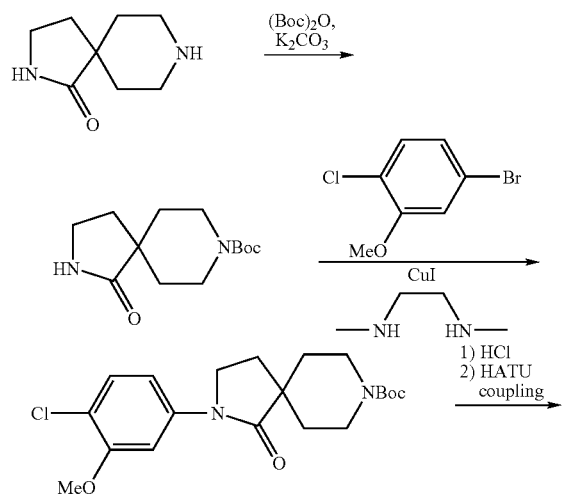

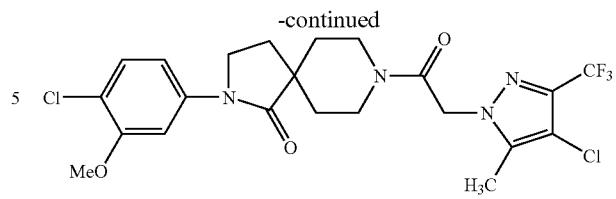

To a solution of 2,8-diaza-spiro[4.5]decan-1-one hydrochloride (763 mg, 4 mmol, 1 equiv) in 10 mL of 1:1 THF and water was added (Boc)₂O (960 mg, 1.1 equiv). The pH of the solution was adjusted to ~10 by addition of K₂CO₃. Upon completion, the mixture was extraction with EtOAc. Organic layer was dried over sodium sulfate, filtered, and evaporated to give 1-oxo-2,8-diaza-spiro[4.5]decane-8-carboxylic acid tert-butyl ester.

A mixture of 1-oxo-2,8-diaza-spiro[4.5]decane-8-carboxylic acid tert-butyl ester (127 mg, 0.5 mmol, 1 equiv), 4-bromo-1-chloro-2-methoxy-benzene (221 mg, 2equiv), N,N-dimethylethylenediamine (14 mg, 0.3 equiv), CuI (29 mg, 0.3 equiv) and Cs₂CO₃ (325 mg, 2 equiv) in 1 mL of dioxane were heated at 110° C. overnight and then cooled to room temperature, taken up in a 1:1 mixture of methanol and EtOAc, filtered through a thin pad of celite and concentrated. The crude product was purified by flash column to give 2-(4-Chloro-3-methoxy-phenyl)-1-oxo-2,8-diaza-spiro[4.5]decane-8-carboxylic acid tert-butyl ester.

2-(4-Chloro-3-methoxy-phenyl)-1-oxo-2,8-diaza-spiro[4.5]decane-8-carboxylic acid tert-butyl ester (39.5 mg, 0.1 mmol, 1 equiv) was treated with 4 mL of 4N HCl in dioxane at rt for 1 h. The volatile was removed and to the residue were added 1 mL of DMF, (4-Chloro-5-methyl-3-trifluoromethyl-pyrazol-1-yl)-acetic acid (24.3 mg, 1 equiv), HATU (42 mg, 1.1 equiv), TEA (50 μL, 3 equiv). After stirring at rt over night, the mixture was taken up in EtOAc, washed with saturated sodium NaHCO₃. Purification by reverse phase HPLC (acetonitrile-H₂O with 0.1% TFA as eluent) gave 2-(4-Chloro-3-methoxy-phenyl)-8-[2-(4-chloro-5-methyl-3-trifluoromethyl-pyrazol-1-yl)-acetyl]-2,8-diaza-spiro[4.5]decan-1-one. LCMS observed for (M+H)⁺: 519. Retention time: 4.75 minutes (Agilent Zorbax SB-C18, 2.1×50 mm, 5μ, 35° C.) using a 4.5 minutes gradient of 20% to 95% B with a 1.1 minutes wash at 95% B (A=0.1 % formic acid/5% acetonitrile/94.9% water, B=0.1 % formic acid/99.9% acetonitrile).

Example 7

This example illustrates the synthesis of 1-[2-(4-Chloro-3-methoxy-phenyl)-2,8-diaza-spiro[4.5]dec-8-yl]-2-(4-chloro-5-methyl-3-trifluoromethyl-pyrazol-1-yl)-ethanone.

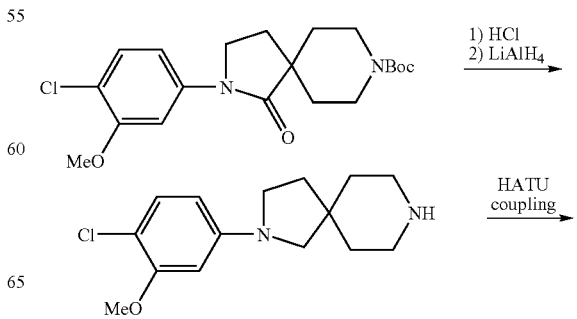

-continued

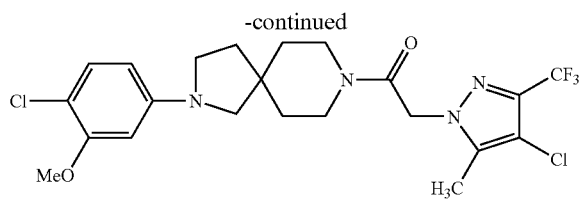

2-(4-Chloro-3-methoxy-phenyl)-1-oxo-2,8-diaza-spiro[4.5]decane-8-carboxylic acid tert-butyl ester (90 mg, 1 equiv) was treated with 4 mL of 4N HCl in dioxane at rt for 1 h. The volatile was removed and to the residue were added 3 mL of THF and 3 mL of dichloromethane. After cooling to 0° C., the solution was treated with 2 mL of 1M LiAlH$_4$ in THF over night (allowed to warm to room temperature). 10 drops of water, 10 drops of 1N NaOH, and then 10 drops of water were added. The organic layer was collected and dried under vacuum. The residue was taken up in 1 mL of DMF, and to the solution were added (4-Chloro-5-methyl-3-trifluoromethyl-pyrazol-1-yl)-acetic acid (55 mg, 1 equiv), HATU (95 mg, 1.1 equiv), TEA (150 μL, 3 equiv). After stirring at rt over night, the mixture was taken up in EtOAc, washed with saturated sodium NaHCO$_3$. Purification by reverse phase HPLC (acetonitrile-H$_2$O with 0.1% TFA as eluent) gave 1-[2-(4-Chloro-3-methoxy-phenyl)-2,8-diaza-spiro[4.5]dec-8-yl]-2-(4-chloro-5-methyl-3-trifluoromethyl-pyrazol-1-yl)-ethanone. LCMS observed for (M+H)+: 505. Retention time: 5.28 minutes (Agilent Zorbax SB-C18, 2.1×50 mm, 5μ, 35° C.) using a 4.5 minutes gradient of 20% to 95% B with a 1.1 minutes wash at 95% B (A=0.1% formic acid/5% acetonitrile/94.9% water, B=0.1% formic acid/99.9% acetonitrile).

Example 8

This example illustrates the synthesis of 1-[5-(4-Chloro-3-methoxybenzyl)-2,5-diazabicyclo[2.2.1]hept-2-yl]-2-(4-chloro-5-methyl-3-trifluoromethylpyrazol-1-yl)ethanone.

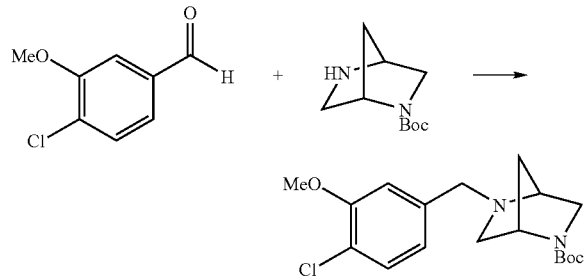

A solution of 4-chloro-3-methoxybenzaldehyde (170 mg) and 2,5-Diazabicyclo[2.2.1]heptane-2-carboxylic acid tert-butyl ester (35 mg) in THF (5 mL) was stirred at room temperature for 1 hour and then sodium triacetoxyborohydride (212 mg) was added in one portion. The mixture was stirred at room temperature for another hour and EtOAc (5 mL) was added followed by the addition of saturated aqueous ammonium chloride (1 mL). The aqueous phase was extracted by EtOAc (3×1 mL) and the combined organic extractants was dried, filtered and concentrated in vacuo. The reaction crude was used as it was.

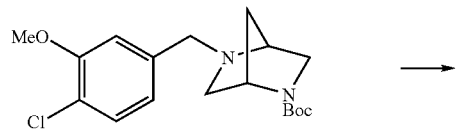

-continued

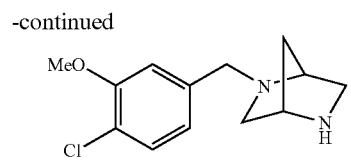

To a solution of crude of the above reaction in CH$_2$Cl$_2$ (3 mL) was slowly added trifluoacetic acid (3 mL). The mixture was stirred at room temperature for 30 minutes and evaporated in vacuo. The residue was purified on preparative HPLC to give 2-(4-Chloro-3-methoxybenzyl)-2,5-diazabicyclo[2.2.1]heptane.

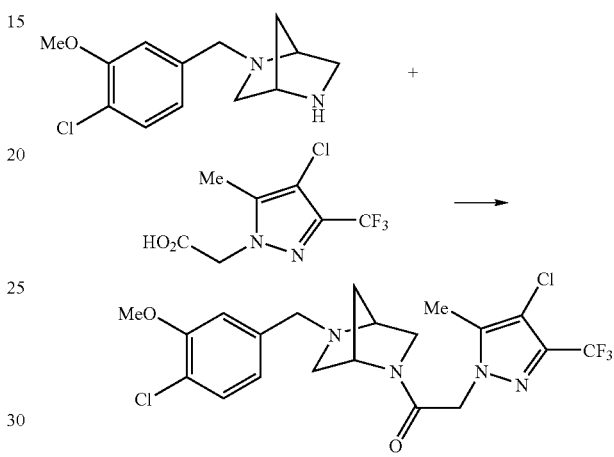

A solution of 2-(4-Chloro-3-methoxybenzyl)-2,5-diazabicyclo[2.2.1]heptane (96 mg), (4-Chloro-5-methyl-3-trifluoromethyl-pyrazol-1-yl)acetic acid (96.8 mg), triethylamine (0.252 mL) in DMF (2 mL) was stirring at room temperature and a solution of T3P (50% in EtOAc, 0.55 mL) was slowly added. The reaction mixture was stirred at room temperature for 1 h and purified on preparative HPLC to afford 1-[5-(4-Chloro-3-methoxybenzyl)-2,5-diazabicyclo[2.2.1]hept-2-yl]-2-(4-chloro-5-methyl-3-trifluoromethylpyrazol-1-yl)ethanone as white powder. LCMS (ES) M+H 477.0, R$_f$ 3.975 min (acetonitrile/H$_2$O 20-95% method).

Example 9

The following example illustrates the synthesis of 1-[5-(4-Chloro-3-methoxyphenyl)hexahydropyrrolo[3,4-c]pyrrol-2-yl]-2-(4-chloro-5-methyl-3-pyrimidin-2-ylpyrazol-1-yl)ethanone.

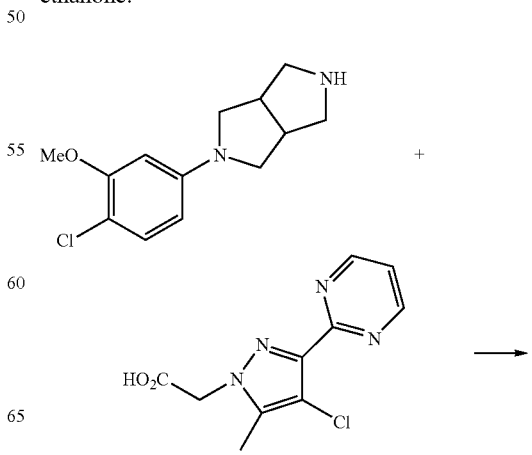

-continued

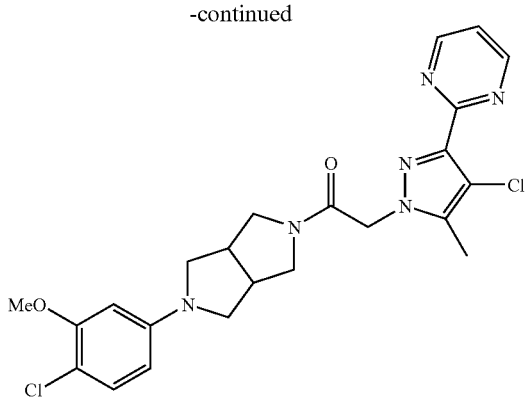

The title compound was synthesized according to procedures in Example 5: LCMS (ES) M+H 487.5, $R_f$ 2.256 min (Agilent Zorbax SB-C18, 2.1×50 mm, 5µ, 35° C., 1 ml/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 10

The following example illustrates the synthesis of 1-[5-(4-Chloro-3-methoxyphenyl)hexahydropyrrolo[3,4-c]pyrrol-2-yl]-2-(4-chloro-5-methyl-3-oxazol-2-ylpyrazol-1-yl)ethanone.

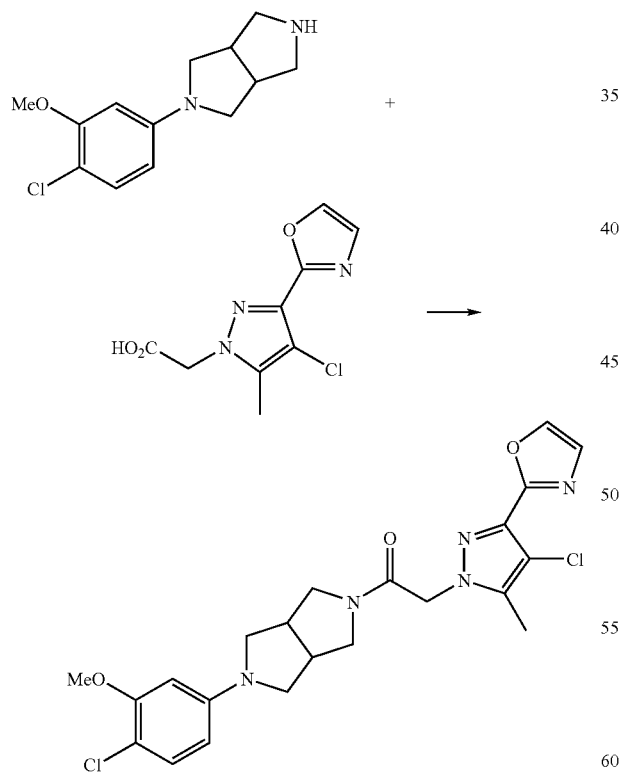

The title compound was synthesized according to procedures in Example 5: LCMS (ES) M+H 476.5, $R_f$ 2.446 min (Agilent Zorbax SB-C18, 2.1×50 mm, 5µ, 35° C., 1 ml/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 11

The following example illustrates the synthesis of 1-[5-(4-Chloro-3-methoxyphenyl)hexahydropyrrolo[3,4-c]pyrrol-2-yl]-2-pyrazolo[3,4-b]pyridin-1-ylethanone.

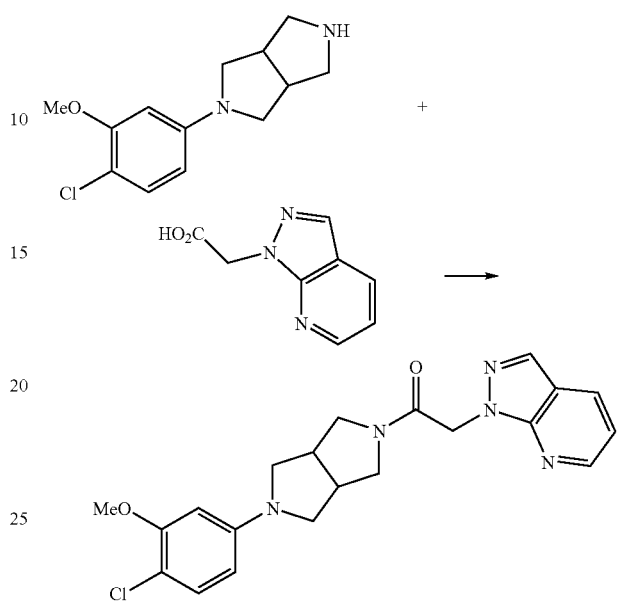

The title compound was synthesized according to procedures in Example 5: LCMS (ES) M+H 412.5, $R_f$ 2.265 min (Agilent Zorbax SB-C18, 2.1×50 mm, 5µ, 35° C., 1 ml/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 12

The following example illustrates the synthesis of 1-[5-(4-Chloro-3-methoxybenzoyl)hexahydropyrrolo[3,4-c]pyrrol-2-yl]-2-(4-chloro-5-methyl-3-trifluoromethylpyrazol-1-yl)ethanone.

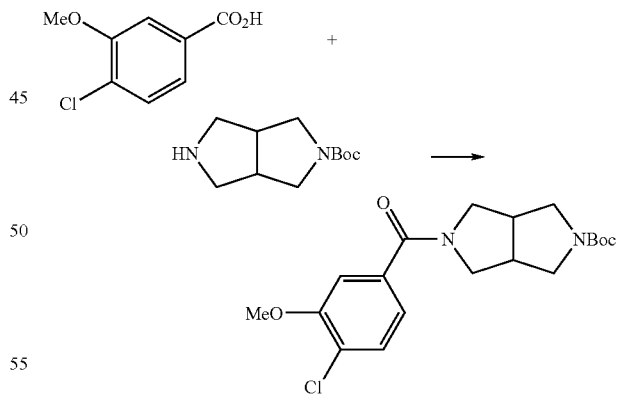

A solution of 4-chloro-3-methoxybenzoic acid (93 mg), hexahydropyrrolo[3,4-c]pyrrole-2-carboxylic acid tert-butyl ester (150 mg), triethylamine (0.42 mL) in DMF (2.5 mL) was stirred at room temperature and to it was slowly added a solution of T3P [please provide full chemical name] (50% in EtOAc, 0.50 mL). The reaction mixture was stirred at room temperature for an additional 30 min and then diluted with ether (10 mL). The reaction solution was washed with water (10 mL) and brine (3 mL). The organic layer was dried over sodium sulfate ($Na_2SO_4$), filtered and evaporated in vacuo. The crude residue was used without further purification.

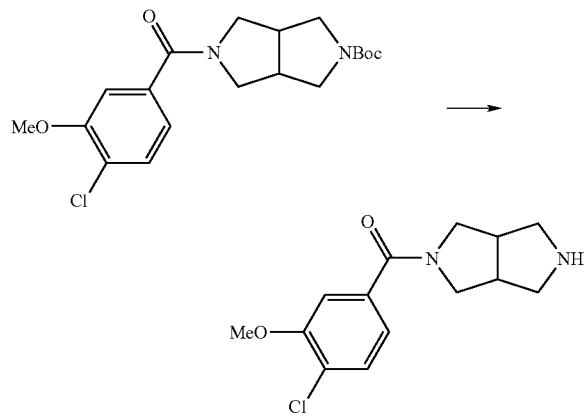

The above residue was dissolved in CH$_2$Cl$_2$ (7 mL) and to it was added trifluoroacetic acid (3 mL). The resultant mixture was stirred at room temperature for another 30 min and then evaporated in vacuo. The crude residue was used without further purification.

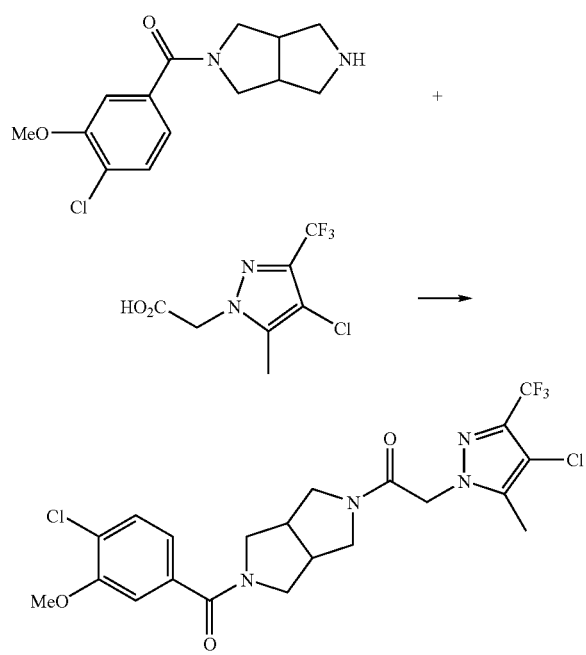

The title compound was synthesized by following the peptide coupling conditions described above for this example: LCMS (ES) M+H 505.5, R$_f$ 2.265 min (Agilent Zorbax SB-C18, 2.1×50 mm, 5μ, 35° C., 1 ml/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 13

The following example illustrates the synthesis of 1-[5-(4-Chlorobenzoyl)hexahydropyrrolo[3,4-c]pyrrol-2-yl]-2-(4-chloro-5-methyl-3-trifluoromethylpyrazol-1-yl)ethanone.

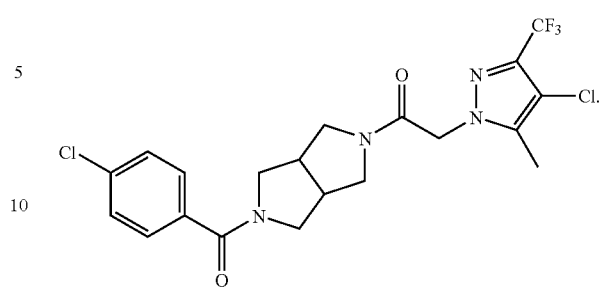

The title compound was synthesized according to procedures in Example 12: LCMS (ES) M+H 475.5, R$_f$ 2.396 min (Agilent Zorbax SB-C18, 2.1×50 mm, 5μ, 35° C., 1 ml/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 14

The following example illustrates the synthesis of 1-[5-(4-Chlorobenzenesulfonyl)hexahydropyrrolo[3,4-c]pyrrol-2-yl]-2-(4-chloro-5-methyl-3-trifluoromethylpyrazol-1-yl)ethanone.

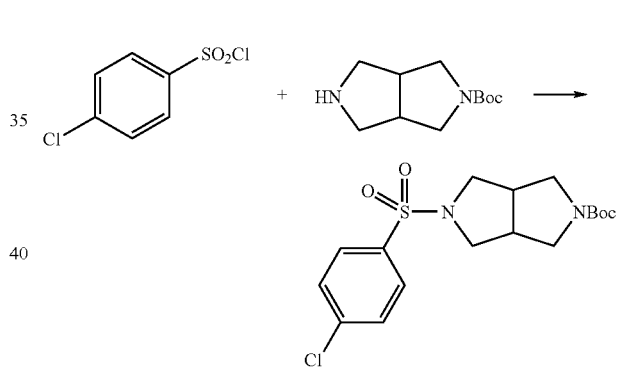

A solution of 4-chlorobenzenesulfonyl chloride (105 mg), hexahydropyrrolo[3,4-c]pyrrole-2-carboxylic acid tert-butyl ester (150 mg), pyridine (0.4 mL) in DMF (2.5 mL) was stirred at room temperature for 30 min then diluted with ether (10 mL). The reaction solution was washed with water (10 mL) and brine (3 mL). The organic layer was dried over sodium sulfate (Na$_2$SO$_4$), filtered and evaporated in vacuo. The crude residue was used without further purification.

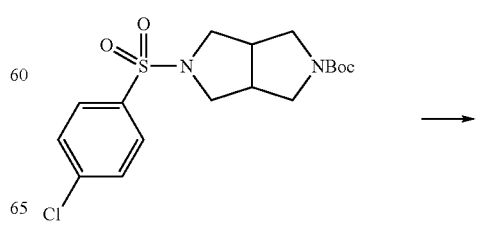

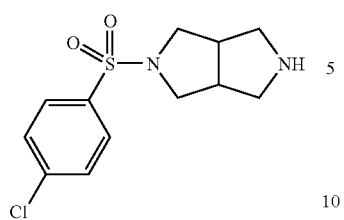

The above residue was dissolved in CH$_2$Cl$_2$ (7 mL) and trifluoroacetic acid (3 mL) was added. The reaction mixture was stirred at room temperature for another 30 min and evaporated in vacuo. The crude residue was used without further purification.

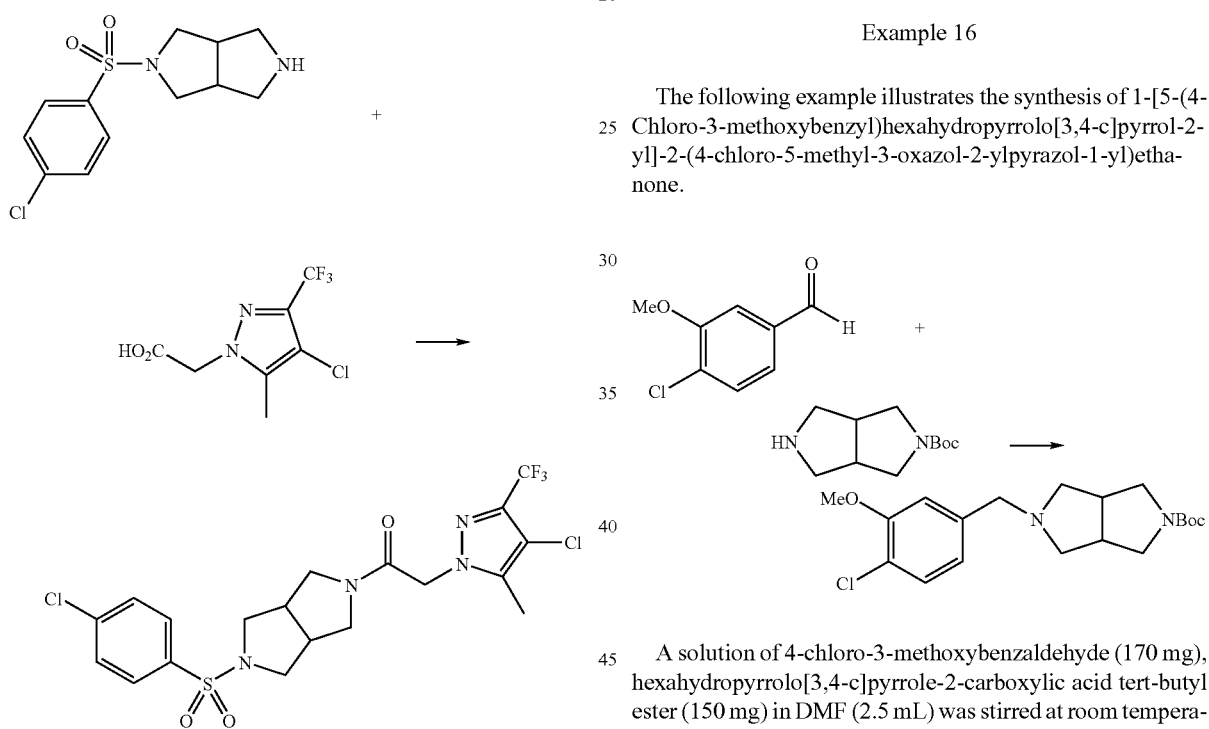

The title compound was synthesized by following the peptide coupling conditions in Example 11: LCMS (ES) M+H 511.4, R$_f$ 2.650 min (Agilent Zorbax SB-C18, 2.1×50 mm, 5μ, 35° C., 1 ml/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 15

The following example illustrates the synthesis of 1-[5-(4-Fluorobenzenesulfonyl)hexahydropyrrolo[3,4-c]pyrrol-2-yl]-2-(4-chloro-5-methyl-3-trifluoromethylpyrazol-1-yl)ethanone.

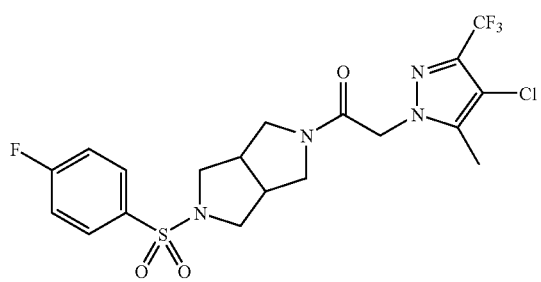

The title compound was synthesized according to procedures in Example 14: LCMS (ES) M+H 495.5, R$_f$ 2.749 min (Agilent Zorbax SB-C18, 2.1×50 mm, 5μ, 35° C., 1 ml/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 16

The following example illustrates the synthesis of 1-[5-(4-Chloro-3-methoxybenzyl)hexahydropyrrolo[3,4-c]pyrrol-2-yl]-2-(4-chloro-5-methyl-3-oxazol-2-ylpyrazol-1-yl)ethanone.

A solution of 4-chloro-3-methoxybenzaldehyde (170 mg), hexahydropyrrolo[3,4-c]pyrrole-2-carboxylic acid tert-butyl ester (150 mg) in DMF (2.5 mL) was stirred at room temperature for 1 hour followed by the addition of NaBH(OAc)$_3$ (1.05 g). The reaction was stirred another 2 hours and aqueous NaHCO$_3$ solution (5 mL) was added followed by the addition of ether (10 mL). The organic layer was dried (Na$_2$SO$_4$), filtered and evaporated in vacuo. The crude residue was used without further purification.

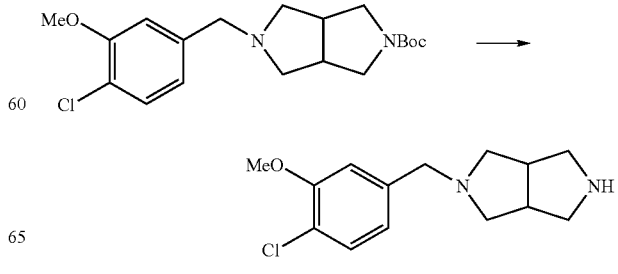

To a solution of the crude residue from the above reaction in CH$_2$Cl$_2$ (10 mL) was slowly added trifluoroacetic acid (5 mL). The mixture was stirred at room temperature for 30 minutes and evaporated in vacuo. The crude residue was used without further purification.

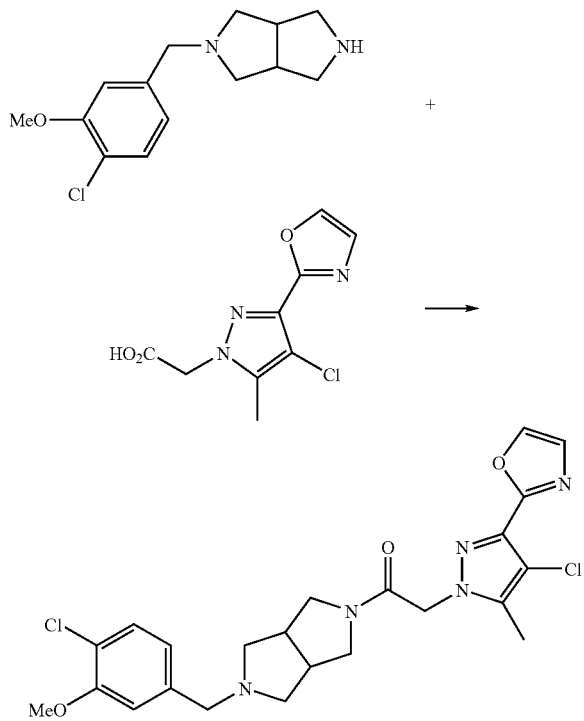

The title compound was synthesized according to peptide coupling procedures in Example 13: LCMS (ES) M+H 490.5, R$_f$ 1.010 min (Agilent Zorbax SB-C18, 2.1×50 mm, 5μ, 35° C., 1 ml/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 17

Materials and Methods for Evaluation of Compounds

A. Cells
  CCR1 Expressing Cells
  a. THP-1 Cells

THP-1 cells were obtained from ATCC and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% CO$_2$/95% air, 100% humidity at 37° C. and subcultured twice weekly at 1:5 and harvested at 1×10$^6$ cells/mL. THP-1 cells express CCR1 and can be used in CCR1 binding and functional assays.
  b. Isolated Human Monocytes Monocytes were isolated from human buffy coats using the Miltenyi bead isolation system (Miltenyi, Auburn, Calif.). Briefly, following a Ficoll gradient separation to isolate peripheral blood mononuclear cells, cells were washed with PBS and the red blood cells lysed using standard procedures. Remaining cells were labeled with anti-CD14 antibodies coupled to magnetic beads (Miltenyi Biotech, Auburn, Calif.). Labeled cells were passed through AutoMACS (Miltenyi, Auburn, Calif.) and positive fraction collected. Monocytes express CCR1 and can be used in CCR1 binding and functional assays.

B. Assays
  Inhibition of CCR1 Ligand Binding

CCR1 expressing cells were centrifuged and resuspended in assay buffer (20 mM HEPES pH 7.1, 140 mM NaCl, 1 mM CaCl$_2$, 5 mM MgCl$_2$, and with 0.2% bovine serum albumin) to a concentration of 2.2×10$^5$ cells/mL for THP-1 cells and 1.1×10$^6$ for monocytes. Binding assays were set up as follows. First, 0.09 mL of cells (1×10$^5$ THP-1 cells/well or 5×10$^5$ monocytes) was added to the assay plates containing the compounds, giving a final concentration of ~2-10 μM each compound for screening (or part of a dose response for compound IC$_{50}$ determinations). Then 0.09 mL of $^{125}$I labeled MIP-1α (obtained from Amersham; Piscataway, N.J.) diluted in assay buffer to a final concentration of ~50 pM, yielding ~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (50 μl; Microscint 20, Packard Instruments) was added to each well, the plates were sealed and radioactivity measured in a Top Count scintillation counter (Packard Instruments). Control wells containing either diluent only (for total counts) or excess MIP-1α or MIP-1β (1 μg/mL, for non-specific binding) were used to calculate the percent of total inhibition for compound. The computer program Prism from GraphPad, Inc. (San Diego, Calif.) was used to calculate IC$_{50}$ values. IC$_{50}$ values are those concentrations required to reduce the binding of labeled MIP-1α to the receptor by 50%.
  Calcium Mobilization To detect the release of intracellular stores of calcium, cells (THP-1 or monocytes) were incubated with 3 μM of INDO-1AM dye (Molecular Probes; Eugene, Oreg.) in cell media for 45 minutes at room temperature and washed with phosphate buffered saline (PBS). After INDO-1AM loading, the cells were resuspended in flux buffer (Hank's balanced salt solution (HBSS) and 1% FBS). Calcium mobilization was measured using a Photon Technology International spectrophotometer (Photon Technology International; New Jersey) with excitation at 350 nm and dual simultaneous recording of fluorescence emission at 400 nm and 490 nm. Relative intracellular calcium levels were expressed as the 400 nm/490 nm emission ratio. Experiments were performed at 37° C. with constant mixing in cuvettes each containing 10$^6$ cells in 2 mL of flux buffer. The chemokine ligands may be used over a range from 1 to 100 nM. The emission ratio was plotted over time (typically 2-3 minutes). Candidate ligand blocking compounds (up to 10 μM) were added at 10 seconds, followed by chemokines at 60 seconds (i.e., MIP-1α; R&D Systems; Minneapolis, Minn.) and control chemokine (i.e., SDF-1α; R&D Systems; Minneapolis, Minn.) at 150 seconds.
  Chemotaxis Assays Chemotaxis assays were performed using 5 μm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e, MIP-1α, Leukotactin; R&D Systems; Minneapolis, Minn.) are use to evaluate compound mediated inhibition of CCR1 mediated migration. Other chemokines (i.e., SDF-1α; R&D Systems; Minneapolis, Minn.) are used as specificity controls. The lower chamber was loaded with 29 μl of chemokine (i.e., 0.1 nM MIP-1α) and varying amounts of compound; the top chamber contained 100,000 THP-1 or monocyte cells in 20

μl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

Identification of Inhibitors of CCR1

A. Assay

To evaluate small organic molecules that prevent the receptor CCR1 from binding ligand, an assay was employed that detected radioactive ligand (i.e, MIP-1α or leukotactin) binding to cells expressing CCR1 on the cell surface (for example, THP-1 cells or isolated human monocytes). For compounds that inhibited binding, whether competitive or not, fewer radioactive counts are observed when compared to uninhibited controls.

THP-1 cells and monocytes lack other chemokine receptors that bind the same set of chemokine ligands as CCR1 (i.e., MIP-1α, MPIF-1, Leukotactin, etc.). Equal numbers of cells were added to each well in the plate. The cells were then incubated with radiolabeled MIP-1α. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

$$\% \text{ inhibition} = (1 - [(\text{sample } cpm) - (\text{nonspecific } cpm)] / [(\text{total } cpm) - (\text{nonspecific } cpm)]) \times 100.$$

Dose Response Curves

To ascertain a candidate compound's affinity for CCR1 as well as confirm its ability to inhibit ligand binding, inhibitory activity was titered over a $1 \times 10^{-10}$ to $1 \times 10^{-4}$ M range of compound concentrations. In the assay, the amount of compound was varied; while cell number and ligand concentration were held constant.

CCR1 Functional Assays

CCR1 is a seven transmembrane, G-protein linked receptor. A hallmark of signaling cascades induced by the ligation of some such receptors is the pulse-like release of calcium ions from intracellular stores. Calcium mobilization assays were performed to determine if the candidate CCR1 inhibitory compounds were able to also block aspects of CCR1 signaling. Candidate compounds able to inhibit ligand binding and signaling with an enhanced specificity over other chemokine and non-chemokine receptors were desired.

Calcium ion release in response to CCR1 chemokine ligands (i.e., MIP-1α, MPIF-1, Leukotactin, etc.) was measured using the calcium indicator INDO-1. THP-1 cells or monocytes were loaded with INDO-1/AM and assayed for calcium release in response to CCR1 chemokine ligand (i.e., MIP-1α) addition. To control for specificity, non-CCR1 ligands, specifically bradykinin, was added, which also signals via a seven transmembrane receptor. Without compound, a pulse of fluorescent signal will be seen upon MIP-1α addition. If a compound specifically inhibits CCR1-MIP-1α signaling, then little or no signal pulse will be seen upon MIP-1α addition, but a pulse will be observed upon bradykinin addition. However, if a compound non-specifically inhibits signaling, then no pulse will be seen upon both MIP-1α and bradykinin addition.

Structures and activities are provided below for representative compounds of the invention, demonstrating that compounds provided herein can significantly and specifically inhibit signaling from CCR1.

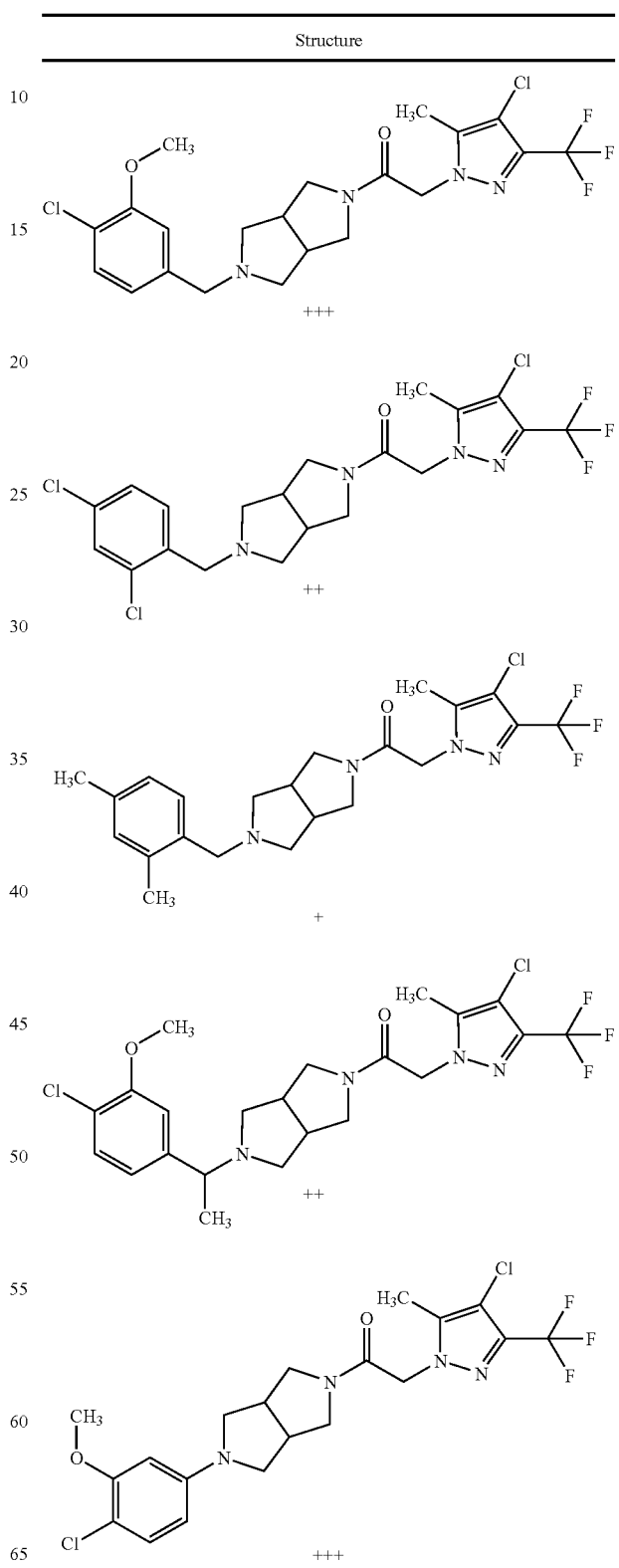

-continued
| Structure |
|---|
| 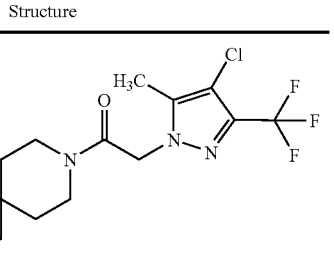<br>++ |
| 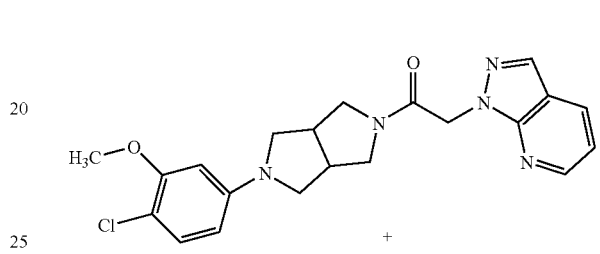<br>++ |
| 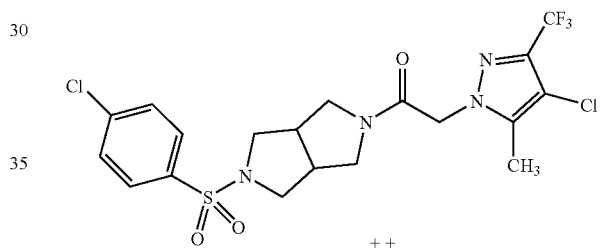<br>++ |
| 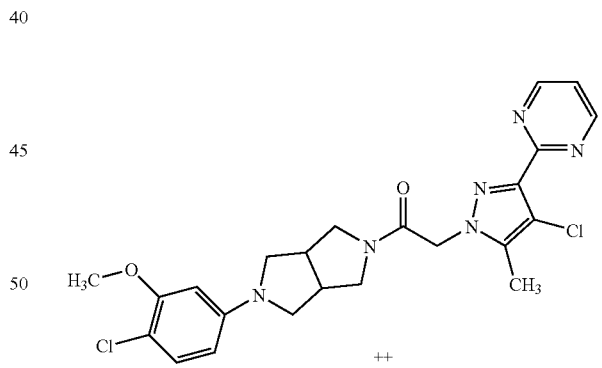<br>++ |
| 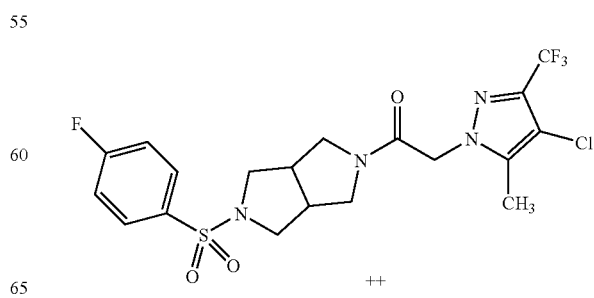<br>+ |
-continued
| Structure |
|---|
| 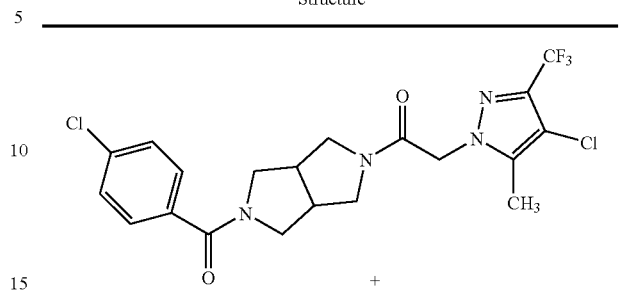 |

-continued

Structure

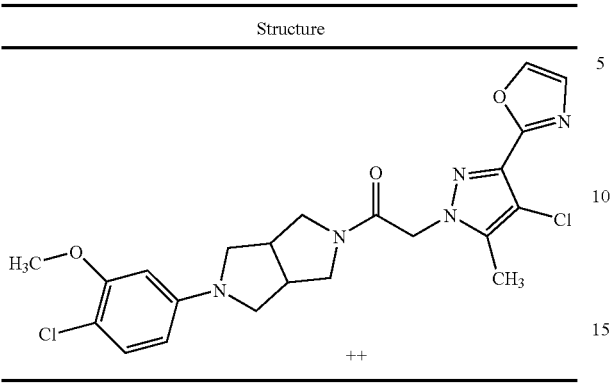

Activities:
+++ IC$_{50}$ < 100 nM
++ 100 nm < IC$_{50}$ < 3 μM
+ 3 μM < IC$_{50}$ < 100 μM One of the primary functions of chemokines is their ability to mediate the migration of chemokine receptor-expressing cells, such as white blood cells. Compounds were confirmed to inhibit not only CCR1 specific binding, but also CCR1 mediated migration via employment of a chemotaxis assay. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were place in the top compartment of a microwell migration chamber, while MIP-1α (or other potent CCR1 chemokine ligand) and increasing concentrations of drug candidate was loaded in the lower chamber. In the absence of inhibitor, cells will migrate to the lower chamber in response to the chemokine agonist; if a compound inhibited CCR1 function, then the majority of cells will remain in the upper chamber. To ascertain a candidate compound's affinity for CCR1 as well as to confirm its ability to inhibit CCR1 mediated cell migration, inhibitory activity was titered over a $1 \times 10^{-10}$ to $1 \times 10^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate IC$_{50}$ values. IC$_{50}$ values are those compound concentrations required to inhibit the number of cells responding to a CCR1 agonist by 50%.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound having the formula:

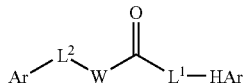

or a pharmaceutically acceptable salt or N-oxide thereof, wherein W is a fused bicyclic diamine moiety having formula B—

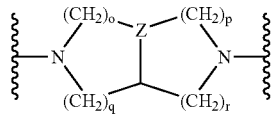

wherein the subscripts o, p, q and r are each independently integers of from 0 to 4, and (i) when o is 0, q is other than 0; (ii) when p is 0, r is other than 0; (iii) when q is 0, r is other than 0; (iv) when p is 0, o is other than 0; (v) the sum of o, p, q and r is 3 to 8; and Z is selected from the group consisting of CH, CR$^1$ and N;

and wherein formula B is optionally substituted with from 1 to 4 R$^1$ groups, and optionally having a double bond joining two ring vertices, and the wavy lines indicate the points of attachment to the remainder of the compound;

each R$^1$ is a substituent independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, —COR$^a$, —CO$_2$R$^a$, —CONR$^a$R$^b$, —NR$^a$COR$^b$, —SO$_2$R$^a$, —X$^1$COR$^a$, —X$^1$CO$_2$R$^a$, —X$^1$CONR$^a$R$^b$, —X$^1$NR$^a$COR$^b$, —X$^1$SO$_2$R$^a$, —X$^1$SO$_2$NR$^a$R$^b$, —X$^1$NR$^a$R$^b$, and —X$^1$OR$^a$; or any two R$^1$ substituents attached to the same atom are optionally replaced with the substituent =O, =NH, =NHOH, =NR$^f$, =S or =CR$^f$R$^g$; wherein X$^1$ is a member selected from the group consisting of C$_{1-4}$ alkylene, C$_{2-4}$ alkenylene and C$_{2-4}$ alkynylene and each R$^a$ and R$^b$ is independently selected from the group consisting of hydrogen, C$_{1-8}$ alkyl, C$_{1-8}$ haloalkyl, C$_{3-6}$ cycloalkyl and aryl-C$_{1-4}$alkyl, and wherein the aliphatic portions of each of said R$^1$ substituents is optionally substituted with from one to three members selected from the group consisting of —OH, —OR$^m$, —OC(O)NHR$^m$, —OC(O)N(R$^m$)$_2$, —SH, —SR$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein each R$^m$ is independently an unsubstituted C$_{1-6}$ alkyl; and optionally two R$^1$ groups on adjacent carbon atoms are joined to form a 5-, 6- or 7-membered carbocyclic or heterocyclic ring;

Ar is selected from the group consisting of phenyl, naphthyl, pyridyl, pyrazinyl, pyridazinyl, pyrimidinyl, triazinyl, quinolinyl, quinoxalinyl and purinyl, each of which is optionally substituted with from one to five R$^2$ substituents independently selected from the group consisting of halogen, —OR$^c$, —OC(O)R$^c$, —NR$^c$R$^d$, —SR$^c$, —R$^e$, —CN, —NO$_2$, —CO$_2$R$^c$, —CONR$^c$R$^d$, —C(O)R$^c$, —OC(O)NR$^c$R$^d$, —NR$^d$C(O)R$^c$, —NR$^d$C(O)$_2$R$^e$, —NR$^c$C(O)NR$^c$R$^d$, —NH—C(NH$_2$)=NH, —NR$^e$C(NH$_2$)=NH, —NH—C(NH$_2$)=NR$^e$, —NH—C(NHR$^e$)=NH, —S(O)R$^e$, —S(O)$_2$R$^e$, —NR$^c$S(O)$_2$R$^e$, —S(O)$_2$NR$^c$R$^d$, —N$_3$, —X$^2$OR$^c$, —O—X$^2$OR$^c$, —X$^2$OC(O)R$^c$, —X$^2$NR$^c$R$^d$, —O—X$^2$NR$^c$R$^d$, —X$^2$SR$^c$, —X$^2$CN, —X$^2$NO$_2$, —X$^2$CO$_2$R$^c$, —O—X²CO₂Rᶜ, —X²CONRᶜRᵈ, —O—X²CONRᶜRᵈ, —X²C(O)Rᶜ, —X²OC(O)NRᶜRᵈ, —X²NRᵈC(O)Rᶜ, —X²NRᵈC(O)₂Rᵉ, —X²NRᶜC(O)NRᶜRᵈ, —X²NH—C(NH₂)=NH, —X²NRᵉC(NH₂)=NH, —X²NH—C(NH₂)=NRᵉ, —X²NH—C(NHRᵉ)=NH, —X²S(O)Rᵉ, —X²S(O)₂Rᵉ, —X²NRᶜS(O)₂Rᵉ, —X²S(O)₂NRᶜRᵈ, —X²N₃, —NRᵈ—X²ORᶜ, —NRᵈ—X²NRᶜRᵈ, —NRᵈ—X²CO₂Rᶜ, and —NRᵈ—X²CONRᶜRᵈ, wherein X² is a member selected from the group consisting of $C_{1-4}$ alkylene, $C_{2-4}$ alkenylene and $C_{2-4}$ alkynylene and each Rᶜ and Rᵈ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or Rᶜ and Rᵈ when attached to the same nitrogen atom can be combined with the nitrogen atom to form a five or six-membered ring having from 0 to 2 additional heteroatoms as ring members; and each Rᵉ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of Rᶜ, Rᵈ and Rᵉ is optionally further substituted with from one to three members selected from the group consisting of —OH, —OR″, —OC(O)NHR″, —OC(O)N(R″)₂, —SH, —SR″, —S(O)R″, —S(O)₂R″, —SO₂NH₂, —S(O)₂NHR″, —S(O)₂N(R″)₂, —NHS(O)₂R″, —NR″S(O)₂R″, —C(O)NH₂, —C(O)NHR″, —C(O)N(R″)₂, —C(O)R″, —NHC(O)R″, —NR″C(O)R″, —NHC(O)NH₂, —NR″C(O)NH₂, —NR″C(O)NHR″, —NHC(O)NHR″, —NR″C(O)N(R″)₂, —NHC(O)N(R″)₂, —CO₂H, —CO₂R″, —NHCO₂R″, —NR″CO₂R″, —CN, —NO₂, —NH₂, —NHR″, —N(R″)₂, —NR″S(O)NH₂ and —NR″S(O)₂NHR″, wherein each R″ is independently an unsubstituted $C_{1-6}$ alkyl;

HAr is a heteroaryl group selected from the group consisting of pyrazolyl, imidazolyl, triazolyl, tetrazolyl, oxazolyl, isoxazolyl, oxadiazolyl, oxathiadiazolyl, pyrrolyl, thiazolyl, isothiazolyl, —wherein HAr is further substituted with 0 to 5 R³ substituents independently selected from the group consisting of halogen, —ORᶠ, —OC(O)Rᶠ, —NRᶠRᵍ, —SRᶠ, —Rʰ, —CN, —NO₂, —CO₂Rᶠ, —CONRᶠRᵍ, —C(O)Rᶠ, —OC(O)NRᶠRᵍ, —NRᵍC(O)Rᶠ, —NRᵍC(O)₂Rʰ, —NRᶠ—C(O)NRᶠRᵍ, —NH—C(NH₂)=NH, —NRʰC(NH₂)=NH, —NH—C(NH₂)=NRʰ, —NH—C(NHRʰ)=NH, —S(O)Rʰ, —S(O)₂Rʰ, —NRᶠS(O)₂Rʰ, —S(O)₂NRᶠRᵍ, —NRᶠS(O)₂NRᶠRᵍ, —N₃, —X³ORᶠ, —X³OC(O)Rᶠ, —X³NRᶠRᵍ, —X³SRᶠ, —X³CN, —X³NO₂, —X³CO₂Rᶠ, —X³CONRᶠRᵍ, —X³C(O)Rᶠ, —X³OC(O)NRᶠRᵍ, —X³NRᵍC(O)Rᶠ, —X³NRᵍC(O)₂Rʰ, —X³NRᶠ—C(O)NRᶠRᵍ, —X³NH—C(NH₂)=NH, —X³NRʰC(NH₂)=NH, —X³NH—C(NH₂)=NRʰ, —X³NH—C(NHRʰ)=NH, —X³S(O)Rʰ, —X³S(O)₂Rʰ, —X³NRᶠS(O)₂Rʰ, —X³S(O)₂NRᶠRᵍ, —Y, —X³Y, —S(O)₂Y, —C(O)Y, —X³N₃, —O—X³ORᶠ, —O—X³NRᶠRᵍ, —O—X³CO₂Rᶠ, —O—X³CONRᶠRᵍ, —NRᵍ—X³ORᶠ, —NRᵍ—X³NRᶠRᵍ, —NRᵍ—X³CO₂Rᶠ, and —NRᵍ—X³CONRᶠRᵍ, wherein Y is a five or six-membered aryl, heteroaryl or heterocyclic ring, optionally substituted with from one to three substituents selected from the group consisting of halogen, —ORᶠ, —OC(O)Rᶠ, —NRᶠRᵍ, —Rʰ, —SRᶠ, —CN, —NO₂, —CO₂Rᶠ, —CONRᶠRᵍ, —C(O)Rᶠ, —NRᵍC(O)Rᶠ, —NRᵍC(O)₂Rʰ, —S(O)Rʰ, —S(O)₂Rʰ, —NRᶠS(O)₂Rʰ, —S(O)₂NRᶠRᵍ, —X³ORᶠ, X³SRᶠ, —X³CN, —X³NO₂, —X³CO₂Rᶠ, —X³CONRᶠRᵍ, —X³C(O)Rᶠ, —X³OC(O)NRᶠRᵍ, —X³NRᵍC(O)Rᶠ, —X³NRᵍC(O)₂Rʰ, —X³NRᶠ—C(O)NRᶠRᵍ, —X³OC(O)Rᶠ, —X³S(O)Rʰ, —X³S(O)₂Rʰ, —X³NRᶠRᵍ, —X³NRᶠS(O)₂Rʰ, —X³S(O)₂NRᶠRᵍ, —O—X³ORᶠ, —O—X³NRᶠRᵍ, —O—X³CO₂Rᶠ, —O—X³CONRᶠRᵍ, —NRᵍ—X³ORᶠ, —NRᵍ—X³NRᶠRᵍ, —NRᵍ—X³CO₂Rᶠ, and —NRᵍ—X³CONRᶠRᵍ; wherein any two R³ substituents attached to the same atom are optionally replaced with the substituent =O, =NH, =NOH, =NRᶠ, =S or =CRᶠRᵍ; and any two R³ substituents on adjacent atoms can be combined to form a 5- to 6-membered ring, and wherein each X³ is independently selected from the group consisting of $C_{1-4}$ alkylene, $C_{2-4}$ alkenylene and $C_{2-4}$ alkynylene; and each Rᶠ and Rᵍ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members; and each Rʰ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of —X³—, Rᶠ, Rᵍ and Rʰ are optionally further substituted with from one to three members selected from the group consisting of —OH, —ORᵒ, —OC(O)NHRᵒ, —OC(O)N(Rᵒ)₂, —SH, —SRᵒ, —S(O)Rᵒ, —S(O)₂Rᵒ, —SO₂NH₂, —S(O)₂NHRᵒ, —S(O)₂N(Rᵒ)₂, —NHS(O)₂Rᵒ, —NRᵒS(O)₂Rᵒ, —C(O)NH₂, —C(O)NHRᵒ, —C(O)N(Rᵒ)₂, —C(O)Rᵒ, —NHC(O)Rᵒ, —NRᵒC(O)Rᵒ, —NHC(O)NH₂, —NRᵒC(O)NH₂, —NRᵒC(O)NHRᵒ, —NHC(O)NHRᵒ, —NRᵒC(O)N(Rᵒ)₂, —NHC(O)N(Rᵒ)₂, —CO₂H, —CO₂Rᵒ, —NHCO₂Rᵒ, —NRᵒCO₂Rᵒ, —CN, —NO₂, —NH₂, —NHRᵒ, —N(Rᵒ)₂, —NRᵒS(O)NH₂ and —NRᵒS(O)₂NHRᵒ, wherein each Rᵒ is independently an unsubstituted $C_{1-6}$ alkyl;

L¹ is a linking group having from one to three main chain atoms selected from the group consisting of C, N, O and S and being optionally substituted with from one to three substituents selected from the group consisting of halogen, —ORⁱ, —OC(O)Rⁱ, —NRⁱRʲ, —SRⁱ, —Rᵏ, —CN, —NO₂, —CO₂Rⁱ, —CONRⁱRʲ, —C(O)Rⁱ, —S(O)Rⁱ, —S(O)₂Rⁱ, —SO₂NH₂, —S(O)₂NHRⁱ, —S(O)₂NRⁱRʲ, —NHS(O)₂Rⁱ, —NRⁱS(O)₂Rⁱ, —OC(O)NRⁱRʲ, —NRʲC(O)Rⁱ, —NRʲC(O)₂Rᵏ, —Y¹, —X⁴Y¹, —X⁴ORⁱ, —X⁴OC(O)Rⁱ, —X⁴NRⁱRʲ, —X⁴SRⁱ, —X⁴S(O)₂Rⁱ, —X⁴S(O)₂NRⁱRʲ, —X⁴CN, —X⁴NO₂, —X⁴CO₂Rⁱ, —X⁴CONRⁱRʲ, —X⁴C(O)Rⁱ, —X⁴OC(O)NRⁱRʲ, —X⁴NRʲS(O)₂Rⁱ, —X⁴NRʲC(O)Rⁱ and —X⁴NRʲC(O)₂Rᵏ, wherein Y¹ is a five or six-membered aryl, heteroaryl or heterocyclic ring, optionally substituted with from one to three substituents independently selected from the group consisting of halogen, —ORⁱ, —OC(O)Rⁱ, —NRⁱRʲ, —SRⁱ, —Rᵏ, —CN, —NO₂, —CO₂Rⁱ, —CONRⁱRʲ, —C(O)Rⁱ, —S(O)Rⁱ, —S(O)₂Rⁱ, —SO₂NH₂, —S(O)₂NHRⁱ, —S(O)₂NRⁱRʲ, —NHS(O)₂Rⁱ, —NRⁱS(O)₂Rⁱ, —OC(O)NRⁱRʲ, —NRʲC(O)Rⁱ, —NRʲC(O)₂Rⁱ, —X⁴ORⁱ, —X⁴OC(O)Rⁱ, —X⁴NRⁱRʲ, —X⁴SRⁱ, —X⁴S(O)₂Rⁱ, —X⁴S(O)₂NRⁱRʲ, —X⁴CN, —X⁴NO₂, —X⁴CO₂Rⁱ, —X⁴CONRⁱRʲ, —X⁴C(O)Rⁱ, —X⁴OC(O)NRⁱRʲ, —X⁴NRʲS(O)₂Rⁱ, —X⁴NRʲC(O)Rⁱ and —X⁴NRʲC(O)₂Rⁱ, and wherein each X⁴ is independently selected from the group consisting of $C_{1-4}$ alkylene, $C_{2-4}$ alkenylene and $C_{2-4}$ alkynylene and each Rⁱ and Rʲ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, or when attached to the same nitrogen atom can be combined with the nitrogen atom to form a five or six-membered ring having from 0 to 2 additional heteroatoms as ring members, and each $R^k$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, wherein the aliphatic portions of —$X^4$—, $R^i$, $R^j$ and $R^k$ are optionally substituted with from one to three members selected from the group consisting of —OH, —$OR^p$, —OC(O)$NHR^p$, —OC(O)N($R^p$)$_2$, —SH, —$SR^p$, —S(O)$R^p$, —S(O)$_2R^p$, —SO$_2$NH$_2$, —S(O)$_2$NHR$^p$, —S(O)$_2$N($R^p$)$_2$, —NHS(O)$_2R^p$, —$NR^p$S(O)$_2R^p$, —C(O)NH$_2$, —C(O)NHR$^p$, —C(O)N($R^p$)$_2$, —C(O)$R^p$, —NHC(O)$R^p$, —$NR^p$C(O)$R^p$, —NHC(O)NH$_2$, —$NR^p$C(O)NH$_2$, —$NR^p$C(O)NHR$^p$, —NHC(O)NHR$^p$, —$NR^p$C(O)N($R^p$)$_2$, —NHC(O)N($R^p$)$_2$, —CO$_2$H, —CO$_2R^p$, —NHCO$_2R^p$, —$NR^p$CO$_2R^p$, —CN, —NO$_2$, —NH$_2$, —NHR$^p$, —N($R^p$)$_2$, —$NR^p$S(O)NH$_2$ and —$NR^p$S(O)$_2$NHR$^p$, wherein each $R^p$ is independently an unsubstituted $C_{1-6}$ alkyl; and $L^2$ is a covalent bond.

2. A compound of claim 1, having the formula

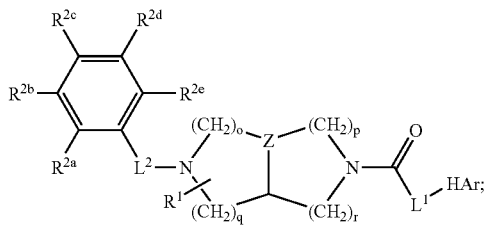

IIId or a pharmaceutically acceptable salt or N-oxide thereof, wherein the subscripts o, p, q and r are 0 to 3;
Z is CH, $CR^1$ or N;
$R^{2a}$, $R^{2b}$, $R^{2c}$, $R^{2d}$ and $R^{2e}$ are each members independently selected from the group consisting of hydrogen, halogen, —$OR^c$, —OC(O)$R^c$, —$NR^cR^d$, —$SR^c$, —$R^e$, —CN, —NO$_2$, —CO$_2R^c$, —$CONR^cR^d$, —C(O)$R^c$, —OC(O)$NR^cR^d$, —$NR^d$C(O)$R^c$, —$NR^d$C(O)$_2R^e$, —$NR^e$—C(O)$NR^cR^d$, —NH—C(NH$_2$)=NH, —$NR^e$C(NH$_2$)=NH, —NH—C(NH$_2$)=$NR^e$, —NH—C(NHR$^e$)=NH, —S(O)$R^e$, —S(O)$_2R^e$, —$NR^c$S(O)$_2R^e$, —S(O)$_2NR^cR^d$, —$N_3$, —$X^2OR^c$, —O—$X^2OR^c$, —$X^2$OC(O)$R^c$, —$X^2NR^cR^d$, —O—$X^2NR^cR^d$, —$X^2SR^c$, —$X^2$CN, —$X^2$NO$_2$, —$X^2CO_2R^c$, —O—$X^2CO_2R^c$, —$X^2CONR^cR^d$, —O—$X^2CONR^cR^d$, —$X^2$C(O)$R^c$, —$X^2$OC(O)$NR^cR^d$, —$X^2NR^d$C(O)$R^c$, —$X^2NR^d$C(O)$_2R^e$, —$X^2NR^e$C(O)$NR^cR^d$, —$X^2$NH—C(NH$_2$)=NH, —$X^2NR^e$C(NH$_2$)=NH, —$X^2$NH—C(NH$_2$)=$NR^e$, —$X^2$NH—C(NHR$^e$)=NH, —$X^2$S(O)$R^e$, —$X^2$S(O)$_2R^e$, —$X^2NR^c$S(O)$_2R^e$, —$X^2$S(O)$_2NR^cR^d$, —$NR^d$—$X^2OR^c$, —$NR^d$—$X^2NR^cR^d$, —$NR^d$—$X^2CO_2R^c$, and —$NR^d$—$X^2CONR^cR^d$, wherein $X^2$ is a member selected from the group consisting of $C_{1-4}$ alkylene, $C_{2-4}$ alkenylene and $C_{2-4}$ alkynylene and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or $R^c$ and $R^d$ when attached to the same nitrogen atom can be combined with the nitrogen atom to form a five or six-membered ring having from 0 to 2 additional heteroatoms as ring members; and each $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of $R^c$, $R^d$ and $R^e$ is optionally further substituted with from one to three members selected from the group consisting of —OH, —$OR''$, —OC(O)$NHR''$, —OC(O)N($R''$)$_2$, —SH, —$SR''$, —S(O)$R''$, —S(O)$_2R''$, —SO$_2$NH$_2$, —S(O)$_2NHR''$, —S(O)$_2$N($R''$)$_2$, —NHS(O)$_2R''$, —$NR''$S(O)$_2R''$, —C(O)NH$_2$, —C(O)$NHR''$, —C(O)N($R''$)$_2$, —C(O)$R''$, —NHC(O)$R''$, —$NR''$C(O)$R''$, —NHC(O)NH$_2$, —$NR''$C(O)NH$_2$, —$NR''$C(O)$NHR''$, —NHC(O)$NHR''$, —$NR''$C(O)N($R''$)$_2$, —NHC(O)N($R''$)$_2$, —CO$_2$H, —CO$_2R''$, —NHCO$_2R''$, —$NR''$CO$_2R''$, —CN, —NO$_2$, —NH$_2$, —$NHR''$, —N($R''$)$_2$, —$NR''$S(O)NH$_2$ and —$NR''$S(O)$_2NHR''$, wherein each $R''$ is independently an unsubstituted $C_{1-6}$ alkyl, such that at least one of $R^{2a}$, $R^{2b}$, $R^{2c}$, $R^{2d}$ and $R^{2e}$ is other than H;
$L^1$ is —CH$_2$—, —CH$_2$NH— or —CH$_2$O— and is optionally substituted with —$R^k$, —$X^4OR^i$, —$X^4$OC(O)$R^i$, —$X^4NR^iR^j$, —$X^4CO_2R^i$, —$X^4CONR^iR^j$, —$X^4SR^i$, —$Y^1$, —$X^4Y^1$, —$X^4$CN or —$X^4$NO$_2$;
$L^2$ is a covalent bond, and
HAr is pyrazolyl, wherein the HAr group is substituted with from 0 to 3 $R^3$ groups.

3. A compound of claim 2, wherein $R^{2c}$ is selected from the group consisting of F, Cl, Br, I, CN, NO$_2$, —CO$_2$CH$_3$, —C(O)CH$_3$ and —S(O)$_2$CH$_3$.

4. A compound of claim 2, wherein $R^{2d}$ is selected from the group consisting of —$SR^c$, —O—$X^2$—$OR^c$, —$X^2$—$OR^c$, —$R^e$ and —$OR^c$.

5. A compound of claim 1, wherein Ar is phenyl substituted with from 1 to 3 $R^2$ groups.

6. A compound of claim 1, wherein HAr is attached to the remainder of the molecule through a nitrogen atom.

7. A compound of claim 1, wherein W is formula B; Ar is phenyl substituted with from 1 to 3 $R^2$ groups; and HAr is pyrazolyl which is substituted with from 1 to 3 $R^3$ groups.

8. A compound of claim 7, wherein $R^2$ is halogen, —$OR^c$, —$R^e$, —CN or —NO$_2$.

9. A compound of claim 2 wherein $L^1$ is —CH$_2$—.

10. A compound of claim 2 wherein the subscripts o, p, q and r are each 1.

11. A compound of claim 2, wherein each $R^3$ moiety on the pyrazole ring is a member independently selected from the group consisting of halogen, —$OR^f$, —$NR^fR^g$, —C(O)$OR^f$, —S(O)$R^h$, —S(O)$_2R^h$, —S(O)$_2NR^fR^g$, —$R^h$, —CN, and —Y.

12. A compound of claim 1, wherein each $R^3$ moiety on the pyrazole ring is flouro, chloro, bromo, iodo, oxazolyl, pyridyl, thiazolyl, —$R^h$ or cyano.

13. A compound of claim 1, selected from the group consisting of:

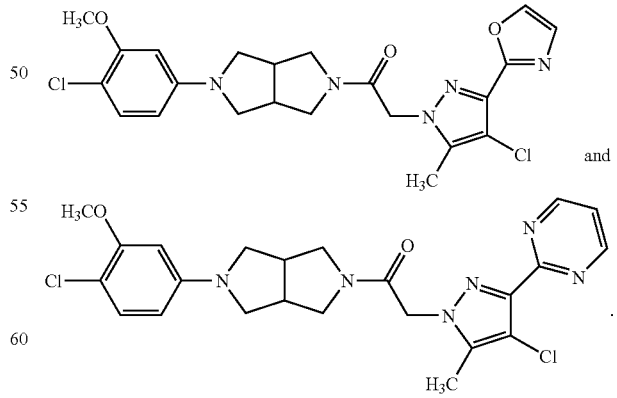

14. A pharmaceutical composition comprising a pharmaceutically acceptable excipient and a compound of claim 1.

* * * * *

UNITED STATES PATENT AND TRADEMARK OFFICE
CERTIFICATE OF CORRECTION

| | |
|---|---|
| PATENT NO. | : 7,435,831 B2 |
| APPLICATION NO. | : 11/219637 |
| DATED | : October 14, 2008 |
| INVENTOR(S) | : Wei Chen et al. |

Page 1 of 1

It is certified that error appears in the above-identified patent and that said Letters Patent is hereby corrected as shown below:

Claim 7, Column 108, Line 31, please insert -- -- -- and -- -- -- before and after "HAr"

Claim 11, Column 108, Line 40, please insert -- -C(O)R$^f$ -- after -NR$^f$R$^g$, and before -C(O)OR$^f$ Signed and Sealed this Sixteenth Day of December, 2008

JON W. DUDAS
*Director of the United States Patent and Trademark Office*